United States Patent
Chartier-Courtaud et al.

(10) Patent No.: US 12,024,718 B2
(45) Date of Patent: *Jul. 2, 2024

(54) CLOSED PROCESS FOR EXPANSION AND GENE EDITING OF TUMOR INFILTRATING LYMPHOCYTES AND USES OF SAME IN IMMUNOTHERAPY

(71) Applicant: Iovance Biotherapeutics, Inc., San Carlos, CA (US)

(72) Inventors: Cecile Chartier-Courtaud, Palo Alto, CA (US); Krit Ritthipichai, Tampa, FL (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 17/810,482

(22) Filed: Jul. 1, 2022

(65) Prior Publication Data

US 2022/0403333 A1 Dec. 22, 2022

Related U.S. Application Data

(63) Continuation of application No. 17/387,357, filed on Jul. 28, 2021, now Pat. No. 11,384,337, which is a continuation of application No. 17/050,552, filed as application No. PCT/US2019/029286 on Apr. 26, 2019.

(60) Provisional application No. 62/680,821, filed on Jun. 5, 2018, provisional application No. 62/663,885, filed on Apr. 27, 2018.

(51) Int. Cl.
| | |
|---|---|
| *C12N 5/0783* | (2010.01) |
| *A01N 1/02* | (2006.01) |
| *A61K 35/17* | (2015.01) |
| *C12N 9/22* | (2006.01) |
| *C12N 15/113* | (2010.01) |

(52) U.S. Cl.
CPC ......... *C12N 5/0638* (2013.01); *A01N 1/0221* (2013.01); *A01N 1/0226* (2013.01); *A61K 35/17* (2013.01); *C12N 9/22* (2013.01); *C12N 15/113* (2013.01); *C12N 2310/20* (2017.05); *C12N 2501/2302* (2013.01); *C12N 2501/2315* (2013.01); *C12N 2501/2321* (2013.01); *C12N 2501/515* (2013.01)

(58) Field of Classification Search
None
See application file for complete search history.

(56) References Cited

U.S. PATENT DOCUMENTS

| | | |
|---|---|---|
| 4,766,106 A | 8/1988 | Katre et al. |
| 4,902,502 A | 2/1990 | Nitecki et al. |
| 5,019,034 A | 5/1991 | Weaver et al. |
| 5,089,261 A | 2/1992 | Nitecki et al. |
| 5,128,257 A | 7/1992 | Baer |
| 5,137,817 A | 8/1992 | Busta et al. |
| 5,173,158 A | 12/1992 | Schmukler |
| 5,206,344 A | 4/1993 | Katre et al. |
| 5,232,856 A | 8/1993 | Firth |
| 5,273,525 A | 12/1993 | Hofmann |
| 5,279,833 A | 1/1994 | Rose |
| 5,304,120 A | 4/1994 | Crandell et al. |
| 5,318,514 A | 6/1994 | Hofmann |
| 5,593,875 A | 1/1997 | Wurm et al. |
| 5,766,902 A | 6/1998 | Craig et al. |
| 5,908,635 A | 6/1999 | Thierry |
| 5,928,893 A | 7/1999 | Kang et al. |
| 6,010,613 A | 1/2000 | Walters et al. |
| 6,025,337 A | 2/2000 | Truong et al. |
| 6,056,938 A | 5/2000 | Unger et al. |
| 6,078,490 A | 6/2000 | Walters |
| 6,110,490 A | 8/2000 | Thierry |
| 6,210,669 B1 | 4/2001 | Aruffo et al. |
| 6,303,121 B1 | 10/2001 | Kwon |
| 6,362,325 B1 | 3/2002 | Kwon |
| 6,410,517 B1 | 6/2002 | Truong et al. |
| 6,475,994 B2 | 11/2002 | Tomalia et al. |
| 6,479,626 B1 | 11/2002 | Kim et al. |
| 6,489,458 B2 | 12/2002 | Hackett et al. |
| 6,534,261 B1 | 3/2003 | Cox et al. |

(Continued)

FOREIGN PATENT DOCUMENTS

| | | |
|---|---|---|
| EP | 0672141 | 5/2003 |
| WO | WO 1995/12673 | 5/1995 |

(Continued)

OTHER PUBLICATIONS

Heon et al. (2015) Biochemical and Biophysical Research Communications 464:360-366.*
Shi et al. (2017) Gene 636:36-41.*
U.S. Appl. No. 15/863,634, filed Jan. 5, 2018, now U.S. Pat. No. 10,894,063.
U.S. Appl. No. 15/874,718, filed Jan. 18, 2018, now U.S. Pat. No. 10,166,257.
U.S. Appl. No. 15/892,311, filed Feb. 8, 2018, now U.S. Pat. No. 10,130,659.

(Continued)

*Primary Examiner* — Michail A Belyavskyi
(74) *Attorney, Agent, or Firm* — Morgan, Lewis & Bockius LLP

(57) ABSTRACT

The present invention provides improved and/or shortened methods for expanding TILs and producing therapeutic populations of TILs, including novel methods for expanding TIL populations in a closed system that lead to improved efficacy, improved phenotype, and increased metabolic health of the TILs in a shorter time period, while allowing for reduced microbial contamination as well as decreased costs. The methods may comprise gene-editing at least a portion of the TILs to enhance their therapeutic efficacy. Such TILs find use in therapeutic treatment regimens.

30 Claims, 26 Drawing Sheets

Specification includes a Sequence Listing.

(56) References Cited

U.S. PATENT DOCUMENTS

| | | |
|---|---|---|
| 6,534,484 B1 | 3/2003 | Wheeler et al. |
| 6,569,997 B1 | 5/2003 | Kwon |
| 6,607,882 B1 | 8/2003 | Cox et al. |
| 6,627,442 B1 | 9/2003 | Humeau et al. |
| 6,706,289 B2 | 3/2004 | Lewis et al. |
| 6,746,838 B1 | 6/2004 | Choo et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,887,673 B2 | 5/2005 | Kunkel et al. |
| 6,903,185 B2 | 6/2005 | Kim et al. |
| 6,905,685 B2 | 6/2005 | Kwon et al. |
| 6,933,113 B2 | 8/2005 | Case et al. |
| 6,974,863 B2 | 12/2005 | Kwon |
| 6,979,539 B2 | 12/2005 | Cox et al. |
| 7,013,219 B2 | 3/2006 | Case et al. |
| 7,030,215 B2 | 4/2006 | Liu et al. |
| 7,189,705 B2 | 3/2007 | Lam et al. |
| 7,214,493 B2 | 5/2007 | Kunkel et al. |
| 7,220,719 B2 | 5/2007 | Case et al. |
| 7,241,573 B2 | 7/2007 | Choo et al. |
| 7,241,574 B2 | 7/2007 | Choo et al. |
| 7,288,638 B2 | 10/2007 | Jure-Kunkel et al. |
| 7,504,101 B2 | 3/2009 | Weinberg |
| 7,550,140 B2 | 6/2009 | Bakker et al. |
| 7,585,849 B2 | 9/2009 | Liu et al. |
| 7,595,376 B2 | 9/2009 | Kim et al. |
| 7,622,444 B2 | 11/2009 | Weinberg |
| 7,687,070 B2 | 3/2010 | Gebeyehu et al. |
| 7,696,175 B2 | 4/2010 | Epstein et al. |
| 7,943,743 B2 | 5/2011 | Korman et al. |
| 7,960,515 B2 | 6/2011 | Min et al. |
| 7,961,515 B2 | 6/2011 | Kato et al. |
| 8,008,449 B2 | 8/2011 | Korman et al. |
| 8,034,334 B2 | 10/2011 | Dudley et al. |
| 8,133,983 B2 | 3/2012 | Bakker et al. |
| 8,236,930 B2 | 8/2012 | Min et al. |
| 8,287,857 B2 | 11/2012 | Dudley et al. |
| 8,337,850 B2 | 12/2012 | Ahrens et al. |
| 8,383,099 B2 | 2/2013 | Dudley et al. |
| 8,450,460 B2 | 5/2013 | Hill et al. |
| 8,586,526 B2 | 11/2013 | Gregory et al. |
| 8,697,359 B1 | 4/2014 | Zhang |
| 8,771,945 B1 | 7/2014 | Zhang |
| 8,795,965 B2 | 8/2014 | Zhang |
| 8,809,050 B2 | 8/2014 | Vera et al. |
| 8,821,867 B2 | 9/2014 | Ahrens et al. |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,921,519 B2 | 12/2014 | Hill et al. |
| 8,932,814 B2 | 1/2015 | Cong et al. |
| 8,945,839 B2 | 2/2015 | Zhang |
| 8,956,860 B2 | 2/2015 | Vera et al. |
| 8,993,233 B2 | 3/2015 | Zhang et al. |
| 8,999,641 B2 | 4/2015 | Zhang et al. |
| 9,006,399 B2 | 4/2015 | Liu et al. |
| 9,028,824 B2 | 5/2015 | Min et al. |
| 9,074,185 B2 | 7/2015 | Dudley et al. |
| 9,163,085 B2 | 10/2015 | Liu et al. |
| 9,340,599 B2 | 5/2016 | Hill et al. |
| 9,359,420 B2 | 6/2016 | Hill et al. |
| 9,458,439 B2 | 10/2016 | Choulika |
| 9,468,678 B2 | 10/2016 | Ahrens et al. |
| 9,844,569 B2 | 12/2017 | Gros et al. |
| 9,914,783 B1 | 3/2018 | Afar et al. |
| 9,982,278 B2 | 5/2018 | Gill et al. |
| 2005/0095244 A1 | 5/2005 | Jure-Kunkel et al. |
| 2005/0106717 A1 | 5/2005 | Wilson et al. |
| 2010/0136030 A1 | 6/2010 | Salah-Eddine et al. |
| 2011/0027218 A1 | 2/2011 | Hill et al. |
| 2011/0052530 A1 | 3/2011 | Dudley et al. |
| 2011/0111494 A1 | 5/2011 | Hill et al. |
| 2011/0136228 A1 | 6/2011 | Vera et al. |
| 2011/0201118 A1 | 8/2011 | Yang et al. |
| 2012/0244133 A1 | 9/2012 | Rosenberg et al. |
| 2013/0102075 A1 | 4/2013 | Vera et al. |
| 2013/0115617 A1 | 5/2013 | Wilson |
| 2013/0117869 A1 | 5/2013 | Duchateau et al. |
| 2013/0315884 A1 | 11/2013 | Gaietto et al. |
| 2014/0227237 A1 | 8/2014 | June et al. |
| 2014/0328791 A1 | 11/2014 | Bossard et al. |
| 2014/0377284 A1 | 12/2014 | Simons et al. |
| 2014/0377739 A1 | 12/2014 | Welch et al. |
| 2015/0110734 A1 | 4/2015 | Hill et al. |
| 2015/0126709 A1 | 5/2015 | Hill et al. |
| 2015/0126710 A1 | 5/2015 | Hill et al. |
| 2015/0132288 A1 | 5/2015 | Simons et al. |
| 2015/0175966 A1 | 6/2015 | Vera et al. |
| 2015/0190506 A1 | 7/2015 | Cheung et al. |
| 2015/0203871 A1 | 7/2015 | Juillerat et al. |
| 2016/0010058 A1 | 1/2016 | Gros et al. |
| 2016/0102324 A1 | 4/2016 | Duchateau et al. |
| 2016/0120906 A1 | 5/2016 | Gaietto et al. |
| 2016/0208216 A1 | 7/2016 | Vera et al. |
| 2016/0215262 A1 | 7/2016 | Powell |
| 2017/0044496 A1 | 2/2017 | Samaik et al. |
| 2017/0081635 A1 | 3/2017 | Samaik et al. |
| 2017/0107490 A1 | 4/2017 | Maeurer |
| 2017/0152478 A1 | 6/2017 | Rosenberg et al. |
| 2018/0021379 A1 | 1/2018 | Gaietto et al. |
| 2018/0127715 A1 | 5/2018 | Veerapathran et al. |
| 2018/0187150 A1 | 7/2018 | De Larichaudy |
| 2018/0207201 A1 | 7/2018 | Wardell et al. |
| 2018/0228841 A1 | 8/2018 | Frank et al. |
| 2019/0010514 A1 | 1/2019 | Poirot et al. |
| 2019/0111153 A1 | 4/2019 | Stephan et al. |

FOREIGN PATENT DOCUMENTS

| | | |
|---|---|---|
| WO | WO 1995/21925 | 8/1995 |
| WO | WO 2004031370 A1 | 4/2004 |
| WO | WO 2006/121810 | 11/2006 |
| WO | WO 2008/025516 A1 | 3/2008 |
| WO | WO 2009/007120 A1 | 1/2009 |
| WO | WO 2009040789 A2 | 4/2009 |
| WO | WO 2010/003766 A1 | 1/2010 |
| WO | WO 2010/010051 A1 | 1/2010 |
| WO | WO 2010/042433 | 4/2010 |
| WO | WO 2012/032433 A1 | 4/2010 |
| WO | WO 2010/078966 A1 | 7/2010 |
| WO | WO 2011072088 A2 | 6/2011 |
| WO | WO 2012/027328 | 3/2012 |
| WO | WO 2012065086 A1 | 5/2012 |
| WO | WO 2012129201 A1 | 9/2012 |
| WO | WO 2012/177788 | 12/2012 |
| WO | WO 2013/028231 | 2/2013 |
| WO | WO 2013/038191 | 3/2013 |
| WO | WO 2013/057500 A1 | 4/2013 |
| WO | WO 2013/088147 A1 | 6/2013 |
| WO | WO 2013/173835 A1 | 11/2013 |
| WO | WO 2013/188427 A1 | 12/2013 |
| WO | WO 2014/148895 | 9/2014 |
| WO | WO 2014/184744 | 11/2014 |
| WO | WO 2014210036 A1 | 12/2014 |
| WO | WO 2015009604 A1 | 1/2015 |
| WO | WO 2015/119923 | 8/2015 |
| WO | WO 2015/164745 A1 | 10/2015 |
| WO | WO 2015157636 A1 | 10/2015 |
| WO | WO 2015/189357 A1 | 12/2015 |
| WO | WO 2015188839 A1 | 12/2015 |
| WO | WO 2015189356 A1 | 12/2015 |
| WO | WO 2015189357 A1 | 12/2015 |
| WO | WO 2016/053338 A1 | 4/2016 |
| WO | WO 2016/096903 A1 | 6/2016 |
| WO | WO 2018/081473 A1 | 5/2018 |
| WO | WO 2018/081476 A2 | 5/2018 |
| WO | WO 2018/081789 | 5/2018 |
| WO | WO 2018/100023 | 6/2018 |
| WO | WO 2018/129332 A1 | 7/2018 |
| WO | WO 2018/129336 | 7/2018 |
| WO | WO 2018/075664 A1 | 10/2018 |

(56) References Cited

FOREIGN PATENT DOCUMENTS

| WO | WO 2018/182817 A1 | 10/2018 |
|---|---|---|
| WO | WO 2018/194176 | 10/2018 |
| WO | WO 2018182817 A1 | 10/2018 |
| WO | WO 2018/209115 | 11/2018 |
| WO | WO 2018/226714 A1 | 12/2018 |

OTHER PUBLICATIONS

U.S. Appl. No. 16/136,147, filed Sep. 19, 2018, now U.S. Pat. No. 10,272,113.
U.S. Appl. No. 16/136,157, filed Sep. 19, 2018, now U.S. Pat. No. 10,420,799.
U.S. Appl. No. 16/201,957, filed Nov. 27, 2018, now U.S. Pat. No. 10,398,734.
U.S. Appl. No. 16/192,707, filed Nov. 15, 2018, now U.S. Pat. No. 10,537,595.
U.S. Appl. No. 16/425,746, filed May 29, 2019, now U.S. Pat. No. 10,639,330.
U.S. Appl. No. 16/203,467, filed Nov. 28, 2018, now U.S. Pat. No. 10,463,697.
U.S. Appl. No. 16/203,478, filed Nov. 28, 2018, now U.S. Pat. No. 10,363,273.
U.S. Appl. No. 16/425,767, filed May 29, 2019, now U.S. Pat. No. 10,695,372.
U.S. Appl. No. 16/425,778, filed May 29, 2019, now U.S. Pat. No. 10,646,517.
U.S. Appl. No. 16/746,416, filed Jan. 17, 2020, now U.S. Pat. No. 10,653,723.
U.S. Appl. No. 16/848,361, filed Apr. 14, 2020, now U.S. Pat. No. 10,905,718.
U.S. Appl. No. 16/848,386, filed Apr. 14, 2020, now U.S. Pat. No. 10,953,046.
U.S. Appl. No. 16/848,454, filed Apr. 14, 2020, now U.S. Pat. No. 10,946,044.
U.S. Appl. No. 16/848,426, filed Apr. 14, 2020, now U.S. Pat. No. 10,953,047.
U.S. Appl. No. 16/848,442, filed Apr. 14, 2020, now U.S. Pat. No. 10,933,094.
U.S. Appl. No. 16/848,474, filed Apr. 14, 2020, now U.S. Pat. No. 10,946,045.
U.S. Appl. No. 16/879,711, filed May 20, 2020, now U.S. Pat. No. 10,925,900.
U.S. Appl. No. 17/110,207, filed Dec. 2, 2020, now U.S. Pat. No. 11,083,752.
U.S. Appl. No. 17/127,768, filed Dec. 18, 2020, now U.S. Pat. No. 11,007,225.
U.S. Appl. No. 17/127,840, filed Dec. 18, 2020, now U.S. Pat. No. 11,052,116.
U.S. Appl. No. 17/127,790, filed Dec. 18, 2020, now U.S. Pat. No. 11,007,226.
U.S. Appl. No. 17/127,795, filed Dec. 18, 2020, now U.S. Pat. No. 11,052,115.
U.S. Appl. No. 17/147,073, filed Jan. 12, 2021, now U.S. Pat. No. 11,013,770.
U.S. Appl. No. 17/147,080, filed Jan. 12, 2021.
U.S. Appl. No. 17/147,090, filed Jan. 12, 2021, now U.S. Pat. No. 11,040,070.
U.S. Appl. No. 17/147,096, filed Jan. 12, 2021.
U.S. Appl. No. 17/326,088, filed May 20, 2021, now U.S. Pat. No. 11,202,803.
U.S. Appl. No. 17/382,831, filed Jul. 22, 2021, now allowed.
U.S. Appl. No. 17/383,272, filed Jul. 22, 2021, now U.S. Pat. No. 11,202,804.
U.S. Appl. No. 17/383,276, filed Jul. 22, 2021, now allowed.
U.S. Appl. No. 17/383,280, filed Jul. 22, 2021, now allowed.
U.S. Appl. No. 17/480,525, filed Sep. 21, 2021, now allowed.
U.S. Appl. No. 17/480,534, filed Sep. 21, 2021.
U.S. Appl. No. 17/480,587, filed Sep. 21, 2021.
U.S. Appl. No. 17/480,596, filed Sep. 21, 2021.
U.S. Appl. No. 15/751,440, filed Feb. 8, 2018, now U.S. Pat. No. 11,026,974.
U.S. Appl. No. 15/892,331, filed Feb. 8, 2018, now U.S. Pat. No. 10,517,894.
U.S. Appl. No. 17/225,993, filed Apr. 8, 2021, now U.S. Pat. No. 11,058,728.
U.S. Appl. No. 17/233,290, filed Apr. 16, 2021, now allowed.
U.S. Appl. No. 17/233,295, filed Apr. 16, 2021, now U.S. Pat. No. 11,123,371.
U.S. Appl. No. 17/233,299, filed Apr. 16, 2021, now U.S. Pat. No. 11,141,438.
U.S. Appl. No. 17/459,988, filed Aug. 27, 2021.
U.S. Appl. No. 17/480,900, filed Sep. 21, 2021.
U.S. Appl. No. 17/480,916, filed Sep. 21, 2021.
U.S. Appl. No. 17/480,919, filed Sep. 21, 2021.
U.S. Appl. No. 17/480,935, filed Sep. 21, 2021.
U.S. Appl. No. 17/480,941, filed Sep. 21, 2021, now allowed.
U.S. Appl. No. 17/548,502, filed Dec. 11, 2021.
U.S. Appl. No. 17/548,504, filed Dec. 11, 2021.
U.S. Appl. No. 17/547,190, filed Dec. 9, 2021.
U.S. Appl. No. 17/547,192, filed Dec. 9, 2021.
U.S. Appl. No. 15/940,901, filed Mar. 29, 2018, now U.S. Pat. No. 10,918,666.
U.S. Appl. No. 17/041,305, filed Sep. 24, 2020.
U.S. Appl. No. 17/110,179, filed Dec. 2, 2020.
U.S. Appl. No. 17/147,412, filed Jan. 12, 2021.
U.S. Appl. No. 17/148,475, filed Jan. 13, 2021, now U.S. Pat. No. 11,168,303.
U.S. Appl. No. 17/148,508, filed Jan. 13, 2021, now U.S. Pat. No. 11,168,304.
U.S. Appl. No. 17/353,430, filed Jun. 21, 2021, now allowed.
U.S. Appl. No. 16/618,039, filed Nov. 27, 2019.
U.S. Appl. No. 16/211,159, filed Dec. 5, 2018.
U.S. Appl. No. 17/050,552, filed Oct. 26, 2020.
U.S. Appl. No. 17/387,357, filed Jul. 28, 2021.
Ahmad, et al., "scFv Antibody: Principles and Clinical Application;" Clin. & Dev. Immunol. 2012, 980250.
Akkok, C. A. et al. "Use of different DMSO concentrations for cryopreservation of autologous peripheral blood stem cell grafts does not have any major impact on levels of leukocyte- and platelet-derived soluble mediators." Cytotherapy vol. 11,6 (2009): 749-60. doi:10.3109/14653240902980443.
Axelsson et al., "Cryopreserved peripheral blood mononuclear cells are suitable for the assessment of immunological markers in type 1 diabetic children", Cryobiology, Aug. 2008, 57, 201-208.
Bachmaier, et al., "Negative regulation of lymphocyteactivation and autoimmunity by themolecular adaptor Cbl-b;" Nature, 2000, 403, 211-216.
Bajgain, P. et al., "Optimizing the production of suspension cells using the G-Rex "M" series", Molecular Therapy—Methods and Clinical Development, vol. 1, Jan. 1, 2014.
Baruch et al., "Adoptive T cell therapy: An overview of obstacles and opportunities : ACT Obstacles and Opportunities", Cancer, vol. 123, No. S11, May 19, 2017, pp. 2154-2162.
Beane, et al., "Clinical Scale Zinc Finger Nuclease-mediated Gene Editing of PD-1 in Tumor Infiltrating Lymphocytes forthe Treatment of Metastatic Melanoma;" Mol. Therapy, 2015, 23 1380-1390.
Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55.
Bloom, et al., "Blockade of BAFF Receptor BR3 on T cells Enhances Their Activation and Cytotoxicity;" J. Immunother., 2018, in press.
Boettcher and McManus, "Choosing the Right Tool for the Job: RNAi, TALEN or CRISPR;" Mol. Cell Review, 2015, 58, 575-585.
Cepko and Pear, "Transduction of Genes Using Retrovirus Vectors;" Cur. Prot. Mol. Biol. 1996, 9.9.1-9.9.16.
Chacon et al., "Co-stimulation through 4-1BB/CD137 Improves the Expansion and Fundtion of CD8+ Melanoma Tumor-Infiltrating Lymphocytes for Adoptive T-Cell Therapy", PLOS ONE, vol. 8, No. 4, Apr. 1, 2013, 25 pages.

(56) References Cited

OTHER PUBLICATIONS

Chang C.-H. et al., "Metabolic competition in the tumor microenvironment is a driver of cancer progression", Cell., Sep. 10, 2015, vol. 162, No. 6, pp. 1229-1241.
Chang et al., "Emerging concepts in immunotherapy T-cell metabolism as a therapeutic target", Nat. Immunol., Apr. 2016, 17(4), 364-368.
Chen and Okayarea, "High-Efficiency Transformation of Mammalian Cells by Plasmid DNA;"*Mol. Cell. Biol.* 1987, 7, 2745-2752.
Cox, et al.; "Therapeutic Genome Editing: Prospects and Challenges;" Nat Med. Feb. 2015; 21(2): 121-131.
Curti, et al., "OX40 is a potent immune stimulating target in late stage cancer Patients;" *Cancer Res.* 2013, 73, 7189-98.
Daboussi et al., "Genome engineering empowers the diatom Phaeodactylum tricomutum for biotechnology;" *Nat Commun* 2014; 5:3831.
Damsky, et al., :Mouse Melanoma Models and Cell Lines; Pigment Cell & Melanoma Res. 2010,23, 853-859.
Dudley et al., "CD8+ Enriched "Young" Tumor Infiltrating Lymphocytes Can Mediate Regression of Metastatic Melanoma" Clin Cancer Res, 16:6122-6131 (2010).
Dudley, et al., "Adoptive Cell Therapy for Patients with Metastatic Melanoma: Evaluation of Intensive Myeloablative Chemoradiation Preparative Regimens" , J. Clin. Oncol., Nov. 2008, 26(32), 5233-39.
Dull, et al., "OX40 is a potent immune stimulating target in late stage cancer Patients;" *J. Virology* 1998.
Eton, et al., "A Phase II Study of "Decrescendo" Interleukin-2 plus Interferon-a-2a in Patients with Progressive Metastatic Melanoma after Chemotherapy;" *Cancer* 2000, 88, 1703-9.
Fantozzi, "Mouse Models of Breast Cancer Metastasis;" *Breast Cancer Res.* 2006, 8, 212.
Fehniger and Caligiuri, "Interleukin 15: biology and relevance to human disease;" Blood 2001, 97, 14-32.
Feigner, et al., "Lipofection: A highly efficient, lipid-mediated DNA-transfection procedure;" *Proc. Natl. Acad. Sci. USA*, 1987, 84, 7413-741.
Fisher, et al., "Targeting of 4-1BB by monoclonal antibody PF-05082566 enhances T-cell function and promotes anti-tumor activity;" *Cancer Immunolog. & Immunother.* 2012, 61, 1721-33.
Fong, et al., "Ovarian Cancer Mouse Models: A Summary of Current Models and Their Limitations;" *J. Ovarian Res.* 2009, 2, 12.
Forget et al., "Activation and propagation of tumor infiltrating lymphocytes on clinical-grade designer artificial antigen presenting cells for adoptive immunotherapy of melanoma", Journal of Immunotherapy, vol. 37 No.9, Nov. 1, 2014, pp. 448-460.
Forget, et al., "A Novel Method to Generate and Expand Clinical-Grade, Genetically Modified, Tumor-Infiltrating Lymphocytes;" Frontiers Immunology 2017, 8, 908.
Forget, Marie-Andree et al. "The beneficial effects of a gas-permeable flask for expansion of Tumor-Infiltrating lymphocytes as reflected in their mitochondrial function and respiration capacity." Oncoimmunology vol. 5,2 e1057386. Jun. 5, 2015, doi: 10.1080/2162402X.2015.1057386.
Frank et al., "Remarkably Stable Tumor-Infiltrating Lymphocytes (HL) for Infusion Phenotype Following Cryopreservation", Nov. 6, 2016, Retrieved from the Internet: http://www.iovance.com/wp-content/uploads/2017/05/LION16701_Frank_POSTER3_final-0005.
Fry and Mackall, "Interleukin-7: from bench to clinic;" Blood 2002, 99, 3892-904.
Garaud, Soizic et al. "A simple and rapid protocol to non-enzymatically dissociate fresh human tissues for the analysis of infiltrating lymphocytes." Journal of visualized experiments : JoVE,94 52392. Dec. 6, 2014, doi:10.3791/52392.
Gassner, et al., "Fludarabine modulates composition and function of the T Cell pool in patients with chronic lymphocytic leukaemia", Cancer. Immunol. Immunother., 2011, 60, 75-85.
Gattinoni, et al., "Adoptive immunotherapy for cancer: building on success", Nat. Rev. Immunol. May 2006, 6(5), 383-393.

Gautron et al., "Fine and Predictable Tuning of Talen Gene Editing Targeting for Improved T Cell Adoptive Immunotherapy;" *Molecular Therapy: Nucleic Acids* Dec. 2017, vol. 9:312-321.
Gieffers, et al., "APG350 Induces Superior Clustering of Trail Receptors and Shows Therapeutic Antitumor Efficacy Independent of Cross-Linking via Fcg Receptors;" *Mol. Cancer Therapeutics* 2013, 12, 2735-47.
Gladstone, D E et al. "Infusion of cryopreserved autologous lymphocytes using a standard peripheral i.v. catheter." Bone marrow transplantation vol. 49,8 (2014): 1119-20. doi:10.1038/bmt.2014. 98.
Glassman, A B, and C E Bennett. "Cryopreservation of human lymphocytes: a brief review and evaluation of an automated liquid nitrogen freezer." Transfusion vol. 19,2 (1979): 178-81. doi: 10.1046/j. 1537-2995.1979.19279160289.x.
Goff SL, et al., "Randomized, Prospective Evaluation Comparing Intensity of Lymphodepletion Before Adoptive Transfer of Tumor-Infiltrating Lymphocytes for Patients With Metastatic Melanoma", J Clin Oncol. Jul. 10, 2016;34(20):2389-79.
Graham and van der Eb, "A New Technique for the Assay of Infectivity of Human Adenovirus 5 DNA;" *Virology* 1973, 52, 456-467.
Hackett, et al., "A Transposon and Transposase System for Human Application;" *Mol. Therapy* 2010, 18, 674-83.
Hall et al., "Expansion of tumor-infiltrating lymphocytes (11L) from human pancreatic tumors", Journal for ImmunoTherapy of Cancer, vol. 4, No. 1, pp. 1-12.
Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.
Henning AL,et al.. Measurement of T-Cell Telomere Length Using Amplified-Signal Fish Staining and Flow Cytometry. Curr Protoc Cytom. Jan. 5, 2017;79:7.47.1-7.47.10. doi: 10.1002/cpcy.11. PubMed PMID 28055115.
Hernandez-Chacon et al., "Costimulation through the CD137/4-1BB Pathway Protects Human Melanoma Tumor-infiltrating Lymphocytes from Activation-induced Cell Death and Enhances Anti-tumor Effector Function", Journal of ImmunoTherapy, vol. 34, No. 3, Apr. 1 2011, pp. 236-250.
Herreros-Villanueva, et al., "Mouse Models of Pancreatic Cancer;" *World J. Gastroenterol.* 2012, 18, 1286-1294.
Hinrichs CS, Rosenberg SA. Exploiting the curative potential of adoptive T-cell therapy for cancer. Immunol Rev. Jan. 2014;257(l):56-71. doi:10.1111/imr.l2132. Review. PubMed PMID: 24329789; PubMed Central Pmcid: PMC3920180.
Huang et al., "Survival, Persistence, and Progressive Differentiation of Adoptively Transferred Tumor-Reactive T Cells Associated with Tumor Regression"; J. Immunother, 28(3), 258-267 (2005).
Ikarashi, H et al., "Solid-phase anti-CD3 antibody activation and cryopre servation of human tumor-infdtrating lymphocytes derived from epithelial ovarian cancer", Japanese Journal of Cancer Research, vol. 83, No. 12, Dec. 1, 1992.
International Search Report and Written Opinion for International Patent Application No. PCT/US2017/058610 dated Mar. 8, 2018, 13 pages.
International Search Report and Written Opinion for International Patent Application No. PCT/US2018/012633 dated May 25, 2018, 14 pages.
International Search Report and Written Opinion for International Patent Application No. PCT/US2018/040474 dated Nov. 14, 2018, 17 pages.
Itzhaki, Orit et al. "Establishment and large-scale expansion of minimally cultured "young" tumor infdtrating lymphocytes for adoptive transfer therapy." Journal of immunotherapy (Hagerstown, Md. : 1997) vol. 34,2 (2011): 212-20. doi:10.1097/CJI. 0b013e318209c94c.
Iyer, R.K. et al., "Industrializing Autologous Adoptive Immunotherapies: Manufacturing Advances and Challenges", Frontiers in Medicine, vol. 5, May 23, 2018.
Jin et al., "Enhanced clinical-scale manufacturing of TCR transduced T-cells using closed culture system modules", Journal of Transactional Medicine, col. 16. No. 1, Jan. 24, 2018.

(56) References Cited

OTHER PUBLICATIONS

Juillerat, et al., "Optimized tuning of Talen specificity using non-conventional RVDs;" *Scientific Reports* 5, Article No. 8150 (2015).
Junker, Niels et al. "Bimodal ex vivo expansion of T cells from patients with head and neck squamous cell carcinoma: a prerequisite for adoptive cell transfer." Cytotherapy vol. 13,7 (2011): 822-34. doi: 10.3109/14653249.2011.563291.
Khalil, et al., Advances in Cancer Research, 2015, 128, 1-68.
Kim, "Animal Models of Cancer in the Head and Neck Region;" *Clin. Exp. Otorhinolaryngol.* 2009, 2, 55-60.
Klapper, J.A. et al., "Single-pass, closed-system rapid expansion of lymphocyte cultures for adoptive cell therapy", Journal of Immunological Methods, vol. 345, No. 1-2, Jun. 30, 2009.
Kleinstiver BP, et al. "High-fidelity CRISPR-Cas9 nucleases with no detectable genome-wide off-target effects;" *Nature*. Jan. 6, 2016.
Kurtulus, et al., "Tigit predominantly regulates the immune response via regulatory T cells;" The Journal of Clinical Investigation, 2015, vol. 125, No. 11, 4053-4062.
Lee et al., "Tumor-Infiltrating Lymphocytes in Melanoma", Curr Oncol Rep. Aug. 2012, 14, 468-474.
Lee, et al., "4-IBB Signaling Activates the T Cell Factor 1 Effector/b-Catenin Pathway with Delayed Kinetics via ERK Signaling and Delayed PI3K/AKT Activation to Promote the Proliferation of CD8+ T Cells;" *PLOS One* 2013, 8, e69677.
Levine, et al., "Gene transfer in humans using a conditionally replicating lentiviral vector;" *Proc. Nat'l Acad. Sci.* 2006, 103, 17372-77.
Marco, "Biotechnological applications of recombinant single-domain antibody fragments;" *Microbial Cell Factories*, 2011,10, 44.
Marin-Acevedo et al., "Next generation of immune checkpoint therapy in cancer: new developments and challenges;" Journal of Hematology & Oncology (2018) 11:39.
Menger, et al., "Talen-Mediated Inactivation of PD-1 in Tumor-Reactive Lymphocytes Promotes Intratumoral T-cell Persistence and Rejection of Established Tumors;" *Cancer Res.*, Apr. 15, 2016; 76(8):2087-93.
Merhavi-Shoham et al., "Adoptive Cell Therapy for Metastatic Melanoma", Cancer Journal, vol. 23, No. 1, Jan. 1, 2017.
Meuwissen, et al., "Mouse Models for Human Lung Cancer;" *Genes & Development*, 2005, 19, 643-664.
Monnier, et al., "In Vivo Applications of Single Chain Fv (Variable Domain) (scFv) Fragments;" *Antibodies*, 2013, 2, 193-208.
Mullany, et al., "Minireview: Animal Models and Mechanisms of Ovarian Cancer Development;" *Endocrinology* 2012, 153, 1585-92.
Mullinax, et al., "Combination of Ipilimumab and Adoptive Cell Therapy with Tumor-Infiltrating Lymphocytes for Patients with Metastatic Melanoma", Frontiers in Oncology, vol. 8, Mar. 2, 2018.
Muranski, et al., "Increased intensity lymphodepletion and adoptive immunotherapy—how far can we go?", Nat. Clin. Pract. Oncol., Dec. 2006, 3, 668-681.
Neuzillet et al., "Targeting the TGFβ pathway for cancer therapy;" Pharmacology & Therapeutics, vol. 147, pp. 22-31 (2015).
Nguyen, Linh T et al. "Expansion and characterization of human melanoma tumorinfiltrating lymphocytes (TILs)." PloS one vol. 5,11 e13940. Nov. 10, 2010, doi: 10.1371/journal.pone.0013940.
O'Day, et al., "Advantages of Concurrent Biochemotherapy Modified by Decrescendo Interleukin-2, Granulocyte Colony-Stimulating Factor, and Tamoxifen for Patients With Metastatic Melanoma;" *J Clin. Oncol.* 1999, 17, 2752-61.
Palmer et al., "Cish actively silences TCR signaling in CD8+ T cells to maintain tumor tolerance;" Journal of Experimental Medicine, 212 (12): 2095 (2015).
Peng, et al., "Transduction of Tumor-Specific T Cells with CXCR2 Chemokine Receptor Improves Migration to Tumor and Antitumor Immune Responses;" Clin. Cancer Res. 2010, 16, 5458.
Ran et al., "Genome engineering using the CRISPR-Cas9 system;" *Nat Protoc.* Nov. 2013; 8(11):2281-2308.

Riddell, et al., "Restoration of Viral Immunity in Immunodeficient Humans by the Adoptive Transfer of T Cell Clones", Science, Jul. 1992, 257, 238-41.
Rohaan et al., "Adoptive transfer of tumor-infiltrating lymphocytes in melanoma: a viable treatment option", Journal for Immunotherapy of Cancer, vol. 6, No. 1, Oct. 3, 2018, pp. 1-16.
Rose, et al., "A New Cationic Liposome Reagent Mediating Nearly Quantitative Transfection of Animal Cells;" *Biotechniques* 1991, 10, 520-525.
Rosenberg SA, et al. "Durable Complete Responses in Heavily Pretreated Patients with Metastatic Melanoma Using T Cell Transfer Immunotherapy", Clinical Cancer research, vol. 17, No. 13, Jul. 1, 2011 pp. 4550-4557.
Rosenberg, S A et al. "A new approach to the adoptive immunotherapy of cancer with tumor-infiltrating lymphocytes." Science (New York, N.Y.) vol. 233,4770 (1986): 1318-21. doi: 10.1126/science. 3489291.
Rosenberg, S A et al. "Treatment of patients with metastatic melanoma with autologous tumor-infiltrating lymphocytes and interleukin 2." Journal of the National Cancer Institute vol. 86,15 (1994): 1159-66. doi:10.1093/jnci/86.15.1159.
Rosenberg, S A et al. "Use of tumor-infiltrating lymphocytes and interleukin-2 in the immunotherapy of patients with metastatic melanoma. A preliminary report." The New England journal of medicine vol. 319,25 (1988): 1676-80. doi: 10.1056/NEJM198812223192527.
Rufer N, et al., "Telomere length dynamics in human lymphocyte subpopulations measured by flow cytometry", Nat Biotechnol. Aug. 1998;16(8):743-7. PubMed PMID: 9702772.
Ruby, et al., "OX40-Enhanced Tumor Rejection and Effector T Cell Differentiation Decreases with Age;" *J. Immunother*. 2009, 182, 1481-89.
Sano, "Xenograft models of head and neck cancers;" *Head Neck Oncol*. 2009, 1, 32.
Sapio et al., "Targeting protein kinase A in cancer therapy: an update;" *EXCLI Journal*; 2014;13: 843-855.
Segal, et al., Clin. Cancer Res. 2016, available athttp:/dx.doi.org/10.1158/1078-0432.CCR-16-1272.
Shen X,et al.. Persistence of tumor infiltrating lymphocytes in adoptive immunotherapy correlates with telomere length. J Immunother. Jan. 2007;30(l): 123-9. PubMed PMID: 17198091; PubMed Central Pmcid: PMC2151201.
Slaymaker IM, et al. "Rationally engineered Cas9 nucleases with improved specificity;" *Science*. Dec. 1, 2015.
Spolski and Leonard, "Interleukin-21: a double-edged sword with therapeutic potential;" Nat. Rev. Drug. Disc. 2014, 13, 379-95.
Steinke and Borish, "Th2 cytokines and asthma Interleukin-4: its role in the pathogenesis of asthma, and targeting it for asthma treatment with interleukin-4 receptor antagonists;" Respir. Res. 2001, 2, 66-70.
Swartz, et al., Cancer Res., 2012, 72, 2473.
Tran KQ, Zhou J, Durflinger KH, et al., "Th2 cytokines and asthma Interleukin-4: its role in the pathogenesis of asthma, and targeting it for asthma treatment with interleukin-4 receptor antagonists;" 2008, *J Immunother.*, 31:742-751.
Tsong, *Biophys. J.* 1991, 60, 297-306.
Tsoukas et al., "Activation of resting T lymphocytes by anti-CD3 (T3) antibodies in the absence of monocytes", J. Immunol. 1985, 135, 1719.
Valton, et al., "Efficient strategies for TALEN-mediated genome editing in mammalian cell lines;" *Methods*, 2014, 69, 151-170.
Van den Bossche, J. et al. "Metabolic Characterization of Polarized M1 and M2 Bone Marrow-derived Macrophages Using Real-time Extracellular Flux Analysis." Journal of visualized experiments : JoVE ,105 53424. Nov. 28, 2015, doi: 10.3791/53424.
Wallner, et al., Clin. Dev. Immunol. 2012, 692639.
Wang & Riviere, "Manufacture of tumor- and virus-specific T lymphocytes for adoptive cell therapies", Cancer Gene Therapy, 2015, 22: 85-94.
Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.

(56) References Cited

OTHER PUBLICATIONS

Weinberg, et al., "Anti-OX40 (CD134) administration to nonhuman primates: immunostimulatory effects and toxicokinetic study;" *J. Immunother*. 2006, 29, 575-585.

Wigler, et al., "DNA-mediated transfer of the adenine phosphoribosyltransferase locus into mammalian cells;" *Proc. Natl. Acad. Sci.* 1979, 76, 1373-1376.

Wilson Wolf—Superior Cell Culture Devices, G-Rex, Oct. 31, 2016.

Yu, et al., "Priming of naive T cells inside tumors leads to eradication of established tumors;" Nature Immunology, 2009, vol. 10, No. 1, 48-57.

Zhou J, et al.. Telomere length of transferred lymphocytes correlates with in vivo persistence and tumor regression in melanoma patients receiving cell transfer therapy. J Immunol. Nov. 1, 20055;175(10):7046-52. PubMed PMID: 16272366; PubMed Central PMCID: PMC135131.

Zhou, et al., "Persistence of Multiple Tumor-Specific T-Cell Clones Is Associated with Complete Tumor Regression in a Melanoma Patient Receiving Adoptive Cell Transfer Therapy"; J. Immunother, 28, 53-62 (2005).

Zufferey, et al., "Multiply attenuated letiviral vector achieves efficient gene deliver in vivo;" *Nat. Biotechnol.* 1997, 15, 871-75.

Zuliani, T. et al., "Value of large scale expansion of tumor infiltrating lymphocytes in a compartmentalised gas-permiable bag: interests for adoptive immunotherapy", Journal of Translational Medicine, vol. 9, No. 1, May 16, 2011.

U.S. National Institutes of Health, "A study of PF-05082566 in combination with Mogamulizumab in Patients with Advanced Solid Tumors", U.S. National Library of Medicine, May 2015, clinicaltrials.gov identifier NCT02444793, 8 pages.

U.S. National Institutes of Health, "A Study of PF-05082566 as a Single Agent and in Combination with Rituximab", U.S. National Library of Medicine, Mar. 2011, clinicaltrials.gov identifier NCTG01307267, 6 pages.

U.S. National Institutes of Health, Study of OX40 Agonist PF-04518600 Alone and in Combination with 4-1BB Agonist PF-05082566, U.S. National Library of Medicine, Dec. 2014, clinicaltrials.gov identifier NCT02315066, 6 pages.

A Study of Avelumab in Combination With Other Cancer Immunotherapies in Advanced Malignancies (Javelin Medley). Available at https://clinicaltrials.gov/ct2/show/NCT02554812.

Andersen et al., Long-lasting Complete Responses in Patients with Metastatic Melanoma After Adoptive Cell Therapy with Tumor-Infiltrating Lymphocytes and an Attenuated IL2 Regimen:, Clin. Cancer Res., 22(15), 3734-3745 (2016).

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes in Patients with Metastatic Melanoma: Intent-to-Treat Analysis and Efficacy after Failure to Prior Immunotherapies"; Clin Cancer Res, 19(17):OF1-OF9 (2013).

Donia M, et al.. Simplified protocol for clinical-grade tumor-infiltrating lymphocyte manufacturing with use of the Wave bioreactor. Cytotherapy. Aug. 2014;16(8):1117-20.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Dudley et al., "Adoptive Cell Transfer Following Non-Myeloablative but Lymphodepleting Chemotherapy forthe Treatment of Patients with Refractory Metastatic Melanoma", J. Clin. Oncol. Apr. 2005, 23(10), 2346-57.

Dudley et al., "Generation of Tumor-Infiltrating Lymphocyte Cultures for Use in Adoptive Transfer Therapy for Melanoma Patients," J Immunother., 2003: 26(4): 332-342.

Dudley, et al.,"Cancer Regression and Autoimmunity in Patients After Clonal Repopulation with Antitumor Lymphocytes", Science, Oct. 2002, 298, 850-54.

He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Jin et al., "Simplified method of the growth of human tumor infiltrating lymphocytes in gas-permiable flasks to Nos. needed for patient treatment", J. Immunotherapy, 2012, 35:283-292.

Li et al. Mart-1-specific melanoma tumor-infiltrating lymphocytes maintaining CD28 expression have improved survival and expansion capability following antigenic restimulation in vitro. J Immunol. Jan. 1, 2010;184(1):452-65.

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg SA, Dudley ME. "Adoptive cell therapy for the treatment of patients with metastatic melanoma", Curr Opin Immunol. Apr. 2009;21(2):233-40.

Rosenberg, "IL-2: The First Effective Immunotherapy for Human Cancer," The Journal of Immunology, col. 192, No. 12, Jun. 6, 2014.

Sadeghi, et al., "Rapid expansion of T cells: Effects of culture and cryopreservation and improtance of short-term cell recovery", Acta Oncologica 2013, 52, 978-986.

Somerville RP, et al., "Clinical scale rapid expansion of lymphocytes for adoptive cell transfer therapy in the Wave® bioreactor", J Transl Med. Apr. 4, 2012;10:69.

Tran et al., "Minimally Cultured tumor-infiltrating lymphocytes display optimal characteristics for adoptive cell therapy", J. Immunother., Oct. 2008; 31(8), 742-751.

Ye, et al., "Engineered artificial antigen presenting cells facilitate direct and efficient expansion of tumor infiltrating lymphocytes", J. of Trans. Med., 2011, 9:131.

International Search Report and Written Opinion dated Oct. 31, 2019 for International Patent Application No. PCT/US2019/029286, 14 pages.

International Preliminary Report on Patentability dated Oct. 27, 2020 for International Patent Application No. PCT/US2019/029286, 10 pages.

Third Party Observation for Application No. EP20200183493 dated Oct. 14, 2021, 5 pages.

Goff et al., "Tumor Infiltrating Lymphocyte Therapy for Metastatic Melanoma: Analysis of Tumors Resected for Til", J. Immunother, 33(8): 840-847, 2010.

\* cited by examiner

Process Development

| Step | Current Process-1C | New Process-2A | Impact |
|---|---|---|---|
| 1 | 4 Fragments/10 G-Rex 10-21 Days | 40 Fragments/1-G-Rex 100 CS- (x2?) 11 Days | Increases Tumor Sample/Container, Shortens Culture, Reduces Steps, Amenable To Closed System |
| 2 | PreREP Freeze-> Testing -> Thaw- ~Day 27- >40e6TIL | Direct To REP- Day 11- <200e6 | Shorten Process, Reduces Steps, Eliminates Testing |
| 3 | 36 G-Rex 100-~Day 30 >5e6TIL - Split ~Day 36 | 4-5 G-Rex 500CS- TIL- Split Day 16 | Reduces Steps, Closed System, Shorter REP |
| 4 | Harvest Day ~43+ Harvesting By Centrifugation | Harvest Day 22 LOVO-Automated Cell Washer | Reduces Steps, Automated, Closed System |
| 5 | Fresh Product- Hypothermosol-Single Infusion Bag | Cryopreserved Product-CS10 In $LN_2$, Multiple Aliquots | Shipping Flexibility, Patient Scheduling, Easier Release Testing, Global Trials |
| 6 | 43+ Day Process Time | 22 Day Process Time | Turnaround To Patient, Clean Room Throughput, COGs |

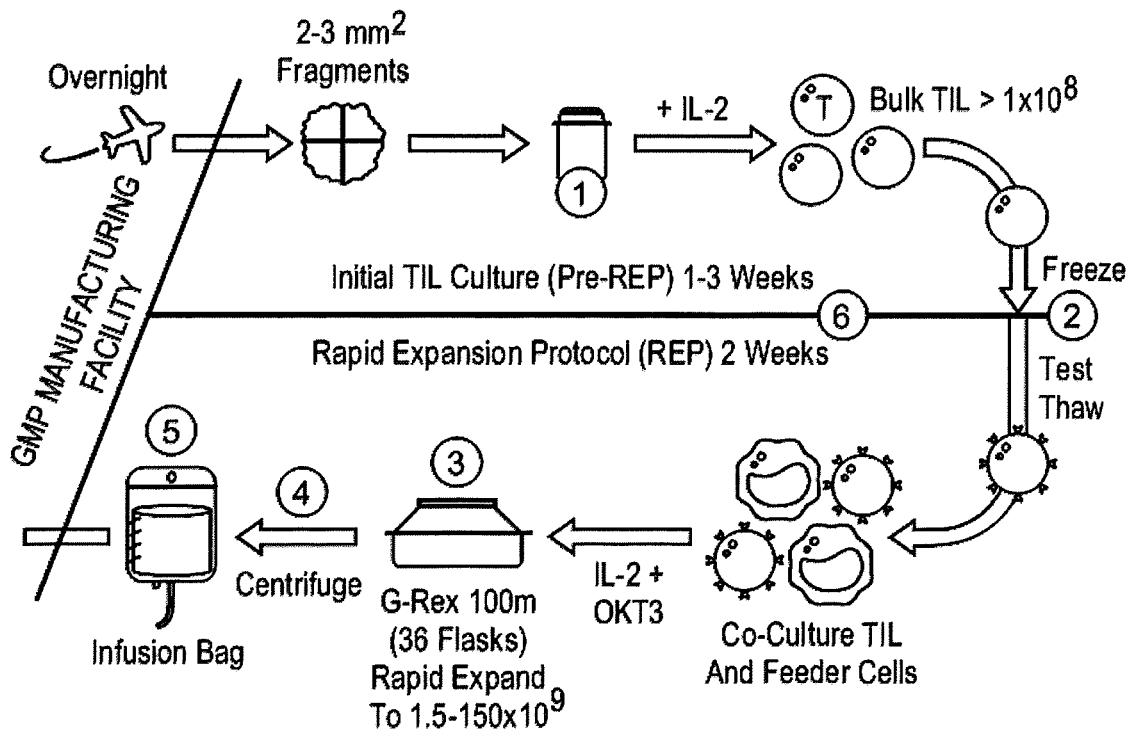

Figure 2

REP PD Process PFD
Page 1/3

REP PD Process PFD
Page 2/3

*Figure 13*

| Process 1C: 43-55 Days for Steps A - E | Process 2A: about 22 days from Steps A - E |
|---|---|
| 1. STEP A<br><br>Obtain Patient Tumor Sample | 2. STEP A<br><br>Obtain Patient Tumor Sample |
| 3. STEP B<br><br>Fragmentation and First Expansion<br><br>11 days to 21 days | 3. STEP B<br><br>Fragmentation and First Expansion<br><br>3 days to 14 days |
| 3. STEP C<br><br>First Expansion to Second Expansion Transition<br><br>Optional Storage until Selection | 4. STEP C<br><br>First Expansion to Second Expansion Transition<br><br>No Storage and Closed System |
| 5. STEP D<br><br>Second Expansion<br><br>IL-2, OKT-3, antigen-presenting feeder cells<br><br>Optionally repeat one or more times | 5. STEP D<br><br>Second Expansion<br><br>IL-2, OKT-3, and antigen-presenting feeder cells<br><br>Closed System |
| 6. STEP E<br><br>Harvest TILS from Step D | 7. STEP E<br><br>Harvest TILS from Step D<br><br>Closed System |
| 6. STEP F<br><br>Final Formulation and/or Transfer to Infusion Bag | 8. STEP F<br><br>Final Formulation and/or Transfer to Infusion Bag<br><br>(optionally cryopreserve) |

*Figure 14*

| Process Step | Process 1C Embodiment | Process 2A Embodiment | Advantages |
|---|---|---|---|
| Pre-REP | • 4 fragments per 10 GREX-10 flasks<br>• 11-21 day duration | • 40 fragments per 1 GREX-100M flask<br>• 11 day duration | • Increased tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day 30)<br>• REP requires >40×10$^6$ TIL | • Pre-REP TIL directly move to REP on day 11<br>• REP requires 25-200×10$^6$ TIL | • Shortened pre-REP-to-REP process<br>• Reduced number of steps<br>• Eliminated phenotyping selection<br>• Amenable to closed system |
| REP | • 6 GREX-100M flasks on REP day 0<br>• 5×10$^6$ TIL and 5×10$^8$ PBMC feeders per flask on REP day 0<br>• Split to 18-36 flasks on REP day 7<br>• 14 day duration | • 1 GREX-500M flask on day 11<br>• 25-200×10$^6$ TIL and 5×10$^9$ PBMC feeders on day 11<br>• Split to ≤6 GREX-500M flasks on day 16<br>• 11 day duration | • Reduced number of steps<br>• Shorter REP duration<br>• Closed system transfer of TIL between flasks<br>• Closed system media exchanges |
| Harvest | • TIL harvested via centrifugation | • TIL harvested via LOVO automated cell washing system$^1$ | • Reduced number of steps<br>• Automated cell washing<br>• Closed system<br>• Reduced loss of product during wash |
| Final Formulation | • Fresh product in Hypothermosol<br>• Single infusion bag<br>• Limited shipping stability | • Cyropreserved product in PlasmaLyte-A + 1% HSA and CS10 stored in LN$_2$<br>• Multiple aliquots<br>• Longer shipping stability | • Shipping flexibility<br>• Flexible patient scheduling<br>• More timely release testing |
| Overall Estimated Process Time | • 43-55 days | • 22 days | • Faster turnaround to patient |

Figure 17

| PROCESS STEP | GEN 1 | GEN 2 | IMPACT |
|---|---|---|---|
| Fragment Culture | ≤21 days, multiple bioreactors, multiple operator interventions | ≤11 days, single closed bioreactor, no intervention | Shortens culture, reduces interventions |
| TIL selection | IL-2 expanded TIL cryopreserved, tested, selection based on phenotype, thaw, rest, co-culture | Bulk TIL direct to co-culture | Reduces steps, eliminates testing, increases clonal diversity |
| Harvest/Wash | Manual volume reduction and harvest. Manual wash and concentration | Closed semi-automated volume reduction and harvest. Automated wash and concentration | Reduces operator interventions, reduces processing time, maintains functionally closed system |
| Formulation | Fresh hypothermic product (2-8°C) | Cryopreserved product (≤ -150°C) | Allows for global trials through increased flexibility in shipping and patient scheduling |
| Manufacturing Time | 38 day process time | 22 day process time | Turnaround to patient, clean room throughput, lower cost of goods |

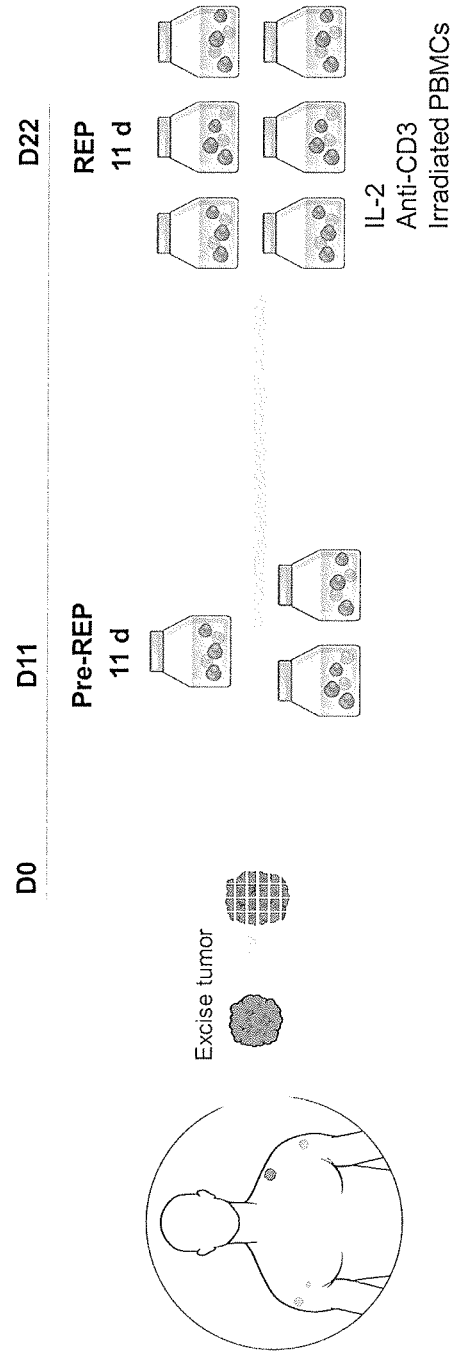

CLOSED PROCESS FOR EXPANSION AND GENE EDITING OF TUMOR INFILTRATING LYMPHOCYTES AND USES OF SAME IN IMMUNOTHERAPY

CROSS-REFERENCE TO RELATED APPLICATIONS

This application is a continuation of U.S. patent application Ser. No. 14/387,357 filed Jul. 28, 2021, which is a continuation of U.S. patent application Ser. No. 17/050,552, filed Oct. 26, 2020; which is a U.S. National Stage of International Application No. PCT/US2019/029286, filed Apr. 26, 2019, which claims the benefit of priority to U.S. Provisional Application No. 62/680,821, filed Jun. 5, 2018, and U.S. Provisional Application No. 62/663,885, filed Apr. 27, 2018, the entireties of which are incorporated herein by reference.

SEQUENCE LISTING

The instant application contains a Sequence Listing which has been submitted electronically in XML format and is hereby incorporated by reference in its entirety. Said XML copy, created on Aug. 12, 2022, is named 116983-5037-US02-ST.26.XML and is 192 kilobytes in size.

FIELD OF THE INVENTION

Methods for expanding tumor infiltrating lymphocytes (TILs) and producing therapeutic populations of TILs are described herein. In addition, methods for gene-editing TILs, and uses of gene-edited TILs in the treatment of diseases such as cancer are disclosed herein.

BACKGROUND OF THE INVENTION

Treatment of bulky, refractory cancers using adoptive transfer of tumor infiltrating lymphocytes (TILs) represents a powerful approach to therapy for patients with poor prognoses. Gattinoni, et al., *Nat. Rev. Immunol.* 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TILs over a 14-day period, although it requires a large excess (e.g., 200-fold) of irradiated allogeneic peripheral blood mononuclear cells (PBMCs, also known as mononuclear cells (MNCs)), often from multiple donors, as feeder cells, as well as anti-CD3 antibody (OKT3) and high doses of IL-2. Dudley, et al., *J. Immunother.* 2003, 26, 332-42. TILs that have undergone an REP procedure have produced successful adoptive cell therapy following host immunosuppression in patients with melanoma. Current infusion acceptance parameters rely on readouts of the composition of TILs (e.g., CD28, CD8, or CD4 positivity) and on fold expansion and viability of the REP product.

Current TIL manufacturing processes are limited by length, cost, sterility concerns, and other factors described herein such that the potential to commercialize such processes is severely limited, and for these and other reasons, at the present time no commercial process has become available. There is an urgent need to provide TIL manufacturing processes and therapies based on such processes that are appropriate for commercial scale manufacturing and regulatory approval for use in human patients at multiple clinical centers. Moreover, there is a strong need for more effective TIL therapies that can increase a patient's response rate and response robustness.

BRIEF SUMMARY OF THE INVENTION

The present invention provides methods for expanding TILs and producing therapeutic populations of TILs. According to exemplary embodiments, at least a portion of the therapeutic population of TILs are gene-edited to enhance their therapeutic effect.

In an embodiment, the present invention provides a method for expanding tumor infiltrating lymphocytes (TILs) into a therapeutic population of TILs comprising:
  (a) obtaining a first population of TILs from a tumor resected from a patient by processing a tumor sample obtained from the patient into multiple tumor fragments;
  (b) adding the tumor fragments into a closed system;
  (c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
  (d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
  (e) harvesting the therapeutic population of TILs obtained from step (d), wherein the transition from step (d) to step (e) occurs without opening the system;
  (f) transferring the harvested TIL population from step (e) to an infusion bag, wherein the transfer from step (e) to (f) occurs without opening the system; and
  (g) at any time during the method, gene-editing at least a portion of the TILs.

In some embodiments, the method further comprises the step of cryopreserving the infusion bag comprising the harvested TIL population in step (f) using a cryopreservation process.

In some embodiments, the cryopreservation process is performed using a 1:1 ratio of harvested TIL population to cryopreservation media.

In some embodiments, the antigen-presenting cells are peripheral blood mononuclear cells (PBMCs). In some embodiments, the PBMCs are irradiated and allogeneic. In some embodiments, the PBMCs are added to the cell culture on any of days 9 through 14 in step (d). In some embodiments, the antigen-presenting cells are artificial antigen-presenting cells.

In some embodiments, the harvesting in step (e) is performed using a membrane-based cell processing system.

In some embodiments, the harvesting in step (e) is performed using a LOVO cell processing system.

In some embodiments, the multiple fragments comprise about 4 to about 50 fragments, wherein each fragment has a volume of about 27 mm$^3$.

In some embodiments, the multiple fragments comprise about 30 to about 60 fragments with a total volume of about 1300 mm$^3$ to about 1500 mm$^3$.

In some embodiments, the multiple fragments comprise about 50 fragments with a total volume of about 1350 mm$^3$.

In some embodiments, the multiple fragments comprise about 50 fragments with a total mass of about 1 gram to about 1.5 grams.

In some embodiments, the cell culture medium is provided in a container selected from the group consisting of a G-container and a Xuri cellbag.

In some embodiments, the cell culture medium in step (d) further comprises IL-15 and/or IL-21.

In some embodiments, the IL-2 concentration is about 10,000 IU/mL to about 5,000 IU/mL.

In some embodiments, the IL-15 concentration is about 500 IU/mL to about 100 IU/mL.

In some embodiments, the IL-21 concentration is about 20 IU/mL to about 0.5 IU/mL.

In some embodiments, the infusion bag in step (f) is a HypoThermosol-containing infusion bag.

In some embodiments, the cryopreservation media comprises dimethlysulfoxide (DMSO). In some embodiments, the cryopreservation media comprises 7% to 10% dimethlysulfoxide (DMSO).

In some embodiments, the first period in step (c) and the second period in step (e) are each individually performed within a period of 10 days, 11 days, or 12 days.

In some embodiments, the first period in step (c) and the second period in step (e) are each individually performed within a period of 11 days.

In some embodiments, steps (a) through (f) are performed within a period of about 10 days to about 22 days.

In some embodiments, steps (a) through (f) are performed within a period of about 20 days to about 22 days.

In some embodiments, steps (a) through (f) are performed within a period of about 15 days to about 20 days.

In some embodiments, steps (a) through (f) are performed within a period of about 10 days to about 20 days.

In some embodiments, steps (a) through (f) are performed within a period of about 10 days to about 15 days.

In some embodiments, steps (a) through (f) are performed in 22 days or less.

In some embodiments, steps (a) through (f) are performed in 20 days or less.

In some embodiments, steps (a) through (f) are performed in 15 days or less.

In some embodiments, steps (a) through (f) are performed in 10 days or less.

In some embodiments, steps (a) through (f) and cryopreservation are performed in 22 days or less.

In some embodiments, the therapeutic population of TILs harvested in step (e) comprises sufficient TILs for a therapeutically effective dosage of the TILs.

In some embodiments, the number of TILs sufficient for a therapeutically effective dosage is from about 2.3×1010 to about 13.7×1010.

In some embodiments, steps (b) through (e) are performed in a single container, wherein performing steps (b) through (e) in a single container results in an increase in TIL yield per resected tumor as compared to performing steps (b) through (e) in more than one container.

In some embodiments, the antigen-presenting cells are added to the TILs during the second period in step (d) without opening the system.

In some embodiments, the third population of TILs in step (d) provides for increased efficacy, increased interferon-gamma production, increased polyclonality, increased average IP-10, and/or increased average MCP-1 when administered to a subject.

In some embodiments, the third population of TILs in step (d) provides for at least a five-fold or more interferon-gamma production when administered to a subject.

In some embodiments, the third population of TILs in step (d) is a therapeutic population of TILs which comprises an increased subpopulation of effector T cells and/or central memory T cells relative to the second population of TILs, wherein the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells obtained from the third population of TILs exhibit increased CD57 expression and decreased CD56 expression relative to effector T cells and/or central memory T cells obtained from the second population of cells.

In some embodiments, the risk of microbial contamination is reduced as compared to an open system.

In some embodiments, the TILs from step (g) are infused into a patient.

In some embodiments, the multiple fragments comprise about 4 fragments.

In some embodiments, the cell culture medium further comprises a 4-1BB agonist and/or an OX40 agonist during the first expansion, the second expansion, or both.

In some embodiments, the gene-editing is carried out after the 4-1BB agonist and/or the OX40 agonist is introduced into the cell culture medium.

In some embodiments, the gene-editing is carried out before the 4-1BB agonist and/or the OX40 agonist is introduced into the cell culture medium.

In some embodiments, the gene-editing is carried out on TILs from one or more of the first population, the second population, and the third population.

In some embodiments, the gene-editing is carried out on TILs from the first expansion, or TILs from the second expansion, or both.

In some embodiments, the gene-editing is carried out after the first expansion and before the second expansion.

In some embodiments, the gene-editing is carried out before step (c), before step (d), or before step (e).

In some embodiments, the cell culture medium comprises OKT-3 during the first expansion and/or during the second expansion, and the gene-editing is carried out before the OKT-3 is introduced into the cell culture medium.

In some embodiments, the cell culture medium comprises OKT-3 during the first expansion and/or during the second expansion, and the gene-editing is carried out after the OKT-3 is introduced into the cell culture medium.

In some embodiments, the cell culture medium comprises OKT-3 beginning on the start day of the first expansion, and the gene-editing is carried out after the TILs have been exposed to the OKT-3.

In some embodiments, the gene-editing causes expression of one or more immune checkpoint genes to be silenced or reduced in at least a portion of the therapeutic population of TILs.

In some embodiments, the one or more immune checkpoint genes is/are selected from the group comprising PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

In some embodiments, the one or more immune checkpoint genes is/are selected from the group comprising PD-1, CTLA-4, LAG-3, HAVCR2 (TIM-3), Cish, TGFβ, and PKA.

In some embodiments, the gene-editing causes expression of one or more immune checkpoint genes to be enhanced in at least a portion of the therapeutic population of TILs, the immune checkpoint gene(s) being selected from the group comprising CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

In some embodiments, the gene-editing comprises the use of a programmable nuclease that mediates the generation of a double-strand or single-strand break at said one or more immune checkpoint genes.

In some embodiments, the gene-editing comprises one or more methods selected from a CRISPR method, a TALE method, a zinc finger method, and a combination thereof.

In some embodiments, the gene-editing comprises a CRISPR method.

In some embodiments, the CRISPR method is a CRISPR/Cas9 method.

In some embodiments, the gene-editing comprises a TALE method.

In some embodiments, the gene-editing comprises a zinc finger method.

In another embodiment, the present invention provides a method for treating a subject with cancer, the method comprising administering expanded tumor infiltrating lymphocytes (TILs) comprising:
(a) obtaining a first population of TILs from a tumor resected from a subject by processing a tumor sample obtained from the patient into multiple tumor fragments;
(b) adding the tumor fragments into a closed system;
(c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) harvesting the therapeutic population of TILs obtained from step (d), wherein the transition from step (d) to step (e) occurs without opening the system; and
(f) transferring the harvested TIL population from step (e) to an infusion bag, wherein the transfer from step (e) to (f) occurs without opening the system;
(g) optionally cryopreserving the infusion bag comprising the harvested TIL population from step (f) using a cryopreservation process;
(h) administering a therapeutically effective dosage of the third population of TILs from the infusion bag in step (g) to the patient; and
(i) at any time during the method steps (a)-(f), gene-editing at least a portion of the TILs.

In some embodiments, the therapeutic population of TILs harvested in step (e) comprises sufficient TILs for administering a therapeutically effective dosage of the TILs in step (h).

In some embodiments, the number of TILs sufficient for administering a therapeutically effective dosage in step (h) is from about $2.3 \times 10^{10}$ to about $13.7 \times 10^{10}$.

In some embodiments, the antigen presenting cells (APCs) are PBMCs.

In some embodiments, the PBMCs are added to the cell culture on any of days 9 through 14 in step (d).

In some embodiments, prior to administering a therapeutically effective dosage of TIL cells in step (h), a non-myeloablative lymphodepletion regimen has been administered to the patient.

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In some embodiments, the method further comprises the step of treating the patient with a high-dose IL-2 regimen starting on the day after administration of the TIL cells to the patient in step (h).

In some embodiments, the high-dose IL-2 regimen comprises 600,000 or 720,000 IU/kg administered as a 15-minute bolus intravenous infusion every eight hours until tolerance.

In some embodiments, the third population of TILs in step (d) is a therapeutic population of TILs which comprises an increased subpopulation of effector T cells and/or central memory T cells relative to the second population of TILs, wherein the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells in the therapeutic population of TILs exhibit increased CD57 expression and decreased CD56 expression relative to effector T cells and/or central memory T cells obtained from the second population of cells.

In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma.

In some embodiments, the cancer is selected from the group consisting of melanoma, HNSCC, cervical cancers, and NSCLC.

In some embodiments, the cancer is melanoma.

In some embodiments, the cancer is HNSCC.

In some embodiments, the cancer is a cervical cancer.

In some embodiments, the cancer is NSCLC.

In some embodiments, the cell culture medium further comprises a 4-1BB agonist and/or an OX40 agonist during the first expansion, the second expansion, or both.

In some embodiments, the gene-editing is carried out after the 4-1BB agonist and/or the OX40 agonist is introduced into the cell culture medium.

In some embodiments, the gene-editing is carried out before the 4-1BB agonist and/or the OX40 agonist is introduced into the cell culture medium.

In some embodiments, the gene-editing is carried out on TILs from one or more of the first population, the second population, and the third population.

In some embodiments, the gene-editing is carried out on TILs from the first expansion, or TILs from the second expansion, or both.

In some embodiments, the gene-editing is carried out after the first expansion and before the second expansion.

In some embodiments, the gene-editing is carried out before step (c), before step (d), or before step (e).

In some embodiments, the cell culture medium comprises OKT-3 during the first expansion and/or during the second expansion, and the gene-editing is carried out before the OKT-3 is introduced into the cell culture medium.

In some embodiments, the cell culture medium comprises OKT-3 during the first expansion and/or during the second expansion, and the gene-editing is carried out after the OKT-3 is introduced into the cell culture medium.

In some embodiments, the cell culture medium comprises OKT-3 beginning on the start day of the first expansion, and the gene-editing is carried out after the TILs have been exposed to the OKT-3.

In some embodiments, the gene-editing causes expression of one or more immune checkpoint genes to be silenced or reduced in at least a portion of the therapeutic population of TILs.

In some embodiments, the one or more immune checkpoint genes is/are selected from the group comprising PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

In some embodiments, the one or more immune checkpoint genes is/are selected from the group comprising PD-1, CTLA-4, LAG-3, HAVCR2 (TIM-3), Cish, TGFβ, and PKA.

In some embodiments, the gene-editing causes expression of one or more immune checkpoint genes to be enhanced in at least a portion of the therapeutic population of TILs, the immune checkpoint gene(s) being selected from the group comprising CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

In some embodiments, the gene-editing comprises the use of a programmable nuclease that mediates the generation of a double-strand or single-strand break at said one or more immune checkpoint genes.

In some embodiments, the gene-editing comprises one or more methods selected from a CRISPR method, a TALE method, a zinc finger method, and a combination thereof.

In some embodiments, the gene-editing comprises a CRISPR method.

In some embodiments, the CRISPR method is a CRISPR/Cas9 method.

In some embodiments, the gene-editing comprises a TALE method.

In some embodiments, the gene-editing comprises a zinc finger method.

In another embodiment, the present invention provides a method for expanding tumor infiltrating lymphocytes (TILs) into a therapeutic population of TILs comprising:
  (a) adding processed tumor fragments from a tumor resected from a patient into a closed system to obtain a first population of TILs;
  (b) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (a) to step (b) occurs without opening the system;
  (c) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (b) to step (c) occurs without opening the system;
  (d) harvesting the therapeutic population of TILs obtained from step (c), wherein the transition from step (c) to step (d) occurs without opening the system;
  (e) transferring the harvested TIL population from step (d) to an infusion bag, wherein the transfer from step (d) to (e) occurs without opening the system; and
  (f) at any time during the method, gene-editing at least a portion of the TILs.

In some embodiments, the therapeutic population of TILs harvested in step (d) comprises sufficient TILs for a therapeutically effective dosage of the TILs.

In some embodiments, the number of TILs sufficient for a therapeutically effective dosage is from about 2.3×10¹⁰ to about 13.7×10¹⁰.

In some embodiments, the method further comprises the step of cryopreserving the infusion bag comprising the harvested TIL population using a cryopreservation process.

In some embodiments, the cryopreservation process is performed using a 1:1 ratio of harvested TIL population to cryopreservation media.

In some embodiments, the antigen-presenting cells are peripheral blood mononuclear cells (PBMCs).

In some embodiments, the PBMCs are irradiated and allogeneic.

The method according to claim 68, wherein the PBMCs are added to the cell culture on any of days 9 through 14 in step (c).

In some embodiments, the antigen-presenting cells are artificial antigen-presenting cells.

In some embodiments, the harvesting in step (d) is performed using a LOVO cell processing system.

In some embodiments, the multiple fragments comprise about 4 to about 50 fragments, wherein each fragment has a volume of about 27 mm³.

In some embodiments, the multiple fragments comprise about 30 to about 60 fragments with a total volume of about 1300 mm³ to about 1500 mm³.

In some embodiments, the multiple fragments comprise about 50 fragments with a total volume of about 1350 mm³.

In some embodiments, the multiple fragments comprise about 50 fragments with a total mass of about 1 gram to about 1.5 grams.

In some embodiments, the multiple fragments comprise about 4 fragments.

In some embodiments, the second cell culture medium is provided in a container selected from the group consisting of a G-container and a Xuri cellbag.

In some embodiments, the infusion bag in step (e) is a HypoThermosol-containing infusion bag.

In some embodiments, the first period in step (b) and the second period in step (c) are each individually performed within a period of 10 days, 11 days, or 12 days.

In some embodiments, the first period in step (b) and the second period in step (c) are each individually performed within a period of 11 days.

In some embodiments, steps (a) through (e) are performed within a period of about 10 days to about 22 days.

In some embodiments, steps (a) through (e) are performed within a period of about 10 days to about 20 days.

In some embodiments, steps (a) through (e) are performed within a period of about 10 days to about 15 days.

In some embodiments, steps (a) through (e) are performed in 22 days or less.

In some embodiments, steps (a) through (e) and cryopreservation are performed in 22 days or less.

In some embodiments, steps (b) through (e) are performed in a single container, wherein performing steps (b) through (e) in a single container results in an increase in TIL yield per resected tumor as compared to performing steps (b) through (e) in more than one container.

In some embodiments, the antigen-presenting cells are added to the TILs during the second period in step (c) without opening the system.

In some embodiments, the third population of TILs in step (d) is a therapeutic population of TILs which comprises an increased subpopulation of effector T cells and/or central memory T cells relative to the second population of TILs, wherein the effector T cells and/or central memory T cells obtained in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells obtained in the therapeutic population of TILs exhibit increased CD57 expression and decreased CD56 expression relative to effector T cells, and/or central memory T cells obtained from the second population of cells.

In some embodiments, the risk of microbial contamination is reduced as compared to an open system.

In some embodiments, the TILs from step (e) are infused into a patient.

In some embodiments, the closed container comprises a single bioreactor.

In some embodiments, the closed container comprises a G-REX-10.

In some embodiments, the closed container comprises a G-REX-100.

In some embodiments, at step (d) the antigen presenting cells (APCs) are added to the cell culture of the second population of TILs at a APC:TIL ratio of 25:1 to 100:1.

In some embodiments, the cell culture has a ratio of $2.5 \times 10^9$ APCs to $100 \times 10^6$ TILs.

In some embodiments, at step (c) the antigen presenting cells (APCs) are added to the cell culture of the second population of TILs at a APC:TIL ratio of 25:1 to 100:1.

In some embodiments, the cell culture has ratio of $2.5 \times 10^9$ APCs to $100 \times 10^6$ TILs.

In some embodiments, the cell culture medium further comprises a 4-1BB agonist and/or an OX40 agonist during the first expansion, the second expansion, or both.

In some embodiments, the gene-editing is carried out after the 4-1BB agonist and/or the OX40 agonist is introduced into the cell culture medium.

In some embodiments, the gene-editing is carried out before the 4-1BB agonist and/or the OX40 agonist is introduced into the cell culture medium.

In some embodiments, the gene-editing is carried out on TILs from one or more of the first population, the second population, and the third population.

In some embodiments, the gene-editing is carried out on TILs from the first expansion, or TILs from the second expansion, or both.

In some embodiments, the gene-editing is carried out after the first expansion and before the second expansion.

In some embodiments, the gene-editing is carried out before step (b), before step (c), or before step (d).

In some embodiments, the cell culture medium comprises OKT-3 during the first expansion and/or during the second expansion, and the gene-editing is carried out before the OKT-3 is introduced into the cell culture medium.

In some embodiments, the cell culture medium comprises OKT-3 during the first expansion and/or during the second expansion, and the gene-editing is carried out after the OKT-3 is introduced into the cell culture medium.

In some embodiments, the cell culture medium comprises OKT-3 beginning on the start day of the first expansion, and the gene-editing is carried out after the TILs have been exposed to the OKT-3.

In some embodiments, the gene-editing causes expression of one or more immune checkpoint genes to be silenced or reduced in at least a portion of the therapeutic population of TILs.

In some embodiments, the one or more immune checkpoint genes is/are selected from the group comprising PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

In some embodiments, the one or more immune checkpoint genes is/are selected from the group comprising PD-1, CTLA-4, LAG-3, HAVCR2 (TIM-3), Cish, TGFβ, and PKA.

In some embodiments, the gene-editing causes expression of one or more immune checkpoint genes to be enhanced in at least a portion of the therapeutic population of TILs, the immune checkpoint gene(s) being selected from the group comprising CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

In some embodiments, the gene-editing comprises the use of a programmable nuclease that mediates the generation of a double-strand or single-strand break at said one or more immune checkpoint genes.

In some embodiments, the gene-editing comprises one or more methods selected from a CRISPR method, a TALE method, a zinc finger method, and a combination thereof.

In some embodiments, the gene-editing comprises a CRISPR method.

In some embodiments, the CRISPR method is a CRISPR/Cas9 method.

In some embodiments, the gene-editing comprises a TALE method.

In some embodiments, the gene-editing comprises a zinc finger method.

In another embodiment, the present invention provides a population of therapeutic TILs that have been expanded in accordance with any of the expansion methods described herein (e.g., for use in the treatment of a subject's cancer), wherein the population of therapeutic TILs has been permanently gene-edited.

In another embodiment, the present invention provides a population of expanded TILs for use in the treatment of a subject with cancer, wherein the population of expanded TILs is a third population of TILs obtainable by a method comprising:
(a) obtaining a first population of TILs from a tumor resected from a subject by processing a tumor sample obtained from the patient into multiple tumor fragments;
(b) adding the tumor fragments into a closed system;
(c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) harvesting the therapeutic population of TILs obtained from step (d), wherein the transition from step (d) to step (e) occurs without opening the system;
(f) transferring the harvested TIL population from step (e) to an infusion bag, wherein the transfer from step (e) to (f) occurs without opening the system;
(g) optionally cryopreserving the infusion bag comprising the harvested TIL population from step (f) using a cryopreservation process; and
(h) at any time during the method, gene-editing at least a portion of the TILs.

In some embodiments, the above method further comprises one or more features recited in any of the methods and compositions described herein.

In some embodiments, the cell culture medium further comprises a 4-1BB agonist and/or an OX40 agonist during the first expansion, the second expansion, or both.

In some embodiments, the gene-editing is carried out after the 4-1BB agonist and/or the OX40 agonist is introduced into the cell culture medium.

In some embodiments, the gene-editing is carried out before the 4-1BB agonist and/or the OX40 agonist is introduced into the cell culture medium.

In some embodiments, the gene-editing is carried out on TILs from one or more of the first population, the second population, and the third population.

In some embodiments, the gene-editing is carried out on TILs from the first expansion, or TILs from the second expansion, or both.

In some embodiments, the gene-editing is carried out after the first expansion and before the second expansion.

In some embodiments, the gene-editing is carried out before step (c), before step (d), or before step (e).

In some embodiments, the cell culture medium comprises OKT-3 during the first expansion and/or during the second expansion, and the gene-editing is carried out before the OKT-3 is introduced into the cell culture medium.

In some embodiments, the cell culture medium comprises OKT-3 during the first expansion and/or during the second expansion, and the gene-editing is carried out after the OKT-3 is introduced into the cell culture medium.

In some embodiments, the cell culture medium comprises OKT-3 beginning on the start day of the first expansion, and the gene-editing is carried out after the TILs have been exposed to the OKT-3.

In some embodiments, the gene-editing causes expression of one or more immune checkpoint genes to be silenced or reduced in at least a portion of the therapeutic population of TILs.

In some embodiments, the one or more immune checkpoint genes is/are selected from the group comprising PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

In some embodiments, the one or more immune checkpoint genes is/are selected from the group comprising PD-1, CTLA-4, LAG-3, HAVCR2 (TIM-3), Cish, TGFβ, and PKA.

In some embodiments, the gene-editing causes expression of one or more immune checkpoint genes to be enhanced in at least a portion of the therapeutic population of TILs, the immune checkpoint gene(s) being selected from the group comprising CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

In some embodiments, the gene-editing comprises the use of a programmable nuclease that mediates the generation of a double-strand or single-strand break at said one or more immune checkpoint genes.

In some embodiments, the gene-editing comprises one or more methods selected from a CRISPR method, a TALE method, a zinc finger method, and a combination thereof.

In some embodiments, the gene-editing comprises a CRISPR method.

In some embodiments, the CRISPR method is a CRISPR/Cas9 method.

In some embodiments, the gene-editing comprises a TALE method.

In some embodiments, the gene-editing comprises a zinc finger method.

In another embodiment, the present invention provides a method for expanding tumor infiltrating lymphocytes (TILs) into a therapeutic population of TILs comprising:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising OKT-3 and/or a 4-1BB agonist antibody for about 2 to 5 days;
(d) optionally adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium, wherein the electroporation step comprises the delivery of a Clustered Regularly Interspersed Short Palindromic Repeat (CRISPR) system, a Transcription Activator-Like Effector (TALE) system, or a zinc finger system for inhibiting the expression of a molecule selected from the group consisting of PD-1, LAG-3, TIM-3, CTLA-4, TIGIT, CISH, TGFβR2, PRA, CBLB, BAFF (BR3), and combinations thereof.

In another embodiment, the present invention provides a method for treating a subject with cancer, the method comprising administering expanded tumor infiltrating lymphocytes (TILs) comprising:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising OKT-3 and/or a 4-1BB agonist antibody for about 2 to 5 days;
(d) optionally adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system;
(j) cryopreserving the harvested TIL population using a dimethylsulfoxide-based cryopreservation medium; and (k) administering a therapeutically effective dosage of the harvested TIL population from the infusion bag to the patient;
wherein the electroporation step comprises the delivery of a Clustered Regularly Interspersed Short Palindromic Repeat (CRISPR) system, a Transcription Activator-Like Effector (TALE) system, or a zinc finger system for inhibiting the expression of a molecule selected from the group consisting of PD-1, LAG-3, TIM-3, CTLA-4, TIGIT, CISH, TGFβR2, PRA, CBLB, BAFF (BR3), and combinations thereof.

In another embodiment, the present invention provides a population of expanded TILs for use in the treatment of a subject with cancer, wherein the population of expanded TILs is a harvested population of TILs obtainable by a method comprising:

(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising OKT-3 and/or a 4-1BB agonist antibody for about 2 to 5 days;
(d) optionally adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium,
wherein the electroporation step comprises the delivery of a Clustered Regularly Interspersed Short Palindromic Repeat (CRISPR) system, a Transcription Activator-Like Effector (TALE) system, or a zinc finger system for inhibiting the expression of a molecule selected from the group consisting of PD-1, LAG-3, TIM-3, CTLA-4, TIGIT, CISH, TGFβR2, PRA, CBLB, BAFF (BR3), and combinations thereof.

In some embodiments, the method comprises performing the first expansion by culturing the first population of TILs in a cell culture medium comprising IL-2, OKT-3 and a 4-1BB agonist antibody, wherein the OKT-3 and the 4-1BB agonist antibody are optionally present in the cell culture medium beginning on Day 0 or Day 1.

In another embodiment, the present invention provides a cryopreservation composition comprising the population of TILs for use to treat a subject with cancer, a cryoprotectant medium comprising DMSO, and an electrolyte solution.

In some embodiments, the cryopreservation composition may further comprise one or more stabilizers (e.g., HSA) and one or more lymphocyte growth factors (e.g., IL-2).

In some embodiments, the cryoprotectant medium comprising DMSO and the electrolyte solution are present in a ratio of about 1.1:1 to about 1:1.1.

In some embodiments, the cryopreservation composition comprises the cryoprotectant medium comprising DMSO in an amount of about 30 mL to about 70 mL, the electrolyte solution in an amount of about 30 mL to about 70 mL, HSA in an amount of about 0.1 g to about 1.0 g, and IL-2 in an amount of about 0.001 mg to about 0.005 mg.

BRIEF DESCRIPTION OF THE DRAWINGS

FIG. 2: Shows a comparison between the 1C process and an embodiment of the 2A process for TIL manufacturing.

FIG. 13: Comparison table of Steps A through F from exemplary embodiments of process 1C and process 2A.

FIG. 14: Detailed comparison of an embodiment of process 1C and an embodiment of process 2A.

FIG. 17: Table of process improvements from Gen 1 to Gen 2.

FIG. 18: An embodiment of a TIL manufacturing process of the present invention.

DETAILED DESCRIPTION OF THE INVENTION

I. Introduction

Figure 1:
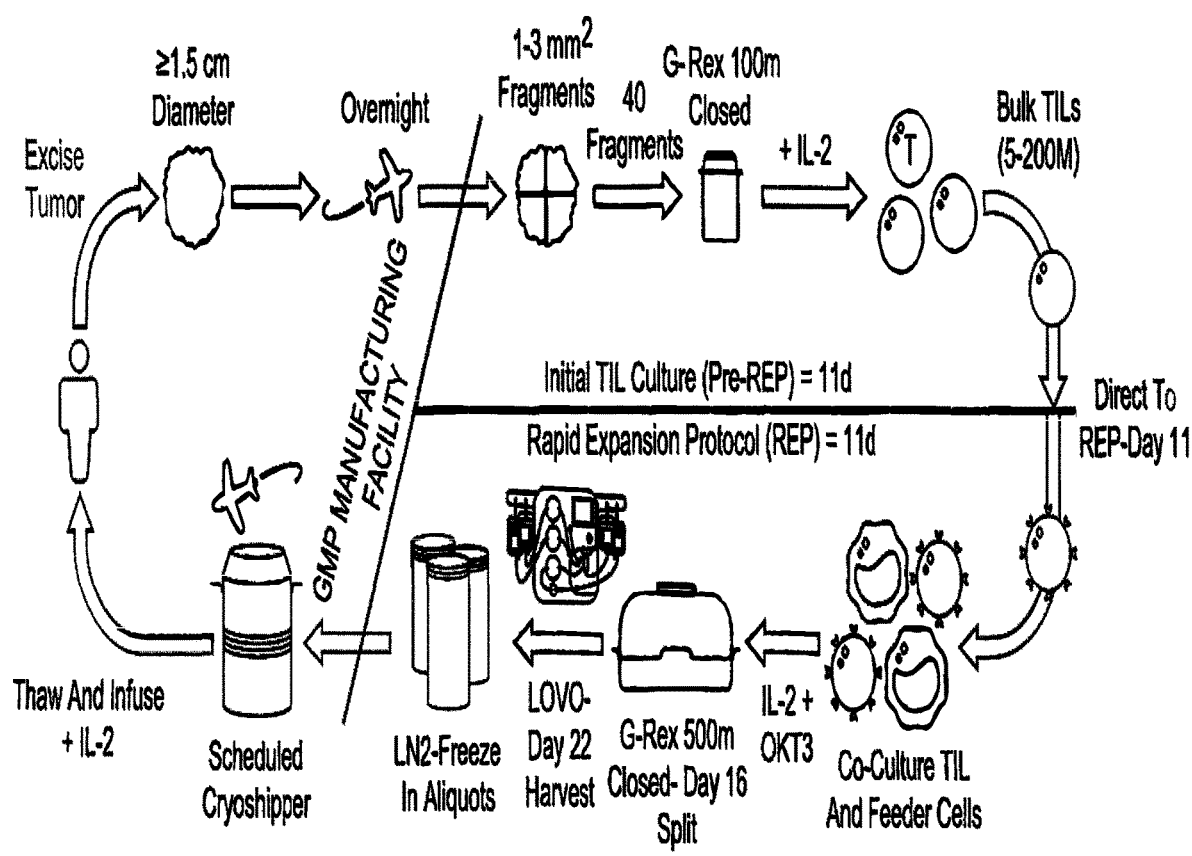
FIG. 1: Shows a diagram of an embodiment of process 2A, a 22-day process for TIL manufacturing.

Adoptive cell therapy utilizing TILs cultured ex vivo by the Rapid Expansion Protocol (REP) has produced successful adoptive cell therapy following host immunosuppression in patients with melanoma. Current infusion acceptance parameters rely on readouts of the composition of TILs (e.g., CD28, CD8, or CD4 positivity) and on the numerical folds of expansion and viability of the REP product.

Current REP protocols give little insight into the health of the TIL that will be infused into the patient. T cells undergo a profound metabolic shift during the course of their maturation from naïve to effector T cells (see Chang, et al., *Nat. Immunol.* 2016, 17, 364, hereby expressly incorporated in its entirety, and in particular for the discussion and markers of anaerobic and aerobic metabolism). For example, naïve T cells rely on mitochondrial respiration to produce ATP, while mature, healthy effector T cells such as TIL are highly glycolytic, relying on aerobic glycolysis to provide the bioenergetics substrates they require for proliferation, migration, activation, and anti-tumor efficacy.

Previous papers report that limiting glycolysis and promoting mitochondrial metabolism in TILs prior to transfer is desirable as cells that are relying heavily on glycolysis will suffer nutrient deprivation upon adoptive transfer which results in a majority of the transferred cells dying. Thus, the art teaches that promoting mitochondrial metabolism might promote in vivo longevity and in fact suggests using inhibitors of glycolysis before induction of the immune response. See Chang, et al., *Nat. Immunol.* 2016, 17(364).

The present invention is further directed in some embodiments to methods for evaluating and quantifying this increase in metabolic health. Thus, the present invention provides methods of assaying the relative health of a TIL population using one or more general evaluations of metabolism, including, but not limited to, rates and amounts of glycolysis, oxidative phosphorylation, spare respiratory capacity (SRC), and glycolytic reserve.

Furthermore, the present invention is further directed in some embodiments to methods for evaluating and quantifying this increase in metabolic health. Thus, the present invention provides methods of assaying the relative health of a TIL population using one or more general evaluations of metabolism, including, but not limited to, rates and amounts of glycolysis, oxidative phosphorylation, spare respiratory capacity (SRC), and glycolytic reserve.

In addition, optional additional evaluations include, but are not limited to, ATP production, mitochondrial mass and glucose uptake.

The present invention is further directed in some embodiments to enhancing the therapeutic effect of TILs with the use of gene editing technology. While adoptive transfer of tumor infiltrating lymphocytes (TILs) offers a promising and effective therapy, there is a strong need for more effective TIL therapies that can increase a patient's response rate and response robustness. As described herein, embodiments of the present invention provide methods for expanding TILs into a therapeutic population that is gene-edited to provide an enhanced therapeutic effect.

II. Definitions

Unless defined otherwise, all technical and scientific terms used herein have the same meaning as is commonly understood by one of skill in the art to which this invention belongs. All patents and publications referred to herein are incorporated by reference in their entireties.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1 \times 10^6$ to $1 \times 10^{10}$ in number, with different TIL populations comprising different numbers. For example, initial growth of primary TILs in the presence of IL-2 results in a population of bulk TILs of roughly $1 \times 10^8$ cells. REP expansion is generally done to provide populations of $1.5 \times 10^9$ to $1.5 \times 10^{10}$ cells for infusion.

By "cryopreserved TILs" herein is meant that TILs, either primary, bulk, or expanded (REP TILs), are treated and stored in the range of about $-150°$ C. to $-60°$ C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS 10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T cell" refers to a subset of T cells that in the human are CD45R0+ and constitutively express CCR7 ($CCR7^{hi}$) and CD62 L ($CD62^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40 L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 ($CCR7^{lo}$) and are heterogeneous or low for CD62 L expression ($CD62\ L^{lo}$). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perform.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "peripheral blood mononuclear cells" and "PBMCs" refers to a peripheral blood cell having a round nucleus, including lymphocytes (T cells, B cells, NK cells) and monocytes. Preferably, the peripheral blood mononuclear cells are irradiated allogeneic peripheral blood mononuclear cells. PBMCs are a type of antigen-presenting cell.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, Calif., USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706. Anti-CD3 antibodies also include the UHCT1 clone (commercially available from BioLegend, San Diego, Calif., USA), also known as T3 and CD3ε.

TABLE 1

Amino acid sequences of muromonab.

| Identifier | Sequence (One-Letter Amino Acid Symbols) | |
|---|---|---|
| SEQ ID NO: 1<br>Muromonab<br>heavy chain | QVQLQQSGAE LARPGASVKM SCKASGYTFT RYTMHWVKQR PGQGLEWIGY INPSRGYTNY<br>NQKFKDKATL TTDKSSSTAY MQLSSLTSED SAVYYCARYY DDHYCLDYWG QGTTLTVSSA<br>KTTAPSVYPL APVCGGTTGS SVTLGCLVKG YFPEPVTLTW NSGSLSSGVH TFPAVLQSDL<br>YTLSSSVTVT SSTWPSQSIT CNVAHPASST KVDKKIEPRP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 2<br>Muromonab<br>light chain | QIVLTQSPAI MSASPGEKVT MTCSASSSVS YMNWYQQKSG TSPKRWIYDT SKLASGVPAH<br>FRGSGSGTSY SLTISGMEAE DAATYYCQQW SSNPFTFGSG TKLEINRADT APTVSIFPPS<br>SEQLTSGGAS VVCFLNNFYP KDINVKWKID GSERQNGVLN SWTDQDSKDS TYSMSSTLTL<br>TKDEYERHNS YTCEATHKTS TSPIVKSFNR NEC | 60<br>120<br>180<br>213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, N.H., USA (CELLGRO GMP) or ProSpec-Tany TechnoGene Ltd., East Brunswick, N.J., USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, Calif., USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4902,502, the disclosures of which are incorporated by reference herein. Formulations of IL-2 suitable for use in the invention are described in U.S. Pat. No. 6,706,289, the disclosure of which is incorporated by reference herein.

TABLE 2

Amino acid sequences of interleukins.

| Identifier | Sequence (One-Letter Amino Acid Symbols) | |
|---|---|---|
| SEQ ID NO: 3<br>recombinant<br>human IL-2<br>(rhIL-2) | MAPTSSSTKK TQLQLEHLLL DLQMILNGIN NYKNPKLTRM LTFKFYMPKK ATELKHLQCL<br>EEELKPLEEV LNLAQSKNFH LRPRDLISNI NVIVLELKGS ETTFMCEYAD ETATIVEFLN<br>RWITFCQSII STLT | 60<br>120<br>134 |
| SEQ ID NO: 4<br>Aldesleukin | PTSSSTKKTQ LQLEHLLLDL QMILNGINNY KNPKLTRMLT FKFYMPKKAT ELKHLQCLEE<br>ELKPLEEVLN LAQSKNFHLR PRDLISNINV IVLELKGSET TFMCEYADET ATIVEFLNRW<br>ITFSQSIIST LT | 60<br>120<br>132 |
| SEQ ID NO: 5<br>recombinant<br>human IL-4<br>(rhIL-4) | MHKCDITLQE IIKTLNSLTE QKTLCTELTV TDIFAASKNT TEKETFCRAA TVLRQFYSHH<br>EKDTRCLGAT AQQFHRHKQL IRFLKRLDRN LWGLAGLNSC PVKEANQSTL ENFLERLKTI<br>MREKYSKCSS | 60<br>120<br>130 |
| SEQ ID NO: 6<br>recombinant<br>human IL-7<br>(rhIL-7) | MDCDIEGKDG KQYESVLMVS IDQLLDSMKE IGSNCLNNEF NFFKRHICDA NKEGMFLFRA<br>ARKLRQFLKM NSTGDFDLHL LKVSEGTTIL LNCTGQVKGR KPAALGEAQP TKSLEENKSL<br>KEQKKLNDLC FLKRLLQEIK TCWNKILMGT KEH | 60<br>120<br>153 |
| SEQ ID NO: 7<br>recombinant<br>human IL-15<br>(rhIL-15) | MNWVNVISDL KKIEDLIQSM HIDATLYTES DVHPSCKVTA MKCFLLELQV ISLESGDASI<br>HDTVENLIIL ANNSLSSNGN VTESGCKECE ELEEKNIKEF LQSFVHIVQM FINTS | 60<br>115 |
| SEQ ID NO: 8<br>recombinant<br>human IL-21<br>(rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and IgG$_1$ expression from B cells. Recombinant human IL-4 suitable for use in the invention is commercially available from multiple suppliers, including ProSpec-Tany TechnoGene Ltd., East Brunswick, N.J., USA (Cat. No. CYT-211) and ThermoFisher Scientific, Inc., Waltham, Mass., USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, N.J., USA (Cat. No. CYT-254) and ThermoFisher Scientific, Inc., Waltham, Mass., USA (human IL-15 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, N.J., USA (Cat. No. CYT-230-b) and ThermoFisher Scientific, Inc., Waltham, Mass., USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human CD4$^+$ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, N.J., USA (Cat. No. CYT-408-b) and ThermoFisher Scientific, Inc., Waltham, Mass., USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., Cancer Res., 2012, 72, 2473. Although tumors express antigens that should be recognized by T cells, tumor clearance by the immune system is rare because of immune suppression by the microenvironment.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, Calif.) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs, expanded TILs ("REP TILs") as well as "reREP TILs" as discussed herein. reREP TILs can include for example second expansion TILs or second additional expansion TILs (such as, for example, those described in Step D of FIG. 9, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR $\alpha\beta$, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 pg/mL, greater than about 100 pg/mL, greater than about 150 pg/mL, or greater than about 200 pg/mL.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

III. Gene-Editing Processes

A. Overview: TIL Expansion+Gene-Editing

Embodiments of the present invention are directed to methods for expanding TIL populations, the methods comprising one or more steps of gene-editing at least a portion of the TILs in order to enhance their therapeutic effect. As used herein, "gene-editing," "gene editing," and "genome editing" refer to a type of genetic modification in which DNA is permanently modified in the genome of a cell, e.g., DNA is inserted, deleted, modified or replaced within the cell's genome. In some embodiments, gene-editing causes the expression of a DNA sequence to be silenced (sometimes referred to as a gene knockout) or inhibited/reduced (sometimes referred to as a gene knockdown). In other embodiments, gene-editing causes the expression of a DNA sequence to be enhanced (e.g., by causing overexpression). In accordance with embodiments of the present invention, gene-editing technology is used to enhance the effectiveness of a therapeutic population of TILs.

A method for expanding tumor infiltrating lymphocytes (TILs) into a therapeutic population of TILs may be carried out in accordance with any embodiment of the methods described herein (e.g., an exemplary TIL expansion method known as process 2A is described below), wherein the method further comprises gene-editing at least a portion of the TILs. According to additional embodiments, a method for expanding TILs into a therapeutic population of TILs is carried out in accordance with any embodiment of the methods described in PCT/US2017/058610, PCT/US2018/012605, or PCT/US2018/012633, which are incorporated by reference herein in their entireties, wherein the method further comprises gene-editing at least a portion of the TILs. Thus, an embodiment of the present invention provides a therapeutic population of TILs that has been expanded in accordance with any embodiment described herein, wherein at least a portion of the therapeutic population has been gene-edited, e.g., at least a portion of the therapeutic population of TILs that is transferred to the infusion bag is permanently gene-edited.

B. Timing of Gene-Editing During TIL Expansion

According to one embodiment, a method for expanding tumor infiltrating lymphocytes (TILs) into a therapeutic population of TILs comprises:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2, and optionally OKT-3 (e.g., OKT-3 may be present in the culture medium beginning on the start date of the expansion process), to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system;

(f) transferring the harvested TIL population from step (e) to an infusion bag, wherein the transfer from step (e) to (f) occurs without opening the system; and (g) at any time during the method, gene-editing at least a portion of the TILs.

As stated in step (g) of the embodiment described above, the gene-editing process may be carried out at any time during the TIL expansion method, which means that the gene editing may be carried out on TILs before, during, or after any of the steps in the expansion method; for example, during any of steps (a)-(f) outlined in the method above, or before or after any of steps (a)-(f) outlined in the method above. According to certain embodiments, TILs are collected during the expansion method (e.g., the expansion method is "paused" for at least a portion of the TILs), and the collected TILs are subjected to a gene-editing process, and, in some cases, subsequently reintroduced back into the expansion method (e.g., back into the culture medium) to continue the expansion process, so that at least a portion of the therapeutic population of TILs that are eventually transferred to the infusion bag are permanently gene-edited. In an embodiment, the gene-editing process may be carried out before expansion by activating TILs, performing a gene-editing step on the activated TILs, and expanding the gene-edited TILs according to the processes described herein.

It should be noted that alternative embodiments of the expansion process may differ from the method shown above; e.g., alternative embodiments may not have the same steps (a)-(g), or may have a different number of steps. Regardless of the specific embodiment, the gene-editing process may be carried out at any time during the TIL expansion method. For example, alternative embodiments may include more than two expansions, and it is possible that gene-editing may be conducted on the TILs during a third or fourth expansion, etc.

According to one embodiment, the gene-editing process is carried out on TILs from one or more of the first population, the second population, and the third population. For example, gene-editing may be carried out on the first population of TILs, or on a portion of TILs collected from the first population, and following the gene-editing process those TILs may subsequently be placed back into the expansion process (e.g., back into the culture medium). Alternatively, gene-editing may be carried out on TILs from the second or third population, or on a portion of TILs collected from the second or third population, respectively, and following the gene-editing process those TILs may subsequently be placed back into the expansion process (e.g., back into the culture medium). According to another embodiment, gene-editing is performed while the TILs are still in the culture medium and while the expansion is being carried out, i.e., they are not necessarily "removed" from the expansion in order to conduct gene-editing.

According to another embodiment, the gene-editing process is carried out on TILs from the first expansion, or TILs from the second expansion, or both. For example, during the first expansion or second expansion, gene-editing may be carried out on TILs that are collected from the culture medium, and following the gene-editing process those TILs may subsequently be placed back into the expansion method, e.g., by reintroducing them back into the culture medium.

According to another embodiment, the gene-editing process is carried out on at least a portion of the TILs after the first expansion and before the second expansion. For example, after the first expansion, gene-editing may be carried out on TILs that are collected from the culture medium, and following the gene-editing process those TILs may subsequently be placed back into the expansion method, e.g., by reintroducing them back into the culture medium for the second expansion.

According to alternative embodiments, the gene-editing process is carried out before step (c) (e.g., before, during, or after any of steps (a)-(b)), before step (d) (e.g., before, during, or after any of steps (a)-(c)), before step (e) (e.g., before, during, or after any of steps (a)-(d)), or before step (f) (e.g., before, during, or after any of steps (a)-(e)).

It should be noted with regard to OKT-3, according to certain embodiments, that the cell culture medium may comprise OKT-3 beginning on the start day (Day 0), or on Day 1 of the first expansion, such that the gene-editing is carried out on TILs after they have been exposed to OKT-3 in the cell culture medium on Day 0 and/or Day 1. According to another embodiment, the cell culture medium comprises OKT-3 during the first expansion and/or during the second expansion, and the gene-editing is carried out before the OKT-3 is introduced into the cell culture medium. Alternatively, the cell culture medium may comprise OKT-3 during the first expansion and/or during the second expansion, and the gene-editing is carried out after the OKT-3 is introduced into the cell culture medium.

It should also be noted with regard to a 4-1BB agonist, according to certain embodiments, that the cell culture medium may comprise a 4-1BB agonist beginning on the start day (Day 0), or on Day 1 of the first expansion, such that the gene-editing is carried out on TILs after they have been exposed to a 4-1BB agonist in the cell culture medium on Day 0 and/or Day 1. According to another embodiment, the cell culture medium comprises a 4-1BB agonist during the first expansion and/or during the second expansion, and the gene-editing is carried out before the 4-1BB agonist is introduced into the cell culture medium. Alternatively, the cell culture medium may comprise a 4-1BB agonist during the first expansion and/or during the second expansion, and the gene-editing is carried out after the 4-1BB agonist is introduced into the cell culture medium.

It should also be noted with regard to IL-2, according to certain embodiments, that the cell culture medium may comprise IL-2 beginning on the start day (Day 0), or on Day 1 of the first expansion, such that the gene-editing is carried out on TILs after they have been exposed to IL-2 in the cell culture medium on Day 0 and/or Day 1. According to another embodiment, the cell culture medium comprises IL-2 during the first expansion and/or during the second expansion, and the gene-editing is carried out before the IL-2 is introduced into the cell culture medium. Alternatively, the cell culture medium may comprise IL-2 during the first expansion and/or during the second expansion, and the gene-editing is carried out after the IL-2 is introduced into the cell culture medium.

As discussed above, one or more of OKT-3, 4-1BB agonist and IL-2 may be included in the cell culture medium beginning on Day 0 or Day 1 of the first expansion. According to one embodiment, OKT-3 is included in the cell culture medium beginning on Day 0 or Day 1 of the first expansion, and/or a 4-1BB agonist is included in the cell culture medium beginning on Day 0 or Day 1 of the first expansion, and/or IL-2 is included in the cell culture medium beginning on Day 0 or Day 1 of the first expansion. According to an example, the cell culture medium comprises OKT-3 and a 4-1BB agonist beginning on Day 0 or Day 1 of the first expansion. According to another example, the cell culture medium comprises OKT-3, a 4-1BB agonist and IL-2 beginning on Day 0 or Day 1 of the first expansion. Of course, one or more of OKT-3, 4-1BB agonist and IL-2 may be added to the cell culture medium at one or more additional time points during the expansion process, as set forth in various embodiments described herein.

According to one embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium.

According to one embodiment, the foregoing method may be used to provide an autologous harvested TIL population for the treatment of a human subject with cancer.

C. Immune Checkpoints

According to particular embodiments of the present invention, a TIL population is gene-edited by genetically modifying one or more immune checkpoint genes in the TIL population. Stated another way, a DNA sequence within the TIL that encodes one or more of the TIL's immune checkpoints is permanently modified, e.g., inserted, deleted or replaced, in the TIL's genome. Immune checkpoints are molecules expressed by lymphocytes that regulate an immune response via inhibitory or stimulatory pathways. In the case of cancer, immune checkpoint pathways are often activated to inhibit the anti-tumor response, i.e., the expression of certain immune checkpoints by malignant cells inhibits the anti-tumor immunity and favors the growth of cancer cells. See, e.g., Marin-Acevedo et al., *Journal of Hematology & Oncology* (2018) 11:39. Thus, certain inhibitory checkpoint molecules serve as targets for immunotherapies of the present invention. According to particular embodiments, TILs are gene-edited to block or stimulate certain immune checkpoint pathways and thereby enhance the body's immunological activity against tumors.

As used herein, an immune checkpoint gene comprises a DNA sequence encoding an immune checkpoint molecule. According to particular embodiments of the present invention, gene-editing TILs during the TIL expansion method causes expression of one or more immune checkpoint genes to be silenced or reduced in at least a portion of the therapeutic population of TILs. For example, gene-editing may cause the expression of an inhibitory receptor, such as PD-1 or CTLA-4, to be silenced or reduced in order to enhance an immune reaction.

The most broadly studied checkpoints include programmed cell death receptor-1 (PD-1) and cytotoxic T lymphocyte-associated molecule-4 (CTLA-4), which are inhibitory receptors on immune cells that inhibit key effector functions (e.g., activation, proliferation, cytokine release, cytoxicity, etc.) when they interact with an inhibitory ligand. Numerous checkpoint molecules, in addition to PD-1 and CTLA-4, have emerged as potential targets for immunotherapy, as discussed in more detail below.

Non-limiting examples of immune checkpoint genes that may be silenced or inhibited by permanently gene-editing TILs of the present invention include PD-1, CTLA-4, LAG- 3, HAVCR2 (TIM-3), Cish, TGFβ, PKA, CBL-B, PPP2CA, PPP2CB, PTPN6, PTPN22, PDCD1, BTLA, CD160, TIGIT, BAFF (BR3), CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3. For example, immune checkpoint genes that may be silenced or inhibited in TILs of the present invention may be selected from the group comprising PD-1, CTLA-4, LAG-3, TIM-3, Cish, TGFβ, and PKA. BAFF (BR3) is described in Bloom, et al., *J. Immunother.*, 2018, in press. According to another example, immune checkpoint genes that may be silenced or inhibited in TILs of the present invention may be selected from the group comprising PD-1, LAG-3, TIM-3, CTLA-4, TIGIT, CISH, TGFβR2, PRA, CBLB, BAFF (BR3), and combinations thereof.

According to one embodiment, a method for expanding tumor infiltrating lymphocytes (TILs) into a therapeutic population of TILs comprises:
 (a) obtaining a first population of TILs from a tumor resected from a patient by processing a tumor sample obtained from the patient into multiple tumor fragments;
 (b) adding the tumor fragments into a closed system;
 (c) performing a first expansion by culturing the first population of TILs in a cell culture medium comprising IL-2 and optionally comprising a 4-1BB agonist antibody for about 2 to 5 days;
 (d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
 (e) performing a sterile electroporation step on the second population of TILs, wherein the sterile electroporation step mediates the transfer of at least one gene editor;
 (f) resting the second population of TILs for about 1 day;
 (g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (1) to step (g) occurs without opening the system;
 (h) harvesting the therapeutic population of TILs obtained from step (g) to provide a harvested TIL population, wherein the transition from step (g) to step (h) occurs without opening the system, wherein the harvested population of TILs is a therapeutic population of TILs;
 (i) transferring the harvested TIL population to an infusion bag, wherein the transfer from step (h) to (i) occurs without opening the system; and
 (j) cryopreserving the harvested TIL population using a dimethylsulfoxide-based cryopreservation medium,
wherein the electroporation step comprises the delivery of a Clustered Regularly Interspersed Short Palindromic Repeat (CRISPR) system, a Transcription Activator-Like Effector (TALE) system, or a zinc finger system for inhibiting the expression of a molecule selected from the group consisting of PD-1, LAG-3, TIM-3, CTLA-4, TIGIT, CISH, TGFβR2, PRA, CBLB, BAFF (BR3), and combinations thereof.

1. PD-1

One of the most studied targets for the induction of checkpoint blockade is the programmed death receptor (PD1 or PD-1, also known as PDCD1), a member of the CD28 super family of T-cell regulators. Its ligands, PD-L1 and PD-L2, are expressed on a variety of tumor cells, including melanoma. The interaction of PD-1 with PD-L1 inhibits T-cell effector function, results in T-cell exhaustion in the setting of chronic stimulation, and induces T-cell apoptosis in the tumor microenvironment. PD1 may also play a role in tumor-specific escape from immune surveillance.

According to particular embodiments, expression of PD1 in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or repressing the expression of PD1. As described in more detail below, the gene-editing process may involve the use of a programmable nuclease that mediates the generation of a double-strand or single-strand break at an immune checkpoint gene, such as PD1. For example, a CRISPR method, a TALE method, or a zinc finger method may be used to silence or reduce the expression of PD1 in the TILs.

2. CTLA-4

CTLA-4 expression is induced upon T-cell activation on activated T-cells, and competes for binding with the antigen presenting cell activating antigens CD80 and CD86. Interaction of CTLA-4 with CD80 or CD86 causes T-cell inhibition and serves to maintain balance of the immune response. However, inhibition of the CTLA-4 interaction with CD80 or CD86 may prolong T-cell activation and thus increase the level of immune response to a cancer antigen.

According to particular embodiments, expression of CTLA-4 in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or repressing the expression of CTLA-4. As described in more detail below, the gene-editing process may comprise the use of a programmable nuclease that mediates the generation of a double-strand or single-strand break at an immune checkpoint gene, such as CTLA-4. For example, a CRISPR method, a TALE method, or a zinc finger method may be used to silence or repress the expression of CTLA-4 in the TILs.

3. LAG-3

Lymphocyte activation gene-3 (LAG-3, CD223) is expressed by T cells and natural killer (NK) cells after major histocompatibility complex (MHC) class II ligation. Although its mechanism remains unclear, its modulation causes a negative regulatory effect over T cell function, preventing tissue damage and autoimmunity. LAG-3 and PD-1 are frequently co-expressed and upregulated on TILs, leading to immune exhaustion and tumor growth. Thus, LAG-3 blockade improves anti-tumor responses. See, e.g., Marin-Acevedo et al., *Journal of Hematology & Oncology* (2018) 11:39.

According to particular embodiments, expression of LAG-3 in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or repressing the expression of LAG-3. As described in more detail below, the gene-editing process may comprise the use of a programmable nuclease that mediates the generation of a double-strand or single-strand break at an immune checkpoint gene, such as LAG-3. According to particular embodiments, a CRISPR method, a TALE method, or a zinc finger method may be used to silence or repress the expression of LAG-3 in the TILs.

4. TIM-3

T cell immunoglobulin-3 (TIM-3) is a direct negative regulator of T cells and is expressed on NK cells and macrophages. TIM-3 indirectly promotes immunosuppression by inducing expansion of myeloid-derived suppressor cells (MDSCs). Its levels have been found to be particularly elevated on dysfunctional and exhausted T-cells, suggesting an important role in malignancy.

According to particular embodiments, expression of TIM-3 in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or repressing the expression of TIM-3. As described in more detail below, the gene-editing process may comprise the use of a programmable nuclease that mediates the generation of a double-strand or single-strand break at an immune checkpoint gene, such as TIM-3. For example, a CRISPR method, a TALE method, or a zinc finger method may be used to silence or repress the expression of TIM-3 in the TILs.

5. Cish

Cish, a member of the suppressor of cytokine signaling (SOCS) family, is induced by TCR stimulation in CD8+ T cells and inhibits their functional avidity against tumors. Genetic deletion of Cish in CD8+ T cells may enhance their expansion, functional avidity, and cytokine polyfunctionality, resulting in pronounced and durable regression of established tumors. See, e.g., Palmer et al., *Journal of Experimental Medicine,* 212 (12): 2095 (2015).

According to particular embodiments, expression of Cish in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or repressing the expression of Cish. As described in more detail below, the gene-editing process may comprise the use of a programmable nuclease that mediates the generation of a double-strand or single-strand break at an immune checkpoint gene, such as Cish. For example, a CRISPR method, a TALE method, or a zinc finger method may be used to silence or repress the expression of Cish in the TILs.

6. TGFβ

The TGFβ signaling pathway has multiple functions in regulating cell growth, differentiation, apoptosis, motility and invasion, extracellular matrix production, angiogenesis, and immune response. TGFβ signaling deregulation is frequent in tumors and has crucial roles in tumor initiation, development and metastasis. At the microenvironment level, the TGFβ pathway contributes to generate a favorable microenvironment for tumor growth and metastasis throughout carcinogenesis. See, e.g., Neuzillet et al., *Pharmacology & Therapeutics,* Vol. 147, pp. 22-31 (2015).

According to particular embodiments, expression of TGFβ in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or reducing the expression of TGFβ. As described in more detail below, the gene-editing process may comprise the use of a programmable nuclease that mediates the generation of a double-strand or single-strand break at an immune checkpoint gene, such as TGFβ. For example, a CRISPR method, a TALE method, or a zinc finger method may be used to silence or repress the expression of TGFβ in the TILs.

In some embodiments, TGFβR2 (TGF beta receptor 2) may be suppressed by silencing TGFβR2 using a CRISPR/Cas9 system or by using a TGFβR2 dominant negative extracellular trap, using methods known in the art.

7. PKA

Protein Kinase A (PKA) is a well-known member of the serine-threonine protein kinase superfamily. PKA, also known as cAMP-dependent protein kinase, is a multi-unit protein kinase that mediates signal transduction of G-protein coupled receptors through its activation upon cAMP binding. It is involved in the control of a wide variety of cellular processes from metabolism to ion channel activation, cell growth and differentiation, gene expression and apoptosis. Importantly, PKA has been implicated in the initiation and progression of many tumors. See, e.g., Sapio et al., *EXCLI Journal;* 2014; 13: 843-855.

According to particular embodiments, expression of PKA in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or repressing the expression of PKA. As described in more detail below, the gene-editing process may comprise the use of a programmable nuclease that mediates the generation of a double-strand or single-strand break at an immune checkpoint gene, such as PKA. For example, a CRISPR method, a TALE method, or a zinc finger method may be used to silence or repress the expression of PKA in the TILs.

8. CBLB

CBLB (or CBL-B) is a E3 ubiquitin-protein ligase and is a negative regulator of T cell activation. Bachmaier, et al., *Nature,* 2000, 403, 211-216; Wallner, et al., *Clin. Dev. Immunol.* 2012, 692639.

According to particular embodiments, expression of CBLB in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or repressing the expression of CBLB. As described in more detail below, the gene-editing process may comprise the use of a programmable nuclease that mediates the generation of a double-strand or single-strand break at an immune checkpoint gene, such as CBLB. For example, a CRISPR method, a TALE method, or a zinc finger method may be used to silence or repress the expression of PKA in the TILs. In some embodiments, CBLB is silenced using a TALEN knockout. In some embodiments, CBLB is silenced using a TALE-KRAB transcriptional inhibitor knock in. More details on these methods can be found in Boettcher and McManus, *Mol. Cell Review,* 2015, 58, 575-585.

9. TIGIT

T-cell immunoreceptor with Ig and ITIM (immunoreceptor tyrosine-based inhibitory motif) domain or TIGIT is a transmembrane glycoprotein receptor with an Ig-like V-type domain and an ITIM in its cytoplasmic domain. Khalil, et al., *Advances in Cancer Research,* 2015, 128, 1-68; Yu, et al., *Nature Immunology,* 2009, Vol. 10, No. 1, 48-57. TIGIT is expressed by some T cells and Natural Killer Cells. Additionally, TIGIT has been shown to be overexpressed on antigen-specific CD8+ T cells and CD8+ TILs, particularly from individuals with melanoma. Studies have shown that the TIGIT pathway contributes to tumor immune evasion and TIGIT inhibition has been shown to increase T-cell activation and proliferation in response to polyclonal and antigen-specific stimulation. Khalil, et al., *Advances in Cancer Research,* 2015, 128, 1-68. Further, coblockade of TIGIT with either PD-1 or TIM3 has shown synergistic effects against solid tumors in mouse models. Id.; see also Kurtulus, et al., *The Journal of Clinical Investigation,* 2015, Vol. 125, No. 11, 4053-4062.

According to particular embodiments, expression of TIGIT in TILs is silenced or reduced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by silencing or repressing the expression of TIGIT. As described in more detail below, the gene-editing process may comprise the use of a programmable nuclease that mediates the generation of a double-strand or single-strand break at an immune checkpoint gene, such as TIGIT. For example, a CRISPR method, a TALE method, or a zinc finger method may be used to silence or repress the expression of TIGIT in the TILs.

D. Overexpression of Co-Stimulatory Receptors or Adhesion Molecules

According to additional embodiments, gene-editing TILs during the TIL expansion method causes expression of one or more immune checkpoint genes to be enhanced in at least a portion of the therapeutic population of TILs. For example, gene-editing may cause the expression of a stimulatory receptor to be enhanced, which means that it is overexpressed as compared to the expression of a stimulatory receptor that has not been genetically modified. Non-limiting examples of immune checkpoint genes that may exhibit enhanced expression by permanently gene-editing TILs of the present invention include certain chemokine receptors and interleukins, such as CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

1. CCRs

For adoptive T cell immunotherapy to be effective, T cells need to be trafficked properly into tumors by chemokines. A match between chemokines secreted by tumor cells, chemokines present in the periphery, and chemokine receptors expressed by T cells is important for successful trafficking of T cells into a tumor bed.

According to particular embodiments, gene-editing methods of the present invention may be used to increase the expression of certain chemokine receptors in the TILs, such as one or more of CCR2, CCR4, CCR5, CXCR2, CXCR3 and CX3CR1. Over-expression of CCRs may help promote effector function and proliferation of TILs following adoptive transfer.

According to particular embodiments, expression of one or more of CCR2, CCR4, CCR5, CXCR2, CXCR3 and CX3CR1 in TILs is enhanced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by enhancing the expression of one or more of CCR2, CCR4, CCR5, CXCR2, CXCR3 and CX3CR1. As described in more detail below, the gene-editing process may comprise the use of a programmable nuclease that mediates the generation of a double-strand or single-strand break at a chemokine receptor gene. For example, a CRISPR method, a TALE method, or a zinc finger method may be used to enhance the expression of certain chemokine receptors in the TILs.

In an embodiment, CCR4 and/or CCR5 adhesion molecules are inserted into a TIL population using a gamma-retroviral or lentiviral method as described herein. In an embodiment, CXCR2 adhesion molecule are inserted into a TIL population using a gamma-retroviral or lentiviral method as described in Forget, et al., *Frontiers Immunology* 2017, 8, 908 or Peng, et al., *Clin. Cancer Res.* 2010, 16, 5458, the disclosures of which are incorporated by reference herein.

According to one embodiment, a method for expanding tumor infiltrating lymphocytes (TILs) into a therapeutic population of TILs comprises:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium,
wherein the electroporation step comprises the delivery of a Clustered Regularly Interspersed Short Palindromic Repeat (CRISPR) system, a Transcription Activator-Like Effector (TALE) system, or a zinc finger system for inhibiting the expression of PD-1 and, optionally, LAG-3, and further wherein a CXCR2 adhesion molecule is inserted by a gammaretroviral or lentiviral method into the first population of TILs, second population of TILs, or harvested population of TILs.

According to one embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium,
wherein the electroporation step comprises the delivery of a Clustered Regularly Interspersed Short Palindromic Repeat (CRISPR) system, a Transcription Activator-Like Effector (TALE) system, or a zinc finger system for inhibiting the expression of PD-1 and, optionally, LAG-3, and further wherein a CCR4 and/or CCR5 adhesion molecule is inserted by a gammaretroviral or lentiviral method into the first population of TILs, second population of TILs, or harvested population of TILs.

According to one embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;

(i) transferring the harvested TIL population to an infusion bag, wherein the transfer from step (h) to (i) occurs without opening the system; and (j) cryopreserving the harvested TIL population using a dimethylsulfoxide-based cryopreservation medium, wherein the electroporation step comprises the delivery of a Clustered Regularly Interspersed Short Palindromic Repeat (CRISPR) system, a Transcription Activator-Like Effector (TALE) system, or a zinc finger system for inhibiting the expression of PD-1 and, optionally, LAG-3, and further wherein an adhesion molecule selected from the group consisting of CCR2, CCR4, CCR5, CXCR2, CXCR3, CX3CR1, and combinations thereof is inserted by a gammaretroviral or lentiviral method into the first population of TILs, second population of TILs, or harvested population of TILs.

2. Interleukins

According to additional embodiments, gene-editing methods of the present invention may be used to increase the expression of certain interleukins, such as one or more of IL-2, IL-4, IL-7, IL-10, IL-15, and IL-21. Certain interleukins have been demonstrated to augment effector functions of T cells and mediate tumor control.

According to particular embodiments, expression of one or more of IL-2, IL-4, IL-7, IL-10, IL-15, and IL-21 in TILs is enhanced in accordance with compositions and methods of the present invention. For example, a method for expanding tumor infiltrating lymphocytes (TILs) into a therapeutic population of TILs may be carried out in accordance with any embodiment of the methods described herein (e.g., process 2A or the methods shown in FIGS. 20 and 21), wherein the method comprises gene-editing at least a portion of the TILs by enhancing the expression of one or more of IL-2, IL-4, IL-7, IL-10, IL-15, and IL-21. As described in more detail below, the gene-editing process may comprise the use of a programmable nuclease that mediates the generation of a double-strand or single-strand break at an interleukin gene. For example, a CRISPR method, a TALE method, or a zinc finger method may be used to enhance the expression of certain interleukins in the TILs.

According to one embodiment, a method for expanding tumor infiltrating lymphocytes (TILs) into a therapeutic population of TILs comprises:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) performing a sterile electroporation step on the second population of TILs, wherein the sterile electroporation step mediates the transfer of at least one gene editor;

(f) resting the second population of TILs for about 1 day;

(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;

(h) harvesting the therapeutic population of TILs obtained from step (g) to provide a harvested TIL population, wherein the transition from step (g) to step (h) occurs without opening the system, wherein the harvested population of TILs is a therapeutic population of TILs;

(i) transferring the harvested TIL population to an infusion bag, wherein the transfer from step (h) to (i) occurs without opening the system; and (j) cryopreserving the harvested TIL population using a dimethylsulfoxide-based cryopreservation medium, wherein the electroporation step comprises the delivery of a Clustered Regularly Interspersed Short Palindromic Repeat (CRISPR) system, a Transcription Activator-Like Effector (TALE) system, or a zinc finger system for inhibiting the expression of PD-1 and, optionally, LAG-3, and further wherein a interleukin selected from the group consisting of IL-2, IL-4, IL-7, IL-10, IL-15, IL-21, and combinations thereof is inserted by a gammaretroviral or lentiviral method into the first population of TILs, second population of TILs, or harvested population of TILs.

E. Gene Editing Methods

As discussed above, embodiments of the present invention provide tumor infiltrating lymphocytes (TILs) that have been genetically modified via gene-editing to enhance their therapeutic effect. Embodiments of the present invention embrace genetic editing through nucleotide insertion (RNA or DNA) into a population of TILs for both promotion of the expression of one or more proteins and inhibition of the expression of one or more proteins, as well as combinations thereof. Embodiments of the present invention also provide methods for expanding TILs into a therapeutic population, wherein the methods comprise gene-editing the TILs. There are several gene-editing technologies that may be used to genetically modify a population of TILs, which are suitable for use in accordance with the present invention.

In some embodiments, a method of genetically modifying a population of TILs includes the step of stable incorporation of genes for production of one or more proteins. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, Cur. Prot. *Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In an embodiment, a method of genetically modifying a population of TILs includes the step of stable incorporation of genes for production or inhibition (e.g., silencing) of one or more proteins. In an embodiment, a method of genetically modifying a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. Other electroporation methods known in the art, such as those described in U.S. Pat. Nos. 5,019,034; 5,128,257; 5,137,817; 5,173,158; 5,232,856; 5,273,525; 5,304,120; 5,318,514; 6,010,613 and 6,078,490, the disclosures of which are incorporated by reference herein, may be used. In an embodiment, the electroporation method is a sterile electroporation method. In an embodiment, the electroporation method is a pulsed electroporation method. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse amplitude. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse width. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to induce pore formation in the TILs, comprising the step of applying a sequence of at least three DC electrical pulses, having field strengths equal to or greater than 100 V/cm, to TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the TILs is maintained. In an embodiment, a method of genetically modifying a population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of genetically modifying a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Feigner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of genetically modifying a population of TILs includes the step of transfection using methods described in U.S. Pat. Nos. 5,766,902; 6,025,337; 6,410,517; 6,475,994; and 7,189,705; the disclosures of each of which are incorporated by reference herein.

According to an embodiment, the gene-editing process may comprise the use of a programmable nuclease that mediates the generation of a double-strand or single-strand break at one or more immune checkpoint genes. Such programmable nucleases enable precise genome editing by introducing breaks at specific genomic loci, i.e., they rely on the recognition of a specific DNA sequence within the genome to target a nuclease domain to this location and mediate the generation of a double-strand break at the target sequence. A double-strand break in the DNA subsequently recruits endogenous repair machinery to the break site to mediate genome editing by either non-homologous end-joining (NHEJ) or homology-directed repair (HDR). Thus, the repair of the break can result in the introduction of insertion/deletion mutations that disrupt (e.g., silence, repress, or enhance) the target gene product.

Major classes of nucleases that have been developed to enable site-specific genomic editing include zinc finger nucleases (ZFNs), transcription activator-like nucleases (TALENs), and CRISPR-associated nucleases (e.g., CRISPR/Cas9). These nuclease systems can be broadly classified into two categories based on their mode of DNA recognition: ZFNs and TALENs achieve specific DNA binding via protein-DNA interactions, whereas CRISPR systems, such as Cas9, are targeted to specific DNA sequences by a short RNA guide molecule that base-pairs directly with the target DNA and by protein-DNA interactions. See, e.g., Cox et al., *Nature Medicine,* 2015, Vol. 21, No. 2.

Non-limiting examples of gene-editing methods that may be used in accordance with TIL expansion methods of the present invention include CRISPR methods, TALE methods, and ZFN methods, embodiments of which are described in more detail below. According to an embodiment, a method for expanding TILs into a therapeutic population may be carried out in accordance with any embodiment of the methods described herein (e.g., process 2A) or as described in PCT/US2017/058610, PCT/US2018/012605, or PCT/US2018/012633, wherein the method further comprises gene-editing at least a portion of the TILs by one or more of a CRISPR method, a TALE method or a ZFN method, in order to generate TILs that can provide an enhanced therapeutic effect. According to an embodiment, gene-edited TILs can be evaluated for an improved therapeutic effect by comparing them to non-modified TILs in vitro, e.g., by evaluating in vitro effector function, cytokine profiles, etc. compared to unmodified TILs.

In some embodiments of the present invention, electroporation is used for delivery of a gene editing system, such as CRISPR, TALEN, and ZFN systems. In some embodiments of the present invention, the electroporation system is a flow electroporation system. An example of a suitable flow electroporation system suitable for use with some embodiments of the present invention is the commercially-available MaxCyte STX system. There are several alternative commercially-available electroporation instruments which may be suitable for use with the present invention, such as the AgilePulse system or ECM 830 available from BTX-Harvard Apparatus, Cellaxess Elektra (Cellectricon), Nucleofector (Lonza/Amaxa), GenePulser MXcell (BIORAD), iPorator-96 (Primax) or siPORTer96 (Ambion). In some embodiments of the present invention, the electroporation system forms a closed, sterile system with the remainder of the TIL expansion method. In some embodiments of the present invention, the electroporation system is a pulsed electroporation system as described herein, and forms a closed, sterile system with the remainder of the TIL expansion method.

1. CRISPR Methods

A method for expanding TILs into a therapeutic population may be carried out in accordance with any embodiment of the methods described herein (e.g., process 2A) or as described in PCT/US2017/058610, PCT/US2018/012605, or PCT/US2018/012633, wherein the method further comprises gene-editing at least a portion of the TILs by a CRISPR method (e.g., CRISPR/Cas9 or CRISPR/Cpf1). According to particular embodiments, the use of a CRISPR method during the TIL expansion process causes expression of one or more immune checkpoint genes to be silenced or reduced in at least a portion of the therapeutic population of TILs. Alternatively, the use of a CRISPR method during the TIL expansion process causes expression of one or more immune checkpoint genes to be enhanced in at least a portion of the therapeutic population of TILs.

CRISPR stands for "Clustered Regularly Interspaced Short Palindromic Repeats." A method of using a CRISPR system for gene editing is also referred to herein as a CRISPR method. CRISPR systems can be divided into two main classes, Class 1 and Class 2, which are further classified into different types and sub-types. The classification of the CRISPR systems is based on the effector Cas proteins that are capable of cleaving specific nucleic acids. In Class 1 CRISPR systems the effector module consists of a multi-protein complex, whereas Class 2 systems only use one effector protein. Class 1 CRISPR includes Types I, III, and IV and Class 2 CRISPR includes Types II, V, and VI. While any of these types of CRISPR systems may be used in accordance with the present invention, there are three types of CRISPR systems which incorporate RNAs and Cas proteins that are preferred for use in accordance with the present invention: Types I (exemplified by Cas3), II (exemplified by Cas9), and III (exemplified by Cas10). The Type II CRISPR is one of the most well-characterized systems.

CRISPR technology was adapted from the natural defense mechanisms of bacteria and archaea (the domain of single-celled microorganisms). These organisms use CRISPR-derived RNA and various Cas proteins, including Cas9, to foil attacks by viruses and other foreign bodies by chopping up and destroying the DNA of a foreign invader. A CRISPR is a specialized region of DNA with two distinct characteristics: the presence of nucleotide repeats and spacers. Repeated sequences of nucleotides are distributed throughout a CRISPR region with short segments of foreign DNA (spacers) interspersed among the repeated sequences. In the type II CRISPR/Cas system, spacers are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Target recognition by the Cas9 protein requires a "seed" sequence within the crRNA and a conserved dinucleotide-containing protospacer adjacent motif (PAM) sequence upstream of the crRNA-binding region. The CRISPR/Cas system can thereby be retargeted to cleave virtually any DNA sequence by redesigning the crRNA. Thus, according to certain embodiments, Cas9 serves as an RNA-guided DNA endonuclease that cleaves DNA upon crRNA-tracrRNA recognition. The crRNA and tracrRNA in the native system can be simplified into a single guide RNA (sgRNA) of approximately 100 nucleotides for use in genetic engineering. The sgRNA is a synthetic RNA that includes a scaffold sequence necessary for Cas-binding and a user-defined approximately 17- to 20-nucleotide spacer that defines the genomic target to be modified. Thus, a user can change the genomic target of the Cas protein by changing the target sequence present in the sgRNA. The CRISPR/Cas system is directly portable to human cells by co-delivery of plasmids expressing the Cas9 endo-nuclease and the RNA components (e.g., sgRNA). Different variants of Cas proteins may be used to reduce targeting limitations (e.g., orthologs of Cas9, such as Cpf1).

According to one embodiment, an engineered, programmable, non-naturally occurring Type II CRISPR-Cas system comprises a Cas9 protein and at least one guide RNA that targets and hybridizes to a target sequence of a DNA molecule in a TIL, wherein the DNA molecule encodes and the TIL expresses at least one immune checkpoint molecule and the Cas9 protein cleaves the DNA molecules, whereby expression of the at least one immune checkpoint molecule is altered; and, wherein the Cas9 protein and the guide RNA do not naturally occur together. According to an embodiment, the expression of two or more immune checkpoint molecules is altered. According to an embodiment, the guide RNA(s) comprise a guide sequence fused to a tracr sequence. For example, the guide RNA may comprise crRNA-tracrRNA or sgRNA. According to aspects of the present invention, the terms "guide RNA", "single guide RNA" and "synthetic guide RNA" may be used interchangeably and refer to the polynucleotide sequence comprising the guide sequence, which is the approximately 17-20 bp sequence within the guide RNA that specifies the target site.

Variants of Cas9 having improved on-target specificity compared to Cas9 may also be used in accordance with embodiments of the present invention. Such variants may be referred to as high-fidelity Cas-9s. According to an embodiment, a dual nickase approach may be utilized, wherein two nickases targeting opposite DNA strands generate a DSB within the target DNA (often referred to as a double nick or dual nickase CRISPR system). For example, this approach may involve the mutation of one of the two Cas9 nuclease domains, turning Cas9 from a nuclease into a nickase. Non-limiting examples of high-fidelity Cas9s include eSpCas9, SpCas9-HF1 and HypaCas9. Such variants may reduce or eliminate unwanted changes at non-target DNA sites. See, e.g., Slaymaker I M, et al. *Science*. 2015 Dec. 1, Kleinstiver B P, et al. *Nature*. 2016 Jan. 6, and Ran et al., *Nat Protoc.* 2013 November; 8(11):2281-2308, the disclosures of which are incorporated by reference herein.

Additionally, according to particular embodiments, Cas9 scaffolds may be used that improve gene delivery of Cas9 into cells and improve on-target specificity, such as those disclosed in U.S. Patent Application Publication No. 2016/0102324, which is incorporated by reference herein. For example, Cas9 scaffolds may include a RuvC motif as defined by (D-[I/L]-G-X-X-S-X-G-W-A) and/or a HNH motif defined by (Y-X-X-D-H-X-X-P-X-S-X-X-X-D-X-S), where X represents any one of the 20 naturally occurring amino acids and [I/L] represents isoleucine or leucine. The HNH domain is responsible for nicking one strand of the target dsDNA and the RuvC domain is involved in cleavage of the other strand of the dsDNA. Thus, each of these domains nick a strand of the target DNA within the protospacer in the immediate vicinity of PAM, resulting in blunt cleavage of the DNA. These motifs may be combined with each other to create more compact and/or more specific Cas9 scaffolds. Further, the motifs may be used to create a split Cas9 protein (i.e., a reduced or truncated form of a Cas9 protein or Cas9 variant that comprises either a RuvC domain or a HNH domain) that is divided into two separate RuvC and HNH domains, which can process the target DNA together or separately.

According to particular embodiments, a CRISPR method comprises silencing or reducing the expression of one or more immune checkpoint genes in TILs by introducing a Cas9 nuclease and a guide RNA (e.g., crRNA-tracrRNA or sgRNA) containing a sequence of approximately 17-20 nucleotides specific to a target DNA sequence of the immune checkpoint gene(s). The guide RNA may be delivered as RNA or by transforming a plasmid with the guide RNA-coding sequence under a promoter. The CRISPR/Cas enzymes introduce a double-strand break (DSB) at a specific location based on a sgRNA-defined target sequence. DSBs may be repaired in the cells by non-homologous end joining (NHEJ), a mechanism which frequently causes insertions or deletions (indels) in the DNA. Indels often lead to frame-shifts, creating loss of function alleles; for example, by causing premature stop codons within the open reading frame (ORF) of the targeted gene. According to certain embodiments, the result is a loss-of-function mutation within the targeted immune checkpoint gene.

Alternatively, DSBs induced by CRISPR/Cas enzymes may be repaired by homology-directed repair (HDR) instead of NHEJ. While NHEJ-mediated DSB repair often disrupts the open reading frame of the gene, homology directed repair (HDR) can be used to generate specific nucleotide changes ranging from a single nucleotide change to large insertions. According to an embodiment, HDR is used for gene editing immune checkpoint genes by delivering a DNA repair template containing the desired sequence into the TILs with the sgRNA(s) and Cas9 or Cas9 nickase. The repair template preferably contains the desired edit as well as additional homologous sequence immediately upstream and downstream of the target gene (often referred to as left and right homology arms).

According to particular embodiments, an enzymatically inactive version of Cas9 (deadCas9 or dCas9) may be targeted to transcription start sites in order to repress transcription by blocking initiation. Thus, targeted immune checkpoint genes may be repressed without the use of a DSB. A dCas9 molecule retains the ability to bind to target DNA based on the sgRNA targeting sequence. According to an embodiment of the present invention, a CRISPR method comprises silencing or reducing the expression of one or more immune checkpoint genes by inhibiting or preventing transcription of the targeted gene(s). For example, a CRISPR method may comprise fusing a transcriptional repressor domain, such as a Kruppel-associated box (KRAB) domain, to an enzymatically inactive version of Cas9, thereby forming, e.g., a dCas9-KRAB, that targets the immune checkpoint gene's transcription start site, leading to the inhibition or prevention of transcription of the gene. Preferably, the repressor domain is targeted to a window downstream from the transcription start site, e.g., about 500 bp downstream. This approach, which may be referred to as CRISPR interference (CRISPRi), leads to robust gene knockdown via transcriptional reduction of the target RNA.

According to particular embodiments, an enzymatically inactive version of Cas9 (deadCas9 or dCas9) may be targeted to transcription start sites in order to activate transcription. This approach may be referred to as CRISPR activation (CRISPRa). According to an embodiment, a CRISPR method comprises increasing the expression of one or more immune checkpoint genes by activating transcription of the targeted gene(s). According to such embodiments, targeted immune checkpoint genes may be activated without the use of a DSB. A CRISPR method may comprise targeting transcriptional activation domains to the transcription start site; for example, by fusing a transcriptional activator, such as VP64, to dCas9, thereby forming, e.g., a dCas9-VP64, that targets the immune checkpoint gene's transcription start site, leading to activation of transcription of the gene. Preferably, the activator domain is targeted to a window upstream from the transcription start site, e.g., about 50-400 bp downstream Additional embodiments of the present invention may utilize activation strategies that have been developed for potent activation of target genes in mammalian cells. Non-limiting examples include co-expression of epitope-tagged dCas9 and antibody-activator effector proteins (e.g., the SunTag system), dCas9 fused to a plurality of different activation domains in series (e.g., dCas9-VPR) or co-expression of dCas9-VP64 with a modified scaffold gRNA and additional RNA-binding helper activators (e.g., SAM activators).

According to other embodiments, a CRISPR-mediated genome editing method referred to as CRISPR assisted rational protein engineering (CARPE) may be used in accordance with embodiments of the present invention, as disclosed in U.S. Pat. No. 9,982,278, which is incorporated by reference herein. CARPE involves the generation of "donor" and "destination" libraries that incorporate directed mutations from single-stranded DNA (ssDNA) or double-stranded DNA (dsDNA) editing cassettes directly into the genome. Construction of the donor library involves cotransforming rationally designed editing oligonucleotides into cells with a guide RNA (gRNA) that hybridizes to a target DNA sequence. The editing oligonucleotides are designed to couple deletion or mutation of a PAM with the mutation of one or more desired codons in the adjacent gene. This enables the entire donor library to be generated in a single transformation. The donor library is retrieved by amplification of the recombinant chromosomes, such as by a PCR reaction, using a synthetic feature from the editing oligonucleotide, namely, a second PAM deletion or mutation that is simultaneously incorporated at the 3' terminus of the gene. This covalently couples the codon target mutations directed to a PAM deletion. The donor libraries are then co-transformed into cells with a destination gRNA vector to create a population of cells that express a rationally designed protein library.

According to other embodiments, methods for trackable, precision genome editing using a CRISPR-mediated system referred to as Genome Engineering by Trackable CRISPR Enriched Recombineering (GEn-TraCER) may be used in accordance with embodiments of the present invention, as disclosed in U.S. Pat. No. 9,982,278, which is incorporated by reference herein. The GEn-TraCER methods and vectors combine an editing cassette with a gene encoding gRNA on a single vector. The cassette contains a desired mutation and a PAM mutation. The vector, which may also encode Cas9, is the introduced into a cell or population of cells. This activates expression of the CRISPR system in the cell or population of cells, causing the gRNA to recruit Cas9 to the target region, where a dsDNA break occurs, allowing integration of the PAM mutation.

Non-limiting examples of genes that may be silenced or inhibited by permanently gene-editing TILs via a CRISPR method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a CRISPR method include CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

Examples of systems, methods, and compositions for altering the expression of a target gene sequence by a CRISPR method, and which may be used in accordance with embodiments of the present invention, are described in U.S. Pat. Nos. 8,697,359; 8,993,233; 8,795,965; 8,771,945; 8,889,356; 8,865,406; 8,999,641; 8,945,839; 8,932,814; 8,871,445; 8,906,616; and 8,895,308, which are incorporated by reference herein. Resources for carrying out CRISPR methods, such as plasmids for expressing CRISPR/Cas9 and CRISPR/Cpf1, are commercially available from companies such as GenScript.

In an embodiment, genetic modifications of populations of TILs, as described herein, may be performed using the CRISPR/Cpf1 system as described in U.S. Pat. No. 9,790,490, the disclosure of which is incorporated by reference herein. The CRISPR/Cpf1 system is functionally distinct from the CRISPR-Cas9 system in that Cpf1-associated CRISPR arrays are processed into mature crRNAs without the need for an additional tracrRNA. The crRNAs used in the CRISPR/Cpf1 system have a spacer or guide sequence and a direct repeat sequence. The Cpf1p-crRNA complex that is formed using this method is sufficient by itself to cleave the target DNA.

According to one embodiment, a method for expanding tumor infiltrating lymphocytes (TILS) into a therapeutic population of TILs comprises:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 and optionally comprising a 4-1BB agonist antibody for about 2 to 5 days;

(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) performing a sterile electroporation step on the second population of TILs, wherein the sterile electroporation step mediates the transfer of at least one gene editor;

(f) resting the second population of TILs for about 1 day;

(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;

(h) harvesting the therapeutic population of TILs obtained from step (g) to provide a harvested TIL population, wherein the transition from step (g) to step (h) occurs without opening the system, wherein the harvested population of TILs is a therapeutic population of TILs;

(i) transferring the harvested TIL population to an infusion bag, wherein the transfer from step (h) to (i) occurs without opening the system; and (j) cryopreserving the harvested TIL population using a dimethylsulfoxide-based cryopreservation medium, wherein the electroporation step comprises the delivery of a Clustered Regularly Interspersed Short Palindromic Repeat (CRISPR)/Cas9 or CRISPR/Cpf1 system for modulating the expression of at least one protein.

According to one embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium,
wherein the electroporation step comprises the delivery of a Clustered Regularly Interspersed Short Palindromic Repeat (CRISPR)/Cas9 or CRISPR/Cpf1 system for inhibiting the expression of PD-1 and LAG-3.

2. TALE Methods

A method for expanding TILs into a therapeutic population may be carried out in accordance with any embodiment of the methods described herein (e.g., process 2A) or as described in PCT/US2017/058610, PCT/US2018/012605, or PCT/US2018/012633, wherein the method further comprises gene-editing at least a portion of the TILs by a TALE method. According to particular embodiments, the use of a TALE method during the TIL expansion process causes expression of one or more immune checkpoint genes to be silenced or reduced in at least a portion of the therapeutic population of TILs. Alternatively, the use of a TALE method during the TIL expansion process causes expression of one or more immune checkpoint genes to be enhanced in at least a portion of the therapeutic population of TILs.

TALE stands for "Transcription Activator-Like Effector" proteins, which include TALENs ("Transcription Activator-Like Effector Nucleases"). A method of using a TALE system for gene editing may also be referred to herein as a TALE method. TALEs are naturally occurring proteins from the plant pathogenic bacteria genus *Xanthomonas*, and contain DNA-binding domains composed of a series of 33-35-amino-acid repeat domains that each recognizes a single base pair. TALE specificity is determined by two hypervariable amino acids that are known as the repeat-variable di-residues (RVDs). Modular TALE repeats are linked together to recognize contiguous DNA sequences. A specific RVD in the DNA-binding domain recognizes a base in the target locus, providing a structural feature to assemble predictable DNA-binding domains. The DNA binding domains of a TALE are fused to the catalytic domain of a type IIS FokI endonuclease to make a targetable TALE nuclease. To induce site-specific mutation, two individual TALEN arms, separated by a 14-20 base pair spacer region, bring FokI monomers in close proximity to dimerize and produce a targeted double-strand break.

Several large, systematic studies utilizing various assembly methods have indicated that TALE repeats can be combined to recognize virtually any user-defined sequence. Strategies that enable the rapid assembly of custom TALE arrays include Golden Gate molecular cloning, high-throughput solid-phase assembly, and ligation-independent cloning techniques. Custom-designed TALE arrays are also commercially available through Cellectis Bioresearch (Paris, France), Transposagen Biopharmaceuticals (Lexington, Ky., USA), and Life Technologies (Grand Island, N.Y., USA). Additionally web-based tools, such as TAL Effector-Nucleotide Target 2.0, are available that enable the design of custom TAL effector repeat arrays for desired targets and also provides predicted TAL effector binding sites. See Doyle, et al., *Nucleic Acids Research*, 2012, Vol. 40, W117-W122. Examples of TALE and TALEN methods suitable for use in the present invention are described in U.S. Patent Application Publication Nos. US 2011/0201118 A1; US 2013/0117869 A1; US 2013/0315884 A1; US 2015/0203871 A1 and US 2016/0120906 A1, the disclosures of which are incorporated by reference herein.

According to an embodiment of the present invention, a TALE method comprises silencing or reducing the expression of one or more immune checkpoint genes by inhibiting or preventing transcription of the targeted gene(s). For example, a TALE method may include utilizing KRAB-TALEs, wherein the method comprises fusing a transcriptional Kruppel-associated box (KRAB) domain to a DNA binding domain that targets the gene's transcription start site, leading to the inhibition or prevention of transcription of the gene.

According to another embodiment, a TALE method comprises silencing or reducing the expression of one or more immune checkpoint genes by introducing mutations in the targeted gene(s). For example, a TALE method may include fusing a nuclease effector domain, such as FokI, to the TALE DNA binding domain, resulting in a TALEN. FokI is active as a dimer; hence, the method comprises constructing pairs of TALENs to position the FOKL nuclease domains to adjacent genomic target sites, where they introduce DNA double strand breaks. A double strand break may be completed following correct positioning and dimerization of FokI. Once the double strand break is introduced, DNA repair can be achieved via two different mechanisms: the high-fidelity homologous recombination pair (HRR) (also known as homology-directed repair or HDR) or the error-prone non-homologous end joining (NHEJ). Repair of double strand breaks via NHEJ preferably results in DNA target site deletions, insertions or substitutions, i.e., NHEJ typically leads to the introduction of small insertions and deletions at the site of the break, often inducing frameshifts that knockout gene function. According to particular embodiments, the TALEN pairs are targeted to the most 5' exons of the genes, promoting early frame shift mutations or premature stop codons. The genetic mutation(s) introduced by TALEN are preferably permanent. Thus, according to one embodiment, the method comprises silencing or reducing expression of an immune checkpoint gene by utilizing dimerized TALENs to induce a site-specific double strand break that is repaired via error-prone NHEJ, leading to one or more mutations in the targeted immune checkpoint gene.

According to additional embodiments, TALENs are utilized to introduce genetic alterations via HRR, such as non-random point mutations, targeted deletion, or addition of DNA fragments. The introduction of DNA double strand breaks enables gene editing via homologous recombination in the presence of suitable donor DNA. According to an embodiment, the method comprises co-delivering dimerized TALENs and a donor plasmid bearing locus-specific homology arms to induce a site-specific double strand break and integrate one or more transgenes into the DNA.

According to another embodiment, a TALEN that is a hybrid protein derived from FokI and AvrXa7, as disclosed in U.S. Patent Publication No. 2011/0201118, may be used in accordance with embodiments of the present invention. This TALEN retains recognition specificity for target nucleotides of AvrXa7 and the double-stranded DNA cleaving activity of FokI. The same methods can be used to prepare other TALEN having different recognition specificity. For example, compact TALENs may be generated by engineering a core TALE scaffold having different sets of RVDs to change the DNA binding specificity and target a specific single dsDNA target sequence. See U.S. Patent Publication No. 2013/0117869. A selection of catalytic domains can be attached to the scaffold to effect DNA processing, which may be engineered to ensure that the catalytic domain is capable of processing DNA near the single dsDNA target sequence when fused to the core TALE scaffold. A peptide linker may also be engineered to fuse the catalytic domain to the scaffold to create a compact TALEN made of a single polypeptide chain that does not require dimerization to target a specific single dsDNA sequence. A core TALE scaffold may also be modified by fusing a catalytic domain, which may be a TAL monomer, to its N-terminus, allowing for the possibility that this catalytic domain might interact with another catalytic domain fused to another TAL monomer, thereby creating a catalytic entity likely to process DNA in the proximity of the target sequences. See U.S. Patent Publication No. 2015/0203871. This architecture allows only one DNA strand to be targeted, which is not an option for classical TALEN architectures.

According to an embodiment of the present invention, conventional RVDs may be used create TALENs that are capable of significantly reducing gene expression. In an embodiment, four RVDs, NI, HD, NN, and NG, are used to target adenine, cytosine, guanine, and thymine, respectively. These conventional RVDs can be used to, for instance, create TALENs targeting the PD-1 gene. Examples of TALENs using conventional RVDs include the T3v1 and T1 TALENs disclosed in Gautron et al., *Molecular Therapy: Nucleic Acids* December 2017, Vol. 9:312-321 (Gautron), which is incorporated by reference herein. The T3v1 and T1 TALENs target the second exon of the PDCD1 locus where the PD-LI binding site is located and are able to considerably reduce PD-1 production. In an embodiment, the T1 TALEN does so by using target SEQ ID NO:127 and the T3v1 TALEN does so by using target SEQ ID NO:128.

According to another embodiment, TALENs are modified using non-conventional RVDs to improve their activity and specificity for a target gene, such as disclosed in Gautron. Naturally occurring RVDs only cover a small fraction of the potential diversity repertoire for the hypervariable amino acid locations. Non-conventional RVDs provide an alternative to natural RVDs and have novel intrinsic targeting specificity features that can be used to exclude the targeting of off-site targets (sequences within the genome that contain a few mismatches relative to the targeted sequence) by TALEN. Non-conventional RVDs may be identified by generating and screening collections of TALEN containing alternative combinations of amino acids at the two hypervariable amino acid locations at defined positions of an array as disclosed in Juillerat, et al., Scientific Reports 5, Article Number 8150 (2015), which is incorporated by reference herein. Next, non-conventional RVDs may be selected that discriminate between the nucleotides present at the position of mismatches, which can prevent TALEN activity at off-site sequences while still allowing appropriate processing of the target location. The selected non-conventional RVDs may then be used to replace the conventional RVDs in a TALEN. Examples of TALENs where conventional RVDs have been replaced by non-conventional RVDs include the T3v2 and T3v3 PD-1 TALENs produced by Gautron. These TALENs had increased specificity when compared to TALENs using conventional RVDs.

According to additional embodiments, TALEN may be utilized to introduce genetic alterations to silence or reduce the expression of two genes. For instance, two separate TALEN may be generated to target two different genes and then used together. The molecular events generated by the two TALEN at their respective loci and potential off-target sites may be characterized by high-throughput DNA sequencing. This enables the analysis of off-target sites and identification of the sites that might result from the use of both TALEN. Based on this information, appropriate conventional and non-conventional RVDs may be selected to engineer TALEN that have increased specificity and activity even when used together. For example, Gautron discloses the combined use of T3v4 PD-1 and TRAC TALEN to produce double knockout CAR T cells, which maintained a potent in vitro anti-tumor function.

In an embodiment, the method of Gautron or other methods described herein may be employed to genetically-edit TILs, which may then be expanded by any of the procedures described herein. In an embodiment, a method for expanding tumor infiltrating lymphocytes (TILs) into a therapeutic population of TILs comprises the steps of:

(a) activating a first population of TILs obtained from a tumor resected from a patient using CD3 and CD28 activating beads or antibodies for 1 to 5 days;

(b) gene-editing at least a portion of the first population of TILs using electroporation of transcription activator-like effector nucleases to obtain a second population of TILs;

(c) optionally incubating the second population of TILs;

(d) performing a first expansion by culturing the second population of TILs in a cell culture medium comprising IL-2, and optionally OKT-3, to produce a third population of TILs, wherein the first expansion is performed in a closed container providing a first gas-permeable surface area, wherein the first expansion is performed for about 3 to 14 days to obtain the third population of TILs;

(e) performing a second expansion by supplementing the cell culture medium of the third population of TILs with additional IL-2, OKT-3, and antigen presenting cells (APCs), to produce a fourth population of TILs, wherein the second expansion is performed for about 7 to 14 days to obtain the fourth population of TILs, wherein the fourth population of TILs is a therapeutic population of TILs;

(f) harvesting the therapeutic population of TILs obtained from step (e);

(g) transferring the harvested TIL population from step (e) to an infusion bag, wherein the transfer from step (e) to (0 occurs without opening the system; and (h) wherein one or more of steps (a) to (g) are performed in a closed, sterile system.

In an embodiment, a method for expanding tumor infiltrating lymphocytes (TILs) into a therapeutic population of TILs comprises the steps of:

(a) activating a first population of TILs obtained from a tumor resected from a patient using CD3 and CD28 activating beads or antibodies for 1 to 5 days;

(b) gene-editing at least a portion of the first population of TILs using electroporation of transcription activator-like effector nucleases in cytoporation medium to obtain a second population of TILs;

(c) optionally incubating the second population of TILs;

(d) performing a first expansion by culturing the second population of TILs in a cell culture medium comprising IL-2, and optionally OKT-3, to produce a third population of TILs, wherein the first expansion is performed in a closed container providing a first gas-permeable surface area, wherein the first expansion is performed for about 6 to 9 days to obtain the third population of TILs;

(e) performing a second expansion by supplementing the cell culture medium of the third population of TILs with additional IL-2, OKT-3, and antigen presenting cells (APCs), to produce a fourth population of TILs, wherein the second expansion is performed for about 9 to 11 days to obtain the fourth population of TILs, wherein the fourth population of TILs is a therapeutic population of TILs;

(f) harvesting the therapeutic population of TILs obtained from step (e);

(g) transferring the harvested TIL population from step (e) to an infusion bag, wherein the transfer from step (e) to (f) occurs without opening the system; and (h) wherein one or more of steps (a) to (g) are performed in a closed, sterile system.

In an embodiment, a method for expanding tumor infiltrating lymphocytes (TILs) into a therapeutic population of TILs comprises the steps of:

(a) activating a first population of TILs obtained from a tumor resected from a patient using CD3 and CD28 activating beads or antibodies for 1 to 5 days;

(b) gene-editing at least a portion of the first population of TILs using electroporation of transcription activator-like effector nucleases in cytoporation medium to obtain a second population of TILs;

(c) optionally incubating the second population of TILs, wherein the incubation is performed at about 30-40° C. with about 5% $CO_2$;

(d) performing a first expansion by culturing the second population of TILs in a cell culture medium comprising IL-2, and optionally OKT-3, to produce a third population of TILs, wherein the first expansion is performed in a closed container providing a first gas-permeable surface area, wherein the first expansion is performed for about 6 to 9 days to obtain the third population of TILs;

(e) performing a second expansion by supplementing the cell culture medium of the third population of TILs with additional IL-2, OKT-3, and antigen presenting cells (APCs), to produce a fourth population of TILs, wherein the second expansion is performed for about 9 to 11 days to obtain the fourth population of TILs, wherein the fourth population of TILs is a therapeutic population of TILs;

(f) harvesting the therapeutic population of TILs obtained from step (e);

(g) transferring the harvested TIL population from step (e) to an infusion bag, wherein the transfer from step (e) to (f) occurs without opening the system; and (h) wherein one or more of steps (a) to (g) are performed in a closed, sterile system.

According to another embodiment, TALENs may be specifically designed, which allows higher rates of DSB events within the target cell(s) that are able to target a specific selection of genes. See U.S. Patent Publication No. 2013/0315884. The use of such rare cutting endonucleases increases the chances of obtaining double inactivation of target genes in transfected cells, allowing for the production of engineered cells, such as T-cells. Further, additional catalytic domains can be introduced with the TALEN to increase mutagenesis and enhance target gene inactivation. The TALENs described in U.S. Patent Publication No. 2013/0315884 were successfully used to engineer T-cells to make them suitable for immunotherapy. TALENs may also be used to inactivate various immune checkpoint genes in T-cells, including the inactivation of at least two genes in a single T-cell. See U.S. Patent Publication No. 2016/0120906. Additionally, TALENs may be used to inactivate genes encoding targets for immunosuppressive agents and T-cell receptors, as disclosed in U.S. Patent Publication No. 2018/0021379, which is incorporated by reference herein. Further, TALENs may be used to inhibit the expression of beta 2-microglobulin (B2M) and/or class II major histocompatibility complex transactivator (CIITA), as disclosed in U.S. Patent Publication No. 2019/0010514, which is incorporated by reference herein.

Non-limiting examples of genes that may be silenced or inhibited by permanently gene-editing TILs via a TALE method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of TALE-nucleases targeting the PD-1 gene are provided in the following table. In these examples, the targeted genomic sequences contain two 17-base pair (bp) long sequences (referred to as half targets, shown in upper case letters) separated by a 15-bp spacer (shown in lower case letters). Each half target is recognized by repeats of half TALE-nucleases listed in the table. Thus, according to particular embodiments, TALE-nucleases according to the invention recognize and cleave the target sequence selected from the group consisting of: SEQ ID NO: 127 and SEQ ID NO: 128. TALEN sequences and gene-editing methods are also described in Gautron, discussed above.

| No. | Target PD-1 Sequence | Repeat Sequence | Half-TALE nuclease |
|---|---|---|---|
| 1 | TTCTCCCCAGCCCTGCT cgtggtgaccgaagg GGACAACGCCACCTTCA (SEQ ID NO: 127) | Repeat PD-1-left (SEQ ID NO: 129) Repeat PD-1-right (SEQ ID NO: 130) | PD-1-left TALEN (SEQ ID NO: 133) PD-1-right TALEN (SEQ ID NO: 134) |
| 2 | TACCTCTGTGGGGCCAT ctccctggcccccaa GGCGCAGATCAAAGAGA (SEQ ID NO: 128) | Repeat PD-1-left (SEQ ID NO: 131) Repeat PD-1-right (SEQ ID NO: 132) | PD-1-left TALEN (SEQ ID NO: 135) PD-1-right TALEN (SEQ ID NO: 136) |

In an embodiment, a method for expanding tumor infiltrating lymphocytes (TILs) into a therapeutic population of TILs comprises the steps of:
  (a) activating a first population of TILs obtained from a tumor resected from a patient using CD3 and CD28 activating beads or antibodies for 1 to 5 days;
  (b) gene-editing at least a portion of the first population of TILs using electroporation of transcription activator-like effector nucleases targeting PDCD1 in cytoporation medium to obtain a second population of TILs;
  (c) optionally incubating the second population of TILs, wherein the incubation is performed at about 30-40° C. with about 5% $CO_2$;
  (d) performing a first expansion by culturing the second population of TILs in a cell culture medium comprising IL-2, and optionally OKT-3, to produce a third population of TILs, wherein the first expansion is performed in a closed container providing a first gas-permeable surface area, wherein the first expansion is performed for about 6 to 9 days to obtain the third population of TILs;
  (e) performing a second expansion by supplementing the cell culture medium of the third population of TILs with additional IL-2, OKT-3, and antigen presenting cells (APCs), to produce a fourth population of TILs, wherein the second expansion is performed for about 9 to 11 days to obtain the fourth population of TILs, wherein the fourth population of TILs is a therapeutic population of TILs;
  (f) harvesting the therapeutic population of TILs obtained from step (e);
  (g) transferring the harvested TIL population from step (e) to an infusion bag, wherein the transfer from step (e) to (f) occurs without opening the system; and
  (h) wherein one or more of steps (a) to (g) are performed in a closed, sterile system.

In an embodiment, a method for expanding tumor infiltrating lymphocytes (TILs) into a therapeutic population of TILs comprises the steps of:
  (a) activating a first population of TILs obtained from a tumor resected from a patient using CD3 and CD28 activating beads or antibodies for 1 to 5 days;
  (b) gene-editing at least a portion of the first population of TILs using electroporation of transcription activator-like effector nucleases targeting SEQ ID NO:128 in cytoporation medium to obtain a second population of TILs;
  (c) optionally incubating the second population of TILs, wherein the incubation is performed at about 30-40° C. with about 5% $CO_2$;
  (d) performing a first expansion by culturing the second population of TILs in a cell culture medium comprising IL-2, and optionally OKT-3, to produce a third population of TILs, wherein the first expansion is performed in a closed container providing a first gas-permeable surface area, wherein the first expansion is performed for about 6 to 9 days to obtain the third population of TILs;
  (e) performing a second expansion by supplementing the cell culture medium of the third population of TILs with additional IL-2, OKT-3, and antigen presenting cells (APCs), to produce a fourth population of TILs, wherein the second expansion is performed for about 9 to 11 days to obtain the fourth population of TILs, wherein the fourth population of TILs is a therapeutic population of TILs;
  (f) harvesting the therapeutic population of TILs obtained from step (e);
  (g) transferring the harvested TIL population from step (e) to an infusion bag, wherein the transfer from step (e) to (f) occurs without opening the system; and
  (h) wherein one or more of steps (a) to (g) are performed in a closed, sterile system.

In an embodiment, a method for expanding tumor infiltrating lymphocytes (TILs) into a therapeutic population of TILs comprises the steps of:
  (a) activating a first population of TILs obtained from a tumor resected from a patient using CD3 and CD28 activating beads or antibodies for 1 to 5 days;
  (b) gene-editing at least a portion of the first population of TILs using electroporation of transcription activator-like effector nuclease mRNA according to SEQ ID NO:135 and SEQ ID NO:136 in cytoporation medium to obtain a second population of TILs;
  (c) optionally incubating the second population of TILs, wherein the incubation is performed at about 30-40° C. with about 5% $CO_2$;
  (d) performing a first expansion by culturing the second population of TILs in a cell culture medium comprising IL-2, and optionally OKT-3, to produce a third population of TILs, wherein the first expansion is performed in a closed container providing a first gas-permeable surface area, wherein the first expansion is performed for about 6 to 9 days to obtain the third population of TILs;
  (e) performing a second expansion by supplementing the cell culture medium of the third population of TILs with additional IL-2, OKT-3, and antigen presenting cells (APCs), to produce a fourth population of TILs, wherein the second expansion is performed for about 9 to 11 days to obtain the fourth population of TILs, wherein the fourth population of TILs is a therapeutic population of TILs;
  (f) harvesting the therapeutic population of TILs obtained from step (e);
  (g) transferring the harvested TIL population from step (e) to an infusion bag, wherein the transfer from step (e) to (f) occurs without opening the system; and (h) wherein one or more of steps (a) to (g) are performed in a closed, sterile system.

Other non-limiting examples of genes that may be enhanced by permanently gene-editing TILs via a TALE method include CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

Examples of systems, methods, and compositions for altering the expression of a target gene sequence by a TALE method, and which may be used in accordance with embodiments of the present invention, are described in U.S. Pat. No. 8,586,526, which is incorporated by reference herein. These disclosed examples include the use of a non-naturally occurring DNA-binding polypeptide that has two or more TALE-repeat units containing a repeat RVD, an N-cap polypeptide made of residues of a TALE protein, and a C-cap polypeptide made of a fragment of a full length C-terminus region of a TALE protein.

Examples of TALEN designs and design strategies, activity assessments, screening strategies, and methods that can be used to efficiently perform TALEN-mediated gene integration and inactivation, and which may be used in accordance with embodiments of the present invention, are described in Valton, et al., *Methods*, 2014, 69, 151-170, which is incorporated by reference herein.

According to one embodiment, a method for expanding tumor infiltrating lymphocytes (TILs) into a therapeutic population of TILs comprises:

(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium, wherein the electroporation step comprises the delivery of a TALE nuclease system for modulating the expression of at least one protein.

According to one embodiment, a method for expanding tumor infiltrating lymphocytes (TILs) into a therapeutic population of TILs comprises:

(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (1) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium, wherein the electroporation step comprises the delivery of a TALE nuclease system for suppressing the expression of PD-1 and LAG-3.

3. Zinc Finger Methods

A method for expanding TILs into a therapeutic population may be carried out in accordance with any embodiment of the methods described herein (e.g., process 2A) or as described in PCT/US2017/058610, PCT/US2018/012605, or PCT/US2018/012633, wherein the method further comprises gene-editing at least a portion of the TILs by a zinc finger or zinc finger nuclease method. According to particular embodiments, the use of a zinc finger method during the TIL expansion process causes expression of one or more immune checkpoint genes to be silenced or reduced in at least a portion of the therapeutic population of TILs. Alternatively, the use of a zinc finger method during the TIL expansion process causes expression of one or more immune checkpoint genes to be enhanced in at least a portion of the therapeutic population of TILs.

An individual zinc finger contains approximately 30 amino acids in a conserved ββα configuration. Several amino acids on the surface of the α-helix typically contact 3 bp in the major groove of DNA, with varying levels of selectivity. Zinc fingers have two protein domains. The first domain is the DNA binding domain, which includes eukaryotic transcription factors and contain the zinc finger. The second domain is the nuclease domain, which includes the FokI restriction enzyme and is responsible for the catalytic cleavage of DNA.

The DNA-binding domains of individual ZFNs typically contain between three and six individual zinc finger repeats and can each recognize between 9 and 18 base pairs. If the zinc finger domains are specific for their intended target site then even a pair of 3-finger ZFNs that recognize a total of 18 base pairs can, in theory, target a single locus in a mammalian genome. One method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Alternatively, selection-based approaches, such as oligomerized pool engineering (OPEN) can be used to select for new zinc-finger arrays from randomized libraries that take into consideration context-dependent interactions between neighboring fingers. Engineered zinc fingers are available commercially; Sangamo Biosciences (Richmond, Calif., USA) has developed a propriety platform (CompoZr®) for zinc-finger construction in partnership with Sigma-Aldrich (St. Louis, Mo., USA).

Non-limiting examples of genes that may be silenced or inhibited by permanently gene-editing TILs via a zinc finger method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a zinc finger method include CCR2, CCR4, CCR5, CXCR2, CXCR3, CX3CR1, IL-2, IL-4, IL-7, IL-10, IL-15, IL-21, the NOTCH 1/2 intracellular domain (ICD), and/or the NOTCH ligand mDLL1.

Examples of systems, methods, and compositions for altering the expression of a target gene sequence by a zinc finger method, which may be used in accordance with embodiments of the present invention, are described in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, which are incorporated by reference herein.

Other examples of systems, methods, and compositions for altering the expression of a target gene sequence by a zinc finger method, which may be used in accordance with embodiments of the present invention, are described in Beane, et al., *Mol. Therapy*, 2015, 23 1380-1390, the disclosure of which is incorporated by reference herein.

According to one embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;
(e) performing a sterile electroporation step on the second population of TILs, wherein the sterile electroporation step mediates the transfer of at least one gene editor;
(f) resting the second population of TILs for about 1 day;
(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;
(h) harvesting the therapeutic population of TILs obtained from step (g) to provide a harvested TIL population, wherein the transition from step (g) to step (h) occurs without opening the system, wherein the harvested population of TILs is a therapeutic population of TILs;
(i) transferring the harvested TIL population to an infusion bag, wherein the transfer from step (h) to (i) occurs without opening the system; and
(j) cryopreserving the harvested TIL population using a dimethylsulfoxide-based cryopreservation medium,
wherein the electroporation step comprises the delivery of a zinc finger nuclease system for modulating the expression of at least one protein.

According to one embodiment, a method for expanding tumor infiltrating lymphocytes (TILs) into a therapeutic population of TILs comprises:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally comprising a 4-1BB agonist antibody for about 2 to 5 days;
(d) adding OKT-3, to produce a second population of TILs, wherein the first expansion is performed in a closed container providing a first gas-permeable surface area, wherein the first expansion is performed for about 1 to 3 days to obtain the second population of TILs, wherein the second population of TILs is at least 50-fold greater in number than the first population of TILs, and wherein the transition from step (c) to step (d) occurs without opening the system;

(e) performing a sterile electroporation step on the second population of TILs, wherein the sterile electroporation step mediates the transfer of at least one gene editor;

(f) resting the second population of TILs for about 1 day;

(g) performing a second expansion by supplementing the cell culture medium of the second population of TILs with additional IL-2, optionally OKT-3 antibody, optionally an OX40 antibody, and antigen presenting cells (APCs), to produce a third population of TILs, wherein the second expansion is performed for about 7 to 11 days to obtain the third population of TILs, wherein the second expansion is performed in a closed container providing a second gas-permeable surface area, and wherein the transition from step (f) to step (g) occurs without opening the system;

(h) harvesting the therapeutic population of TILs obtained from step (g) to provide a harvested TIL population, wherein the transition from step (g) to step (h) occurs without opening the system, wherein the harvested population of TILs is a therapeutic population of TILs;

(i) transferring the harvested TIL population to an infusion bag, wherein the transfer from step (h) to (i) occurs without opening the system; and (j) cryopreserving the harvested TIL population using a dimethylsulfoxide-based cryopreservation medium, wherein the electroporation step comprises the delivery of a zinc finger nuclease system for suppressing the expression of PD-1 and LAG-3.

IV. TIL Manufacturing Processes

Figure 3:
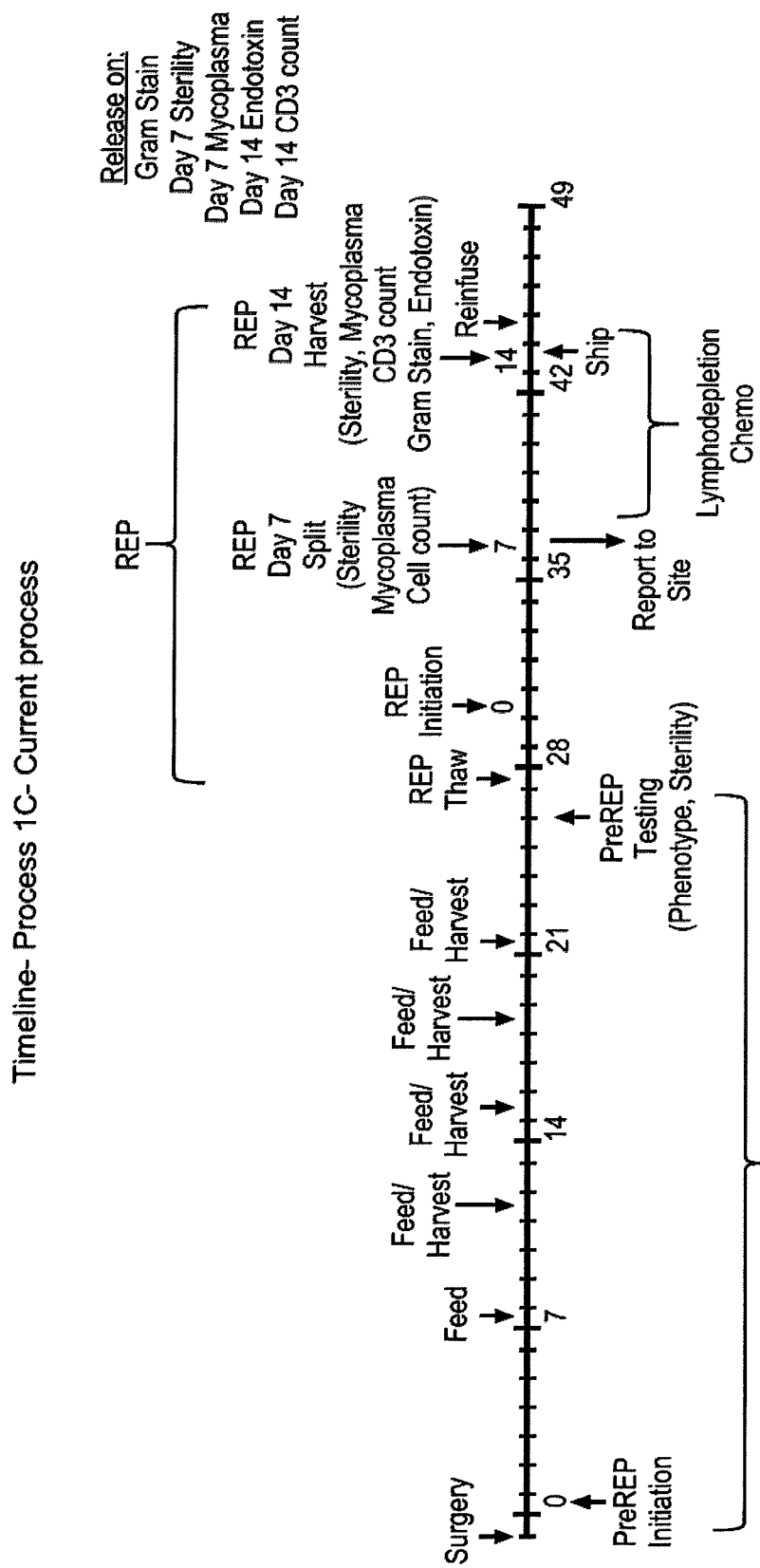
FIG. 3: Shows the IC process timeline.
Figure 4:
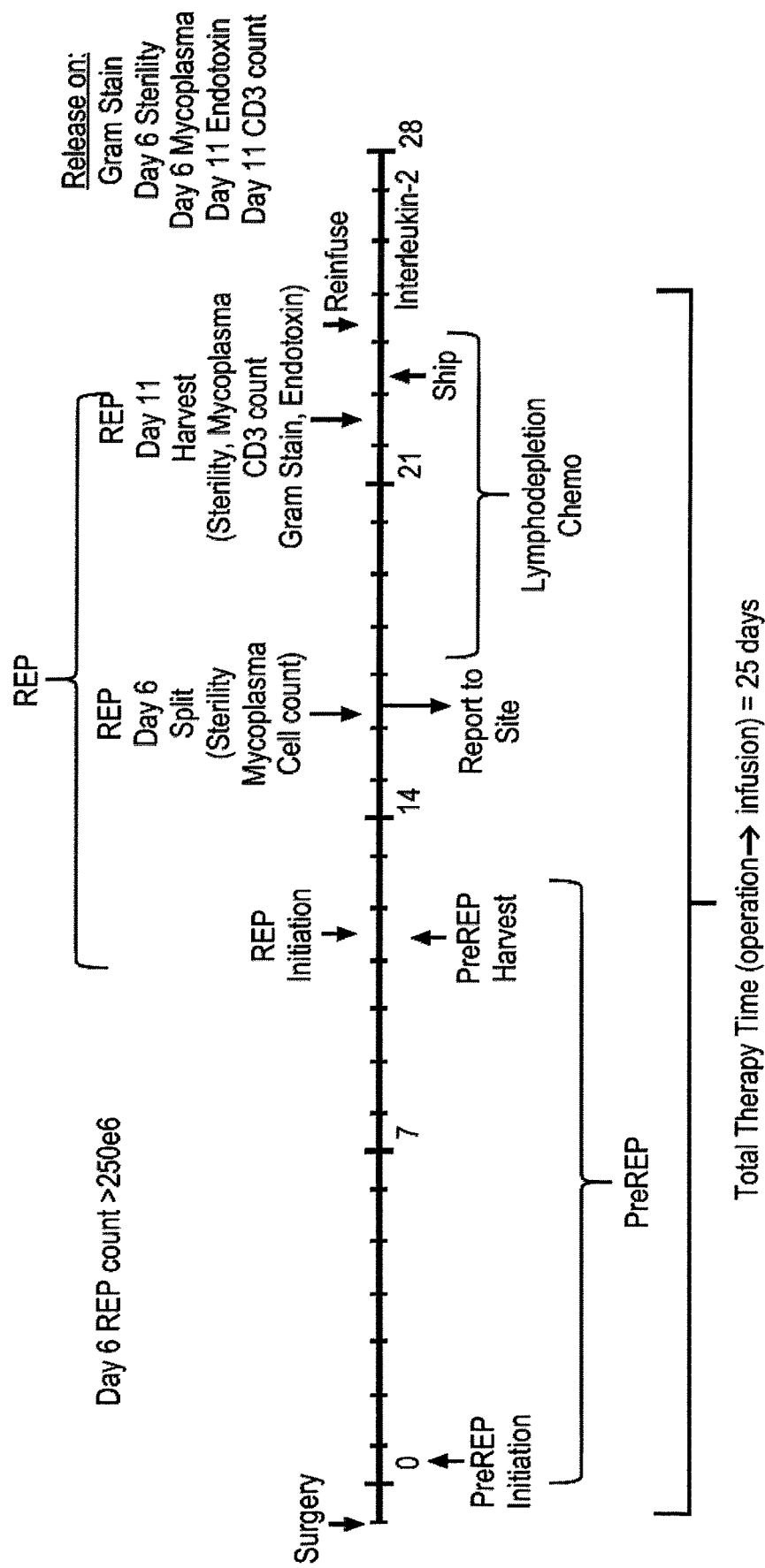
FIG. 4: Shows the process of an embodiment of TIL therapy using process 2A for TIL manufacturing, including administration and co-therapy steps, for higher cell counts.

An exemplary TIL process known as process 2A containing some of these features is depicted in FIG. 1, and some of the advantages of this embodiment of the present invention over process 1C are described in FIG. 2, as does FIG. 14. Process 1C is shown for comparison in FIG. 3. Two alternative timelines for TIL therapy based on process 2A are shown in FIG. 4 (higher cell counts) and FIG. 5 (lower cell counts). An embodiment of process 2A is shown in FIG. 6 as well as FIG. 9. FIGS. 13 and 14 further provides an exemplary 2A process compared to an exemplary 1C process.

As discussed herein, the present invention can include a step relating to the restimulation of cryopreserved TILs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 9 as Step A) is shortened to 3 to 14 days and the second expansion (including processes shown in FIG. 9 as Step B) is shorted to 7 to 14 days, as discussed in detail below as well as in the examples and figures. In some embodiments, the first expansion (for example, an expansion described as Step B in FIG. 9) is shortened to 11 days and the second expansion (for example, an expansion as described in Step D in FIG. 9) is shortened to 11 days, as discussed in the Examples and shown in FIGS. 4, 5 and 27. In some embodiments, the combination of the first expansion and second expansion (for example, expansions described as Step B and Step D in FIG. 9) is shortened to 22 days, as discussed in detail below and in the examples and figures.

The "Step" Designations A, B, C, etc., below are in reference to FIG. 9 and in reference to certain embodiments described herein. The ordering of the Steps below and in FIG. 9 is exemplary and any combination or order of steps, as well as additional steps, repetition of steps, and/or omission of steps is contemplated by the present application and the methods disclosed herein.

A. STEP A: Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, useful TILs are obtained from malignant melanoma tumors, as these have been reported to have particularly high levels of TILs.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer (including, for example, head and neck squamous cell carcinoma (HNSCC)) glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

Once obtained, the tumor sample is generally fragmented using sharp dissection into small pieces of between 1 to about 8 mm$^3$, with from about 2-3 mm$^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicin, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

Figure 9:
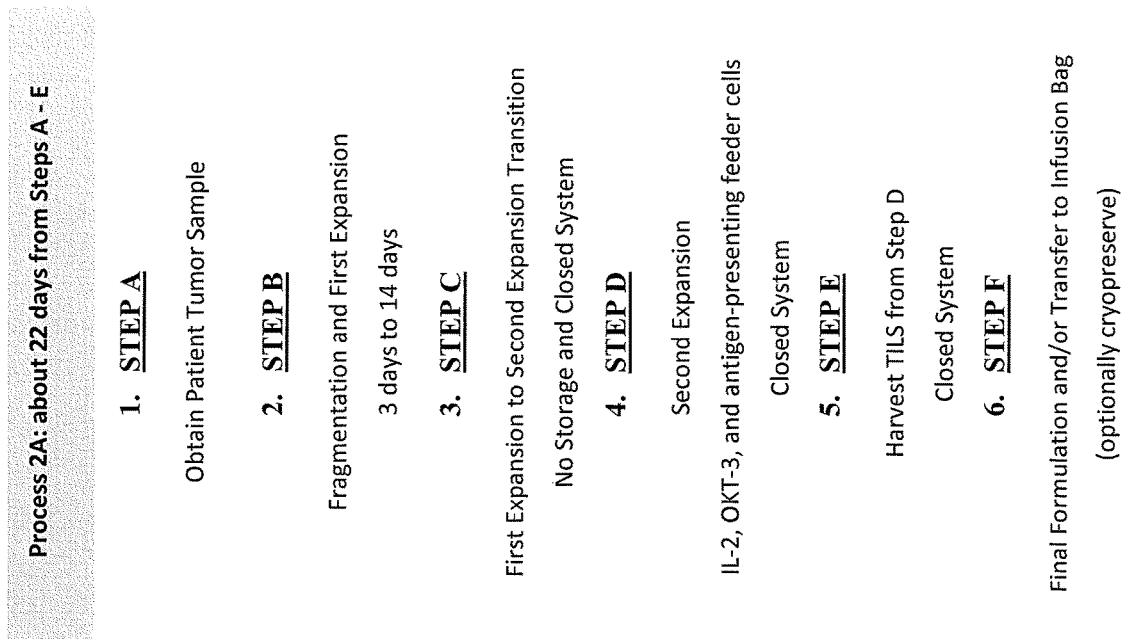
FIG. 9: Exemplary Process 2A chart providing an overview of Steps A through F.
Figure 10:
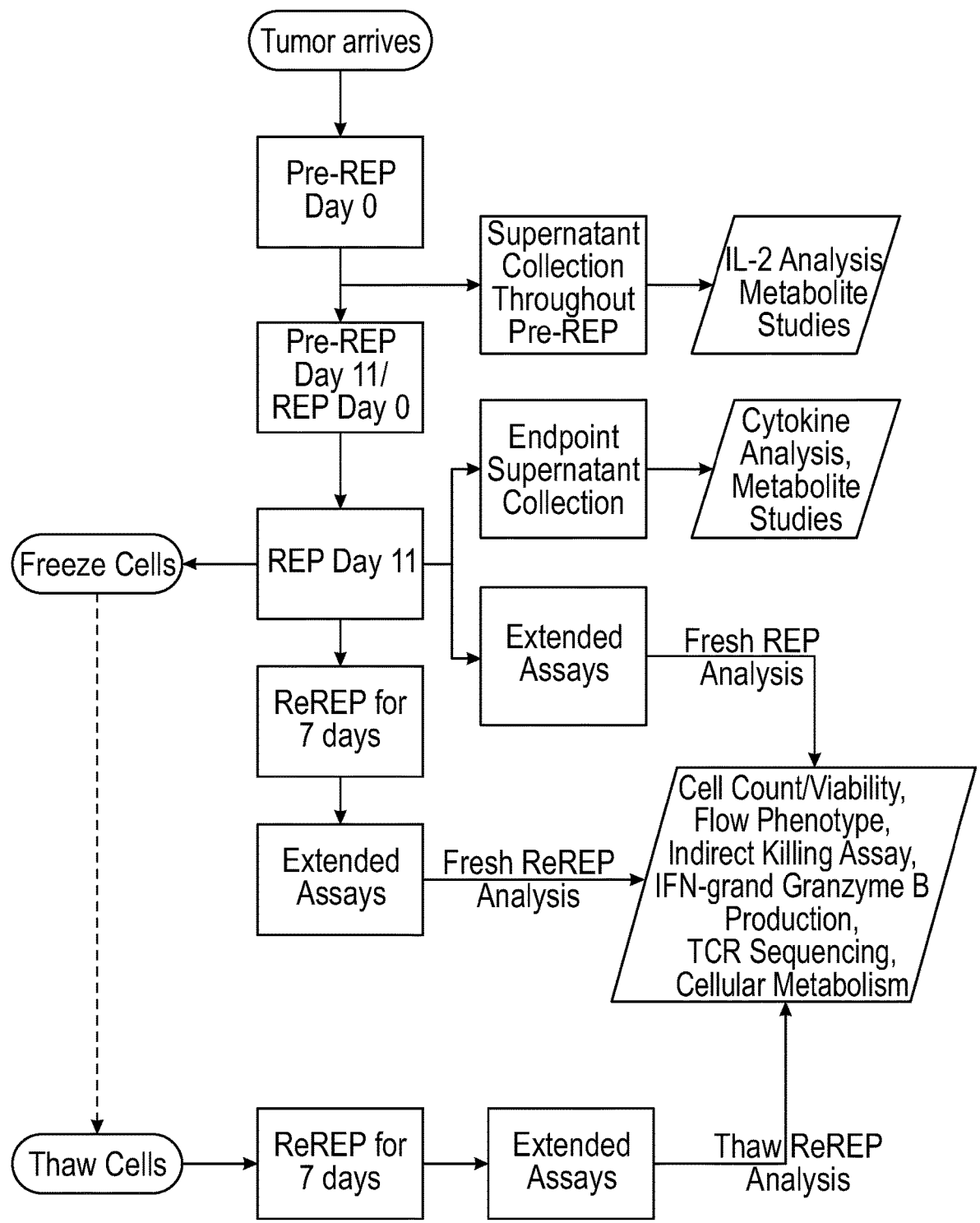
FIG. 10: Process Flow Chart on Process 2A Data Collection Plan
Figure 11:
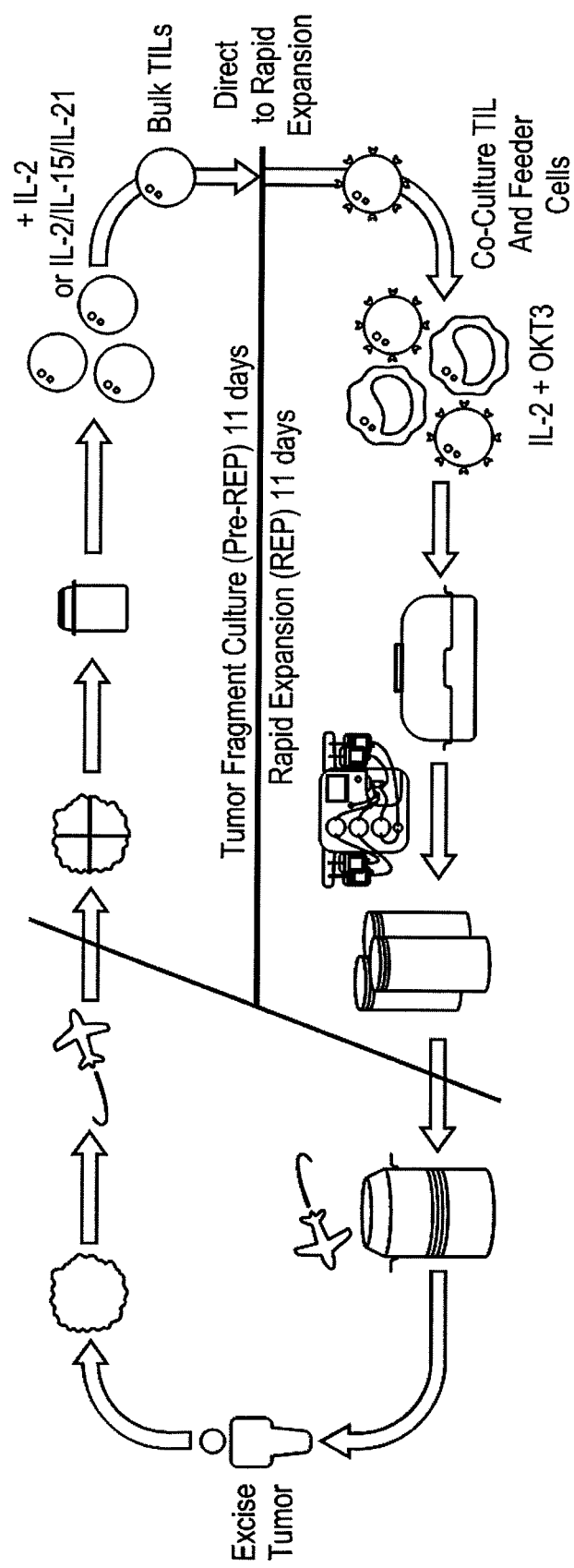
FIG. 11: Scheme of on exemplary embodiment of the Rapid Expansion Protocol (REP). Upon arrival the tumor is fragmented, placed into G-Rex flasks with IL-2 for TIL expansion (pre-REP expansion), for 11 days. For the triple cocktail studies, IL-2/IL-15/IL-21 is added at the initiation of the pre-REP. For the Rapid Expansion Protocol (REP), TIL are cultured with feeders and OKT3 for REP expansion for an additional 11 days.
Figure 12:
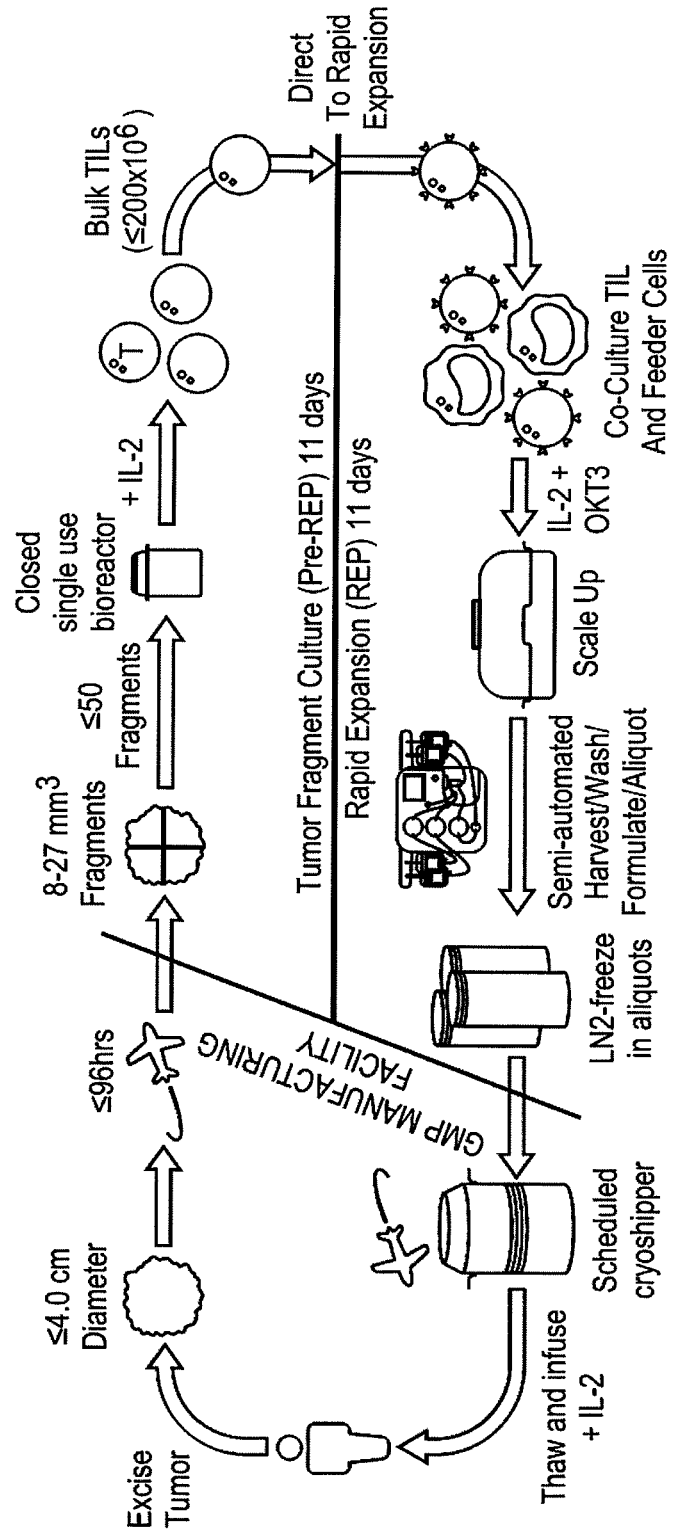
FIG. 12: Shows a diagram of an embodiment of process 2A, a 22-day process for TIL manufacturing.
Figure 15:
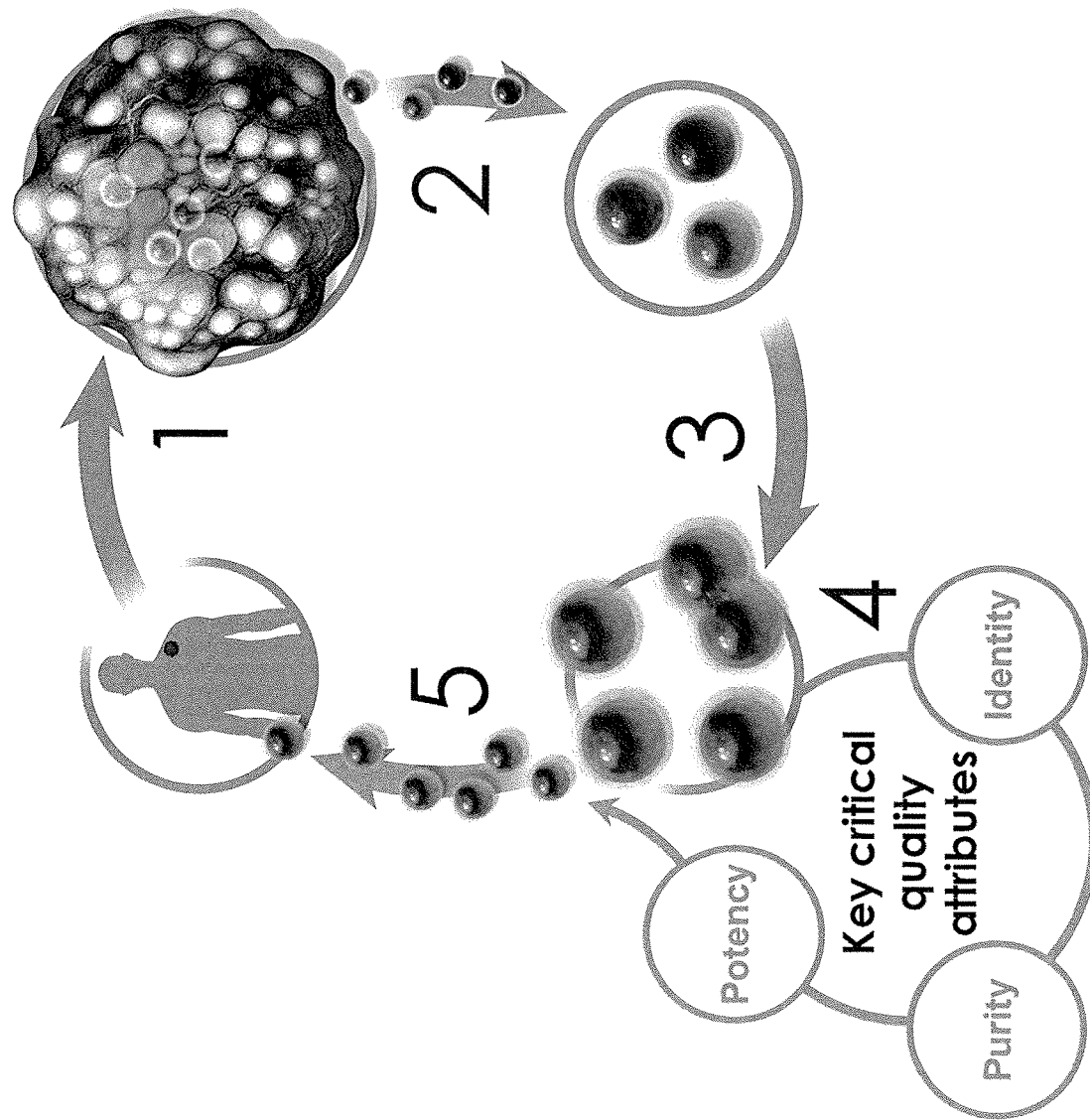
FIG. 15: Detailed scheme of an embodiment of a TIL therapy process.
Figure 16:
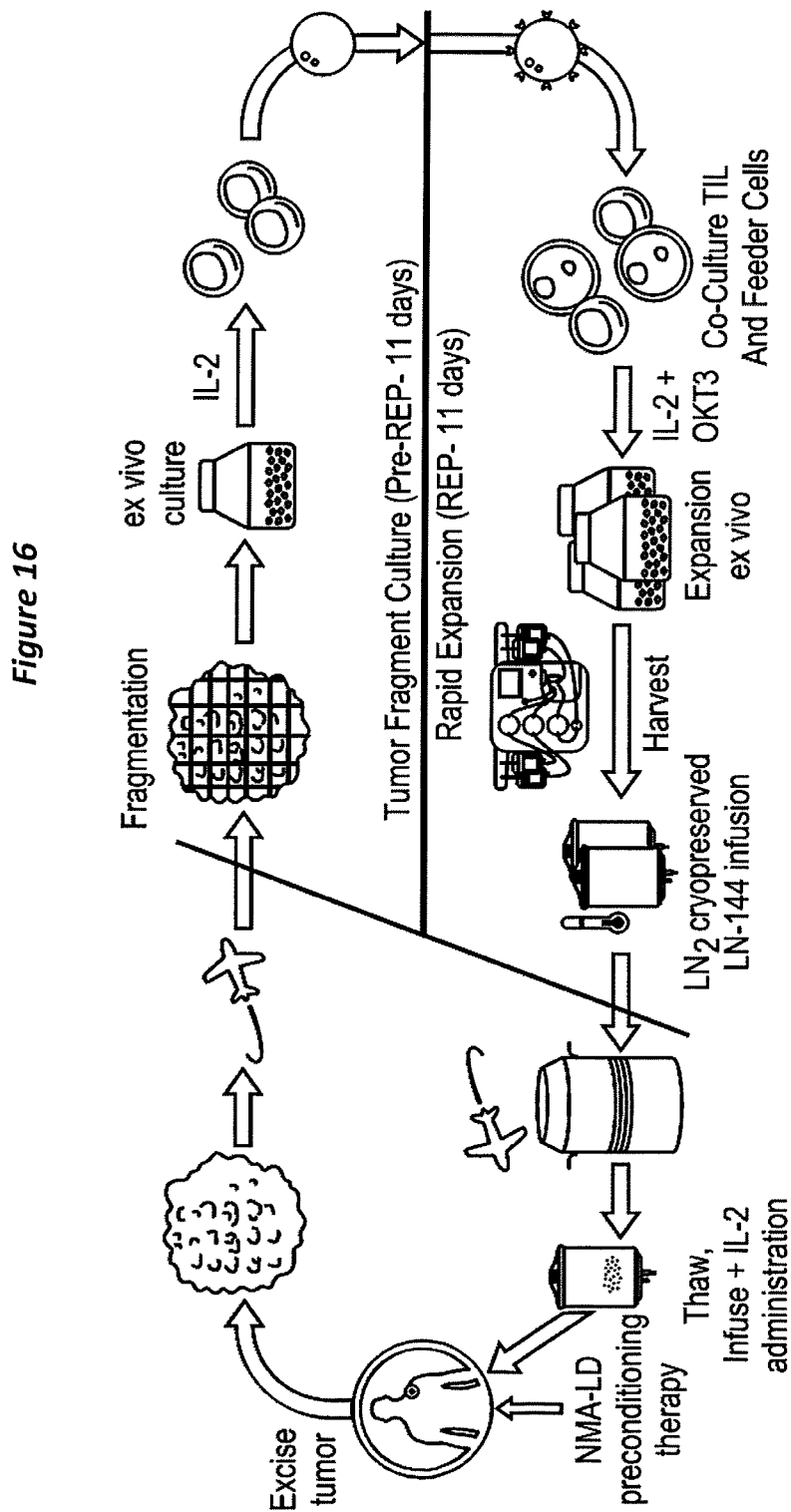
FIG. 16: Depiction of an embodiment of a cryopreserved TIL manufacturing process (22 days).
Figure 19A:
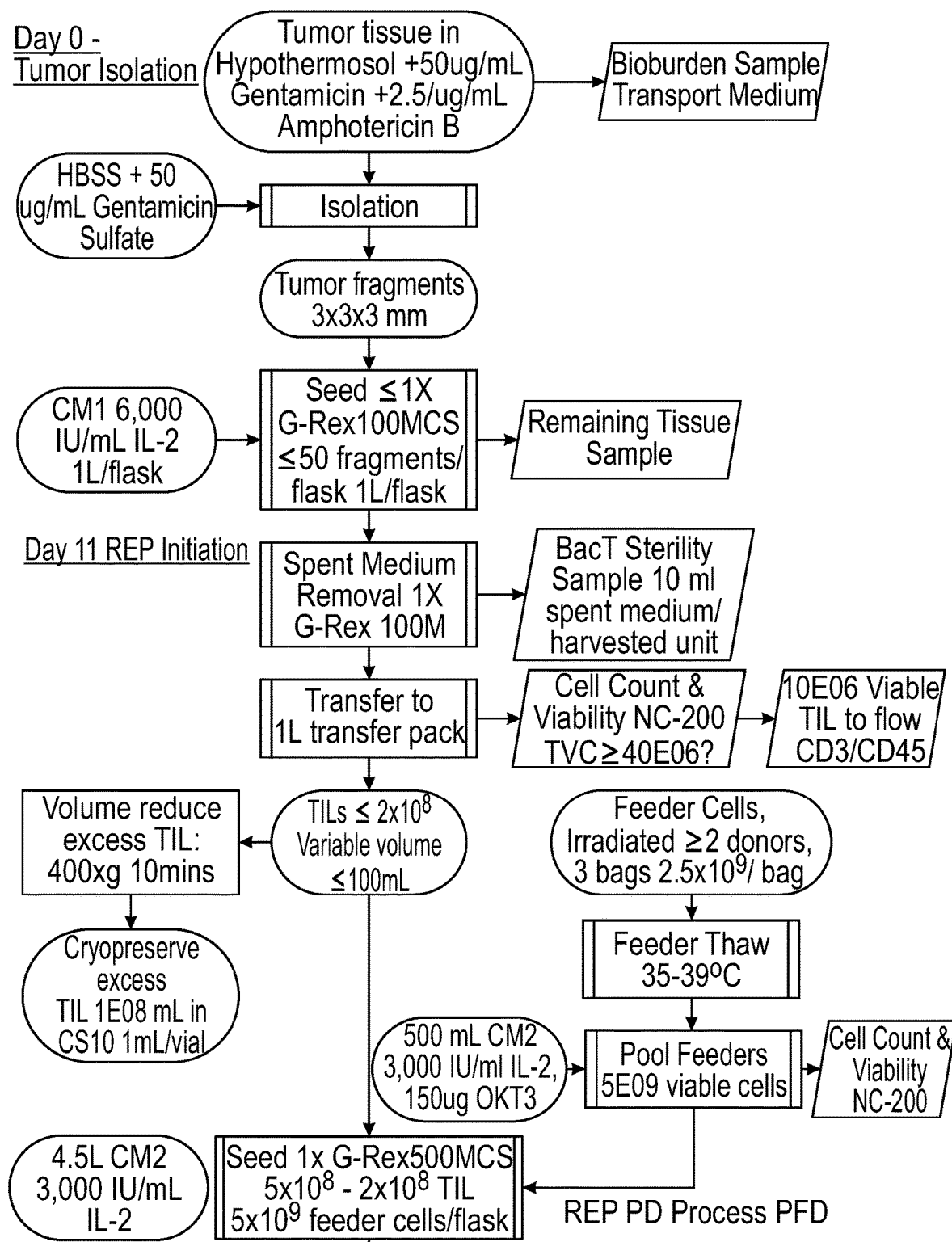
FIGS. 19A, 19B, and 19C: Process Flow Chart of Process 2A.
Figure 19B:
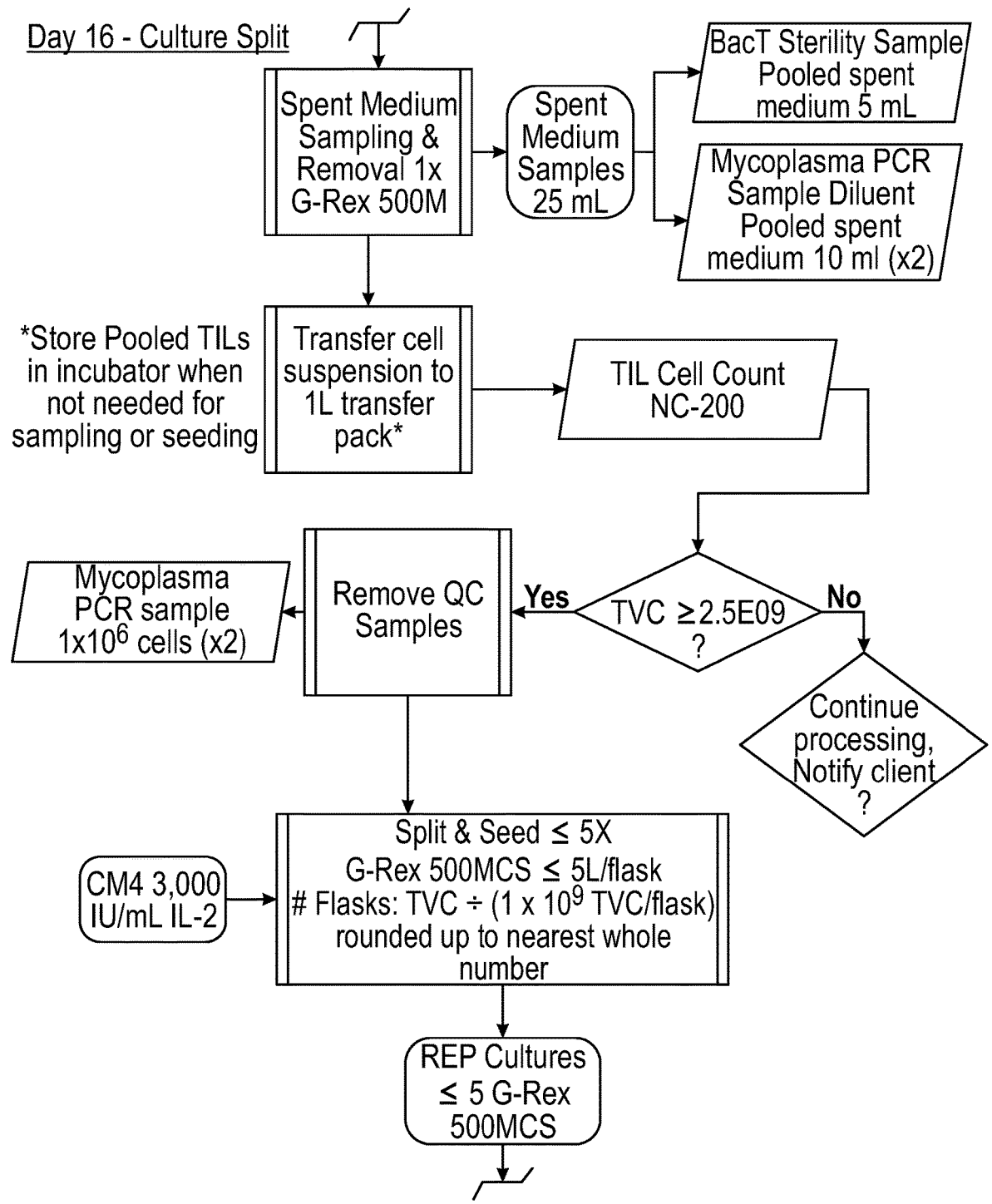
Figure 19C:
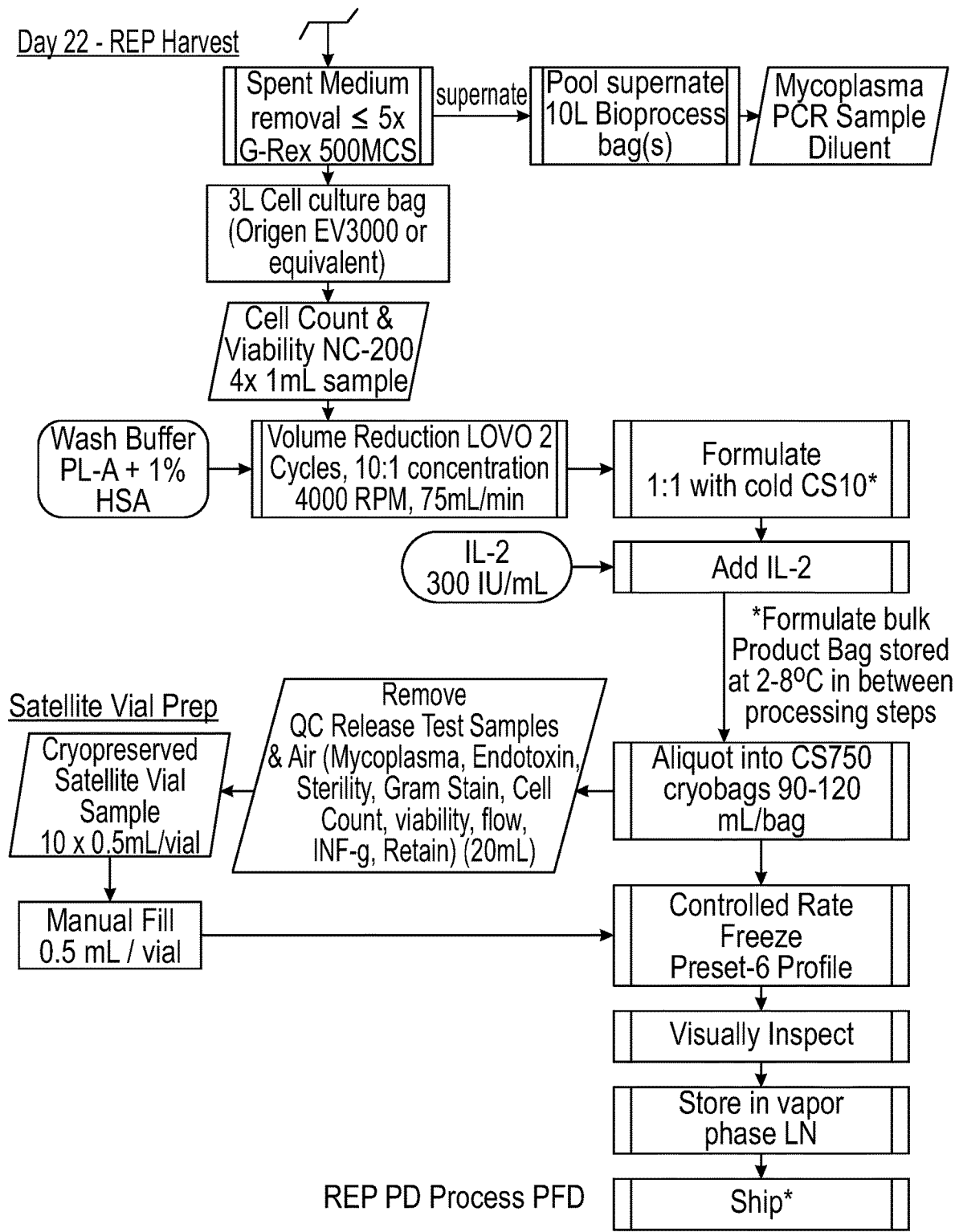

In some embodiments, where the tumor is a solid tumor, the tumor undergoes physical fragmentation after the tumor sample is obtained in, for example, Step A (as provided in FIG. 9). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 mm$^3$. In some embodiments, the multiple fragments comprise about 30 to about 60 fragments with a total volume of about 1300 mm$^3$ to about 1500 mm$^3$. In some embodiments, the multiple fragments comprise about 50 fragments with a total volume of about 1350 mm$^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 mm$^3$ and 10 mm$^3$. In some embodiments, the tumor fragment is between about 1 mm$^3$ and 8 mm$^3$. In some embodiments, the tumor fragment is about 1 mm$^3$. In some embodiments, the tumor fragment is about 2 mm$^3$. In some embodiments, the tumor fragment is about 3 mm$^3$. In some embodiments, the tumor fragment is about 4 mm$^3$. In some embodiments, the tumor fragment is about 5 mm$^3$. In some embodiments, the tumor fragment is about 6 mm$^3$. In some embodiments, the tumor fragment is about 7 mm$^3$. In some embodiments, the tumor fragment is about 8 mm$^3$. In some embodiments, the tumor fragment is about 9 mm$^3$. In some embodiments, the tumor fragment is about 10 mm$^3$.

In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, Calif.). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 9.

B. STEP B: First Expansion

1. Young TILs

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology*, 75:157-167 (2012); Dudley et al., *Clin Cancer Res*, 16:6122-6131 (2010); Huang et al., *J Immunother*, 28(3):258-267 (2005); Besser et al., *Clin Cancer Res*, 19(17):OF1-OF9 (2013); Besser et al., *J Immunother* 32:415-423 (2009); Robbins, et al., *J Immunol* 2004; 173: 7125-7130; Shen et al., J Immunother, 30:123-129 (2007); Zhou, et al., *J Immunother*, 28:53-62 (2005); and Tran, et al., J Immunother, 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 9. In some embodiments, the TILs obtained by the present method exhibit an increase in the T-cell repertoire diversity as compared to freshly harvested TILs and/or TILs prepared using methods referred to as process 1C, as exemplified in FIG. 13. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

After dissection or digestion of tumor fragments, for example such as described in Step A of FIG. 9, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step (for example such as those described in Step B of FIG. 9, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, N.Y., each well can be seeded with $1\times10^6$ tumor digest cells or one tumor fragment in 2 mL of complete medium (CM) with IL-2 (6000 IU/mL; Chiron Corp., Emeryville, Calif.). In some embodiments, the tumor fragment is between about 1 mm$^3$ and 10 mm$^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, Minn.) (FIG. 1), each flask was loaded with 10-40$\times10^6$ viable tumor digest cells or 5-30 tumor fragments in 10-40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of 20-30$\times10^6$ IU/mg for a 1 mg vial. In some embodiments the IL-2 stock solution has a specific activity of 20$\times10^6$ IU/mg for a 1 mg vial. In some embodiments the IL-2 stock solution has a specific activity of 25$\times10^6$ IU/mg for a 1 mg vial. In some embodiments the IL-2 stock solution has a specific activity of 30$\times10^6$ IU/mg for a 1 mg vial. In some embodiments, the IL-2 stock solution has a final concentration of 4-8$\times10^6$ IU/mg of IL-2. In some embodiments, the IL-2 stock solution has a final concentration of 5-7$\times10^6$ IU/mg of IL-2. In some embodiments, the IL-2 stock solution has a final concentration of 6$\times10^6$ IU/mg of IL-2. In some embodiments, the IL-2 stock solution is prepare as described in Example 4. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In an embodiment, the cell culture medium comprises OKT-3 antibody. The OKT-3 antibody may be present in the cell culture medium beginning on day 0 of the REP (i.e., the start day of the REP) and/or day 0 of the second expansion (i.e., the start day of the second expansion). In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 pg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, between 50 ng/mL and 100 ng/mL of OKT-3 antibody. In some embodiments, the cell culture medium does not comprise OKT-3 antibody.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, Minn.) (FIG. 1), each flask was loaded with 10-40×10$^6$ viable tumor digest cells or 5-30 tumor fragments in 10-40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days. In some embodiments, the CM is the CM1 described in the Examples, see, Example 5. In some embodiments, the first expansion occurs in an initial cell culture medium or a first cell culture medium. In some embodiments, the initial cell culture medium or the first cell culture medium comprises IL-2.

In some embodiments, the first expansion (including processes such as for example those described in Step B of FIG. 9, which can include those sometimes referred to as the pre-REP) process is shortened to 3-14 days, as discussed in the examples and figures. In some embodiments, the first expansion (including processes such as for example those described in Step B of FIG. 9, which can include those sometimes referred to as the pre-REP) is shortened to 7 to 14 days, as discussed in the Examples and shown in FIGS. 4 and 5, as well as including for example, an expansion as described in Step B of FIG. 9. In some embodiments, the first expansion of Step B is shortened to 10-14 days, as discussed in the Examples and shown in FIGS. 4 and 5. In some embodiments, the first expansion is shortened to 11 days, as discussed in the Examples and shown in FIGS. 4 and 5, as well as including for example, an expansion as described in Step B of FIG. 9.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 9, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 9 and as described herein.

In some embodiments, the first expansion (including processes referred to as the pre-REP; for example, Step B according to FIG. 9) process is shortened to 3 to 14 days, as discussed in the examples and figures. In some embodiments, the first expansion of Step B is shortened to 7 to 14 days, as discussed in the Examples and shown in FIGS. 4 and 5. In some embodiments, the first expansion of Step B is shortened to 10 to 14 days, as discussed in the Examples and shown in FIGS. 4, 5, and 9. In some embodiments, the first expansion is shortened to 11 days, as discussed in the Examples and shown in FIGS. 4, 5, and 9.

In some embodiments, the first expansion, for example, Step B according to FIG. 9, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, the first expansion is performed using an additional 4-1BB agonist antibody added to the cell culture medium at the start of the expansion, using any of the 4-1BB agonist antibodies described hereinafter.

C. STEP C: First Expansion to Second Expansion Transition

In some cases, the bulk TIL population obtained from the first expansion, including for example the TIL population obtained from for example, Step B as indicated in FIG. 9, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 9) are stored until phenotyped for selection. In some embodiments, the TILs obtained from the first expansion (for example, from Step B as indicated in FIG. 9) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 9). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 9, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

D. STEP D: Second Expansion

In some embodiments, the TIL cell population is expanded in number after harvest and initial bulk processing for example, after Step A and Step B, and the transition referred to as Step C, as indicated in FIG. 9). This further expansion is referred to herein as the second expansion, which can include expansion processes generally referred to in the art as a rapid expansion process (REP; as well as processes as indicated in Step D of FIG. 9). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 9) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 9). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, N.J. or Miltenyi Biotech, Auburn, Calif.) or UHCT-1 (commercially available from BioLegend, San Diego, Calif., USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 µM MART-1:26-35 (27 L) or gp1 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In a some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT3 antibody. The OKT-3 antibody may be present in the cell culture medium beginning on day 0 of the REP (i.e., the start day of the REP) and/or day 0 of the second expansion (i.e., the start day of the second expansion). In some embodiments, the cell culture medium comprises about 30 ng/mL of OKT3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT3 antibody. In some embodiments, the cell culture medium does not comprise OKT-3 antibody.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 9, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 9 and as described herein.

In some embodiments, the second expansion can be conducted in a supplemented cell culture medium comprising IL-2, OKT-3, and antigen-presenting feeder cells. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally ⅔ media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks). In some embodiments, the second expansion (including expansions referred to as rapid expansions) is performed in T-175 flasks, and about 1×10$^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and 2.0×10$^6$ cells/mL.

In an embodiment, the second expansion (which can include expansions referred to as REP, as well as those referred to in Step D of FIG. 9) may be performed in 500 mL capacity gas permeable flasks with 100 cm gas-permeable silicon bottoms (G-Rex 100, commercially available from Wilson Wolf Manufacturing Corporation, New Brighton, Minn., USA), $5\times10^6$ or $10\times10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 ml media. In some embodiments, media replacement is done until the cells are transferred to an alternative growth chamber. In some embodiments, ⅔ of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, Mass.). In some embodiments, viability is determined according to the Cellometer K2 Image Cytometer Automatic Cell Counter protocol described, for example, in Example 15.

In some embodiments, the second expansion (including expansions referred to as REP) of TIL can be performed using T-175 flasks and gas-permeable bags as previously described (Tran K Q, Thou J, Durflinger K H, et al., 2008, *J Immunother.*, 31:742-751, and Dudley M E, Wunderlich J R, Shelton T E, et al. 2003, *J Immunother.*, 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about $1\times10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0\times10^6$ cells/mL.

In some embodiments, the second expansion (including expansions referred to as REP) are performed in 500 mL capacity flasks with 100 $cm^2$ gas-permeable silicon bottoms (G-Rex 100, Wilson Wolf) (FIG. 1), about $5\times10^6$ or $10\times10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% $CO_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% $CO_2$ and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 9, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

1. Feeder Cells and Antigen Presenting Cells

In an embodiment, the second expansion procedures described herein (for example including expansion such as those described in Step D from FIG. 9, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, in particular example 14, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion). See, for example, Example 14.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2. See, for example, Example 13.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/ml IL-2. In some embodiments, the PBMCs are cultured in the presence of 10-50 ng/ml OKT3 antibody and 2000-5000 IU/ml IL-2. In some embodiments, the PBMCs are cultured in the presence of 20-40 ng/ml OKT3 antibody and 2000-4000 IU/ml IL-2. In some embodiments, the PBMCs are cultured in the presence of 25-35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5 \times 10^9$ feeder cells to about $100 \times 10^6$ TILs. In another embodiment, the second expansion procedures described herein require a ratio of about $2.5 \times 10^9$ feeder cells to about $50 \times 10^6$ TILs. In yet another embodiment, the second expansion procedures described herein require about $2.5 \times 10^9$ feeder cells to about $25 \times 10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

Figure 5:
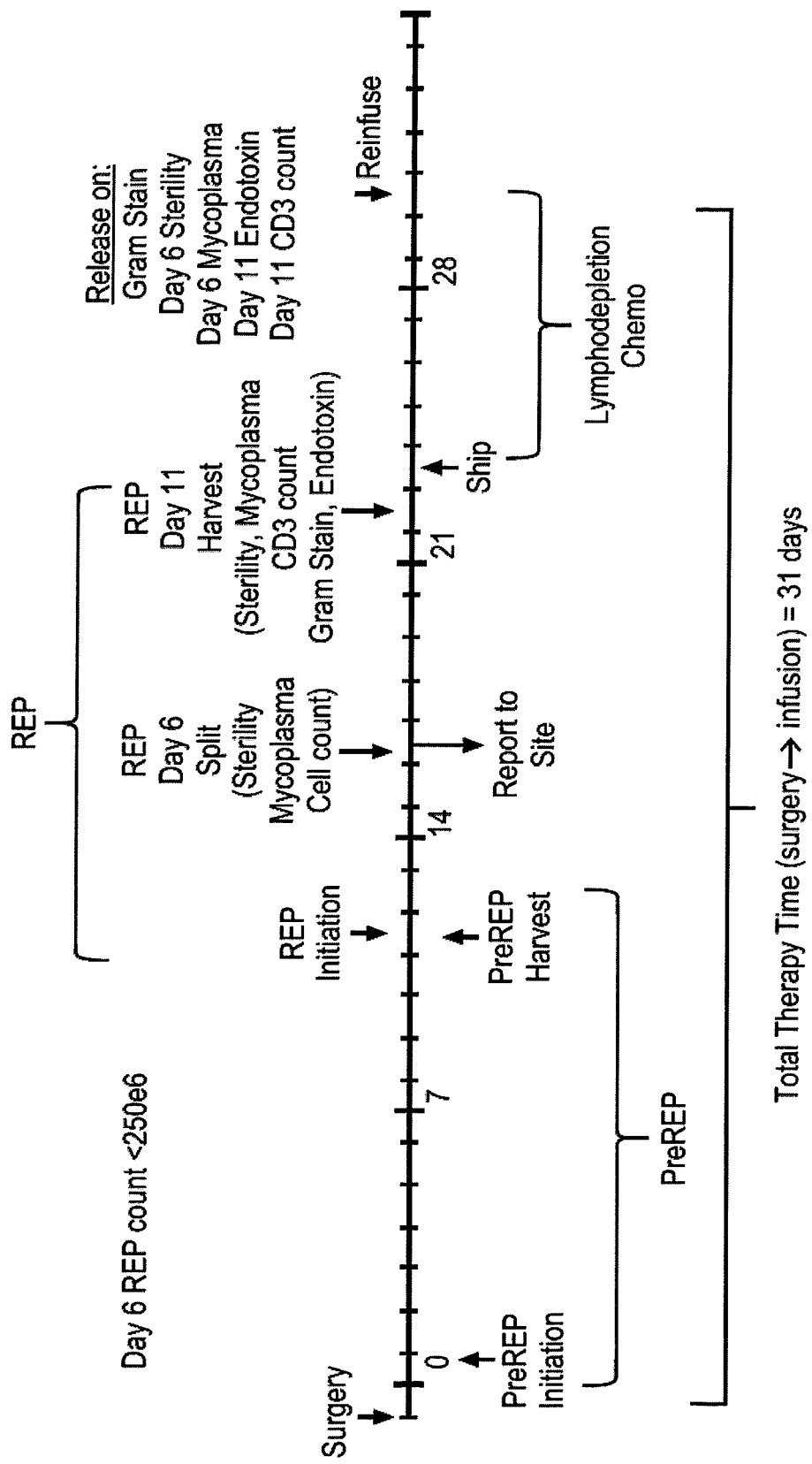
FIG. 5: Shows the process of an embodiment of TIL therapy using process 2A for TIL manufacturing, including administration and co-therapy steps, for lower cell counts.
Figure 6:
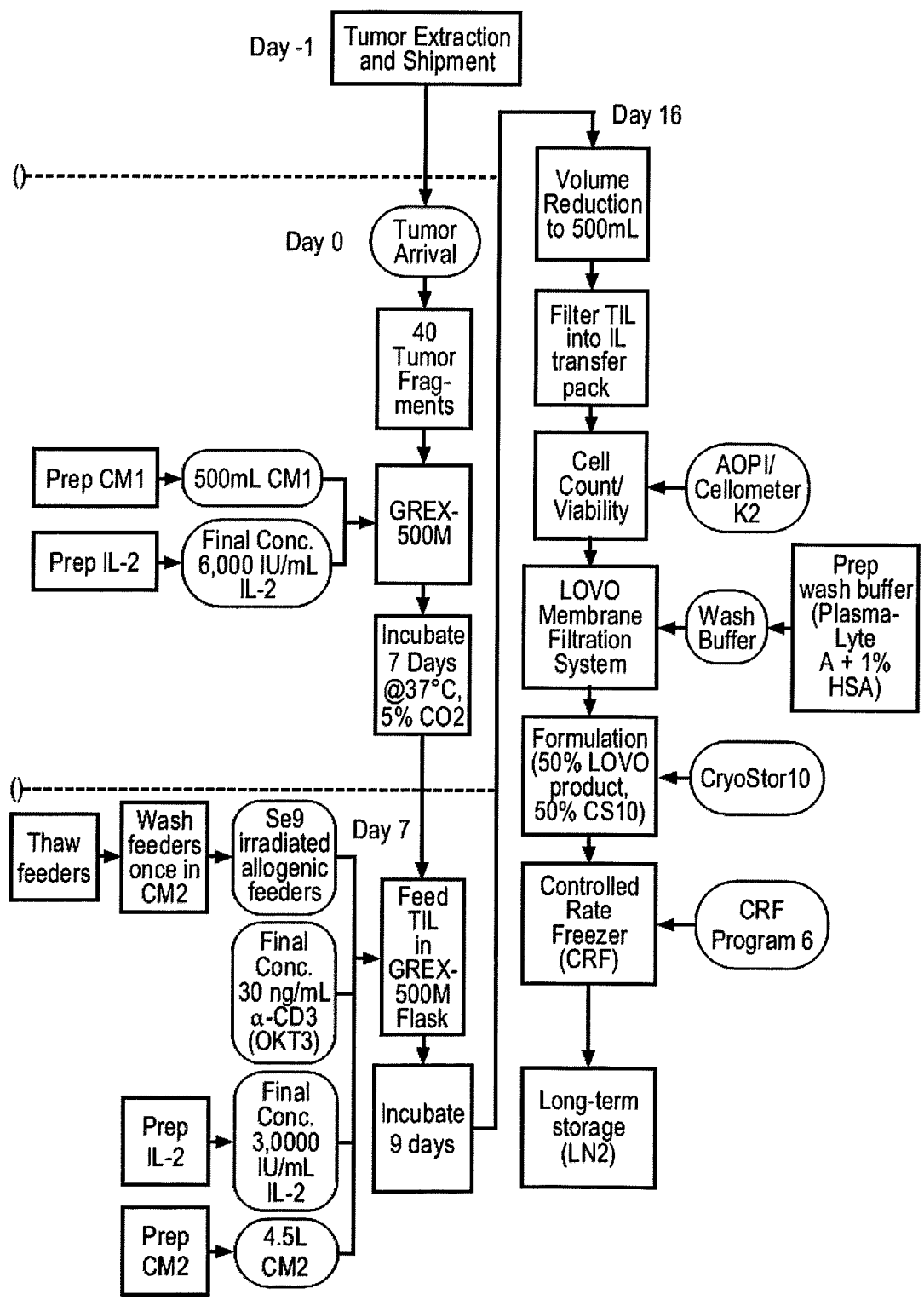
FIG. 6: Shows a detailed schematic for an embodiment of the 2A process.
Figures 7A, 7B:
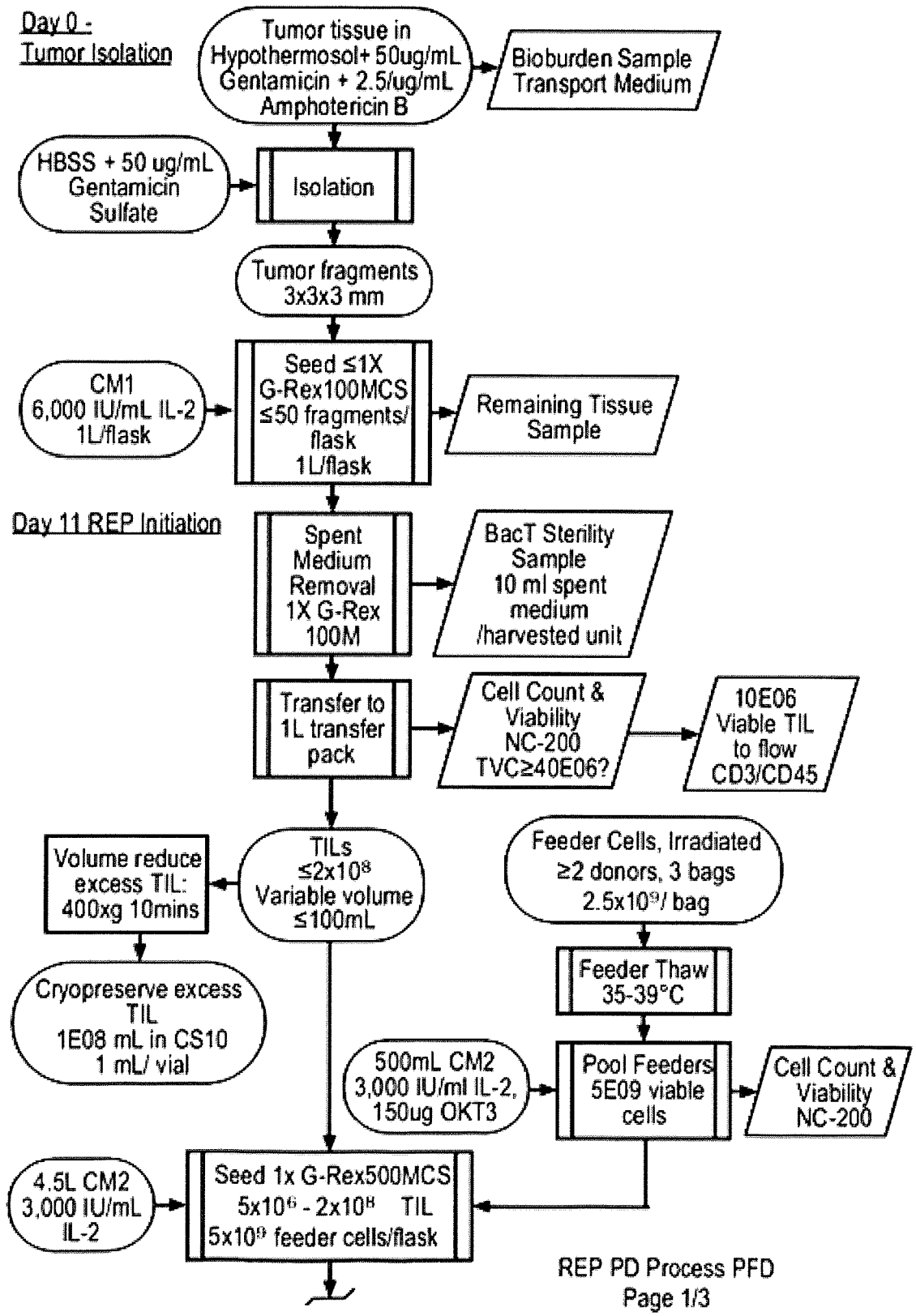
FIGS. 7a, 7b and 7c: Depict the major steps of an embodiment of process 2A including the cryopreservation steps.
Figure 7B:
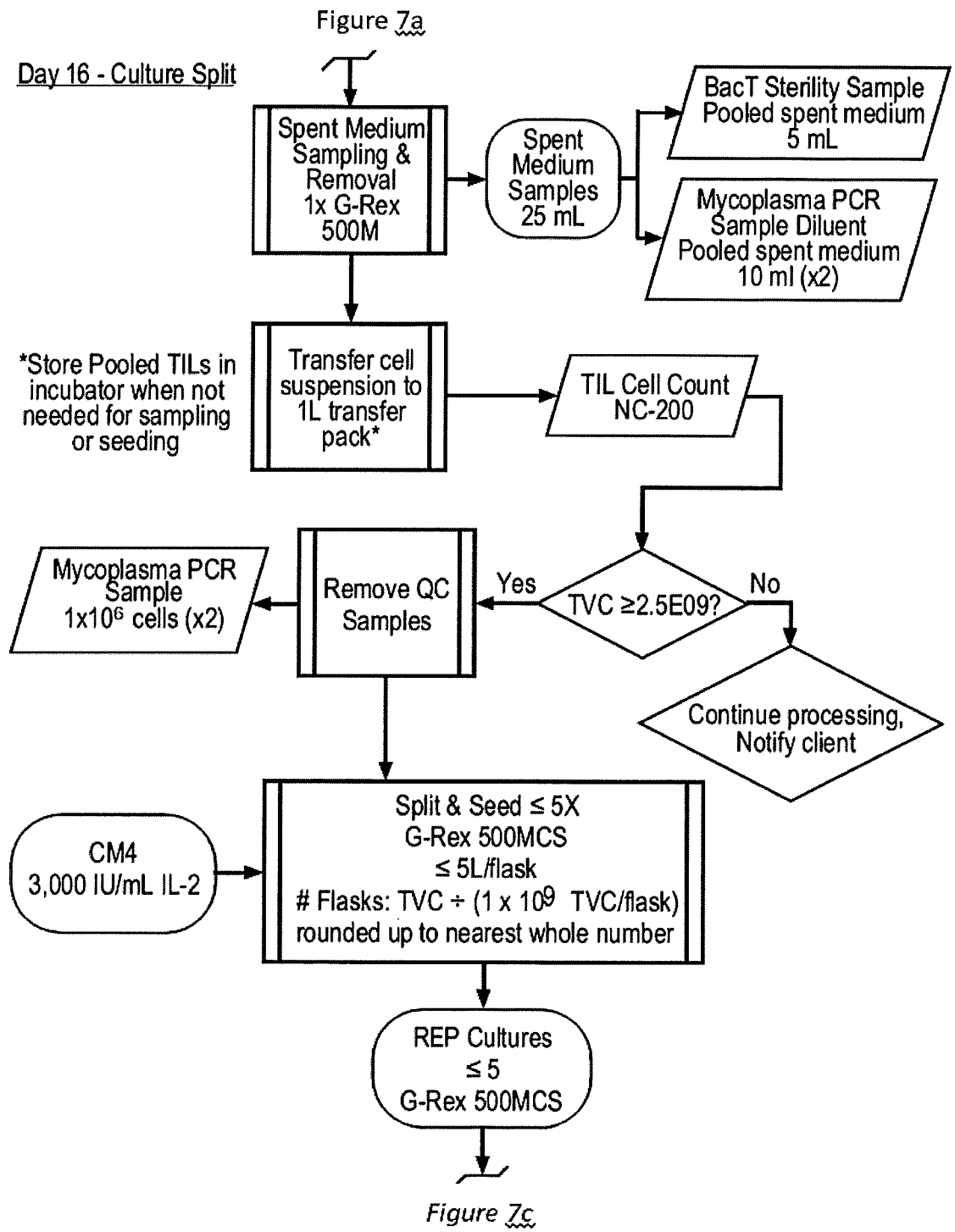
Figure 7C:
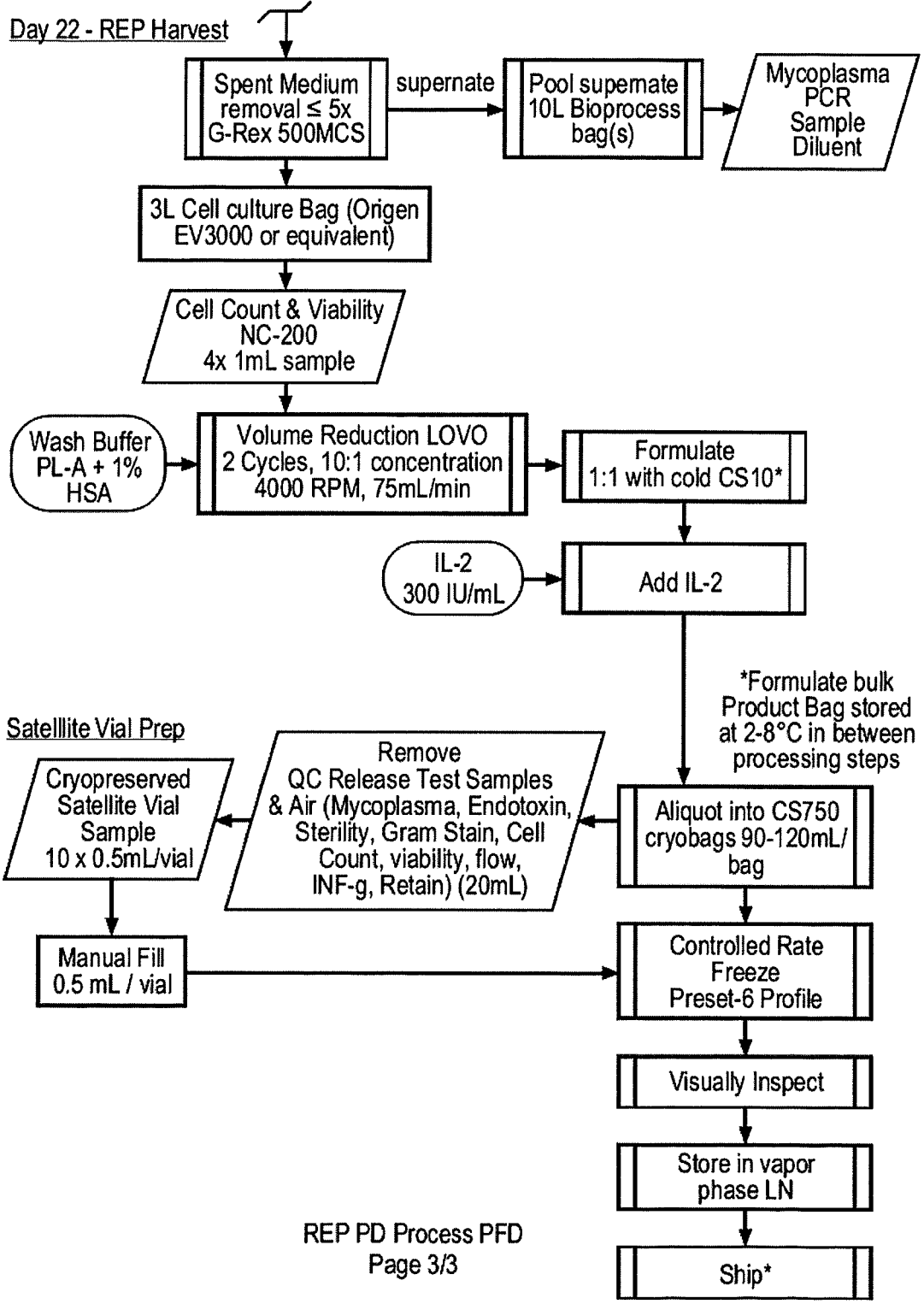
Figure 8:
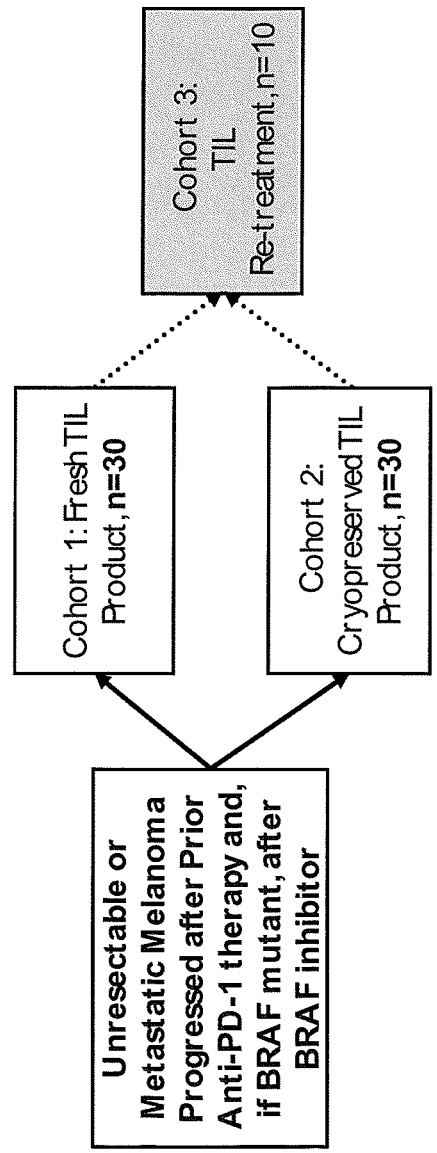
FIG. 8: Depicts the clinical trial design including cohorts treated with process 1C and an embodiment of process 2A.

In general, the allogenic PBMCs are inactivated, either via irradiation or heat treatment, and used in the TIL expansion procedures described herein, including the exemplary procedures described in FIGS. 4, 5, and 9.

In an embodiment, artificial antigen presenting cells are used in the second expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

3. Anti-CD3 Antibodies

In some embodiments, the culture media used in expansion methods described herein (including those referred to as REP, see for example, FIG. 9) also includes an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, N.J. or Miltenyi Biotech, Auburn, Calif.).

In some embodiments, the anti-CD3 antibody, such as OKT3, may be added to TIL culture 2 days, 3 days, 4 days, or 5 days prior to an electroporation step. In some embodiments, the anti-CD3 antibody, such as OKT3, may be added immediately before an electroporation step. In some embodiments, the anti-CD3 antibody, such as OKT3, may be added immediately after an electroporation step. In some embodiments, the anti-CD3 antibody, such as OKT3, may be added 2 days, 3 days, 4 days, or 5 days after an electroporation step.

4. 4-1BB and OX40 Agonists

According to an embodiment, the cell culture medium further comprises a 4-1BB (CD137) agonist and/or an OX40 agonist during the first expansion, the second expansion, or both. The gene-editing may be carried out after the 4-1BB agonist and/or the OX40 agonist are introduced into the cell culture medium. Alternatively, the gene-editing may be carried out before the 4-1BB agonist and/or the OX40 agonist are introduced into the cell culture medium.

The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 3.

TABLE 3

Amino acid sequences of 4-1BB antigens.

| Identifier | Sequence (One-Letter Amino Acid Symbols) | | | | | |
|---|---|---|---|---|---|---|
| SEQ ID NO: 9 | MGNSCYNIVA | TLLLVLNFER | TRSLQDPCSN | CPAGTFCDNN | RNQICSPCPP | NSFSSAGGQR 60 |
| human 4-1BB, | TCDICRQCKG | VFRTRKECSS | TSNAECDCTP | GFHCLGAGCS | MCEQDCKQGQ | ELTKKGCKDC 120 |
| Tumor necrosis | CFGTFNDQKR | GICRPWTNCS | LDGKSVLVNG | TKERDVVCGP | SPADLSPGAS | SVTPPAPARE 180 |
| factor receptor | PGHSPQIISF | FLALTSTALL | FLLFFLTLRF | SVVKRGRKKL | LYIFKQPFMR | PVQTTQEEDG 240 |
| superfamily, | CSCRFPEEEE | GGCEL | | | | 255 |
| member 9 (*Homo sapiens*) | | | | | | |

TABLE 3-continued

Amino acid sequences of 4-1BB antigens.

| Identifier | Sequence (One-Letter Amino Acid Symbols) | |
|---|---|---|
| SEQ ID NO: 10 murine 4-1BB, Tumor necrosis factor receptor superfamily, member 9 (Mus musculus) | MGNNCYNVVV IVLLLVGCEK VGAVQNSCDN CQPGTFCRKY NPVCKSCPPS TFSSIGGQPN<br>CNICRVCAGY FRFKKFCSST HNAECECIEG FHCLGPQCTR CEKDCRPGQE LTKQGCKTCS<br>LGTFNDQNGT GVCRPWTNCS LDGRSVLKTG TTEKDVVCGP PVVSFSPSTT ISVTPEGGPG<br>GHSLQVLTLF LALTSALLLA LIFITLLFSV LKWIRKKFPH IFKQPFKKTT GAAQEEDACS<br>CRCPQEEEGG GGGYEL | 60<br>120<br>180<br>240<br>256 |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5 \times 10^5$ 1/M·s or faster, binds to human or murine 4-1BB with a $k_{assoc}$ of about $7.5 \times 10^5$ 1/M·s or faster, binds to human or murine 4-1BB with a $k_{assoc}$ of about $8 \times 10^5$ 1/M·s or faster, binds to human or murine 4-1BB with a $k_{assoc}$ of about $8.5 \times 10^5$ 1/M·s or faster, binds to human or murine 4-1BB with a $k_{assoc}$ of about $9 \times 10^5$ 1/M·s or faster, binds to human or murine 4-1BB with a $k_{assoc}$ of about $9.5 \times 10^5$ 1/M·s or faster, or binds to human or murine 4-1BB with a $k_{assoc}$ of about $1 \times 10^6$ 1/M·s or faster.

In some embodiments, the compositions, processes and methods described include a 4-1BB agonist that binds to human or murine 4-1BB with a $k_{dissoc}$ of about $2 \times 10^{-5}$ 1/s or slower, binds to human or murine 4-1BB with a $k_{dissoc}$ of about $2.1 \times 10^{-5}$ 1/s or slower, binds to human or murine 4-1BB with a $k_{dissoc}$ of about $2.2 \times 10^{-5}$ 1/s or slower, binds to human or murine 4-1BB with a $k_{dissoc}$ of about $2.3 \times 10^{-5}$ 1/s or slower, binds to human or murine 4-1BB with a $k_{dissoc}$ of about $2.4 \times 10^{-5}$ 1/s or slower, binds to human or murine 4-1BB with a $k_{dissoc}$ of about $2.5 \times 10^{-5}$ 1/s or slower, binds to human or murine 4-1BB with a $k_{dissoc}$ of about $2.6 \times 10^{-5}$ 1/s or slower or binds to human or murine 4-1BB with a $k_{dissoc}$ of about $2.7 \times 10^{-5}$ 1/s or slower, binds to human or murine 4-1BB with a $k_{dissoc}$ of about $2.8 \times 10^{-5}$ 1/s or slower, binds to human or murine 4-1BB with a $k_{dissoc}$ of about $2.9 \times 10^{-5}$ 1/s or slower, or binds to human or murine 4-1BB with a $k_{dissoc}$ of about $3 \times 10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[Homo sapiens TNFRSF9 (tumor necrosis factor receptor (TNFR) superfamily member 9, 4-1BB, T cell antigen ILA, CD137)], Homo sapiens (fully human) monoclonal antibody. The amino acid sequences of utomilumab are set forth in Table 4. Utomilumab comprises glycosylation sites at Asn59 and Asn292; heavy chain intrachain disulfide bridges at positions 22-96 ($V_H$-$V_L$), 143-199 ($C_H$1-$C_L$), 256-316 ($C_H$2) and 362-420 ($C_H$3); light chain intrachain disulfide bridges at positions 22'-87' ($V_H$-$V_L$) and 136'-195' ($C_H$1-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., Cancer Immunolog. & Immunother. 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 4

Amino acid sequences for 4-1BB agonist antibodies related to utomilumab.

| Identifier | Sequence (One-Letter Amino Acid Symbols) | |
|---|---|---|
| SEQ ID NO: 11<br>heavy chain for<br>utomilumab | EVQLVQSGAE VKKPGESLRI SCKGSGYSFS TYWISWVRQM PGKGLEWMGK IYPGDSYTNY<br>SPSFQGQVTI SADKSISTAY LQWSSLKASD TAMYYCARGY GIFDYWGQGT LVTVSSASTK<br>GPSVFPLAPC SRSTSESTAA LGCLVKDYFP EPVTVSWNSG ALTSGVHTFP AVLQSSGLYS<br>LSSVVTVPSS NFGTQTYTCN VDHKPSNTKV DKTVERKCCV ECPPCPAPPV AGPSVFLFPP<br>KPKDTLMISR TPEVTCVVVD VSHEDPEVQF NWYVDGVEVH NAKTKPREEQ FNSTFRVVSV<br>LTVVHQDWLN GKEYKCKVSN KGLPAPIEKT ISKTKGQPRE PQVYTLPPSR EEMTKNQVSL<br>TCLVKGFYPS DIAVEWESNG QPENNYKTTP PMLDSDGSFF LYSKLTVDKS RWQQGNVFSC<br>SVMHEALHNH YTQKSLSLSP G | 60<br>120<br>180<br>240<br>300<br>360<br>420<br>441 |
| SEQ ID NO: 12<br>light chain for<br>utomilumab | SYELTQPPSV SVSPGQTASI TCSGDNIGDQ YAHWYQQKPG QSPVLVIYQD KNRPSGIPER<br>FSGSNSGNTA TLTISGTQAM DEADYYCATY TGFGSLAVFG GGTKLTVLGQ PKAAPSVTLF<br>PPSSEELQAN KATLVCLISD FYPGAVTVAW KADSSPVKAG VETTTPSKQS NNKYAASSYL<br>SLTPEQWKSH RSYSCQVTHE GSTVEKTVAP TECS | 60<br>120<br>180<br>214 |
| SEQ ID NO: 13<br>heavy chain<br>variable region<br>for utomilumab | EVQLVQSGAE VKKPGESLRI SCKGSGYSFS TYWISWVRQM PGKGLEWMG KIYPGDSYTN<br>YSPSFQGQVT ISADKSISTA YLQWSSLKAS DTAMYYCARG YGIFDYWGQ GTLVTVSS | 60<br>118 |
| SEQ ID NO: 14<br>light chain<br>variable region<br>for utomilumab | SYELTQPPSV SVSPGQTASI TCSGDNIGDQ YAHWYQQKPG QSPVLVIYQD KNRPSGIPER<br>FSGSNSGNTA TLTISGTQAM DEADYYCATY TGFGSLAVFG GGTKLTVL | 60<br>108 |
| SEQ ID NO: 15<br>heavy chain CDR1<br>for utomilumab | STYWIS | 6 |

TABLE 4-continued

Amino acid sequences for 4-1BB agonist antibodies related to utomilumab.

| Identifier | Sequence (One-Letter Amino Acid Symbols) | |
|---|---|---|
| SEQ ID NO: 16 heavy chain CDR2 for utomilumab | KIYPGDSYTN YSPSFQG | 17 |
| SEQ ID NO: 17 heavy chain CDR3 for utomilumab | RGYGIFDY | 8 |
| SEQ ID NO: 18 light chain CDR1 for utomilumab | SGDNIGDQYA H | 11 |
| SEQ ID NO: 19 light chain CDR2 for utomilumab | QDKNRPS | 7 |
| SEQ ID NO: 20 light chain CDR3 for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table 5. Urelumab comprises N-glycosylation sites at positions 298 (and 298"); heavy chain intrachain disulfide bridges at positions 22-95 ($V_H$-$V_L$), 148-204 ($C_H1$-$C_L$), 262-322 ($C_H2$) and 368-426 ($C_H3$) (and at positions 22"-95", 148"-204", 262"-322", and 368"-426"); light chain intrachain disulfide bridges at positions 23'-88' ($V_H$-$V_L$) and 136'-196' ($C_H1$-$C_L$) (and at positions 23'''-88''' and 136'''-196'''); interchain heavy chain-heavy chain disulfide bridges at positions 227-227" and 230-230"; and interchain heavy chain-light chain disulfide bridges at 135-216' and 135"-216'''. The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., *Clin. Cancer Res.* 2016, available at http:/dx.doi.org/10.1158/1078-0432.CCR-16-1272. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1BB agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO:23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO:24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 5

Amino acid sequences for 4-1BB agonist antibodies related to urelumab.

| Identifier | Sequence (One-Letter Amino Acid Symbols) | | | | | |
|---|---|---|---|---|---|---|
| SEQ ID NO: 21 heavy chain for urelumab | QVQLQQWGAG | LLKPSETLSL | TCAVYGGSFS | GYYWSWIRQS | PEKGLEWIGE | INHGGYVTYN | 60 |
| | PSLESRVTIS | VDTSKNQFSL | KLSSVTAADT | AVYYCARDYG | PGNYDWYFDL | WGRGTLVTVS | 120 |
| | SASTKGPSVF | PLAPCSRSTS | ESTAALGCLV | KDYFPEPVTV | SWNSGALTSG | VHTFPAVLQS | 180 |
| | SGLYSLSSVV | TVPSSSLGTK | TYTCNVDHKP | SNTKVDKRVE | SKYGPPCPPC | PAPEFLGGPS | 240 |
| | VFLFPPKPKD | TLMISRTPEV | TCVVVDVSQE | DPEVQFNWYV | DGVEVHNAKT | KPREEQFNST | 300 |
| | YRVVSVLTVL | HQDWLNGKEY | KCKVSNKGLP | SSIEKTISKA | KGQPREPQVY | TLPPSQEEMT | 360 |
| | KNQVSLTCLV | KGFYPSDIAV | EWESNGQPEN | NYKTTPPVLD | SDGSFFLYSR | LTVDKSRWQE | 420 |
| | GNVFSCSVMH | EALHNHYTQK | SLSLSLGK | | | | 448 |
| SEQ ID NO: 22 light chain for urelumab | EIVLTQSPAT | LSLSPGERAT | LSCRASQSVS | SYLAWYQQKP | GQAPRLLIYD | ASNRATGIPA | 60 |
| | RFSGSGSGTD | FTLTISSLEP | EDFAVYYCQQ | RSNWPPALTF | CGGTKVEIKR | TVAAPSVFIF | 120 |
| | PPSDEQLKSG | TASVVCLLNN | FYPREAKVQW | KVDNALQSGN | SQESVTEQDS | KDSTYSLSST | 180 |
| | LTLSKADYEK | HKVYACEVTH | QGLSSPVTKS | FNRGEC | | | 216 |
| SEQ ID NO: 23 variable heavy chain for urelumab | MKHLWFFLLL | VAAPRWVLSQ | VQLQQWGAGL | LKPSETLSLT | CAVYGGSFSG | YYWSWIRQSP | 60 |
| | EKGLEWIGEI | NHGGYVTYNP | SLESRVTISV | DTSKNQFSLK | LSSVTAADTA | VYYCARDYGP | 120 |
| SEQ ID NO: 24 variable light chain for urelumab | MEAPAQLLFL | LLLWLPDTTG | EIVLTQSPAT | LSLSPGERAT | LSCRASQSVS | SYLAWYQQKP | 60 |
| | GQAPRLLIYD | ASNRATGIPA | RFSGSGSGTD | FTLTISSLEP | EDFAVYYCQQ | | 110 |
| SEQ ID NO: 25 heavy chain CDR1 for urelumab | GYYWS | | | | | | 5 |
| SEQ ID NO: 26 heavy chain CDR2 for urelumab | EINHGGYVTY | NPSLES | | | | | 16 |
| SEQ ID NO: 27 heavy chain CDR3 for urelumab | DYGPGNYDWY | FDL | | | | | 13 |
| SEQ ID NO: 28 light chain CDR1 for urelumab | RASQSVSSYL | A | | | | | 11 |
| SEQ ID NO: 29 light chain CDR2 for urelumab | DASNRAT | | | | | | 7 |
| SEQ ID NO: 30 light chain CDR3 for urelumab | QQRSDWPPAL | T | | | | | 11 |

In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031)), antibodies disclosed in U.S. Pat. No. 6,887,673 (such as 4E9 or BMS-554271), antibodies disclosed in U.S. Pat. No. 7,214,493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362,325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303,121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

Figure 22:
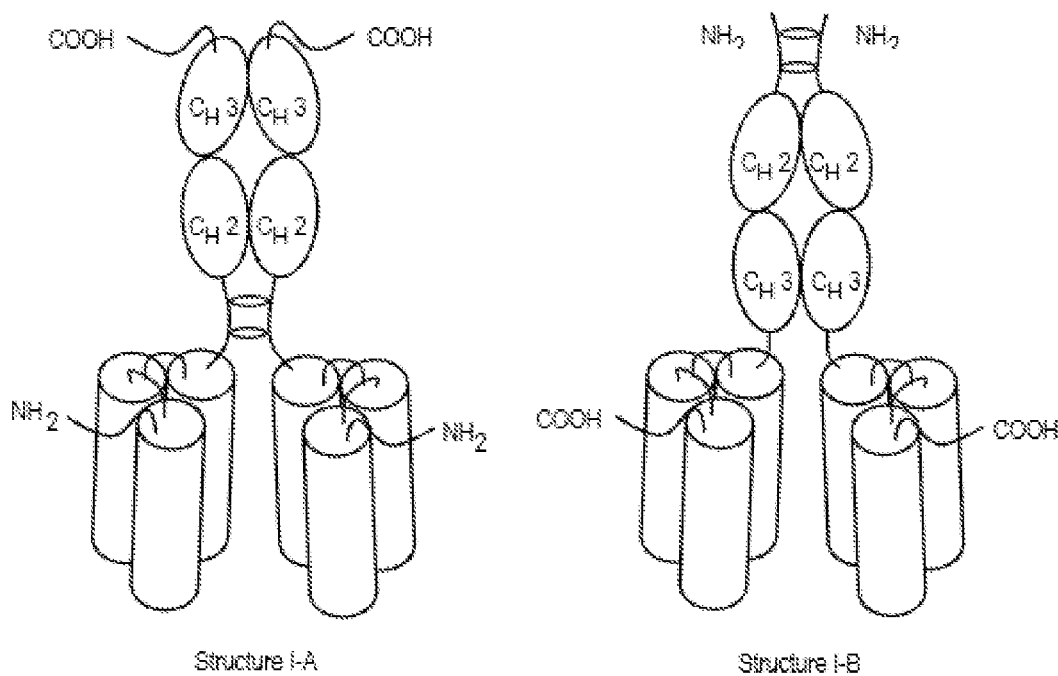
FIG. 22: Depiction of the structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a VH and a VL chain connected by a linker that may comprise hydrophilic residues and Gly and Ser sequences for flexibility, as well as Glu and Lys for solubility.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein) of FIG. 22, or a fragment, derivative, conjugate, variant, or biosimilar thereof.

In structures I-A and I-B of FIG. 22, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories,* 2011, 10, 44; Ahmad, et al., *Clin. & Dev. Immunol.* 2012, 980250; Monnier, et al., *Antibodies,* 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 6. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 6

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | |
|---|---|---|
| SEQ ID NO: 31<br>Fc domain | KSCDKTHTCP PCPAPELLGG PSVFLFPPKP KDTLMISRTP EVTCVVVDVS HEDPEVKFNW<br>YVDGVEVHNA KTKPREEQYN STYRVVSVLT VLHQDWLNGK EYKCKVSNKA LPAPIEKTIS<br>KAKGQPREPQ VYTLPPSREE MTKNQVSLTC LVKGFYPSDI AVEWESNGQP ENNYKTTPPV<br>LDSDGSFFLY SKLTVDKSRW QQGNVFSCSV MHEALHNHYT QKSLSLSPGK | 60<br>120<br>180<br>230 |
| SEQ ID NO: 32<br>linker | GGPGSSKSCD KTHTCPPCPA PE | 22 |
| SEQ ID NO: 33<br>linker | GGSGSSKSCD KTHTCPPCPA PE | 22 |
| SEQ ID NO: 34<br>linker | GGPGSSSSSS SKSCDKTHTC PPCPAPE | 27 |
| SEQ ID NO: 35<br>linker | GGSGSSSSSS SKSCDKTHTC PPCPAPE | 27 |
| SEQ ID NO: 36<br>linker | GGPGSSSSSS SSSKSCDKTH TCPPCPAPE | 29 |
| SEQ ID NO: 37<br>linker | GGSGSSSSSS SSSKSCDKTH TCPPCPAPE | 29 |

TABLE 6-continued

Amino acid sequences for TNFRSF fusion proteins,
including 4-1BB fusion proteins, with C-terminal Fc-antibody
fragment fusion protein design (structure I-A).

| Identifier | Sequence (One-Letter Amino Acid Symbols) | |
|---|---|---|
| SEQ ID NO: 38 linker | GGPGSSGSGS SDKTHTCPPC PAPE | 24 |
| SEQ ID NO: 39 linker | GGPGSSGSGS DKTHTCPPCP APE | 23 |
| SEQ ID NO: 40 linker | GGPSSSGSDK THTCPPCPAP E | 21 |
| SEQ ID NO: 41 linker | GGSSSSSSSS GSDKTHTCPP CPAPE | 25 |

Amino acid sequences for the other polypeptide domains of structure I-B are given in Table 7. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SEQ ID NO:43 to SEQ ID NO:45.

NO:46. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:47.

TABLE 7

Amino acid sequences for TNFRSF fusion proteins,
including 4-1BB fusion proteins, with N-terminal Fc-antibody
fragment fusion protein design (structure I-B).

| Identifier | Sequence (One-Letter Amino Acid Symbols) | |
|---|---|---|
| SEQ ID NO: 42 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B of FIG. 22 comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 8, any combination of a variable heavy chain and variable light chain of the foregoing, and fragments, derivatives, conjugates, variants, and biosimilars thereof.

In an embodiment, a 4-1BB agonist fusion protein according to structures I-A or I-B of FIG. 22 comprises one or more 4-1BB binding domains comprising a 4-1BBL sequence. In an embodiment, a 4-1BB agonist fusion protein according to structures I-A or I-B comprises one or more 4-1BB binding domains comprising a sequence according to SEQ ID NO:46.

In an embodiment, a 4-1BB agonist fusion protein according to structures I-A or I-B of FIG. 22 comprises one or more 4-1BB binding domains that is a scFv domain comprising $V_H$ and $V_L$ regions that are each at least 95% identical to the sequences shown in SEQ ID NO:13 and SEQ ID NO:14, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the $V_H$ and $V_L$ sequences given in Table 8, wherein the $V_H$ and $V_L$ domains are connected by a linker.

TABLE 8

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 46<br>4-1BBL | MEYASDASLD PEAPWPPAPR ARACRVLPWA LVAGLLLLLL LAAACAVFLA CPWAVSGARA | 60 |
| | SPGSAASPRL REGPELSPDD PAGLLDLRQG MFAQLVAQNV LLIDGPLSWY SDPGLAGVSL | 120 |
| | TGGLSYKEDT KELVVAKAGV YYVFFQLELR RVVAGEGSGS VSLALHLQPL RSAAGAAALA | 180 |
| | LTVDLPPASS EARNSAFGFQ GRLLHLSAGQ RLGVHLHTEA RARHAWQLTQ GATVLGLFRV | 240 |
| | TPEIPAGLPS PRSE | 254 |
| SEQ ID NO: 47<br>4-1BBL soluble<br>domain | LRQGMFAQLV AQNVLLIDGP LSWYSDPGLA GVSLTGGLSY KEDTKELVVA KAGVYYVFFQ | 60 |
| | LELRRVVAGE GSGSVSLALH LQPLRSAAGA AALALTVDLP PASSEARNSA FGFQGRLLHL | 120 |
| | SAGQRLGVHL HTEARARHAW QLTQGATVLG LFRVTPEIPA GLPSPRSE | 168 |
| SEQ ID NO: 48<br>variable heavy<br>chain for 4B4-1-<br>1 version 1 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVS | 118 |
| SEQ ID NO: 49<br>variable light<br>chain for 4B4-1-<br>1 version 1 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIK | 107 |
| SEQ ID NO: 50<br>variable heavy<br>chain for 4B4-1-<br>1 version 2 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVSA | 119 |
| SEQ ID NO: 51<br>variable light<br>chain for 4B4-1-<br>1 version 2 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIKR | 108 |
| SEQ ID NO: 52<br>variable heavy<br>chain for H39E3-<br>2 | MDWTWRILFL VAAATGAHSE VQLVESGGGL VQPGGSLRLS CAASGFTFSD YWMSWVRQAP | 60 |
| | GKGLEWVADI KNDGSYTNYA PSLTNRFTIS RDNAKNSLYL QMNSLRAEDT AVYYCARELT | 120 |
| SEQ ID NO: 53<br>variable light<br>chain for H39E3-<br>2 | MEAPAQLLFL LLLWLPDTTG DIVMTQSPDS LAVSLGERAT INCKSSQSLL SSGNQKNYL | 60 |
| | WYQQKPGQPP KLLIYYASTR QSGVPDRFSG SGSGTDFTLT ISSLQAEDVA | 110 |

In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, Calif., USA. In an embodiment, the 4-1BB agonist is Creative Biolabs 4-1BB agonist antibody catalog no. MOM-18179, commercially available from Creative Biolabs, Shirley, N.Y., USA.

The OX40 (CD134) agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40 L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40 L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 9.

TABLE 9

Amino acid sequences of OX40 antigens.

| Identifier | Sequence (One-Letter Amino Acid Symbols) | |
|---|---|---|
| SEQ ID NO: 54<br>human OX40<br>(Homo sapiens) | MCVGARRLGR GPCAALLLLG LGLSTVTGLH CVGDTYPSND RCCHECRPGN GMVSRCSRSQ<br>NTVCRPCGPG FYNDVVSSKP CKPCTWCNLR SGSERKQLCT ATQDTVCRCR AGTQPLDSYK<br>PGVDCAPCPP GHFSPGDNQA CKPWTNCTLA GKHTLQPASN SSDAICEDRD PPATQPQETQ<br>GPPARPITVQ PTEAWPRTSQ GPSTRPVEVP GGRAVAAILG LGLVLGLLGP LAILLALYLL<br>RRDQRLPPDA HKPPGGGSFR TPIQEEQADA HSTLAKI | 60<br>120<br>180<br>240<br>277 |
| SEQ ID NO: 55<br>murine OX40<br>(Mus musculus) | MYVWVQQPTA LLLLGLTLGV TARRLNCVKH TYPSGHKCCR ECQPGHGMVS RCDHTRDTLC<br>HPCETGFYNE AVNYDTCKQC TQCNHRSGSE LKQNCTPTQD TVCRCRPGTQ PRQDSGYKLG<br>VDCVPCPPGH FSPGNNQACK PWTNCTLSGK QTRHPASDSL DAVCEDRSLL ATLLWETQRP<br>TFRPTTVQST TVWPRTSELP SPPTLVTPEG PAFAVLLGLG LGLLAPLTVL LALYLLRKAW<br>RLPNTPKPCW GNSFRTPIQE EHTDAHFTLA KI | 60<br>120<br>180<br>240<br>272 |

In some embodiments, the compositions, processes and methods described include a OX40 agonist that binds human or murine OX40 with a $K_D$ of about 100 pM or lower, binds human or murine OX40 with a $K_D$ of about 90 pM or lower, binds human or murine OX40 with a $K_D$ of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5 \times 10^5$ 1/M·s or faster, binds to human or murine OX40 with a $k_{assoc}$ of about $7.5 \times 10^5$ 1/M·s or faster, binds to human or murine OX40 with a $k_{assoc}$ of about $8 \times 10^5$ 1/M·s or faster, binds to human or murine OX40 with a $k_{assoc}$ of about $8.5 \times 10^5$ 1/M·s or faster, binds to human or murine OX40 with a $k_{assoc}$ of about $9 \times 10^5$ 1/M·s or faster, binds to human or murine OX40 with a $k_{assoc}$ of about $9.5 \times 10^5$ 1/M·s or faster, or binds to human or murine OX40 with a $k_{assoc}$ of about $1 \times 10^6$ 1/M·s or faster.

In some embodiments, the compositions, processes and methods described include a OX40 agonist that binds to human or murine OX40 with a $k_{dissoc}$ of about $2 \times 10^{-5}$ 1/s or slower, binds to human or murine OX40 with a $k_{dissoc}$ of about $2.1 \times 10^{-5}$ 1/s or slower, binds to human or murine OX40 with a $k_{dissoc}$ of about $2.2 \times 10^{-5}$ 1/s or slower, binds to human or murine OX40 with a $k_{dissoc}$ of about $2.3 \times 10^{-5}$ 1/s or slower, binds to human or murine OX40 with a $k_{dissoc}$ of about $2.4 \times 10^{-5}$ 1/s or slower, binds to human or murine OX40 with a $k_{dissoc}$ of about $2.5 \times 10^{-5}$ 1/s or slower, binds to human or murine OX40 with a $k_{dissoc}$ of about $2.6 \times 10^{-5}$ 1/s or slower or binds to human or murine OX40 with a $k_{dissoc}$ of about $2.7 \times 10^{-5}$ 1/s or slower, binds to human or murine OX40 with a $k_{dissoc}$ of about $2.8 \times 10^{-5}$ 1/s or slower, binds to human or murine OX40 with a $k_{dissoc}$ of about $2.9 \times 10^{-5}$ 1/s or slower, or binds to human or murine OX40 with a $k_{dissoc}$ of about $3 \times 10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 10. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H1$-$C_L$), 265-325 ($C_H2$) and 371-429 ($C_H3$) (and at positions 22"-95", 148"-204", 265"-325", and 371"-429"); light chain intrachain disulfide bridges at positions 23'-88' ($V_H$-$V_L$) and 134'-194' ($C_H1$-$C_L$) (and at positions 23'"-88" and 134"-194"); interchain heavy chain-heavy chain disulfide bridges at positions 230-230" and 233-233"; and interchain heavy chain-light chain disulfide bridges at 224-214' and 224"-214". Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO:56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises $V_H$ and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO:58 and SEQ ID NO:59, respectively. In an embodiment, a OX40 agonist comprises $V_H$ and $V_L$ regions that are each at least 95% identical to the sequences shown in SEQ ID NO:58 and SEQ ID NO:59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO:65, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 10

Amino acid sequences for OX40 agonist antibodies related to tavolixizumab.

| Identifier | Sequence (One-Letter Amino Acid Symbols) | |
|---|---|---|
| SEQ ID NO: 56<br>heavy chain for<br>tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVTVS<br>SASTKGPSVF PLAPSSKSTS GGTAALGCLV KDYFPEPVTV SWNSGALTSG VHTFPAVLQS<br>SGLYSLSSVV TVPSSSLGTQ TYICNVNHKP SNTKVDKRVE PKSCDKTHTC PPCPAPELLG<br>GPSVFLFPPK PKDTLMISRT PEVTCVVVDV SHEDPEVKFN WYVDGVEVHN AKTKPREEQY<br>NSTYRVVSVL TVLHQDWLNG KEYKCKVSNK ALPAPIEKTI SKAKGQPREP QVYTLPPSRE<br>EMTKNQVSLT CLVKGFYPSD IAVEWESNGQ PENNYKTTPP VLDSDGSFFL YSKLTVDKSR<br>WQQGNVFSCS VMHEALHNHY TQKSLSLSPG K | 60<br>120<br>180<br>240<br>300<br>360<br>420<br>451 |
| SEQ ID NO: 57<br>light chain for<br>tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 58<br>heavy chain<br>variable region<br>for<br>tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVT | 60<br>118 |
| SEQ ID NO: 59<br>light chain<br>variable region<br>for<br>tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKR | 60<br>108 |
| SEQ ID NO: 60<br>heavy chain CDR1<br>for<br>tavolixizumab | GSFSSGYWN | 9 |
| SEQ ID NO: 61<br>heavy chain CDR2<br>for<br>tavolixizumab | YIGYISYNGI TYH | 13 |
| SEQ ID NO: 62<br>heavy chain CDR3<br>for<br>tavolixizumab | RYKYDYDGGH AMDY | 14 |
| SEQ ID NO: 63<br>light chain CDR1<br>for<br>tavolixizumab | QDISNYLN | 8 |
| SEQ ID NO: 64<br>light chain CDR2<br>for<br>tavolixizumab | LLIYYTSKLH S | 11 |
| SEQ ID NO: 65<br>light chain CDR3<br>for<br>tavolixizumab | QQGSALPW | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 11.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO:66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region (V$_H$) comprises the sequence shown in SEQ ID NO:68, and the OX40 agonist light chain variable region (V$_L$) comprises the sequence shown in SEQ ID NO:69, and conservative amino acid substitutions thereof. In an embodiment, a OX40 agonist comprises V$_H$ and V$_L$ regions that are each at least 99% identical to the sequences shown in SEQ ID NO:68 and SEQ ID NO:69, respectively. In an embodiment, a OX40 agonist comprises V$_H$ and V$_L$ regions that are each at least 98% identical to the sequences shown in SEQ ID NO:68 and SEQ ID NO:69, respectively. In an embodiment, a OX40 agonist comprises V$_H$ and V$_L$ regions that are each at least 97% identical to the sequences shown in SEQ ID NO:68 and SEQ ID NO:69, respectively. In an embodiment, a OX40 agonist comprises V$_H$ and V$_L$ regions that are each at least 96% identical to the sequences shown in SEQ ID NO:68 and SEQ ID NO:69, respectively. In an embodiment, a OX40 agonist comprises V$_H$ and V$_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO:75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 11

Amino acid sequences for OX40 agonist antibodies related to 11D4.

| Identifier | Sequence (One-Letter Amino Acid Symbols) | |
|---|---|---|
| SEQ ID NO: 66<br>heavy chain for<br>11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSSAS<br>TKGPSVFPLA PCSRSTSEST AALGCLVKDY FPEPVTVSWN SGALTSGVHT FPAVLQSSGL<br>YSLSSVVTVP SSNFGTQTYT CNVDHKPSNT KVDKTVERKC CVECPPCPAP PVAGPSVFLF<br>PPKPKDTLMI SRTPEVTCVV VDVSHEDPEV QFNWYVDGVE VHNAKTKPRE EQFNSTFRVV<br>SVLTVVHQDW LNGKEYKCKV SNKGLPAPIE KTISKTKGQP REPQVYTLPP SREEMTKNQV<br>SLTCLVKGFY PSDIAVEWES NGQPENNYKT TPPMLDSDGS FFLYSKLTVD KSRWQQGNVF<br>SCSVMHEALH NHYTQKSLSL SPGK | 60<br>120<br>180<br>240<br>300<br>360<br>420<br>444 |
| SEQ ID NO: 67<br>light chain for<br>11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 68<br>heavy chain<br>variable region<br>for 11D4 | EVQLVESGGG LVQPGGSLRL SCAASGFTFS SYSMNWVRQA PGKGLEWVSY ISSSSSTIDY<br>ADSVKGRFTI SRDNAKNSLY LQMNSLRDED TAVYYCARES GWYLFDYWGQ GTLVTVSS | 60<br>118 |
| SEQ ID NO: 69<br>light chain<br>variable region<br>for 11D4 | DIQMTQSPSS LSASVGDRVT ITCRASQGIS SWLAWYQQKP EKAPKSLIYA ASSLQSGVPS<br>RFSGSGSGTD FTLTISSLQP EDFATYYCQQ YNSYPPTFGG GTKVEIK | 60<br>107 |
| SEQ ID NO: 70<br>heavy chain CDR1<br>for 11D4 | SYSMN | 5 |
| SEQ ID NO: 71<br>heavy chain CDR2<br>for 11D4 | YISSSSSTID YADSVKG | 17 |
| SEQ ID NO: 72<br>heavy chain CDR3<br>for 11D4 | ESGWYLFDY | 9 |

TABLE 11-continued

Amino acid sequences for OX40 agonist antibodies related to 11D4.

| Identifier | Sequence (One-Letter Amino Acid Symbols) | |
|---|---|---|
| SEQ ID NO: 73 light chain CDR1 for 11D4 | RASQGISSWL A | 11 |
| SEQ ID NO: 74 light chain CDR2 for 11D4 | AASSLQS | 7 |
| SEQ ID NO: 75 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 12.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to the sequences shown in SEQ ID NO:76 and SEQ ID NO:77, respectively. In an embodiment, a OX40 agonist comprises heavy and light chains that are each at least 96% identical to the sequences shown in SEQ ID NO:76 and SEQ ID NO:77, respectively. In an embodiment, a OX40 agonist comprises heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region ($V_L$) comprises the sequence shown in SEQ ID NO:79, and conservative amino acid substitutions thereof. In an embodiment, a OX40 agonist comprises $V_H$ and $V_L$ regions that are each at least 99% identical to the sequences shown in SEQ ID NO:78 and SEQ ID NO:79, respectively. In an embodiment, a OX40 agonist comprises $V_H$ and $V_L$ regions that are each at least 98% identical to the sequences shown in SEQ ID NO:78 and SEQ ID NO:79, respectively. In an embodiment, a OX40 agonist comprises $V_H$ and $V_L$ regions that are each at least 97% identical to the sequences shown in SEQ ID NO:78 and SEQ ID NO:79, respectively. In an embodiment, a OX40 agonist comprises $V_H$ and $V_L$ regions that are each at least 96% identical to the sequences shown in SEQ ID NO:78 and SEQ ID NO:79, respectively. In an embodiment, a OX40 agonist comprises $V_H$ and $V_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO:85, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 12

Amino acid sequences for OX40 agonist antibodies related to 18D8.

| Identifier | Sequence (One-Letter Amino Acid Symbols) | |
|---|---|---|
| SEQ ID NO: 76<br>heavy chain for<br>18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSSASTKGP SVFPLAPCSR STSESTAALG CLVKDYFPEP VTVSWNSGAL TSGVHTFPAV<br>LQSSGLYSLS SVVTVPSSNF GTQTYTCNVD HKPSNTKVDK TVERKCCVEC PPCPAPPVAG<br>PSVFLFPPKP KDTLMISRTP EVTCVVVDVS HEDPEVQFNW YVDGVEVHNA KTKPREEQFN<br>STFRVVSVLT VVHQDWLNGK EYKCKVSNKG LPAPIEKTIS KTKGQPREPQ VYTLPPSREE<br>MTKNQVSLTC LVKGFYPSDI AVEWESNGQP ENNYKTTPPM LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 77<br>light chain for<br>18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |
| SEQ ID NO: 78<br>heavy chain<br>variable region<br>for 18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSS | 60<br>120<br>124 |
| SEQ ID NO: 79<br>light chain<br>variable region<br>for 18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIK | 60<br>106 |
| SEQ ID NO: 80<br>heavy chain CDR1<br>for 18D8 | DYAMH | 5 |
| SEQ ID NO: 81<br>heavy chain CDR2<br>for 18D8 | GISWNSGSIG YADSVKG | 17 |
| SEQ ID NO: 82<br>heavy chain CDR3<br>for 18D8 | DQSTADYYFY YGMDV | 15 |
| SEQ ID NO: 83<br>light chain CDR1<br>for 18D8 | RASQSVSSYL A | 11 |
| SEQ ID NO: 84<br>light chain CDR2<br>for 18D8 | DASNRAT | 7 |
| SEQ ID NO: 85<br>light chain CDR3<br>for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 13.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodiment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO:93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

In some embodiments, the OX40 agonist is Hu106-222, which is a humanized antibody available from GlaxoSmithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 14.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

TABLE 13

Amino acid sequences for OX40 agonist antibodies related to Hu119-122.

| Identifier | Sequence (One-Letter Amino Acid Symbols) | |
|---|---|---|
| SEQ ID NO: 86 heavy chain variable region for Hu119-122 | EVQLVESGGG LVQPGGSLRL SCAASEYEFP SHDMSWVRQA PGKGLELVAA INSDGGSTYY PDTMERRFTI SRDNAKNSLY LQMNSLRAED TAVYYCARHY DDYYAWFAYW GQGTMVTVSS | 60 120 |
| SEQ ID NO: 87 light chain variable region for Hu119-122 | EIVLTQSPAT LSLSPGERAT LSCRASKSVS TSGYSYMHWY QQKPGQAPRL LIYLASNLES GVPARFSGSG SGTDFTLTIS SLEPEDFAVY YCQHSRELPL TFGGGTKVEI K | 60 111 |
| SEQ ID NO: 88 heavy chain CDR1 for Hu119-122 | SHDMS | 5 |
| SEQ ID NO: 89 heavy chain CDR2 for Hu119-122 | AINSDGGSTY YPDTMER | 17 |
| SEQ ID NO: 90 heavy chain CDR3 for Hu119-122 | HYDDYYAWFA Y | 11 |
| SEQ ID NO: 91 light chain CDR1 for Hu119-122 | RASKSVSTSG YSYMH | 15 |
| SEQ ID NO: 92 light chain CDR2 for Hu119-122 | LASNLES | 7 |
| SEQ ID NO: 93 light chain CDR3 for Hu119-122 | QHSRELPLT | 9 |

In an embodiment, a OX40 agonist comprises heavy chain CDR1, CDR2 and CDR3 domains having the sequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO:100, and SEQ ID NO:101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 14

Amino acid sequences for OX40 agonist antibodies related to Hu106-222.

| Identifier | Sequence (One-Letter Amino Acid Symbols) | |
|---|---|---|
| SEQ ID NO: 94 heavy chain variable region for Hu106-222 | QVQLVQSGSE LKKPGASVKV SCKASGYTFT DYSMHWVRQA PGQGLKWMGW INTETGEPTY ADDFKGRFVF SLDTSVSTAY LQISSLKAED TAVYYCANPY YDYVSYYAMD YWGQGTTVTV SS | 60 120 122 |
| SEQ ID NO: 95 light chain variable region for Hu106-222 | DIQMTQSPSS LSASVGDRVT ITCKASQDVS TAVAWYQQKP GKAPKLLIYS ASYLYTGVPS RFSGSGSGTD FTFTISSLQP EDIATYYCQQ HYSTPRTFGQ GTKLEIK | 60 107 |
| SEQ ID NO: 96 heavy chain CDR1 for Hu106-222 | DYSMH | 5 |
| SEQ ID NO: 97 heavy chain CDR2 for Hu106-222 | WINTETGEPT YADDFKG | 17 |
| SEQ ID NO: 98 heavy chain CDR3 for Hu106-222 | PYYDYVSYYA MDY | 13 |
| SEQ ID NO: 99 light chain CDR1 for Hu106-222 | KASQDVSTAV A | 11 |
| SEQ ID NO: 100 light chain CDR2 for Hu106-222 | SASYLYT | 7 |
| SEQ ID NO: 101 light chain CDR3 for Hu106-222 | QQHYSTPRT | 9 |

In some embodiments, the OX40 agonist antibody is MEDI6469 (also referred to as 9B12). MEDI6469 is a murine monoclonal antibody. Weinberg, et al., *J. Immunother.* 2006, 29, 575-585. In some embodiments the OX40 agonist is an antibody produced by the 9B12 hybridoma, deposited with Biovest Inc. (Malvem, Mass., USA), as described in Weinberg, et al., *J. Immunother.* 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, N.H.

In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table 6. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table 7. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SED ID NO:43 to SEQ ID NO:45.

In an embodiment, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 15, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40 L sequence. In an embodiment, an OX40 agonist fusion protein according to structures I-A or I-B comprises one or more OX40 binding domains comprising a sequence according to SEQ ID NO:102. In an embodiment, an OX40 agonist fusion protein according to structures I-A or I-B comprises one or more OX40 binding domains comprising a soluble OX40 L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 15, wherein the $V_H$ and $V_L$ domains are connected by a linker.

TABLE 15

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 102 OX40L | MERVQPLEEN VGNAARPRFE RNKLLLVASV IQGLGLLLCF TYICLHFSAL QVSHRYPRIQ | 60 |
| | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVNGGEL ILIHQNPGEF | 180 |
| | CVL | 183 |
| SEQ ID NO: 103 OX40L soluble domain | SHRYPRIQSI FTEYKKEKGF ILTSQKEDEI MKVQNNSVII NCDGFYLISL KGYFSQEVNI | 60 |
| | VNISLHYQKD EEPLFQLKKV RSVNSLMVAS LTYKDKVYLN VTTDNTSLDD FHVNGGELIL | 120 |
| | IHQNPGEFCV L | 131 |
| SEQ ID NO: 104 OX40L soluble domain (alternative) | YPRIQSIKVQ FTEYKKEKGF ILTSQKEDEI MKVQNNSVII NCDGFYLISL KGYFSQEVNI | 60 |
| | SLHYQKDEEP LFQLKKVRSV NSLMVASLTY KDKVYLNVTT DNTSLDDFHV NGGELILIHQ | 120 |
| | NPGEFCVL | 128 |
| SEQ ID NO: 105 variable heavy chain for 008 | EVQLVESGGG LVQPGGSLRL SCAASGFTFS NYTMNWVRQA PGKGLEWVSA ISGSGGSTYY | 60 |
| | ADSVKGRFTI SRDNSKNTLY LQMNSLRAED TAVYYCAKDR YSQVHYALDY WGQGTLVTVS | 120 |
| SEQ ID NO: 106 variable light chain for 008 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 107 variable heavy chain for 011 | EVQLVESGGG VVQPGRSLRL SCAASGFTFS DYTMNWVRQA PGKGLEWVSS ISGGSTYYAD | 60 |
| | SRKGRFTISR DNSKNTLYLQ MNNLRAEDTA VYYCARDRYF RQQNAFDYWG QGTLVTVSSA | 120 |
| SEQ ID NO: 108 variable light chain for 011 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 109 variable heavy chain for 021 | EVQLVESGGG LVQPRGSLRL SCAASGFTFS SYAMNWVRQA PGKGLEWVAV ISYDGSNKYY | 60 |
| | ADSVKGRFTI SRDNSKNTLY LQMNSLRAED TAVYYCAKDR YITLPNALDY WGQGTLVTVS | 120 |
| SEQ ID NO: 110 variable light chain for 021 | DIQMTQSPVS LPVTPGEPAS ISCRSSQSLL HSNGYNYLDW YLQKPGQSPQ LLIYLGSNRA | 60 |
| | SGVPDRFSGS GSGTDFTLKI SRVEAEDVGV YYCQQYKSNP PTFGQGTK | 108 |
| SEQ ID NO: 111 variable heavy chain for 023 | EVQLVESGGG LVHPGGSLRL SCAGSGFTFS SYAMHWVRQA PGKGLEWVSA IGTGGGTYYA | 60 |
| | DSVMGRFTIS RDNSKNTLYL QMNSLRAEDT AVYYCARYDN VMGLYWFDYW GQGTLVTVSS | 120 |
| SEQ ID NO: 112 variable light chain for 023 | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPAFGG GTKVEIKR | 108 |
| SEQ ID NO: 113 heavy chain variable region | EVQLQQSGPE LVKPGASVKM SCKASGYTFT SYVMHWVKQK PGQGLEWIGY INPYNDGTKY | 60 |
| | NEKFKGKATL TSDKSSSTAY MELSSLTSED SAVYYCANYY GSSLSMDYWG QGTSVTVSS | 119 |
| SEQ ID NO: 114 light chain variable region | DIQMTQTTSS LSASLGDRVT ISCRASQDIS NYLNWYQQKP DGTVKLLIYY TSRLHSGVPS | 60 |
| | RFSGSGSGTD YSLTISNLEQ EDIATYFCQQ GNTLPWTFGG GTKLEIKR | 108 |
| SEQ ID NO: 115 heavy chain variable region | EVQLQQSGPE LVKPGASVKI SCKTSGYTFK DYTMHWVKQS HGKSLEWIGG IYPNNGGSTY | 60 |
| | NQNFKDKATL TVDKSSSTAY MEFRSLTSED SAVYYCARMG YHGPHLDFDV WGAGTTVTVS | 120 |
| | P | 121 |
| SEQ ID NO: 116 light chain variable region | DIVMTQSHKF MSTSLGDRVS ITCKASQDVG AAVAWYQQKP GQSPKLLIYW ASTRHTGVPD | 60 |
| | RFTGGGSGTD FTLTISNVQS EDLTDYFCQQ YINYPLTFGG GTKLEIKR | 108 |
| SEQ ID NO: 117 heavy chain variable region of humanized antibody | QIQLVQSGPE LKKPGETVKI SCKASGYTFT DYSMHWVKQA PGKGLKWMGW INTETGEPTY | 60 |
| | ADDFKGRFAF SLETSASTAY LQINNLKNED TATYFCANPY YDYVSYYAMD YWGHGTSVTV | 120 |
| | SS | 122 |
| SEQ ID NO: 118 heavy chain variable region of humanized antibody | QVQLVQSGSE LKKPGASVKV SCKASGYTFT DYSMHWVRQA PGQGLKWMGW INTETGEPTY | 60 |
| | ADDFKGRFVF SLDTSVSTAY LQISSLKAED TAVYYCANPY YDYVSYYAMD YWGQGTTVTV | 120 |
| | SS | 122 |

TABLE 15-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 119 light chain variable region of humanized antibody | DIVMTQSHKF MSTSVRDRVS ITCKASQDVS TAVAWYQQKP GQSPKLLIYS ASYLYTGVPD RFTGSGSGTD FTFTISSVQA EDLAVYYCQQ HYSTPRTFGG GTKLEIK | 60 107 |
| SEQ ID NO: 120 light chain variable region of humanized antibody | DIVMTQSHKF MSTSVRDRVS ITCKASQDVS TAVAWYQQKP GQSPKLLIYS ASYLYTGVPD RFTGSGSGTD FTFTISSVQA EDLAVYYCQQ HYSTPRTFGG GTKLEIK | 60 107 |
| SEQ ID NO: 121 heavy chain variable region of humanized antibody | EVQLVESGGG LVQPGESLKL SCESNEYEFP SHDMSWVRKT PEKRLELVAA INSDGGSTYY PDTMERRFII SRDNTKKTLY LQMSSLRSED TALYYCARHY DDYYAWFAYW GQGTLVTVSA | 60 120 |
| SEQ ID NO: 122 heavy chain variable region of humanized antibody | EVQLVESGGG LVQPGGSLRL SCAASEYEFP SHDMSWVRQA PGKGLELVAA INSDGGSTYY PDTMERRFTI SRDNAKNSLY LQMNSLRAED TAVYYCARHY DDYYAWFAYW GQGTMVTVSS | 60 120 |
| SEQ ID NO: 123 light chain variable region of humanized antibody | DIVLTQSPAS LAVSLGQRAT ISCRASKSVS TSGYSYMHWY QQKPGQPPKL LIYLASNLES GVPARFSGSG SGTDFTLNIH PVEEEDAATY YCQHSRELPL TFGAGTKLEL K | 60 111 |
| SEQ ID NO: 124 light chain variable region of humanized antibody | EIVLTQSPAT LSLSPGERAT LSCRASKSVS TSGYSYMHWY QQKPGQAPRL LIYLASNLES GVPARFSGSG SGTDFTLTIS SLEPEDFAVY YCQHSRELPL TFGGGTKVEI K | 60 111 |
| SEQ ID NO: 125 heavy chain variable region | MYLGLNYVFI VFLLNGVQSE VKLEESGGGL VQPGGSMKLS CAASGFTFSD AWMDWVRQSP EKGLEWVAEI RSKANNHATY YAESVNGRFT ISRDDSKSSV YLQMNSLRAE DTGIYYCTWG EVFYFDYWGQ GTTLTVSS | 60 120 138 |
| SEQ ID NO: 126 light chain variable region | MRPSIQFLGL LLFWLHGAQC DIQMTQSPSS LSASLGGKVT ITCKSSQDIN KYIAWYQHKP GKGPRLLIHY TSTLQPGIPS RFSGSGSGRD YSFSISNLEP EDIATYYCLQ YDNLLTFGAG TKLELK | 60 120 126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, N.Y., USA.

In an embodiment, the OX40 agonist is OX40 agonistic antibody clone Ber-ACT35 commercially available from BioLegend, Inc., San Diego, Calif., USA.

E. STEP E: Harvest TILS

After the second expansion step, cells can be harvested. In some embodiments the TILs are harvested after one, two, three, four or more expansion steps, for example as provided in FIG. 9. In some embodiments the TILs are harvested after two expansion steps, for example as provided in FIG. 9.

TILs can be harvested in any appropriate and sterile manner, including for example by centrifugation. Methods for TEL harvesting are well known in the art and any such know methods can be employed with the present process. In some embodiments, TILS are harvest using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 9, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

F. STEP F: Final Formulation and Transfer to Infusion Bag

After Steps A through E as provided in an exemplary order in FIG. 9 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

G. Pharmaceutical Compositions, Dosages, and Dosing Regimens

In an embodiment, TILs expanded using the methods of the present disclosure are administered to a patient as the pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3 \times 10^{10}$ to about $13.7 \times 10^{10}$ TILs are administered, with an average of around $7.8 \times 10^{10}$ TILs, particularly if the cancer is melanoma. In an embodiment, about $1.2 \times 10^{10}$ to about $4.3 \times 10^{10}$ of TILs are administered. In some embodiments, about $3 \times 10^{10}$ to about $12 \times 10^{10}$ TILs are administered. In some embodiments, about $4 \times 10^{10}$ to about $10 \times 10^{10}$ TILs are administered. In some embodiments, about $5 \times 10^{10}$ to about $8 \times 10^{10}$ TILs are administered. In some embodiments, about $6 \times 10^{10}$ to about $8 \times 10^{10}$ TILs are administered. In some embodiments, about $7 \times 10^{10}$ to about $8 \times 10^{10}$ TILs are administered. In some embodiments, the therapeutically effective dosage is about $2.3 \times 10^{10}$ to about $13.7 \times 10^{10}$. In some embodiments, the therapeutically effective dosage is about $7.8 \times 10^{10}$ TILs, particularly of the cancer is melanoma. In some embodiments, the therapeutically effective dosage is about $1.2 \times 10^{10}$ to about $4.3 \times 10^{10}$ of TILs. In some embodiments, the therapeutically effective dosage is about $3 \times 10^{10}$ to about $12 \times 10^{10}$ TILs. In some embodiments, the therapeutically effective dosage is about $4 \times 10^{10}$ to about $10 \times 10^{10}$ TILs. In some embodiments, the therapeutically effective dosage is about $5 \times 10^{10}$ to about $8 \times 10^{10}$ TILs. In some embodiments, the therapeutically effective dosage is about $6 \times 10^{10}$ to about $8 \times 10^{10}$ TILs. In some embodiments, the therapeutically effective dosage is about $7 \times 10^{10}$ to about $8 \times 10^{10}$ TILs.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{11}$, $2 \times 10^{12}$, $3 \times 10^{11}$, $4 \times 10^{12}$, $5 \times 10^{12}$, $6 \times 10^{11}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the TILs provided in the pharmaceutical compositions of the invention is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25%

13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$ $5\times10^8$ $6\times10^8$, $7\times10^8$ $8\times10^8$, $9\times10^8$, $1\times10^9$ $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

H. Cryopreservation of TILs

As discussed above, and exemplified in Steps A through E as provided in FIG. 9, cryopreservation can occur at numerous points throughout the TIL expansion process. In some embodiments, the expanded population of TILs after the second expansion (as provided for example, according to Step D of FIG. 9) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Examples 8 and 9.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

I. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, at http://www.fda.gov/cber/guidelines.htm and https://www.fda.gov/BiologicsBloodVaccines/GuidanceComplianceRegulatoryInformation/Guidances/Blood/ucm076779.htm.

As provided on the FDA website, closed systems with sterile methods are known and well described. See, https://www.fda.gov/BiologicsBloodVaccines/GuidanceComplianceRegulatoryInformation/Guidances/Blood/ucm076779.htm, as referenced above and provided in pertinent part below.

Sterile connecting devices (STCDs) produce sterile welds between two pieces of compatible tubing. This procedure permits sterile connection of a variety of containers and tube diameters. This guidance describes recommended practices and procedures for use of these devices. This guidance does not address the data or information that a manufacturer of a sterile connecting device must submit to FDA in order to obtain approval or clearance for marketing. It is also important to note that the use of an approved or cleared sterile connecting device for purposes not authorized in the labeling may cause the device to be considered adulterated and misbranded under the Federal Food, Drug and Cosmetic Act.

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

C. Cell Cultures

In an embodiment, a method for expanding TILs, including those discuss above as well as exemplified in FIG. 9, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the first expansion is serum free. In some embodiments, the media in the second expansion is serum free. In some embodiments, the media in the first expansion and the second are both serum free. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad Calif.). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium for a duration of about 7 to 14 days, e.g., about 11 days. In some embodiments pre-REP is about 7 to 14 days, e.g., about 11 days. In some embodiments, REP is about 7 to 14 days, e.g., about 11 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5\times10^5$ cells/cm$^2$ to between $10\times10^6$ and $30\times10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

D. Optional Cryopreservation of TILs

Either the bulk TIL population or the expanded population of TILs can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIG. 9. In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS 10 and cell culture media. In a preferred embodiment, a population of TILs is cryopreserved using about a 1:1 (vol:vol) ratio of CS10 and cell culture media, further comprising additional IL-2.

According to particular embodiments, a cryopreservation composition (also referred to herein as a "dimethylsulfoxide-based cryopreservation medium") comprises a population of TILs prepared in accordance with the present invention (e.g., in an amount of $1\times10^6$ to $9\times10^{13}$), a cryoprotectant medium comprising DMSO that is suitable for preserving cells in low-temperature environments such as −70° C. to −196° C. (e.g., CryoStor® CS10) and an electrolyte solution (e.g., an isotonic solution such as PlasmaLyte® A). In a preferred embodiment, the cryoprotectant medium and electrolyte solution are present in a ratio of between about 1.2:1 and about 1:1.2, or between about 1.1:1 and about 1:1.1, or preferably about 1:1. According to one embodiment, the electrolyte solution comprises one or more of sodium, potassium, magnesium, acetate, chloride and gluconate, or a combination thereof; for example, the electrolyte solution may comprise sodium chloride, sodium gluconate, sodium acetate trihydrate, potassium chloride and magnesium chloride. According to an embodiment, the electrolyte solution has a pH between about 7 and about 8, preferably between about 7.2 and about 7.6, or about 7.4. Preferably, the cryopreservation composition further comprises one or more stabilizers (e.g., human serum albumin) and/or one or more lymphocyte growth factors (e.g., IL-2). For example, each of the cryoprotectant medium and the electrolyte solution may be present in the cryopreservation composition in an amount of about 20 mL to about 100 mL, or about 30 mL to about 70 mL, or about 40 mL to about 60 mL, or about 50 mL; human serum albumin may be present in an amount of about 0.01 g to about 2.0 g, or about 0.1 g to about 1.0 g, or about 0.5 g; and IL-2 may be present in an amount of about 0.001 mg to about 0.005 mg, or about 0.0015 mg to about 0.0025 mg, or about 0.0018 mg. The cryopreservation medium may optionally comprise one or more additional additives or excipients, such as pH adjusters, preservatives, etc.

According to one embodiment, a cryopreservation composition containing a population of TILs is composed of the following:

| Nominal Composition (% v/V) of Drug Product (100 mL basis) | | |
|---|---|---|
| Ingredient | Nominal Quantity per 100 mL fill | Function |
| Tumor Infiltrating Lymphocytes | $83 \times 10^7$ to $3.0 \times 10^{10}$ | Active Ingredient |
| CryoStor® CS10* | 50 mL | Cryopreservation medium |
| PlasmaLyte A | 50 mL | Isotonic agent |
| Human Serum Albumin (HSA) | 0.5 g | Stabilizer |
| Interleukin-2 | 0.0018 mg (30,000 IU) | Lymphocyte growth factor |
| Total | 100 mL | |

*Cryostor CS10 contains 10% dimethylsulfoxide (DMSO)

As discussed above in Steps A through E, cryopreservation can occur at numerous points throughout the TIL expansion process. In some embodiments, the bulk TIL population after the first expansion according to Step B or the expanded population of TILs after the one or more second expansions according to Step D can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

V. Methods of Treating Cancers and Other Diseases

The compositions and methods described herein can be used in a method for treating diseases. In an embodiment, they are for use in treating hyperproliferative disorders. They may also be used in treating other disorders as described herein and in the following paragraphs.

In some embodiments, the hyperproliferative disorder is cancer. In some embodiments, the hyperproliferative disorder is a solid tumor cancer. In some embodiments, the solid tumor cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma. In some embodiments, the hyperproliferative disorder is a hematological malignancy. In some embodiments, the solid tumor cancer is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m²/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the TILs described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32.

In some embodiments, IFN-gamma (IFN-γ) is indicative of treatment efficacy for hyperproliferative disorder treatment. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood of a subject treated with TILs prepared by the methods of the present invention, including those as described for example in FIG. 20 or FIG. 21. In some embodiments, the TILs obtained by the present method provide for increased IFN-γ in the blood of subjects treated with the TILs of the present method as compared to subjects treated with TILs prepared using methods referred to as process 1C, as exemplified in FIG. 13. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 20 or FIG. 21. In some embodiments, IFN-γ secretion is increased one-fold as compared to an untreated patient and/or as compared to a patient treated with TILs prepared using other methods than those provide herein including for example, methods other than those embodied in FIG. 20 or FIG. 21. In some embodiments, IFN-γ secretion is increased two-fold as compared to an untreated patient and/or as compared to a patient treated with TILs prepared using other methods than those provide herein including for example, methods other than those embodied in FIG. 20 or FIG. 21. In some embodiments, IFN-γ secretion is increased three-fold as compared to an untreated patient and/or as compared to a patient treated with TILs prepared using other methods than those provide herein including for example, methods other than those embodied in FIG. 20 or FIG. 21. In some embodiments, IFN-γ secretion is increased four-fold as compared to an untreated patient and/or as compared to a patient treated with TILs prepared using other methods than those provide herein including for example, methods other than those embodied in FIG. 20 or FIG. 21. In some embodiments, IFN-γ secretion is increased five-fold as compared to an untreated patient and/or as compared to a patient treated with TILs prepared using other methods than those provide herein including for example, methods other than those embodied in FIG. 20 or FIG. 21. In some embodiments, IFN-γ is measured using a Quantikine ELISA kit. In some embodiments, IFN-γ is measured using a Quantikine ELISA kit. In some embodiments, IFN-γ is measured in TILs ex vivo from a patient treated with the TILs produced by the methods of the present invention. In some embodiments, IFN-γ is measured in blood in a patient treated with the TILs produced by the methods of the present invention. In some embodiments, IFN-γ is measured in serum in a patient treated with the TILs produced by the methods of the present invention.

Figure 20:
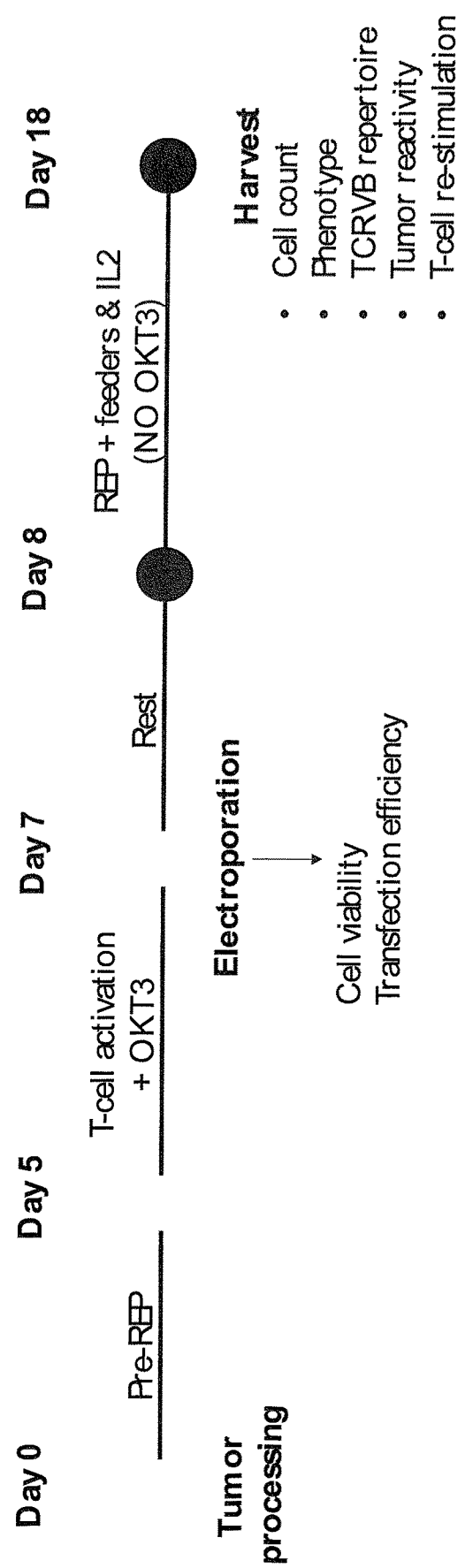
FIG. 20: Depiction of an embodiment of a TIL manufacturing process including electroporation step for use with gene-editing processes (including TALEN, zinc finger nuclease, and CRISPR methods as described herein).
Figure 21:
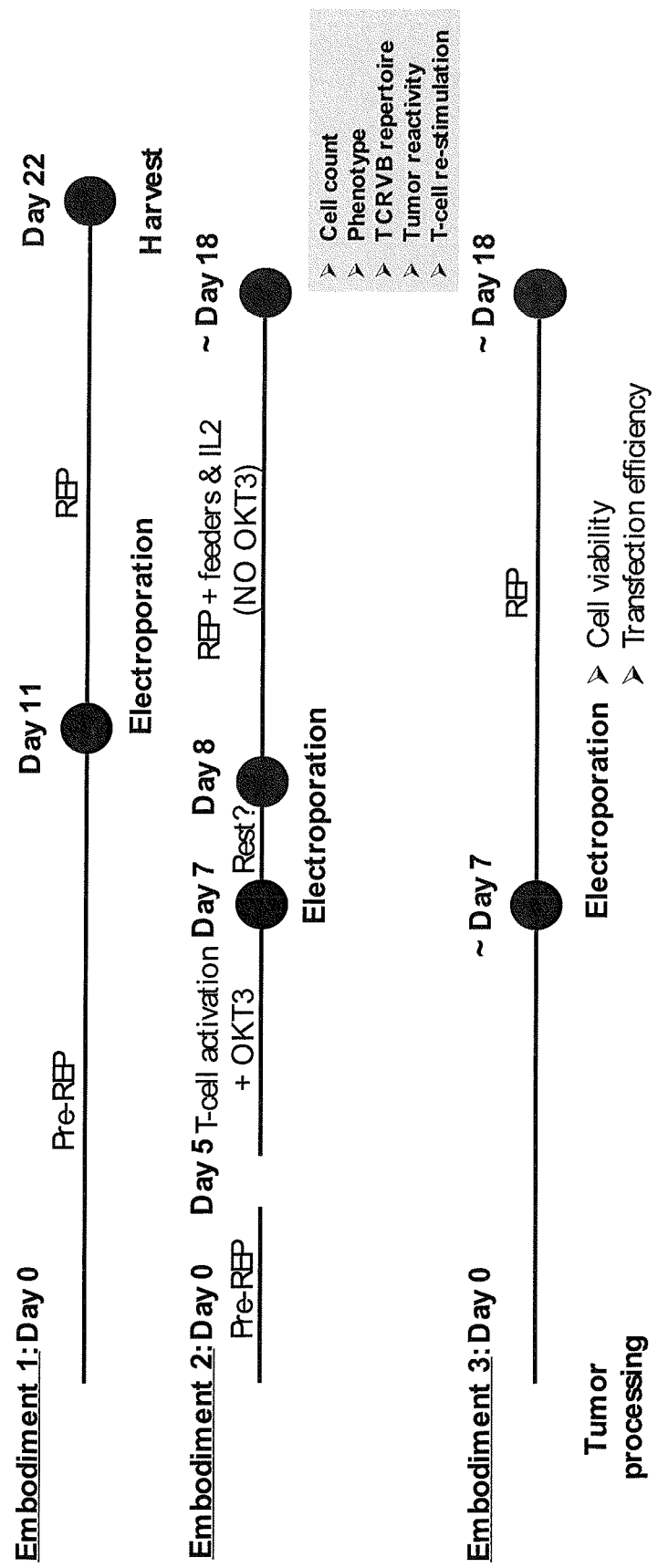
FIG. 21: Depiction of embodiments of TIL manufacturing processes including electroporation step for use with gene-editing processes (including TALEN, zinc finger nuclease, and CRISPR methods as described herein).

In some embodiments, the TILs prepared by the methods of the present invention, including those as described for example in FIG. 20 or FIG. 21, exhibit increased polyclonality as compared to TILs produced by other methods, including those not exemplified in FIG. 20 or FIG. 21, such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 20 or FIG. 21. In some embodiments, polyclonality is increased one-fold as compared to an untreated patient and/or as compared to a patient treated with TILs prepared using other methods than those provide herein including for example, methods other than those embodied in FIG. 9. In some embodiments, polyclonality is increased two-fold as compared to an untreated patient and/or as compared to a patient treated with TILs prepared using other methods than those provide herein including for example, methods other than those embodied in FIG. 9. In some embodiments, polyclonality is increased ten-fold as compared to an untreated patient and/or as compared to a patient treated with TILs prepared using other methods than those provide herein including for example, methods other than those embodied in FIG. 9. In some embodiments, polyclonality is increased 100-fold as compared to an untreated patient and/or as compared to a patient treated with TILs prepared using other methods than those provide herein including for example, methods other than those embodied in FIG. 9. In some embodiments, polyclonality is increased 500-fold as compared to an untreated patient and/or as compared to a patient treated with TILs prepared using other methods than those provide herein including for example, methods other than those embodied in FIG. 9. In some embodiments, polyclonality is increased 1000-fold as compared to an untreated patient and/or as compared to a patient treated with TILs prepared using other methods than those provide herein including for example, methods other than those embodied in FIG. 9.

1. Methods of Co-Administration

In some embodiments, the TILs produced as described herein, including for example TILs derived from a method described in FIG. 20 or FIG. 21, can be administered in combination with one or more immune checkpoint regulators, such as the antibodies described below. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)-BioXcell cat BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs produced according to Steps A through F as described herein. In some embodiments, the subject administered the combination of TILs produced according to Steps A through F is co administered with a and anti-PD-1 antibody when the patient has a cancer type that is refractory to administration of the anti-PD-1 antibody alone. In some embodiments, the patient is administered TILs in combination with and anti-PD-1 when the patient has refractory melanoma. In some embodiments, the patient is administered TILs in combination with and anti-PD-1 when the patient has non-small-cell lung carcinoma (NSCLC).

2. Optional Lymphodepletion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.*, 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 µg/mL to 10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 ng/mL-10 ng/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day, 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

3. IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., *Cancer* 2000, 88, 1703-9, the disclosures of which are incorporated herein by reference. In an embodiment, a decrescendo IL-2 regimen comprises 18×10$^6$ IU/m$^2$ administered intravenously over 6 hours, followed by 18×10$^6$ IU/m$^2$ administered intravenously over 12 hours, followed by 18×10$^6$ IU/m$^2$ administered intravenously over 24 hrs, followed by 4.5×10$^6$ IU/m$^2$ administered intravenously over 72 hours. This treatment cycle may be repeated every 28 days for a maximum of four cycles. In an embodiment, a decrescendo IL-2 regimen comprises 18,000,000 IU/m² on day 1, 9,000,000 IU/m² on day 2, and 4,500,000 IU/m² on days 3 and 4.

In an embodiment, the IL-2 regimen comprises administration of pegylated IL-2 every 1, 2, 4, 6, 7, 14 or 21 days at a dose of 0.10 mg/day to 50 mg/day.

4. Adoptive Cell Transfer

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). TILs for ACT can be prepared as described herein. In some embodiments, the TILs are prepared, for example, according to a method as described in FIG. 9. They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods. In some embodiments, TILs can be administered as described herein. In some embodiments, TILs can be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1. Production of a Cryopreserved TIL Therapy

This example describes the cGMP manufacture of TIL therapy in G-Rex Flasks according to current Good Tissue Practices and current Good Manufacturing Practices.

PROCESS REFERENCE Expansion Plan

| Estimated Day (post-seed) | Activity | Target Criteria | Anticipated Vessels | Estimated Total Volume (mL) |
|---|---|---|---|---|
| 0 | Tumor Dissection | ≤50 desirable tumor fragments per G-Rex100MCS | G-Rex100MCS 1 flask | ≤1000 |
| 11 | REP Seed | 5-200 × 10⁶ viable cells per G-Rex500MCS | G-Rex500MCS 1 flasks | ≤5000 |
| 16 | REP Split | 1 × 10⁹ viable cells per G-Rex500MCS | G-Rex500MCS ≤5 flasks | ≤25000 |
| 22 | Harvest | Total available cells | 3-4 CS-750 bags | ≤530 |

Flask Volumes:

| Flask Type | Working Volume/Flask (mL) |
|---|---|
| G-Rex100MCS | 1000 |
| G-Rex500MCS | 5000 |

Equipment
Equipment List: Day 0 CM1 Media Preparation/Tumor Wash Preparation/Tumor Dissection:
Magnehelic Gauge
Biological Safety Cabinet (BSC)
Incubator
CO2 Analyzer
Micropipetter (100-1000 μL)
Pipet-Aid
Baxa Repeater Pump
Sebra Tube Sealer
2-8° C. Refrigerator
−80° C. Freezer
−20° C. Freezer
Timer
Equipment List: CM2 Preparation/Day 11 REP Seed
Magnehelic Gauge
Biological Safety Cabinet (BSC)
Incubator
Incubator
CO2 Analyzer
Dry Bath
Water Bath
CytoTherm
Welder
Gatherex
NC200 NucleoCounter
Baxa Repeater Pump
Sebra Tube Sealer Balance
Equipment List: CM2 Preparation/Day 11 REP Seed
Centrifuge
Micropipetter (100-1000 μL)
Pipet-Aid
Timer
2-8° C. Refrigerator
−80° C. Freezer
Controlled Rate Freezer LN2 Storage Freezer (Quarantine)
−20° C. Freezer
Equipment List: CM4 Preparation/Day 16
Magnehelic Gauge
Biological Safety Cabinet (BSC)
Incubator
Incubator
CO2 Analyzer
Welder
Welder
Gatherex
NC200 NucleoCounter
Baxa Repeater Pump
Sebra Tube Sealer Balance
Micropipetter (100-1000 μL)
Pipet-Aid
2-8° C. Refrigerator
−80° C. Freezer
Equipment List: Day 22 Formulation, Fill, Cryopreservation
  Magnehelic Gauge
  Biological Safety Cabinet (BSC)
  Incubator
  Incubator
  CO2 Analyzer
  Welder
  Gatherex
  NC200 NucleoCounter
  Baxa Repeater Pump
  Sebra Tube Sealer Balance
  Micropipetter (20-200 μL) Pipet-Aid
Equipment List: Day 22 Formulation, Fill, Cryopreservation
  Pipet-Aid
  2-8° C. Refrigerator
  −80° C. Freezer
  Controlled Rate Freezer
  LN2 Storage Freezer
  LN2 Storage Freezer (Quarantine)
  LOVO Cell Processing System
7.0 Materials
  Materials: Day 0 CM1 Media Preparation/Tumor Wash Preparation/Tumor Dissection
  Disposable Scalpels, Sterile
  50 mL Serological Pipets, Sterile
  1 mL Serological Plastic Pipet, Sterile
  10 mL Serological Pipet, Sterile
  Centrifuge Tube, 50 mL, 28×114 mm, Conical Base, Screw Cap, PP, Sterile
  25 mL Serological Pipet, Sterile
  5 mL Serological Pipet, Sterile
  MF75 Series, Disposable Tissue Culture Filter, 1000 mL, aPES Filter, 0.2 μm, Sterile
  Pipets, Serological 100 mL
  2-mercaptoethanol 1000×, liquid, 55 mM in D-PBS
  Hank's Balanced Sodium Salt Solution (1×), Liquid, w/o Calcium Chloride, Magnesium Chloride, Magnesium Sulfate
  GlutaMAX 1-200 mM (100×), liquid
  ART Barrier Pipet Tips, 10004, Individually Wrapped, Sterile
  150 mm Petri Dish, Extra-Depth, Sterile
  6-well, Ultra-Low Attachment Plates, 9.5 cm$^2$ Well Growth Area, PS, Sterile
  Thermo Scientific Samco General-Purpose Transfer Pipettes. 7.7 mL, Sterile
  Repeater Pump Fluid Transfer Set Male Luer Lock End
  Long Forceps 8", Sterile
  Gentamicin Sulfate, 50 mg/mL stock
  Scientific Disposable Forceps, 4.5", Stainless Steel, Sterile
  100 mm petri dish, Sterile Extra Depth
  Pumpmatic Liquid-Dispensing System
  Gentamicin Sulfate, 50 mg/mL stock
  Syringe Cap Dual Function, Red
  RPMI-1640, 1 L Bottle
  G-Rex 100M Flask Closed System
  Sterile rulers
  Reconstituted IL-2
  Human Tumor Sample, Head and Neck ☐ N/A
  Human Tumor Sample, Cervical ☐ N/A
  GemCell Human Serum AB, Heat Inactivated ☐ N/A
  Human Tumor Sample, Melanoma
  GemCell Human Serum AB, Heat Inactivated
  Materials: CM2 Preparation/Day 11 REP Seed
  Luer-Lok Syringe, 60 mL Sterile Needle 16G×1.5" Sterile
  50 mL Serological Pipets, Sterile
  1 mL Serological Plastic, Pipet, Sterile
  Nunc Internally Threaded Cryotube Vials, Sterile
  10 mL Serological Pipet, Sterile
  Centrifuge Tube, 15 mL
  Centrifuge Tube, 50 mL
  Pipets, Serological 100 mL
  Syringe, 1 cc Sterile Luer-Lok
  3 mL Syringe, Luer-Lok Tip, Sterile
  5 mL Serological Pipet, Sterile
  Nalgene *MF75* Series Filter Unit Receiver, 250 mL, Sterile
  Nalgene MF75 Series Filter Unit Receiver, 500 mL, Sterile
  1000 mL Nalgene Rapid-Flow Sterile Disposable Filter Unit, 0.22 μm PES
  CryoStor CS-10
  2-mercaptoethanol 1000× Liquid, 55 mM in D-PBS
  GlutaMAX 1-200 mM (100×), liquid
  1,000 μL ART Barrier Sterile Pipet Tips, Individual Wrap
  VIA1 Cassettes
  Transfer Pack Container, 1000 mL w/ Coupler, Sterile
  Transfer Pack 300 mL w/ Coupler
  Sterile Alcohol Pads
  Repeater Pump Fluid Transfer Set Male Luer Lock Ends
  CTS AIM V 1 L Bottle
  MACS GMP CD3 pure (OKT-3)
  Gentamicin Sulfate, 50 mg/mL stock
  4" Tubing w/ Piercing Pin and Syringe Adapter
  Syringe Only Luer-Lok 10 mL
  Tubing, Four Spike Male Luer Manifold
  Gravity Blood Administration Set Y-type with No injection site, 170 μm blood filter
  Pumpmatic Liquid-Dispensing System
  10 L Labtainer 3 Port Bag
  Gentamicin Sulfate, 50 mg/mL stock
  100 mL Syringe
  3000 mL Culture Bag
  Origen Cell Connect CC2
  Syringe Cap Dual Function Red
  RPMI-1640, 1 L Bottle
  G-Rex 500M Flask Closed System
  Reconstituted IL-2
  Allogeneic Irradiated Feeder Cells
  Allogeneic Irradiated Feeder Cells
  Human Serum, type AB(HI) Gemini
  Human Serum, type AB(HI) Gemini Materials: CM4 Preparation/Day 16
Luer-Lok Syringe, 60 mL Sterile
1 mL Serological Plastic Pipet, Sterile
Nunc Internally Threaded Cyrotube Vials, Sterile
10 mL Serological Pipets, Sterile
Centrifuge Tube, 15 mL
Centrifuge Tube, 50 mL
Pipets, Serological 100 mL
Syringe with Luer-Lock, sterile, 3 mL
5 mL Serological Pipet, Sterile
Syringe only Luer-Lok 10 mL
Nalgene *MF75* Series
Filter Unit Receiver, 250 mL, Sterile
GlutaMAX1-200 mM (100×), liquid
ART Barrier Pipet Tips, 1000 µl, Individually Wrapped, Sterile
VIA1 Cassettes
Materials: CM4 Preparation/Day 16
Transfer Pack Container, 1000 mL with Coupler, Sterile
Sterile Alcohol Pads
Repeater Pump Fluid Transfer Set Male Luer Lock Ends
CTS AIM-V 1000 mL ☐ N/A
Plasma Transfer Set 4" Tubing with Female Luer Adapter
30 mL Luer-Lok Sterile Syringe
CTS AIM V 10 L bag
Pumpmatic Liquid-Dispensing System
10 L Labtainer 3 Port Bag
Syringe Cap Dual Function Red
G-Rex500M Flask Closed System
Reconstituted IL-2
Materials: Day 22 Formulation, Fill, Cryopreservation
Luer-Lok Syringe, 60 mL Sterile
Needle 16G×1.5" Sterile
50 mL Serological Pipets, Sterile
Nunc Internally Threaded Cryotubes Vials, Sterile
10 mL Serological Pipet, Sterile
Centrifuge Tube, 15 mL
Centrifuge Tube, 50 mL
Syringe, 1 cc Sterile Luer-Lok
3 mL Syringe, Luer-Lok Tip, Sterile
25 mL Serological Pipet, Sterile
5 mL Serological Pipet, Sterile
Syringe only Luer-Lok 10 mL
Pipets, Serological 100 mL
ART Barrier Sterile Pipet Tips, 200 µL Individual Wrap
VIA1-Cassettes
Plasma-Lyte A Injection 1 L
LOVO Cell Washing Disposable Set
LOVO Ancillary Bag Kit
Sterile Alcohol Pads
Repeater Pump Fluid Transfer Set Male Luer Lock Ends
CTS AIM V 1 L Bottle
Human Albumin 25%
Plasma Transfer Set 4" Tubing with Female Luer Adapter
Tubing, Four Male Luer Manifold
Gravity Blood Administration
Set Y-type with No injection site, 170 µm blood filter
Pumpmatic Liquid-Dispensing System
10 L Labtainer 3 Port Bag
100 mL Syringe
Cryo bag CS750
3 L Culture Bag
Origen Cell Connect CC2
Syringe Cap Dual Function Red
Cryostor CS10, 100 mL Bag
Dispensing Spike, Vented
Reconstituted IL-2

Process
8.1 Day 0 CM1 Media Preparation
    8.1.1 Checked room sanitization, line clearance, and materials. Confirmed room sanitization,
    8.1.2 Ensured completion of pre-processing table.
    8.1.3 Environmental Monitoring. Prior to processing, ensured pre-process environmental monitoring had been initiated.
    8.1.4 Prepared RPMI 1640 Media In the BSC, using an appropriately sized pipette, removed 100.0 mL from 1000 mL RPMI 1640 Media and placed into an appropriately sized container labeled "Waste".
    8.1.5 In the BSC added reagents to RPMI 1640 Media bottle. Added the following reagents to the RPMI 1640 Media bottle as shown in in table. Recorded volumes added.
Amount Added per bottle: Heat Inactivated Human AB Serum (100.0 mL); GlutaMax (10.0 mL); Gentamicin sulfate, 50 mg/mL (1.0 mL); 2-mercaptoethanol (1.0 mL)
    8.1.6 Mixed Media. Capped RPMI 1640 Media bottle from Step 8.1.5 and swirled bottle to ensure reagents were mixed thoroughly.
    8.1.7 Filtered RPMI media. Filtered RPMI 1640 Media from Step 8.1.6 through 1 L 0.22-micron filter unit.
    8.1.8 Labeled filtered media. Aseptically capped the filtered media and labeled with the following information.
    8.1.9 Removed unnecessary materials from BSC. Passed out media reagents from BSC, left Gentamicin Sulfate and HBSS in BSC for Formulated Wash Media preparation in Section 8.2.
    8.1.10 Stored unused consumables. Transferred any remaining opened/thawed media reagents to appropriate storage conditions or disposed into waste.
NOTE: Assigned the appropriate open expiry to media reagents per Process Note 5.9 and labeled with batch record lot number
    8.1.11 Thawed IL-2 aliquot. Thawed one 1.1 mL IL-2 aliquot ($6\times10^6$ IU/mL) (BR71424) until all ice had melted. Recorded IL-2: Lot # and Expiry (NOTE: Ensured IL-2 label was attached).
    8.1.12 Transferred IL-2 stock solution to media. In the BSC, transferred 1.0 mL of IL-2 stock solution to the CM1 Day 0 Media Bottle prepared in Step 8.1.8. Added CM1 Day 0 Media 1 bottle and IL-2 ($6\times10^6$ IU/mL) 1.0 mL.
    8.1.13 Mixed and Relabeled. Capped and swirled the bottle to mix media containing IL-2. Relabeled as "Complete CM1 Day 0 Media" and assigned new lot number.
    8.1.14 Sample Media per Sample Plan. Removed 20.0 mL of media using an appropriately sized pipette and dispensed into a 50 mL conical tube.
    8.1.15 Labeled and stored. Sample labeled with sample plan inventory label and stored "Media Retain" sample at 2-8° C. until submitted to Login for testing per Sample Plan.
    8.1.16 Signed for Sampling. Ensured that LIMS sample plan sheet was completed for removal of the sample.
    8.1.17 Prepared "Tissue Pieces" conical tube. In BSC, transferred 25.0 mL of "Complete CM1 Day 0 Media" (prepared in Step 8.1.13) to a 50 mL conical tube. Labeled the tube as "Tissue Pieces" and batch record lot number.
    8.1.18 Passed G-Rex100MCS into BSC. Aseptically passed G-Rex100MCS (W3013130) into the BSC.

8.1.19 Prepared G-Rex100MCS. In the BSC, closed all clamps on the G-Rex100MCS, leaving vent filter clamp open.

8.1.20 Prepared G-Rex100MCS. Connected the red line of G-Rex100MCS flask to the larger diameter end of the repeater pump fluid transfer set (W3009497) via luer connection.

8.1.21 Prepared Baxa Pump. Staged Baxa pump next to BSC. Removed pump tubing section of repeater pump fluid transfer set from BSC and installed in repeater pump.

8.1.22 Prepared to pump media. Within the BSC, removed the syringe from Pumpmatic Liquid-Dispensing System (PLDS) (W3012720) and discarded. NOTE: Ensured to not compromise the sterility of the PLDS pipette.

8.1.23 Prepared to pump media. Connected PLDS pipette to the smaller diameter end of repeater pump fluid transfer set via luer connection and placed pipette tip in "Complete CM1 Day 0 Media" (prepared in Step 8.1.13) for aspiration.

Opened all clamps between media and G-Rex100MCS.

8.1.24 Pumped Complete CM1 media into G-Rex100MCS flask. Set the pump speed to "High" and "9" and pumped all Complete CM1 Day 0 Media into G-Rex100MCS flask. Once all media was transferred, cleared the line and stopped pump.

8.1.25 Disconnected pump from flask. Ensured all clamps were closed on the flask, except vent filter. Removed the repeater pump fluid transfer set from the red media line, and placed a red cap (W3012845) on the red media line.

8.1.26 Heated seal. Removed G-Rex100MCS flask from BSC, heated seal (per Process Note 5.12) off the red cap from the red line near the terminal luer.

8.1.27 Labeled G-Rex100MCS. Labeled G-Rex100MCS flask with QA provided in-process "Day 0" label. Attached sample "Day 0" label below.

8.1.28 Monitored Incubator. Incubator parameters: Temperature LED Display: 37.0±2.0° C.; CO2 Percentage: 5.0±1.5% CO2

8.1.29 Warmed Media. Placed the 50 mL conical tube labeled "Tissue Fragments" prepared in Step 8.1.17 and the G-Rex100MCS prepared in Step 8.1.27 in incubator for ≥30 minutes of warming.

Recorded warming times below. Recorded if Warm Time was ≥30 minutes (Yes/No).

[Tissue Fragments Conical or GRex100MCS]

8.1.30 Reviewed Section 8.1.

8.2 Day 0 Tumor Wash Media Preparation 8.2.1 Added Gentamicin to HBSS. In the BSC, added 5.0 mL Gentamicin (W3009832 or W3012735) to 1×500 mL HBSS Media (W3013128) bottle. Recorded volumes. Added per bottle: HBSS (500.0 mL); Gentamicin sulfate, 50 mg/ml (5.0 mL)

8.2.2 Capped HBSS bottle and swirled. Capped HBSS containing gentamicin prepared in Step 8.2.1 and swirled bottle to ensure reagents are mixed thoroughly.

8.2.3 Filtered Solution. Filtered HBSS containing gentamicin prepared in Step 8.2.1 through a 1 L 0.22-micron filter unit (W1218810).

8.2.4 Aseptically capped the filtered media and label. Aseptically capped the filtered media and labeled with the following information. Proceeded to SECTION 8.3.

8.2.5 Reviewed Section 8.2.

8.3 Day 0 Tumor Processing 8.3.1 Obtained Tumor. Obtained tumor specimen from QAR and transferred into suite at 2-8° C. immediately for processing. Ensured all necessary information is recorded on the Tumor Shipping Batch Record.

8.3.2 Recorded Tumor Information.

8.3.3 Affixed Tumor Label. Affixed tumor Attachment. QAR release sticker below. Attached Tumor Shipping Batch Record as #5.

8.3.4 Passed in necessary materials for tumor dissection into the BSC.

8.3.5 Opened Materials. Opened all materials inside the BSC, ensuring not to compromise the sterility of the items.

8.3.6 Labeled Materials. Labeled three 50 ml conical tubes: the first as "Forceps," the second as "Scalpel," and the third as "Fresh Tumor Wash Media". Labeled 5×100 mm petri dishes as "Wash 1," "Wash 2," "Wash 3," "Holding," and "Unfavorable." Labeled one 6 well plate as "Favorable Intermediate Fragments."

8.3.7 Aliquoted Tumor Wash Media. Using an appropriately sized pipette, transferred 5.0 mL of "Tumor Wash Media" prepared in Step 8.2.4 into each well of one 6-well plate for favorable intermediate tumor fragments (30.0 mL total). NOTE: The forceps and scalpels were stored in their respective tumor wash media conicals as needed during the tumor washing and dissection processes.

8.3.8 Aliquoted Tumor Wash Media Using an appropriately sized pipette, transferred 50.0 mL of "Tumor Wash Media" prepared in Step 8.2.4 into each 100 mm petri dish for "Wash 1," "Wash 2," "Wash 3," and "Holding" (200.0 mL total).

8.3.9 Aliquoted Tumor Wash Media Using an appropriately sized pipette, transfer 20.0 mL of "Tumor Wash Media" prepared in Step 8.2.4 into each 50 mL conical (60.0 mL total).

8.3.10 Prepared Lids for Tumor Pieces. Aseptically removed lids from two 6-well plates. The lids were utilized for selected tumor pieces. NOTE: Throughout tumor processing, DID NOT cross over open tissue culture plates and lids.

8.3.11 Passed the tumor into the BSC. Aseptically passed the tumor into the BSC. Recorded processing start time.

8.3.12 Tumor Wash 1 Using 8" forceps (W3009771), removed the tumor from the specimen bottle and transferred to the "Wash 1" dish prepared in Step 8.3.8.

NOTE: Retained the solution in specimen bottle.

8.3.13 Tumor Wash 1 Using forceps, gently washed tumor time from timer below: specimen and allowed it to sit for ≥3 minutes. Recorded wash time (MM:SS).

8.3.14 Prepared Bioburden Sample per Sample Plan. Transferred 20.0 mL (or available volume) of solution from the tumor specimen bottle into a 50 mL conical per sample plan.

8.3.15 Labeled and stored sample. Labeled with sample plan inventory label and stored bioburden sample collected in Step 8.3.14 at 2-8° C. until submitted for testing.

8.3.16 Signed for sampling. Ensured that LIMS sample plan sheet was completed for removal of the sample.

8.3.17 Tumor Wash 2. Using a new set of forceps removed the tumor from the "Wash 1" dish and transferred to the "Wash 2" dish prepared in Step 8.3.8.

8.3.18 Tumor Wash 2. Using forceps, washed tumor specimen by gently agitating for ≥3 minutes and allowed it to sit. Recorded time.

8.3.19 Prepared drops of Tumor Wash Media for desired tumor pieces. Using a transfer pipette, placed 4 individual drops of Tumor Wash Media from the conical prepared in Step 8.3.9 into each of the 6 circles on the upturned lids of the 6-well plates (2 lids). Placed an extra drop on two circles for a total of 50 drops.

8.3.20 Tumor Wash 3. Using forceps, removed the tumor from the "Wash 2" dish and transferred to the "Wash 3" dish prepared in Step 8.3.8.

8.3.21 Tumor Wash 3. Using forceps, washed tumor specimen by gently agitating and allowed it to sit for ≥3 minutes. Recorded time.

8.3.22 Prepared tumor dissection dish. Placed a ruler under 150 mm dish lid.

8.3.23 Transferred Tumor to Dissection Dish. Using forceps, aseptically transferred tumor specimen to the 150 mm dissection dish lid.

8.3.24 Measured Tumor. Arranged all pieces of tumor specimen end to end and recorded the approximate overall length and number of fragments. Took a clear picture of each tumor specimen.

8.3.25 Assessed Tumor. Assessed the tumor for necrotic/fatty tissue. Assessed whether >30% of entire tumor area observed to be necrotic and/or fatty tissue; if yes, contacted area management to ensure tumor was of appropriate size, then proceeded to Step 8.3.26. Assessed whether <30% of entire tumor area were observed to be necrotic or fatty tissue; if yes, proceeded to Step 8.3.27 and clean-up dissection was NOT performed.

8.3.26 If applicable: Clean-Up Dissection. If tumor was large and >30% of tissue exterior was observed to be necrotic/fatty, performed "clean up dissection" by removing necrotic/fatty tissue while preserving tumor inner structure using a combination of scalpel and/or forceps. NOTE: To maintain tumor internal structure, used only vertical cutting pressure. Did not cut in a sawing motion with scalpel. NOTE: Fat, necrotic, and extraneous tissue were placed in unfavorable dish.

8.3.27 Dissect Tumor Using a combination of scalpel and/or forceps, cut the tumor specimen into even, appropriately sized fragments (up to 6 intermediate fragments). NOTE: To maintain tumor internal structure, use only vertical cutting pressure. Did not cut in a sawing motion with scalpel. NOTE: Ensured to keep non-dissected intermediate fragments completely submerged in "Tumor Wash Media" (prepared in Step 8.2.4).

8.3.28 Transferred intermediate tumor fragments. Transferred each intermediate fragment to the "holding" dish from Step 8.3.8.

8.3.29 Dissected Tumor Fragments. Manipulated one intermediate fragment at a time, dissected the tumor intermediate fragment in the dissection dish into pieces approximately 3×3×3 mm in size, minimizing the amount of hemorrhagic, necrotic, and/or fatty tissues on each piece. NOTE: To maintain tumor internal structure, used only vertical cutting pressure. Did not cut in a sawing motion with scalpel.

8.3.30 Selected Tumor Pieces. Selected up to eight (8) tumor pieces without hemorrhagic, necrotic, and/or fatty tissue. Used the ruler for reference. Continued dissection until 8 favorable pieces have been obtained, or the entire intermediate fragment has been dissected. Transferred each selected piece to one of the drops of "Tumor Wash Media" prepared in Step 8.3.19.

8.3.31 Stored Intermediate Fragments to Prevent Drying. After selecting up to eight (8) pieces from the intermediate fragment, placed remnants of intermediate fragment into a new single well of "Favorable Intermediate Fragments" 6-well plate prepared in Step 8.3.7. NOTE: Fatty or necrotic tissue was placed in the "Unfavorable" dish (prepared in step 8.3.6).

8.3.32 Repeated Intermediate Fragment Dissection. Proceeded to the next intermediate fragment, repeated Steps 8.3.29-8.3.31 until all intermediate fragments had been processed, obtained fresh scalpels and forceps as needed.

8.3.33 Determined number of pieces collected. If desirable tissue remains, selected additional Favorable Tumor Pieces from the "favorable intermediate fragments" 6-well plate to fill the drops for a maximum of 50 pieces. Recorded the total number of dissected pieces created. NOTE: Ensuring to keep the tumor intermediate fragments hydrated with Wash Medium as necessary throughout dissection. Recorded Total quantity of dissected pieces collected.

8.3.34 Removed Conical Tube from Incubator. Removed the "Tissue Pieces" 50 mL conical tube from the incubator. Recorded time in Step 8.1.29. Ensured conical tube was warmed for ≥30 min.

8.3.35 Prepared Conical Tube. Passed "Tissue Pieces" 50 mL conical into the BSC, ensuring not to compromise the sterility of open processing surfaces.

8.3.36 Transferred Tumor Pieces to 50 mL Conical Tube. Using a transfer pipette, scalpel, forceps or combination, transferred the selected 50 best tumor fragments from favorable dish lids to the "Tissue Pieces" 50 mL conical tube. NOTE: If a tumor piece was dropped during transfer and desirable tissue remains, additional pieces from the favorable tumor intermediate fragment wells were added. Recorded numbers of pieces.

8.3.37 Prepared BSC for G-REX100MCS. Removed all unnecessary items from BSC for vessel seed, retaining the favorable tissue plates if they contained extra fragments.

8.3.38 Removed G-REX100MCS from Incubator. Removed G-Rex100MCS containing media from incubator. Completed Step 8.1.29.

8.3.39 Passed flask into BSC. Aseptically passed G-Rex100MCS flask into the BSC. NOTE: When transferring the flask, did not hold from the lid or the bottom of the vessel. Transferred the vessel by handling the sides. NOTE: Only utilized IPA WIPES when handling G-Rex flasks.

8.3.40 Added tumor fragments to G-Rex100MCS flask. In the BSC, lifted G-Rex100MCS flask cap, ensuring that sterility of internal tubing was maintained. Swirled conical tube with tumor pieces to suspend and quickly poured the contents into the G-Rex100MCS flask.

8.3.41 Evenly distributed pieces. Ensured that the tumor pieces were evenly distributed across the membrane of the flask. Gently tilted the flask back and forth if necessary to evenly distribute the tumor pieces.

8.3.42 Recorded total number of tumor fragments in vessel. Recorded number of tumor fragments on bottom membrane of vessel and number of observed to be floating in vessel. NOTE: If the number of fragments seeded were NOT equivalent to number of collected in Step 8.3.36H, contacted Area Management, and document in Section 10.0.

8.3.43 Incubate G-Rex flask Incubated G-Rex100MCS at the following parameters: Incubated G-Rex flask: Temperature LED Display: 37.0±2.0° C.; CO2 Percentage: 5.0±1.5% CO2

8.3.44 Calculated incubation window. Performed calculations to determine the proper time to remove G-Rex100MCS incubator on Day 11. Calculations: Time of incubation; lower limit=time of incubation+252 hours; upper limit=time of incubation+276 hours 8.3.45 Environmental Monitoring. After processing, verified BSC and personnel monitoring were performed.

8.3.46 Discarded materials. Stored remaining unwarmed media at 2-8° C. and labeled. After process was complete, discarded any remaining warmed media and thawed aliquots of IL-2.

8.3.47 Sample submission. Ensured all Day 0 samples were submitted to Login and transferred in LIMS.

8.3.48 Review Section 8.3.

8.4 Day 11—Media Preparation 8.4.1 Checked room, sanitization, line clearance, and materials. Confirmed room sanitization, line clearance, and that materials are within expiry.

8.4.2 Pre-processing table. Equipment list: BSC; Balance; Sebra Tube Sealer; Gatherex™ Media Removal and Cell Recovery Device; Ensure QA provided placard is placed on the appropriate BSC; Ensure QA provided placard lot number and patient ID display matches the lot number and patient ID in this Batch Record.

8.4.3 Monitored Incubator. Monitored Incubator. Incubator parameters: Temperature LED Display: 37.0±2.0° C.; CO2 Percentage: 5.0±1.5% CO2. NOTE: Section 8.4 may be run concurrently with section 8.5.

8.4.4 Warmed media. Warmed 3×1000 mL RPMI 1640 Media (W3013112) bottles and 3×1000 mL AIM-V (W3009501) bottles in an incubator for ≥30 minutes. Recorded time. Media: RPMI 1640 and AIM-V. NOTE: Placed an additional 1×1000 ml bottle of AIM-V Media (W3009501) at room temperature for use in Step 8.5.34. Labeled the bottle "For Cell Count Dilutions Only" and the batch record lot number.

8.4.5 Environmental monitoring. Prior to processing, ensured pre-process environmental monitoring was performed as per SOP-00344.

8.4.6 Removed RPMI 1640 Media from incubator. Removed the RPMI 1640 Media when time was reached. Record end incubation time in Step 8.4.4. Ensure media was warmed for ≥30 min.

8.4.7 Prepared RPMI 1640 Media. In the BSC, removed 100.0 mL from each of the three pre-warmed 1000 mL RPMI 1640 Media bottles and placed into an appropriately sized container labeled "Waste".

8.4.8 In BSC add reagents to RPMI 1640 Media bottle. In the BSC added the following reagents to each of the three RPMI 1640 Media bottles. Recorded volumes added to each bottle. GemCell Human serum, Heat Inactivated Type AB (100.0 mL), GlutaMax (10.0 mL), Gentamicin sulfate, 50 mg/nil (1.0 mL), 2-mercaptoethanol (1.0 mL)

8.4.9 Filter Media. Caped bottles from Step 8.4.8 and swirled to ensure reagents were mixed thoroughly. Filtered each bottle of media through a separate 1 L 0.22-micron filter unit.

8.4.10 Labeled filtered media. Aseptically capped the filtered media and labeled each bottle with CM1 Day 11 Media.

8.4.11 Thawed IL-2 aliquot. Thawed 3×1.1 mL aliquots of IL-2 (6×106 IU/mL) (BR71424) until all ice had melted Recorded IL 2 lot # and Expiry. NOTE: EnsureIL-2 label is attached.

8.4.12 Removed AIM-V Media from the incubator. Removed the three bottles of AIM-V Media from the incubator. Recorded end incubation time in Step 8.4.4. Ensured media had been warmed for ≥30 minutes.

8.4.13 Add IL-2 to AIM-V. In the BSC, using a micropipette, added 3.0 mL of thawed IL-2 into one 1 L bottle of pre-warmed AIM-V media. Rinse micropipette tip with media after dispensing IL-2. Use a new sterile micropipette tip for each aliquot. Recorded the total volume added. Labeled bottle as "AIM-V Containing IL-2".

8.4.14 Transferred materials. Aseptically transferred a 10 L Labtainer Bag and a repeater pump transfer set into the BSC.

8.4.15 Prepared 10 L Labtainer media bag. Closed all lines on a 10 L Labtainer bag. Attached the larger diameter tubing end of a repeater pump transfer set to the middle female port of the 10 L Labtainer Bag via luer lock connection.

8.4.16 Prepare Baxa pump. Staged the Baxa pump next to the BSC. Fed the transfer set tubing through the Baxa pump situated outside of the BSC. Set the Baxa Pump to "High" and "9".

8.4.17 Prepared 10 L Labtainer media bag. In BSC, removed syringe from Pumpmatic Liquid-Dispensing System (PLDS) and discarded. NOTE: Ensured to not compromise the sterility of the PLDS pipette.

8.4.18 Prepared 10 L Labtainer media bag. Connected PLDS pipette to smaller diameter end of repeater pump fluid transfer set via luer connection and placed pipette tip in AIM-V media containing IL-2 bottle (prepared in Step 8.4.13) for aspiration. Opened all clamps between media bottle and 10 L Labtainer.

8.4.19 Pumped media into 10 L Labtainer. In the BSC, using the PLDS, transfer pre-warmed AIM-V media containing IL-2 prepared in Step 8.4.13, as well as two additional AIM-V bottles into the 10 L Labtainer bag. Added the three bottles of filtered CM1 Day 11 Media from Step 8.4.10. After addition of final bottle, cleared the line to the bag. NOTE: Stopped the pump between addition of each bottle of media.

8.4.20 Removed pumpmatic from Labtainer bag. Removed PLDS from the transfer set and placed a red cap on the luer of the line in the BSC.

8.4.21 Mixed media. Gently massaged the bag to mix.
8.4.22 Labeled media. In the BSC, labeled the media bag with the following information. Expiration date was 24 hours from the preparation date.
8.4.23 Sample media per sample plan. In the BSC, attached a 60 mL syringe to the available female port of the "Complete CM2 Day 11 Media" bag prepared in step 8.4.22. Removed 20.0 mL of media and place in a 50 mL conical tube. Placed a red cap on the female port of the "Complete CM2 Day 11 Media" Bag.
8.4.24 Labeled and stored sample. Labeled with sample plan inventory label and stored Media Retain Sample at 2-8° C. until submitted to Login for testing.
8.4.25 Sign for Sampling. Ensured that LIMS sample plan sheet was completed for removal of the sample.
8.4.26 Sealed the transfer set line. Outside the BSC, heat sealed off (per Process Note 5.12) the red cap on the transfer set line, close to red cap. Kept the transfer set on the bag.
8.4.27 Prepared Cell Count Dilution Tubes In the BSC, added 4.5 mL of AIM-V Media that had been labelled with "For Cell Count Dilutions" and lot number to four 15 mL conical tubes. Labeled the tubes with the lot number and tube number (1-4). Labeled 4 cryovials "Feeder" and vial number (1-4). Kept vials under BSC to be used in Step 8.5.30.
8.4.28 Transferred reagents from the BSC to 2-8° C. Transferred any remaining 2-mercaptoethanol, GlutaMax, and human serum from the BSC to 2-8° C. Ensured all reagents were labeled with the batch record lot number, and the appropriate open expiry per Process Note 5.9.
8.4.29 Prepared 1 L Transfer Pack. Outside of the BSC weld (per Process Note 5.11) a 1 L Transfer Pack to the transfer set attached to the "Complete CM2 Day 11 Media" bag prepared in step 8.4.22. Labeled transfer pack as "Feeder Cell CM2 Media" and lot number.
8.4.30 Prepared 1 L Transfer Pack. Made a mark on the tubing of the 1 L Transfer Pack tubing a few inches away from the bag. Placed the empty Transfer Pack onto the scale so that the tubing was on the scale to the point of the mark.
8.4.31 Tared scale. Tared the scale and left the empty Transfer Pack on the scale.
8.4.32 Prepared feeder cell transfer pack. Set the Baxa pump to "Medium" and "4." Pumped 500.0±5.0 mL of "Complete CM2 Day 11" media prepared in Step 8.4.22 into Cell CM2 Media" transfer pack. Measured by weight and recorded the volume of Complete CM2 media added to the Transfer Pack.
8.4.33 Heated seal line. Once filled, heated seal the line per Process Note 5.12. Separated CM2 Day 11 media bag with transfer set from feeder cell media transfer pack, kept weld toward 1 L transfer pack.
8.4.34 If applicable: Incubated feeder cell media transfer pack. When applicable, placed the "Feeder Cell CM2 Media" transfer pack in incubator until used in Step 8.6.6.
8.4.35 Incubated Complete CM2 Day 11 Media. Placed "Complete CM2 Day 11 Media" prepared in Step 8.4.22 in incubator until use in Step 8.7.2.
8.4.36 Reviewed Section 8.4.
8.5 Day 11—TIL Harvest
 8.5.1 Preprocessing table. Monitored incubator. Incubator parameters: Temperature LED Display: 37.0±2.0° C.; CO2 Percentage: 5.0±1.5% CO2. NOTE: Section 8.5 may be run concurrently with Sections 8.4 and 8.6.
 8.5.2 Removed G-Rex100MCS from incubator. Performed check below to ensure incubation parameters are met before removing G-Rex100MCS from incubator. Lower limit from Step 8.3.44 B. Upper limit from Step 8.3.44 C. Record Time of Removal from incubator. Determined: Is 8.3.44 B≤Time of Removal from incubator <Step 8.3.44 C? *IF NO CONTACT AREA MANAGEMENT. Carefully removed G-Rex100MCS from incubator and ensured all clamps were closed except large filter line. Recorded processing start time.
 8.5.3 Prepared 300 mL Transfer Pack. Labeled a 300 mL Transfer pack as "TIL Suspension".
 8.5.4 Prepared 300 mL Transfer Pack. Sterile welded (per Process Note 5.11) the TIL Suspension transfer (single line) of a Gravity Blood Filter. See, for example.
 8.5.5 Prepared 300 mL Transfer Pack. Placed the 300 mL Transfer Pack on a scale and record dry weight.
 8.5.6 Prepared 1 L Transfer Pack. Labeled 1 L Transfer Pack as "Supernatant" and Lot number.
 8.5.7 Welded transfer packs to G-Rex100MCS. Sterile welded (per Process Note 5.11) the red media removal line from the G-Rex100MCS to the "Supernatant" transfer pack. Sterile welded the clear cell removal line from the G-Rex100MCS to one of the two spike lines on the top of the blood filter connected to the "TIL Suspension" transfer pack prepared in Step 8.5.4. See, for example.
 8.5.8 GatheRex Setup. Placed G-Rex100MCS on the left side of the GatheRex and the "Supernatant" and "TIL Suspension" transfer packs to the right side.
 8.5.9 GatheRex Setup. Install the red media removal line from the G Rex100MCS to the top clamp (marked with a red line) and tubing guides on the GatheRex. Installed the clear harvest line from the G-Rex100MCS to the bottom clamp (marked with a blue line) and tubing guides on the GatheRex.
 8.5.10 GatheRex Setup. Attached the gas line from the GatheRex to the sterile filter of the G-Rex100MCS flask. NOTE: Before removing the supernatant from the G-Rex100MCS flask, ensured all clamps on the cell removal lines were closed.
 8.5.11 Volume Reduction of G-Rex100MCS. Transferred ~900 mL of culture supernatant from the G-Rex100MCS to the 1 L Transfer Pack. Visually inspect G-Rex100MCS flask to ensure flask is level and media has been reduced to the end of the aspirating dip tube. NOTE: If the Gatherex stops prematurely, it was restarted by pressing the button with the arrow pointing to the right again.
 8.5.12 Prepare flask for TIL Harvest. After removal of the supernatant, closed all clamps to the red line.
 8.5.13 Initiation of TIL Harvest. Recorded the start time of the TIL harvest.
 8.5.14 Initiation of TIL Harvest. Vigorously tapped flask and swirled media to release cells. Performed an inspection of the flask to ensure all cells have detached. NOTE: Contacted area management if cells did not detach.
 8.5.15 Initiation of TIL Harvest. Tilt flask away from collection tubing and allowed tumor pieces to settle along edge. Slowly tipped flask toward collection tubing so pieces remained on the opposite side of the flask. NOTE: If the cell collection straw is not at the junction of the wall and bottom membrane, rapping the flask while tilted at a 450 angle is usually sufficient to properly position the straw.

8.5.16 TIL Harvested. Released all clamps leading to the TIL Suspension transfer pack.

8.5.17 TIL Harvested. Using the GatheRex, transferred the cell suspension through the blood filter into the 300 mL transfer pack. NOTE: Be sure to maintain the tilted edge until all cells and media are collected.

8.5.18 TIL Harvested. Inspect membrane for adherent cells.

8.5.19 Rinsed flask membrane. Rinsed the bottom of the G-Rex100MCS. Cover ~¼ of gas exchange membrane with rinse media. NOTE: If tumor pieces obstruct the harvest line, pause collection by pressing the "X" on the cell collection line. Press the "Release Clamps" button on the Gatherex and pick the transfer pack up and gently squeeze with increasing pressure until the fragment is removed. Do not squeeze the bag too hard, as this may cause the line or bag to rupture. Resume collection once obstruction has been removed.

8.5.20 Closed clamps on G-Rex100MCS. Ensured all clamps are closed.

8.5.21 Heat sealed. Heat sealed (per Process Note 5.12) the TIL suspension transfer pack as close to the weld as possible so that the overall tubing length remains approximately the same.

8.5.22 Heat sealed. Heat sealed the "Supernatant" transfer pack per Process Note 5.12. Maintained enough line to weld.

8.5.23 Calculated volume of TIL suspension. Recorded weight of TIL Suspension transfer pack and calculated the volume of cell suspension.

8.5.24 Prepared Supernatant Transfer Pack for Sampling. Welded (per Process Note 5.11) a 4" plasma transfer set to "supernatant" transfer pack, retaining the luer connection on the 4" plasma transfer set, and transferred into the BSC.

8.5.25 Prepared TIL Suspension Transfer Pack for Sampling. Welded (per Process Note 5.11) a 4" plasma transfer set to 300 mL "TIL Suspension" transfer pack, retained the luer connection on the 4" plasma transfer set, and transferred into the BSC.

8.5.26 Pulled Bac-T Sample. In the BSC, using an appropriately sized syringe, draw up approximately 20.0 mL of supernatant from the 1 L "Supernatant" transfer pack and dispense into a sterile 50 mL conical tube labeled "Bac-T." Keep in BSC for use in Step 8.5.27.

8.5.27 Inoculated BacT per Sample Plan. Removed a 1.0 mL sample from the 50 mL conical labeled BacT prepared in Step 8.5.26 using an appropriately sized syringe and inoculated the anaerobic bottle. Recorded the time the bottle was inoculated using the space provided on the bottle label. Repeated the above for the aerobic bottle. NOTE: This step may be performed out of sequence.

8.5.28 Labeled and stored sample. Labeled with sample plan inventory label and stored Bac-T sample at room temperature, protected from light, until submitted to Login for testing per Sample Plan. NOTE: Did not cover barcode on bottle with label.

8.5.29 Signed for Sampling. Ensured that LIMS sample plan sheet was completed for removal of the sample.

8.5.30 TIL Cell Count Samples. Labeled 4 cry ovials with vial number (1-4). Using separate 3 mL syringes, pulled 4×1.0 mL cell count samples from TIL Suspension Transfer Pack using the luer connection, and placed in respective cryovials.

8.5.31 Closed the luer connection. Placed a red cap (W3012845) on the line.

8.5.32 Incubated TIL. Placed TIL Transfer Pack in incubator until needed.

8.5.33 Perform Cell Counts Perform cell counts and calculations utilizing NC-200 and Process Note 5.14. Perform initial cell counts undiluted.

8.5.34 Recorded Cell Count sample volumes. NOTE: If no dilution needed, "Sample [μL]"=200, "Dilution [μL]"=0.

8.5.35 Determined Multiplication Factor. Total cell count sample Volume:

8.5.34A+8.5.34B. Multiplication Factor C÷8.5.34A.

8.5.36 Selected protocols and entered multiplication factors. Ensured the "Viable Cell Count Assay" protocol had been selected, all multiplication factors, and sample and diluent volumes had been entered. NOTE: If no dilution needed, enter "Sample [μL]"=200, "Dilution [μL]"=0

8.5.37 Recorded File Name, Viability and Cell Counts from Nucleoview 8.5.38 Determined the Average of Viable Cell Concentration and Viability of the cell counts performed. Viability (8.5.37A+8.5.37B)÷2. Viable Cell Concentration (8.5.37C+8.5.37D)÷2

8.5.39 Determined Upper and Lower Limit for counts. Lower Limit: 8.5.38F×0.9. Upper Limit: 8.5.38F×1.1.

8.5.40 Were both counts within acceptable limits? Lower Limit: 8.5.37 C and D≥8.5.39G. Upper Limit: 8.5.37 C and D≤8.5.39H. *If either result was "No" performed second set of counts in steps 8.5.41-8.5.48*.

8.5.41 If Applicable: Performed cell counts. Performed cell counts and calculations in utilizing NC-200 and Process Note 5.14. NOTE: Dilution was adjusted according based off the expected concentration of cells. Performed 8.5.42 If Applicable: Recorded Cell Count sample volumes.

8.5.43 If Applicable: Determined Multiplication Factor. Total cell count sample Volume: 8.5.42A+8.5.42B. Multiplication Factor C÷8.5.42A D 8.5.44 If Applicable: Selected protocols and entered multiplication factors. Ensured the "Viable Cell Count Assay" protocol was selected, all multiplication factors, and sample and diluent volumes were entered. NOTE: If no dilution needed, enter "Sample [μL]"=200, "Dilution μL"=0.

8.5.45 If Applicable: Recorded Cell Counts from Nucleoview 8.5.46 If Applicable: Determined the Average of Viable Cell Concentration and Viability of the cell counts performed. Determined averaged viable cell concentration.

8.5.47 If Applicable: Determined Upper and Lower Limit for counts. Lower Limit: 8.5.46F×0.9. Upper Limit: 8.5.46F×1.1.

8.5.48 If Applicable: Were counts within acceptable limits? Lower Limit:

8.5.45 C and D≥8.5.47G. Upper Limit: 8.5.45 C and D≤8.5.47H. NOTE: If either result is "No" continue to Step 8.5.49 to determine an average.

8.5.49 If Applicable: Determined an average Viable Cell Concentration from all four counts performed. Average Viable Cell Concentration (A+B+C+D)÷4=AVERAGE 8.5.50 Adjusted Volume of TIL Suspension Calculate the adjusted volume of TIL suspension after removal of cell count samples. Total TIL Cell Volume from Step 8.5.23C (A). Volume of Cell Count Sample Removed (4.0 ml) (B) Adjusted Total TIL Cell Volume C=A−B.

8.5.51 Calculated Total Viable TIL Cells. Average Viable Cell Concentration*: 8.5.38 F* or 8.5.46 F* or *8.5.49E*; Total Volume: 8.5.50; Total Viable Cells: C=A×B. *Circle step reference used to determine Viable Cell Concentration. NOTE: If Total Viable TIL Cells is <5×10$^6$ cells contact Area Management and proceed to Step 8.7.1. If Total Viable TIL Cells is >5×10$^6$, proceed to Step 8.5.52.

8.5.52 Calculation for flow cytometry. If the Total Viable TIL Cell count from Step 8.5.51C was ≥4.0× 10$^7$, calculated the volume to obtain 1.0×10$^7$ cells for the flow cytometry sample. *If there are <4.0×10$^7$ cells, N/A the remaining fields in the table. Proceed to Step 8.7.1. Total viable cells required for flow cytometry: 1.0×10$^7$ cells. Volume of cells required for flow cytometry: Viable cell concentration from 8.5.51 divided by 1.0×10$^7$ cells A.

8.5.53 If Applicable: Removed TIL from incubator. Removed TIL Suspension from incubator and recorded end incubation time in Step 8.5.32.

8.5.54 If Applicable: Removed flow cytometry sample as per Sample Plan. Using an appropriately sized syringe, removed the calculated volume (8.5.52 C) for the phenotyping sample from the TIL Suspension transfer pack and place in a 50 mL conical tube.

8.5.55 If Applicable: Labeled and stored flow cytometry sample. Labeled with sample plan inventory label and store Flow Cytometry sample at 2-8° C. until submitted to Login for testing per Sampling Plan.

8.5.56 Signed for Sampling. Ensure that LIMS sample plan sheet was completed for removal of the sample.

8.5.57 If Applicable: Recalculated Total Viable Cells and Volume flow. Calculated the remaining Total Viable Cells and remaining volume after the removal of cytometry sample below.

| Parameter | Formula | Result |
|---|---|---|
| Total Viable TIL | Step 8.5.51C | A. cells |
| TIL removed for Flow Cytometry | 1 × 10$^7$ cells | B. 1 × 10$^7$ cells |
| Remaining Total Viable TIL | C = A − B | C. cells |
| Volume of TIL | Step 8.5.50C | D. mL |
| Volume of TIL removed | Step 8.5.52 C | E. mL |
| Remaining Volume of TIL | F = D − E | F. mL |

8.5.58 If Applicable: Calculated TIL volume. Calculated the volume of TIL suspension equal to 2.0×10$^8$ viable cells.

| Total Viable Cells Required | Viable Cell Concentration from Step 8.5.51A | Volume of TIL Suspension containing 2.0 × 10$^8$ viable cells C = A ÷ B |
|---|---|---|
| A. 2.0 × 10$^8$ cells | B. cells/mL | C. mL |

8.5.59 If Applicable: Calculated TIL volume to remove Calculate the excess volume of TIL cells to remove.

| Total Volume of TIL Suspension from Step 8.5.57F | Volume of suspension containing 2.0 × 10$^8$ TIL from Step 8.5.58C | Volume of excess TIL to Remove C = A − B |
|---|---|---|
| A. mL | B. mL | C. mL |

8.5.60 If Applicable: Removed excess TIL. In the BSC, using an appropriately sized syringe, remove the calculated volume (Step 8.5.59C) from the TIL Suspension transfer pack. NOTE: Do not use a syringe more than once. Use multiple syringes if applicable. Placed in appropriately sized sterile container and label as date, and lot number. Placed a red cap on the "TIL Suspension" transfer pack line.

8.5.61 If Applicable: Placed TIL in Incubator. Placed TIL Suspension Transfer Pack in incubator until needed. Recorded time.

8.5.62 If Applicable: Calculations. Calculated total excess TIL removed.

Step 8.5.51A Volume of TIL to Remove from Step 8.5.59C. Calculated Total Excess TIL removed.

| Viable Cell Concentration from Step 8.5.51A | Volume of TIL to Remove from Step 8.5.59C | Total Excess TIL removed C = A × B |
|---|---|---|
| A. cells/mL | B. mL | C. cells |

8.5.63 If Applicable: Calculations. Calculated amount of CS-10 media to add to excess TIL cells from Step 8.5.62C. Target cell concentration for freezing is 1.0×10$^8$ cells/ml.

| Total Excess TIL Removed Step 8.5.62C | Target Concentration to Freeze | Volume of CS-10 to Add (mL) C = A ÷ B |
|---|---|---|
| A. cells | B. 1.0 × 10$^8$ cells/mL | C. mL |

8.5.64 If Applicable: Centrifuged excess TIL. Centrifuged the excess TIL cell suspension. Speed: 350×g. Time: 10:00 minutes. Temperature: Ambient Brake: Full (9). Acceleration: Full (9).

8.5.65 If Applicable: Observed conical tube. Recorded observations: Pellet observed? Supernatant was clear? *NOTE: If either answer was no, contact Area Management.

8.5.66 If Applicable: Added CS-10. In BSC, aseptically aspirate supernatant. Gently tap bottom of tube to resuspend cells in remaining fluid.

8.5.67 If Applicable: Added CS10. Slowly add the volume of CS10 calculated in Step 8.5.63C
8.5.68 If Applicable: Labeled vials. Labeled vials with QA provided labels. Attached a sample label.
8.5.69 If Applicable: Filled Vials. Aliquoted 1.0 mL cell suspension, into appropriately sized cryovials. NOTE: Did not fill more than 10 vials of Excess TIL.
8.5.70 If Applicable: Filled Vials. Aliquoted residual volume into appropriately sized cryovial per SOP-00242. If volume is ≤0.5 mL, add CS10 to vial until volume is 0.5 mL.
8.5.71 If Applicable: Filled Vials. Filled one vial with 1.0 mL of CS10 and label as "Blank".
8.5.72 If Applicable: Recorded number of vials filled. Recorded number of vials filled below, not including blank.
8.5.73 If Applicable: Environmental Monitoring. After processing, verified BSC and personnel monitoring had been performed TIL Cryopreservation of Sample 8.5.74 If Applicable: Calculated Volume for Cryopreservation. Calculated the volume of cells required to obtain $1 \times 10^7$ cells for cryopreservation.

| Total Viable TIL required for cryopreservation | Viable Cell Concentration From Step 8.5.51A | Volume of Cells required for cryopreservation $C = A \div B$ |
|---|---|---|
| A. $1 \times 10^7$ cells | B. cells/mL | C. mL |

8.5.75 If Applicable: Removed sample for Cryopreservation. In the BSC, using the appropriately sized syringe, removed the calculated volume (Step 8.5.74C) from the TIL Suspension transfer pack. Placed in appropriately sized conical tube and label as "Cryopreservation Sample $1 \times 10^7$ cells," dated, and lot number. Placed a red cap (W3012845) on the TIL Suspension transfer pack.
8.5.76 If Applicable: Placed TIL in Incubator. Placed TIL Suspension Transfer Pack in incubator until needed.
8.5.77 If Applicable: Cryopreservation sample. Centrifuged the "Cryopreservation Sample $1 \times 10^7$ cells" according to the following parameters: Speed: 350× g, Time: 10:00 minutes, Temperature: Ambient, Brake: Full (9) Acceleration: Full (9). NOTE: Ensure proper units are set for speed and time on the centrifuge.
8.5.78 If Applicable: Observed conical tube. Recorded observations: Pellet observed? Supernatant is clear? *NOTE: If either answer is no, contact Area Management.
8.5.79 If Applicable: Added CS-10. In BSC, aseptically aspirate supernatant. Gently tap bottom of tube to resuspend cells in remaining fluid.
8.5.80 If Applicable: Added CS-10. Slowly added. 0.5 mL of CS10. Recorded volume added.
8.5.81 If Applicable: Labeled vial. Labeled vial with QA issued label.
8.5.82 If Applicable: Filled Vials. Aliquoted resuspended volume into labeled cryovial.
8.5.83 If Applicable: Filled blank. Filled another vial with 0.5 mL of CS10 and label as "Blank".
8.5.84 If Applicable: Recorded number of vials filled, not including "blank". Cryopreservation Sample Vials Filled at –0.0.5 mL 8.5.85 If Applicable: Environmental Monitoring. After processing, verify BSC and personnel monitoring have been performed.
8.5.86 Review Section 8.5
8.6 Day 11—Feeder Cells
8.6.1 Obtained feeder cells. Obtained 3 bags of feeder cells with at least two different lot numbers from LN2 freezer. Kept cells on dry ice until ready to thaw. NOTE: Section 8.6 could be performed concurrently with Section 8.5.
8.6.2 Obtained feeder cells. Recorded feeder cell information. Confirmed that at least two different lots of feeder cells were obtained.
8.6.3 Prepared waterbath or Cryotherm. Prepared water bath or Cytotherm for Feeder Cell thaw.
8.6.4 Thawed Feeder Cells. Placed the Feeder Cell bags into individual zip top bags, based on Lot number, and thawed 37.0±2.0° C. water bath or cytotherm for ~3-5 minutes or until ice has just disappeared. Recorded thaw times below from timer.
8.6.5 Feeder cell harness preparation. Welded (per Process Note 5.11) 4S-4M60 to a CC2 Cell Connect (W3012820), replacing a single spike of the Cell Connect apparatus (B) with the 4-spike end of the 4S-4M60 manifold at (G). Welded H to G.
8.6.6 If applicable: Removed media from incubator. Removed the Feeder Cell CM2 Media transfer pack prepared in Step 8.4.34 from the incubator.
8.6.7 Attached media transfer pack Weld (per Process Note 5.11) the "Feeder Cell CM2 Media" transfer pack to a CC2 Luer. NOTE: The bag will be attached to the side of the harness with the needless injection port.
8.6.8 Transfer harness. Transferred the assembly containing the Complete CM2 Day 11 Media into the BSC.
8.6.9 Pool thawed feeder cells. Within the BSC, pulled 10 mL of air into a 100 mL syringe. Used this to replace the 60 mL syringe on the CC2.
8.6.10 Pool thawed feeder cells. Wiped each port on the feeder cell bags with an alcohol pad prior to removing the cover. Spike the three feeder bags using three of the spikes of the CC2. NOTE: Maintained constant pressure while turning the spike in one direction. Ensure to not puncture the side of the port.
8.6.11 Pool Thawed Feeder Cells. Opened the stopcock so that the line from the feeder cell bags is open and the line to the needless injection port is closed.
8.6.12 Pool Thawed Feeder Cells. Drew up the contents of the feeder cell bags into the syringe. All three bags drained at once. Once feeder cell bags had been drained, while maintaining pressure on the syringe, clamped off the line to the feeder cell bags.
8.6.13 Recorded volume of feeder cells. Did not detach syringe below. the syringe from the harness. Recorded the total volume of feeder cells in the syringe.
8.6.14 Added feeder cells to transfer pack. Turned the stopcock so the line to the feeder cell bag is closed and the line to the media Transfer Pack was open. Ensured the line to media transfer pack is unclamped.
8.6.15 Added feeder cells to transfer pack Dispensed the feeder cells from the syringe into the "Feeder Cell CM2 Media" transfer pack. Clamped off the line to the transfer pack containing the feeder cells and leave the syringe attached to the harness.

8.6.16 Mixed pooled feeder cells. Massaged bag to mix the pooled feeder cells in the transfer pack.

8.6.17 Labeled transfer pack. Labeled bag as "Feeder Cell Suspension" and Lot number.

8.6.18 Calculated total volume in Transfer Pack Calculated the total volume of feeder cell suspension.

8.6.19 Removed cell count samples. Using a separate 3 mL syringe for each sample, pulled 4×1.0 mL cell count samples from Feeder Cell Suspension Transfer Pack using the needless injection port. Aliquoted each sample into the cryovials labeled in Step 8.4.27. NOTE: Wiped the needless injection port with a sterile alcohol pad (W3009488) and mixed Feeder Cell Suspension between each sampling for cell counts.

8.6.20 Performed Cell Counts. Performed cell counts and calculations utilizing NC-200 and Process Note 5.14. Diluted cell count samples by adding 0.5 mL of cell suspension into 4.5 mL of AIM-V media labelled with the lot number and "For Cell Count Dilutions". This will give a 1:10 dilution. Adjusted if necessary.

8.6.21 Recorded Cell Count. Sample volumes 8.6.22 Determine Multiplication Factor

| Parameter | Formula | Result |
|---|---|---|
| Total cell count sample Volume | 8.6.21A + 8.6.21B | C. µL |
| Multiplication Factor | C ÷ 8.6.21A | D. |

8.6.23 Selected protocols and entered multiplication factors. Ensured the "Viable Cell Count Assay" protocol had been selected, all multiplication factors, and sample and diluent volumes had been entered.

8.6.24 Recorded File Name, Viability and Cell Counts from Nucleoview.

8.6.25 Determined the Average of Viable Cell Concentration and Viability of the cell counts performed.

| Parameter | Formula | Result |
|---|---|---|
| Viability | (8.6.24A + 8.6.24B) ÷ 2 | E. % |
| Viable Cell Concentration | (8.6.24C + 8.6.24D) ÷ 2 | F. cells/mL |

8.6.26 Determined Upper and Lower Limit for counts.

| Parameter | Formula | Result |
|---|---|---|
| Lower Limit | 8.6.25F × 0.9 | G. cells/mL |
| Upper Limit | 8.6.25F × 1.1 | H. cells/mL |

8.6.27 Were both counts within acceptable limits?

| Parameter | Formula | Result (Yes/No) |
|---|---|---|
| Lower Limit | 8.6.24 C and D ≥ 8.6.26G | |
| Upper Limit | 8.6.24 C and D ≤ 8.6.26H | |

NOTE: If either result was "No" performed second set of counts in steps 8.6.28-8.6.35.

8.6.28 If Applicable: Performed cell counts Perform cell counts and calculations in utilizing NC-200 per SOP-00314 and Process Note 5.14 NOTE: Dilution could be adjusted according based off the expected concentration of cells.

8.6.29 If Applicable: Recorded Cell Count, sample volumes. NOTE: If no dilution needed, enter "Sample [µL]"=200, "Dilution [µL]"=0.

8.6.30 If Applicable: Determined Multiplication Factor.

| Parameter | Formula | Result |
|---|---|---|
| Total cell count sample Volume | 8.6.29A + 8.6.29B | C. mL |
| Multiplication Factor | C ÷ 8.6.29A | D. |

8.6.31 Select protocols and enter multiplication factors. Ensure the "Viable Cell Count Assay" protocol was selected, all multiplication factors, and sample and diluent volumes were entered. NOTE: If no dilution needed, enter "Sample [µL]"=200, "Dilution [µL]"=0.

8.6.32 If Applicable: Recorded Cell Counts from Nucleoview 8.6.33 If Applicable: Determined the Average of Viable Cell Concentration and Viability of the cell counts performed.

| Parameter | Formula | Result |
|---|---|---|
| Viability | (8.6.32A + 8.6.32B) ÷ 2 | E. % |
| Viable Cell Concentration | (8.6.32C + 8.6.32D) ÷ 2 | F. cells/mL |

8.6.34 if Applicable: Determined Upper and Lower Limit for counts.

| Parameter | Formula | Result |
|---|---|---|
| Lower Limit | 8.6.33F × 0.9 | G. cells/mL |
| Upper Limit | 8.6.33F × 1.1 | H. cells/mL |

8.6.35 If Applicable: Were counts within acceptable limits?

| Parameter | Formula | Result (Yes/No) |
|---|---|---|
| Lower Limit | 8.6.32 C and D ≥ 8.6.34G | |
| Upper Limit | 8.6.32 C and D ≤ 8.6.34H | |

NOTE: If either result was "No," continued to step 8.6.36 to find a total Average Viable Cell Concentration and proceed with calculations.

8.6.36 If Applicable: Determined an average Viable Cell Concentration from all four counts performed.

8.6.37 Adjusted Volume of Feeder Cell Suspension. Calculated the adjusted volume of Feeder Cell suspension after removal of cell count samples. Total Feeder Cell Volume from Step 8.6.18C minus 4.0 ml removed.

8.6.38 Calculated Total Viable Feeder Cells.

| Parameter | Formula | Result |
|---|---|---|
| Average Viable Cell Concentration* | 8.6.25 F* -or- 8.6.33 F* -or- 8.6.36 E* | A. cells/mL |

| Parameter | Formula | Result |
|---|---|---|
| Total Volume | 8.6.37 C | B. mL |
| Total Viable Cells | A × B | C. cells |

If Total Viable Cells are $<5\times10^9$, proceed to Step 8.6.39. If Total Viable Cells are $\geq 5\times10^9$, proceed to Step 8.5.70.

8.6.39 If Applicable: Obtained additional Feeder Cells. Obtained an additional bag of feeder cells from LN2 freezer. Kept cells on dry ice until ready to thaw.

8.6.40 If Applicable: Obtained additional Feeder Cells. Recorded feeder cell information.

8.6.41 If Applicable: Thawed Additional Feeder Cells. Placed the 4th Feeder Cell bag into a zip top bag and thaw in a 37.0±2.0° C. water bath or cytotherm for ~3-5 minutes or until ice has just disappeared. Recorded thaw time.

8.6.42 If applicable: Pooled additional feeder cells. In the BSC, pulled 10 mL of air into a new 100 mL syringe. Used this to replace the syringe on the harness.

8.6.43 If applicable: Pooled additional feeder cells Wiped the port of the feeder cell bag with an alcohol pad prior to removing the cover. Spiked the feeder cell bag using one of the remaining spikes of the harness prepared in Step 8.6.7 NOTE: Maintained constant pressure while turning the spike in one direction. Ensured to not puncture the side of the port.

8.6.44 If applicable: Pooled additional feeder cells. Opened the stopcock so that the line from the feeder cell bag was open and the line to the needless injection port was closed.

8.6.45 If applicable: Pooled additional feeder cells. Drew up the contents of the feeder cell bag into the syringe. Recorded volume.

8.6.46 If Applicable: Measured Volume. Measured the volume of the feeder cells in the syringe and recorded below (B). Calculated the new total volume of feeder cells.

| Feeder Cell Volume from Step 8.6.37C | Feeder Cell Volume from Step 8.6.45 | Total Feeder Cell Volume C = A + B |
|---|---|---|
| A. mL | B. mL | C. mL |

8.6.47 If Applicable: Added Feeder Cells to Transfer Pack. Turned the stopcock so the line to the feeder cell bag was closed and the line to the "Feeder Cell Suspension" transfer pack was open. Ensured the line to the transfer pack was unclamped. Dispensed the feeder cells from the syringe into the "Feeder Cell Suspension" transfer pack. Clamped the line to the transfer pack and left the syringe attached to the harness.

8.6.48 If Applicable: Added Feeder Cells to Transfer Pack. Massaged bag to mix the pooled feeder cells in the Feeder Cell Suspension transfer pack.

8.6.49 If Applicable: Prepared dilutions. In the BSC, add 4.5 mL of AIM-V Media that has been labelled with "For Cell Count Dilutions" and lot number to four 15 mL conical tubes. Label the tubes with the lot number and tube number (1-4). Labeled 4 cryovials "Additional Feeder" and vial number (1-4).

8.6.50 If Applicable: Prepared cell counts. Using a separate 3 mL syringe for each sample, removed 4×1.0 mL cell count samples from Feeder Cell Suspension transfer pack, using the needless injection port. Aliquoted each sample into cryovials labeled in Step 8.6.49. NOTE: Wiped the needless injection port with a sterile alcohol pad and mix Feeder Cell Suspension between each sampling for cell counts.

8.6.51 If Applicable: Performed Cell Counts. Performed cell counts and calculations utilizing NC-200 and Process Note 5.14. Diluted cell count samples by adding 0.5 mL of cell suspension into 4.5 mL of AIM-V media labelled with the lot number and "For Cell Count Dilutions". This will give a 1:10 dilution. Adjusted if necessary.

8.6.52 If Applicable: Recorded Cell Count sample volumes.

8.6.53 If Applicable: Determined Multiplication Factor

| Parameter | Formula | Result |
|---|---|---|
| Total cell count samnle Volume | 8.6.52A + 8.6.52B | C. µL |
| Multiplication Factor | C ÷ 8.6.52A | D. |

8.6.54 If Applicable: Selected protocols and entered multiplication factors. Ensured the "Viable Cell Count Assay" protocol had been selected, all multiplication factors, and sample and diluent volumes had been entered.

8.6.55 If Applicable: Recorded File Name, Viability and Cell Counts from Nucleoview.

8.6.56 If Applicable: Determine the Average of Viable Cell Concentration and Viability of the cell counts performed.

| Parameter | Formula | Result |
|---|---|---|
| Viability | (8.6.55A + 8.6.55B) ÷ 2 | E. % |
| Viable Cell Concentration | (8.6.55C + 8.6.55D) ÷ 2 | F. cells/mL |

8.6.57 If Applicable: Determine Upper and Lower Limit for counts.

| Parameter | Formula | Result |
|---|---|---|
| Lower Limit | 8.6.56F × 0.9 | G. cells/mL |
| Upper Limit | 8.6.56F × 1.1 | H. cells/mL |

Are both counts within acceptable limits? NOTE: If either result is "No" perform second set of counts in Steps 8.5.59-8.5.65

8.6.59 If Applicable: Performed cell counts. Performed cell counts and calculations in utilizing NC-200 and Process Note 5.14. NOTE: Dilution could be adjusted according based off the expected concentration of cells.

8.6.60 If Applicable: Recorded Cell Count sample volumes. NOTE: If no dilution was needed, entered "Sample [µL]"=200, "Dilution [4]"=0

8.6.61 If Applicable: Determined Multiplication Factor.

| Parameter | Formula | Result |
|---|---|---|
| Total cell count sample Volume | 8.6.60A + 8.6.60B | C. μL |
| Multiplication Factor | C ÷ 8.6.60A | D. |

8.6.62 If Applicable: Select protocols and enter multiplication factors. Ensured the "Viable Cell Count Assay" protocol has been selected, all multiplication factors, and sample and diluent volumes had been entered. NOTE: If no dilution was needed, entered "Sample [μL]"=200, "Dilution [μL]"=0

8.6.63 If Applicable: Recorded Cell Counts from Nucleoview.

8.6.64 If Applicable: Determined the Average of Viable Cell Concentration and Viability of the cell counts performed.

| Parameter | Formula | Result |
|---|---|---|
| Viability | (8.6.63A + 8.6.63B) ÷ 2 | E. % |
| Viable Cell Concentration | (8.6.63C + 8.6.63D) ÷ 2 | F. |

8.6.65 If Applicable: Determined Upper and Lower Limit for counts

| Parameter | Formula | Result |
|---|---|---|
| Lower Limit | 8.6.64F × 0.9 | G. cells/mL |
| Upper Limit | 8.6.64F × 1.1 | H. cells/mL |

8.6.66 If Applicable: Were counts within acceptable limits?

| Parameter | Formula | Result (Yes/No) |
|---|---|---|
| Lower Limit | 8.6.63 C and D ≥ 8.6.65G | |
| Upper Limit | 8.6.63 C and D ≤ 8.6.65H | |

NOTE: If either result was "No," continue to Step 8.6.67 to find a total Average Viable Cell Concentration and proceeded with calculations.

8.6.67 If Applicable: Determined an average Viable Cell Concentration from all four counts performed.

8.6.68 If Applicable: Adjusted Volume of Feeder Cell Suspension. Calculated the adjusted volume of Feeder Cell suspension after removal of cell count samples. Total Feeder Cell Volume from Step 8.6.46C minus 4.0 mL removed.

8.6.69 If Applicable: Calculated Total Viable Feeder Cells.

| Parameter | Formula | Result |
|---|---|---|
| Average Viable Cell Concentration* | 8.6.56 F* -or- 8.6.64 F* -or- 8.6.67 E* | A. cells/mL |
| Total Volume | 8.6.68 C | B. mL |
| Total Viable Cells | A × B | C. cells |

*Circled step reference used to determine Viable Cell Concentration.

8.6.70 Calculated Volume of Feeder Cells. Calculated the volume of Feeder Cell Suspension that was required to obtain $5 \times 10^9$ viable feeder cells.

| Number of Feeder Cells Required | Viable Cell Concentration from Step 8.6.38A* or Step 8.6.69A* | Volume of Feeder Cells = $5 \times 10^9$ viable cells C = A ÷ B |
|---|---|---|
| A. $5 \times 10^9$ Viable Cells | B. cells/mL | C. mL |

*Circle applicable step 8.6.71 Calculated excess feeder cell volume. Calculated the volume of excess feeder cells to remove. Round down to nearest whole number.

| Total Volume of Feeder Cells in Transfer Pack from Step 8.6.46C* or Step 8.6.68C* | Volume of Feeder Cells = $5 \times 10^9$ viable cells from Step 8.6.70C | Volume of Excess Feeder Cells to remove, viable cells C = A − B |
|---|---|---|
| A. mL | B. mL | C. mL |

*Circle applicable step 8.6.72 Removed excess feeder cells. In a new 100 mL syringe, pulled up 10 mL of air and attached the syringe to the harness.

8.6.73 Removed excess feeder cells. Opened the line to the "Feeder Cell Suspension" transfer pack. Using the syringe drew up the volume of feeder cells calculated in Step 8.6.71C plus an additional 10.0 mL from the Transfer Pack into a 100 mL syringe. Closed the line to the Feeder Cell Suspension transfer pack once the volume of feeder cells is removed. Did not remove final syringe. NOTE: Once a syringe has been filled, replaced it with a new syringe. Multiple syringes could be used to remove total volume. With each new syringe, pulled in 10 mL of air.

8.6.74 Recorded volume. Recorded the total volume (including the additional 10 mL) of feeder cells removed.

8.6.75 Added OKT3. In the BSC, using a 1.0 mL syringe and 16G needle, drew up 0.15 mL of OKT3.

8.6.76 Added OKT3. Aseptically removed the needle from the syringe and attach the syringe to the needless injection port. Injected the OKT3.

8.6.77 Added OKT3. Opened the stopcock to the "Feeder Cell Suspension" transfer pack and added 10 mL of feeder cells removed in Step 8.6.73 to flush OKT3 through the line.

8.6.78 Added OKT3. Turned the syringe upside down and push air through to clear the line to the Feeder Cell Suspension transfer pack.

8.6.79 Added OKT3. Left the remaining feeder cell suspension in the syringe. Closed all clamps and remove the harness from the BSC.

8.6.80 Heat Sealed. Heat sealed (per Process Note 5.12) the Feeder Cell Suspension transfer pack, leaving enough tubing to weld. Discarded the harness.

8.6.81 Review Section 8.6

8.7 Day 11 G-Rex Fill and Seed 8.7.1 Set up G-Rex500MCS. Outside the BSC, removed a G-Rex500MCS from packaging and inspected the flask for any cracks or kinks in the tubing. Ensured all luer connections and closures were tight. Closed all clamps on the G-Rex500MCS lines except for the vent filter line. Using a marker drew a line at the 4.5 L gradation.

8.7.2 Removed media from incubator. Removed the "Complete CM2 Day 11 Media", prepared in Step 8.4.35, from the incubator.

8.7.3 Prepared to pump media. Welded (per Process Note 5.11) the red line of the G-Rex500MCS to the repeater pump transfer set attached to the complete CM2 Day 11 Media.

8.7.4 Prepare to pump media. Hung the "Complete CM2 Day 11 Media" bag on an IV pole. Fed the pump tubing through the Baxa pump.

8.7.5 Pumped media into G-Rex500MCS. Set the Baxa pump to "High" and "9". Pumped 4.5 L of media into the G-Rex500MCS, filling to the line marked on the flask in Step 8.7.1.

8.7.6 Heat sealed. Heat sealed the red line (per Process Note 5.12) of the G-Rex500MCS near the weld created in Step 8.7.3.

8.7.7 Labeled Flask. Labeled the flask with the Attach a sample "Day 11 QA provided in-process "Day 11" label.

8.7.8 If applicable: Incubated flask. Held flask in incubator while waiting to seed with TIL.

8.7.9 Welded the Feeder Cell: Suspension transfer pack to the flask. Sterile welded (per Process Note 5.11) the red line of the G-Rex500MCS to the "Feeder Cell Suspension" transfer pack.

8.7.10 Added Feeder Cells to G-Rex500MCS. Opened all clamps between Feeder Cell Suspension and G-Rex500MCS and added Feeder Cell Suspension to flask by gravity feed. Ensured the line has been completely cleared.

8.7.11 Heat sealed. Heat sealed (per Process Note 5.12) the red line near the weld created in Step 8.7.9.

8.7.12 Welded the TIL Suspension transfer pack to the flask. Sterile weld (per Process Note 5.11) the red line of the G-Rex500MCS to the "TIL Suspension" transfer pack.

8.7.13 Added TIL to G-Rex500MCS. Opened all clamps between TIL Suspension and G-Rex500MCS and added TIL Suspension to flask by gravity feed. Ensured the line has been completely cleared.

8.7.14 Heat sealed. Heat sealed (per process note 5.12) the red line near the weld created in Step 8.7.12 to remove the TIL suspension bag.

8.7.15 Incubated G-Rex500MCS. Checked that all clamps on the G-Rex500MCS were closed except the large filter line and place in the incubator. Incubator parameters: Temperature LED Display: 37.0±12.0° C., CO2 Percentage: 5.01±1.5% CO2.

8.7.16 Calculated incubation window. Performed calculations to determine the proper time to remove G-Rex500MCS from incubator on Day 16. Time of incubation (Step 8.7.15). Lower limit: Time of incubation+108 hours. Upper limit: Time of incubation+132 hours.

8.7.17 Environmental Monitoring. After processing, verified BSC and personnel monitoring had been performed.

8.7.18 Submit Samples. Submit samples to Login.

8.7.19 Review Section 8.7

8.8 Day 11 Excess TIL Cryopreservation 8.8.1 If Applicable: Froze Excess TIL Vials. Verified the CRF has been set up prior to freeze. Perform Cryopreservation.

8.8.2 If Applicable: Started CRF. Recorded the total number of vials placed into the CRF (not including blank). Verify number of vials transferred into the CRF matches total number of vials prepared in Step 8.5.72 or Step 8.5.84 Step 8.5.72C or Step 8.5.84

8.8.3 If applicable: Initiated automated portion of the freezing profile. Recorded START TIME for the initiation of the automated portion of the freezing profile.

8.8.4 If Applicable: Transferred vials from Controlled Rate Freezer to the appropriate storage. Upon completion of freeze, transfer vials from CRF to the appropriate storage container.

8.8.5 If applicable: Transferred vials to appropriate storage. Recorded storage location in LN2.

8.8.6 Review Section 8.8

8.9 Day 16 Media Preparation 8.9.1 Pre-warmed AIM-V Media. Removed three CTS AIM V 10 L media bags from 2-8° C. at least 12 hours prior to use and place at room temperature protected from light. Verify each bag is within expiry. Labeled each bag with Bag Number (1-3). lot number, date, and "warming start time HHMM". Record warming start time and date.

8.9.2 Calculated time Media from step 8.9.1 was warmed. Calculated the warming time of media bags 1, 2, and 3 from step 8.9.1. Ensured all bags have been warmed for a duration between 12 and 24 hours.

8.9.3 Checked room sanitization, line clearance, and materials. Confirmed room sanitization, line clearance, and materials.

8.9.4 Ensured completion of pre-processing table.

8.9.5 Environmental Monitoring. Prior to processing, ensured pre-process environmental monitoring had been initiated.

8.9.6 Setup 10 L Labtainer for Supernatant. In the BSC attached the larger diameter end of a fluid pump transfer set to one of the female ports of a 10 L Labtainer bag using the Luer connectors.

8.9.7 Setup 10 L Labtainer for Supernatant Label as "Supernatant" and Lot number.

8.9.8 Setup 10 L Labtainer for Supernatant Ensure all clamps were closed prior to removing from the BSC. NOTE: Supernatant bag was used during TIL Harvest (Section 8.10), which may be performed concurrently with media preparation.

8.9.9 Thawed IL-2. Thawed 5×1.1 mL aliquots of IL-2 ($6\times10^6$ IU/mL) (BR71424) per bag of CTS AIM V media until all ice had melted. Recorded IL-2 Lot number and Expiry. Attached IL-2 labels.

8.9.10 Aliquoted GlutaMax. In BSC, aliquoted 100.0 mL of Glutamax into an appropriately sized receiver. Recorded the volume added to each receiver NOTE: Initially prepared one bag of AIM-V media following Step 8.9.10-Step 8.9.28. Additional bags required were determined in Step 8.10.59.

8.9.11 Labeled receivers. Labeled each receiver as "GlutaMax."

8.9.12 Added IL-2 to GlutaMax. Using a micropipette, added 5.0 mL of IL-2 to each GlutaMax receiver. Ensured to rinse the tip per process note 5.18 and used a new pipette tip for each mL added. Recorded volume added to each Glutamax receiver below.

8.9.13 Labeled receivers. Labeled each receiver as "GlutaMax+IL-2" and receiver number.

8.9.14 Prepared CTS AIM V media bag for formulation. Ensured CTS AIM V 10 L media bag (W3012717) was warmed at room temperature and protected from light for 12-24 hours prior to use. Recorded end incubation time in Step 8.9.2.

8.9.15 Prepared CTS AIM V media bag for formulation. In the BSC, closed clamp on a 4" plasma transfer set, then connected to the bag using the spike ports. NOTE: Maintained constant pressure while turning the spike in one direction. Ensured to not puncture the side of the port.

8.9.16 Prepared CTS AIM V media bag for formulation. Connected the larger diameter end of a repeater pump fluid transfer set to the 4" plasma transfer set via luer.

8.9.17 Stage Baxa Pump. Stage Baxa pump next to BSC. Removed pump tubing section of repeater pump fluid transfer set from BSC and installed in repeater pump.

8.9.18 Prepared to formulate media. In BSC, removed syringe from Pumpmatic Liquid-Dispensing System (PLDS) and discarded. NOTE: Ensured to not compromise the sterility of the PLDS pipette.

8.9.19 Prepared to formulate media. Connected PLDS pipette to smaller diameter end of repeater pump fluid transfer set via luer connection and placed pipette tip in "GlutaMax+IL-2" prepared in Step 8.9.13 for aspiration Open all clamps between receiver and 10 L bag.

8.9.20 Pumped GlutaMax+IL-2 into bag. Set the pump speed to "Medium" and "3" and pump all "GlutaMax+IL-2" into 10 L CTS AIM V media bag. Once no solution remains, clear line and stop pump. Recorded the volume of GlutaMax containing IL-2 added to each Aim V bag below. Recorded/8.9.21 Removed PLDS. Ensured all clamps were closed, and removed the PLDS pipette from the repeater pump fluid transfer set. Removed repeater pump fluid transfer set and red cap the 4" plasma transfer set.

8.9.22 Labeled Bags. Labeled each bag of "Complete CM4 Day 16 media" prepared.

8.9.23 Removed Media Retain per Sample Plan. Using a 30 mL syringe, removed 20.0 mL of "Complete CM4 Day 16 media" by attaching syringe to the 4" plasma transfer set and dispensed sample into a 50 mL conical tube. NOTE: Only removed the Media Retain Sample from the first bag of media prepared. NOTE: Ensure 4" plasma transfer set was either clamped or red capped after removal of syringe.

8.9.24 Attached new repeater pump fluid transfer set. Attached the larger diameter end of a new fluid pump transfer set onto the 4" plasma transfer set that was connected to the "Complete CM4 Day 16 media" bag.

8.9.25 Labeled and stored sample. Labeled with sample plan inventory label and stored media retain sample at 2-8° C. until submitted to Login for testing per Sample Plan.

8.9.26 Signed for Sampling. Ensured that LIMS sample plan sheet was completed for removal of the sample.

8.9.27 Monitor Incubator. Monitored Incubator. If applicable, per Step 8.9.10, monitor for additional bags prepared. Incubator parameters: Temperature LED Display: 37.0±2.0° C., CO2 Percentage: 5.0±1.5% CO2.

8.9.28 Warmed Complete CM4 Day 16 Media. Warmed the first bag of Complete CM4 Day 16 Media in incubator for ≥30 minutes until ready for use. If applicable, per Step 8.10.59, warmed additional bags.

8.9.29 Prepared Dilutions. In the BSC, added 4.5 mL of AIM-V Media that had been labelled with Batch record Lot Number and "For Cell Count Dilutions" to each 4×15 mL conical tube. Labeled the conical tubes with the lot number and tube number (1-4). Labeled 4 cryovials with vial number (1-4). Kept vials under BSC to be used in Step 8.10.31.

8.9.30 Reviewed Section 8.9

8.10 Day 16 REP Spilt 8.10.1 Pre-processing table.

8.10.2 Monitored Incubator. Monitored Incubator. Incubator parameters: Temperature LED Display: 37.0±2.0° C., CO2 Percentage: 5.0±1.5% CO2

8.10.3 Removed G-Rex500MCS from Incubator. Performed check below to ensure incubation parameters are met before removing G-Rex500MCS from incubator.

| Lower limit from Step 8.7.16B (DDMMYY HHMM) | Upper limit from Step 8.7.16C (DDMMYY HHMM) | Time of Removal from incubator (DDMMYY HHMM) | Is 8.7.16B < Time of Removal from incubator < Step 8.7.16C Yes/No* |
|---|---|---|---|

Removed G-Rex500MCS from the incubator.

8.10.4 Setup 1 L Transfer Pack. Heat sealed a 1 L transfer pack (W3006645) per Processed Note 5.12, leaving ~12" of line.

8.10.5 Prepared 1 L Transfer Pack. Labeled 1 L transfer pack as TIL Suspension.

8.10.6 Weighed 1 L Transfer Pack Place 1 L transfer pack, including the entire line, on a scale and record dry weight.

8.10.7 GatheRex Setup. Sterile welded (per Process Note 5.11) the red media removal line from the G-Rex500MCS to the repeater pump transfer set on the 10 L labtainer bag "Supernatant" prepared in Step 8.9.8. Sterile welded the clear cell removal line from the G-Rex500MCS to the TIL Suspension transfer pack prepared in Step 8.10.5.

8.10.8 GatheRex Setup. Placed G-Rex500MCS flask on the left side of the GatheRex. Placed the supernatant labtainer bag and TIL suspension transfer pack to the right side.

8.10.9 GatheRex Setup. Installed the red media removal line from the G-Rex500MCS to the top clamp (marked with a red line) and tubing guides on the GatheRex. Installed the clear harvest line from the G-Rex500MCS to the bottom clamp (marked with a blue line) and tubing guides on the GatheRex.

8.10.10 GatheRex Setup. Attached the gas line from the GatheRex to the sterile filter of the G-Rex500 MCS. NOTE: Before removing the supernatant from the G-Rex500MCS, ensured all clamps on the cell removal lines were closed.

8.10.11 Volume Reduction of G-Rex500MCS. Transferred ~4.5 L of culture supernatant from the G-Rex500MCS to the 10 L Labtainer per SOP-01777. Visually inspect G-Rex500MCS to ensure 8.10.12 Prepared flask for TIL Harvest. After removal of the supernatant, closed all clamps to the red line.

8.10.13 Initiation of TIL Harvest. Recorded the start time of the TIL harvest.

8.10.14 Initiation of TIL Harvest. Vigorously tap flask and swirl media to release cells. Performed an inspection of the flask to ensure all cells have detached. NOTE: Contact area management if cells did not detach.

8.10.15 Initiation of TIL Harvest. Tilted the flask to ensure hose is at the edge of the flask. Note: If the cell collection straw is not at the junction of the wall and bottom membrane, rapping the flask while tilted at a 450 angle is usually sufficient to properly position the straw.

8.10.16 TIL Harvest. Released all clamps leading to the TIL suspension transfer pack.

8.10.17 TIL Harvest. Using the GatheRex transferred the cell suspension into the TIL Suspension transfer pack. NOTE: Be sure to maintain the tilted edge until all cells and media are collected.

8.10.18 TIL Harvest. Inspected membrane for adherent cells.

8.10.19 Rinse flask membrane. Rinse the bottom of the G-Rex500MCS. Cover ~¼ of gas exchange membrane with rinse media.

8.10.20 Closed clamps on G-Rex500MCS. Ensured all clamps are closed on the G-Rex500MCS.

8.10.21 Heat sealed. Heat sealed (per Process Note 5.12) the Transfer Pack containing the TIL as close to the weld as possible so that the overall tubing length remained approximately the same.

8.10.22 Heat sealed. Heat sealed the 10 L Labtainer containing the supernatant (per Process Note 5.12) and passed into the BSC for sample collection in Step 8.10.25.

8.10.23 Calculated volume of TIL suspension. Recorded weight of Transfer Pack with cell suspension and calculate the volume suspension.

8.10.24 Prepared transfer pack for sample removal. Welded (per Process Note 5.11) a 4" Plasma Transfer Set, to the TIL Suspension transfer pack from Step 8.10.21, leaving the female luer end attached as close to the bag as possible.

8.10.25 Removed testing samples from cell supernatant. In the BSC, remove 10.0 mL of supernatant from 10 L labtainer using female luer port and appropriately sized syringe. Placed into a 15 mL conical tube and label as "BacT" Retain the tube for BacT sample in Step 8.10.28.

8.10.26 Removed testing samples from cell supernatant. Using a separate syringe, removed 10.0 mL of supernatant and placed into a 15 mL conical tube. Retained the tube for *mycoplasma* sample for use in Step 8.10.32. Labeled tube as "*Mycoplasma* diluent"

8.10.27 Closed supernatant bag. Placed a red cap on the luer port to close the bag, and pass out of BSC.

8.10.28 Sterility & BacT Testing Sampling. In the BSC, removed a 1.0 mL sample from the 15 mL conical labeled BacT prepared in Step 8.10.25 using an appropriately sized syringe and inoculate the anaerobic bottle. Repeat the above for the aerobic bottle. NOTE: This step may be performed out of sequence.

8.10.29 Labeled and store samples. Labeled with sample plan inventory label and store BacT sample at room temperature, protected from light, until submitted to Login for testing per Sample Plan. NOTE: Did not cover barcode on bottle with label.

8.10.30 Signed for Sampling. Ensured that LIMS sample plan sheet is completed for removal of the sample.

8.10.31 Removed Cell Count Samples. In the BSC, using separate 3 mL syringes for each sample, removed 4×1.0 mL cell count samples from "TIL Suspension" transfer pack using the luer connection. Placed samples in cryovials prepared in Step 8.9.29.

8.10.32 Removed *Mycoplasma* Samples. Using a 3 mL syringe, removed 1.0 mL from TIL Suspension transfer pack and place into 15 mL conical labeled "*Mycoplasma* diluent" prepared in Step 8.10.26.

8.10.33 Label and store sample. Labeled with sample plan inventory label and stored *Mycoplasma* sample at 2-8° C. until submitted to Login for testing per Sample Plan.

8.10.34 Signed for Sampling. Ensured that LIMS sample plan sheet was completed for removal of the sample.

8.10.35 Prepared Transfer Pack for Seeding. In the BSC, attached the large diameter tubing end of a Repeater Pump Fluid Transfer Set to the Luer adapter on the transfer pack containing the TIL. Clamped the line close to the transfer pack using a hemostat. Placed a red cap onto the end of the transfer set.

8.10.36 Placed TIL in Incubator. Removed cell suspension from the BSC and place in incubator until needed. Recorded time.

8.10.37 Performed Cell Counts. Performed cell counts and calculations utilizing NC-200 and Process Note 5.14. Diluted cell count samples initially by adding 0.5 mL of cell suspension into 4.5 mL of AIM-V media prepared in Step 8.9.29. This gave a 1:10 dilution.

8.10.38 Recorded Cell Count sample volumes 8.10.39 Determined Multiplication Factor.

| Parameter | Formula | Result |
|---|---|---|
| Total cell count | 8.10.38A + 8.10.38B | C. uL |
| samnle Volume | | |
| Multiplication Factor | C ÷ 8.10.38A | D. |

8.10.40 Selected protocols and enter multiplication factors. Ensured the "Viable Cell Count Assay" protocol had been selected, all multiplication factors, and sample and diluent volumes had been entered.

8.10.41 Recorded File Name, Viability and Cell Counts from Nucleoview.

8.10.42 Determined the Average of Viable Cell Concentration and Viability of the cell counts performed.

| Parameter | Formula | Result |
|---|---|---|
| Viability | (8.10.41A + 8.10.41B) ÷ 2 | E. % |
| Viable Cell Concentration | (8.10.41C + 8.10.41D) ÷ 2 | F. cells/mL |

8.10.43 Determined Upper and Lower Limit for counts.

| Parameter | Formula | Result |
|---|---|---|
| Lower Limit | 8.10.42F × 0.9 | G. cells/mL |
| Upper Limit | 8.10.42F × 1.1 | H. cells/mL |

8.10.44 Were both counts within acceptable limits?

| Parameter | Formula | Result (Yes/No) |
|---|---|---|
| Lower Limit | 8.10.41C and D ≥ 8.10.43G | |
| Upper Limit | 8.10.41C and D ≤ 8.10.43H | |

8.10.45 If Applicable: Performed cell counts. Performed cell counts and calculations in utilizing NC-200 and Process Note 5.14. NOTE: Dilution may be adjusted according based off the expected concentration of cells.

8.10.46 If Applicable: Recorded Cell Count sample volumes. NOTE: If no dilution was needed, enter "Sample [µL]"=200, "Dilution [µL]"=0

8.10.47 If Applicable: Determined Multiplication Factor.

| Parameter | Formula | Result |
|---|---|---|
| Total cell count sample Volume | 8.10.46A + 8.10.46B | C. mL |
| Multiplication Factar | C ÷ 8.10.46A | D. |

8.10.48 If Applicable: Select protocols and enter multiplication factors.

Ensure the "Viable Cell Count Assay" protocol has been selected, all multiplication factors, and sample and diluent volumes have been entered. NOTE: If no dilution needed, enter "Sample [µL]"=200, "Dilution [µL]"=0

8.10.49 If Applicable: Recorded Cell Counts from Nucleoview 8.10.50 If Applicable: Determined the Average of Viable Cell Concentration and Viability of the cell counts performed.

| Parameter | Formula | Result |
|---|---|---|
| Viability | (8.10.49A + 8.10.49B) ÷ 2 | E. % |
| Viable Cell | (8.10.49C + 8.10.49D) ÷ 2 | F. cells/mL |

8.10.51 If Applicable: Determined Upper and Lower Limit for counts.

| Parameter | Formula | Result |
|---|---|---|
| Lower Limit | 8.10.50F × 0.9 | G. cells/mL |
| Upper Limit | 8.10.50F × 1.1 | H. cells/mL |

8.10.52 If Applicable: Were counts within acceptable limits?

| Parameter | Formula | Result (Yes/No) |
|---|---|---|
| Lower Limit | 8.10.49 C and D ≥ 8.10.51G | |
| Upper Limit | 8.10.49 C and D ≤ 8.10.51H | |

NOTE: If either result is "No" continue to Step 8.10.53 to determine an average of all cell counts collected.

8.10.53 If Applicable: Determined an average Viable Cell Concentration from all four counts performed.

8.10.54 Adjusted Volume of TIL Suspension. Calculated the adjusted volume of TIL suspension after removal of cell count samples. Total TIL Cell Volume from Step 8.10.23C minus 5.0 mL removed for testing.

8.10.55 Calculated Total Viable TIL Cells.

| Parameter | Formula | Result |
|---|---|---|
| Average Viable Cell Concentration* | 8.10.42 F* -or- 8.10.50 F* -or- | A. cells/mL |
| Total Volume | 8.10.54 C | B. mL |
| Total Viable Cells | A × B | C. cells |

8.10.56 Calculated flasks for subculture. Calculated the total number of flasks to seed. NOTE: Rounded the number of G-Rex500MCS flasks to see up to the neared whole number.

| Total Viable Cell Count from Step 8.10.55C A | Target Cells Required per Flask B | Number of G-Rex500MCS Flasks to Seed C = A ÷ B |
|---|---|---|
| cells | 1.0 × 10⁹ cells/flask | flasks |

NOTE: The maximum number of G-Rex500MCS flasks to seed was five. If the calculated number of flasks to seed exceeded five, only five were seeded USING THE ENTIRE VOLUME OF CELL SUSPENSION AVAILABLE NOTE: The maximum number of G-Rex500MCS flasks to seed was five. If the calculated number of flasks to seed exceeded five, only five were seeded USING THE ENTIRE VOLUME OF CELL SUSPENSION AVAILABLE 8.10.57 Calculate number of flasks for subculture

| Criteria | Yes/No |
|---|---|
| Number of G-Rex500MCS Flasks to Seed Step 8.10.56C ≤ 5 | |
| Number of G-Rex500MCS Flasks to Seed Step 8.10.56C > 5 | |
| If yes, seed 5 flasks with ALL available | |

8.10.58 QA Review of Cell Count calculations performed in steps 8.10.38-8.10.57.

8.10.59 Determined number of additional media bags needed. Calculated the number of media bags required in addition to the bag prepared in Step 8.9.28.

| Number of G-Rex500MCS Flasks to Seed (Step 8.10.56C) A | Number of Media Bag Required B = A ÷ 2* | Number of Bags Prepared in Step 8.9.22 C | Number of Additional Bags to Prepare D = B − C |
|---|---|---|---|
| | | 1 | |

*Round the number of media bags required up to the next whole number.

8.10.60 If Applicable: Prepared additional media. Prepared one 10 L bag of "CM4 Day 16 Media" for every two G-Rex-500M flask needed calculated in Step 8.10.59D. Proceeded to Step 8.10.62 and seeded the first GREX-500M flask(s) while additional media is prepared and warmed.

8.10.61 If Applicable: Prepared additional media bags. Prepared and warmed the calculated number of additional media bags determined in Step 8.10.59D, repeating Step 8.9.10-Step 8.9.28.

8.10.62 Filled G-Rex500MCS. Opened a G-Rex500MCS on the benchtop and inspected for cracks in the vessel or kinks in the tubing. Ensured all luer connections and closures were tight. Made a mark at the 4500 mL line on the outside of the flask with a marker. Closed all clamps on the G-Rex500MCS except the large filter line.

8.10.63 Filled G-Rex500MCS. Sterile welded (per Process Note 5.11) the red media line of a G-Rex500MCS to the fluid transfer set on the media bag prepared in Step 8.9.28.

8.10.64 Prepared to pump media. Hung "CM4 Day 16 Media" on an IV pole. Fed the pump tubing through the Baxa pump.

8.10.65 Pump media into G-Rex500MCS. Set the Baxa pump on "High" and "9" and pump 4500 mL of media into the flask. Pumped 4.5 L of "CM4 Day 16 Media" into the G-Rex500MCS, filling to the line marked on the flask in Step 8.10.62. Once 4.5 L of media had been transferred, stopped the pump.

8.10.66 Heat Sealed. Heat sealed (per Process Note 5.12) the red media line of G-Rex500MCS, near the weld created in Step 8.10.63, removing the media bag.

8.10.67 Repeated Fill. Repeat Steps 8.10.62-8.10.66 for each flask calculated in Step 8.10.56C as media is warmed and prepared for use. NOTE: Multiple flasks may be filled at the same time using gravity fill or multiple pumps. NOTE: Fill only two flasks per bag of media.

8.10.68 Recorded and labelled flask(s) filled. Labeled each flask alphabetically as it is filled and with QA provided in-process "Day 16" labels.

8.10.69 Sample Labeled. Attached a sample "Day 16" label below.

8.10.70 If applicable: Incubated flask. Held flask in incubator while waiting to seed with TIL.

8.10.71 Verified Number of Flasks Filled. Recorded the total number of flasks filled.

8.10.72 Calculated volume of cell suspension to add. Calculated the target volume of TIL suspension to add to the new G-Rex500MCS flasks.

| Total Volume of TIL suspension from Step 8.10.54C A | Number of flask(s) filled from Step 8.10.71 | Target Volume of cell suspension to transfer to each flask C = A ÷ B |
|---|---|---|
| mL | | mL |

8.10.56C exceeds five only five will be seeded, USING THE ENTIRE VOLUME OF CELL SUSPENSION.

8.10.73 Prepared Flasks for Seeding. Removed G-Rex500MCS from Step 8.10.70 from the incubator.

8.10.74 Prepared for pumping. Closed all clamps on G-Rex500MCS except large filter line. Fed the pump tubing through the Baxa pump.

8.10.75 Removed TIL from incubator. Removed "TIL Suspension" transfer pack from the incubator and record incubation end time in Step 8.10.36.

8.10.76 Prepared cell suspension for seeding. Sterile welded (per Process Note 5.11) "TIL Suspension" transfer pack from Step 8.10.75 to pump inlet line.

8.10.77 Tared scale. Placed TIL suspension bag on a scale. Primed the line from the TIL suspension bag to the weld using the Baxa pump set to "Low" and "2". Tared the scale.

8.10.78 Seeded flask with TIL Suspension. Set Baxa pump to "Medium" and "5". Pump the volume of TIL suspension calculated in Step 8.10.72C into flask. Record the volume of TIL Suspension added to each flask.

8.10.79 Heat sealed. Heat sealed (per Process Note 5.12) the "TIL Suspension" transfer pack, leaving enough tubing to weld on the next flask. Used the line stripper to clear the residual TIL suspension in the G-Rex flask line into the vessel.

8.10.80 Filled remaining flasks. Between each flask seeded, ensured to mix "TIL Suspension" transfer pack and repeat Steps 8.10.76-8.10.79 to seed all remaining flaks. Filled flask(s) in alphabetical order.

8.10.81 Monitored Incubator. NOTE: If flasks must be split among two incubators, ensure to monitor both. Incubator parameters: Temperature LED Display: 37.0±2.0° C., CO2 Percentage: 5.0±1.5% CO2.

8.10.82 Incubated Flasks. Recorded the time each flask is placed in the incubator.

8.10.83 Calculated incubation window. Performed calculations below to determine the time range to remove G-Rex500MCS from incubator on Day 22.

| Flask | 8.10.83A Time of incubation (Step 8.10.82) (DDMMMYY HHMM) | 8.10.83B Lower limit: Time of incubation + 132 hours (DDMMMYY HHMM) | 8.10.83C Upper limit: Time of incubation + 156 hours (DDMMMYY HHMM) |
|---|---|---|---|

8.10.84 Environmental Monitoring. After processing, verified BSC and personnel monitoring had been performed.
8.10.85 Sample Submission. Ensured all Day 16 Samples were submitted to Login.
8.10.86 Reviewed Section 8.10.

8.11 Day 22 Wash Buffer Preparation
8.11.1 Checked room sanitization, line clearance, and materials.
8.11.2 Ensured completion of pre-processing checklist.
8.11.3 Environmental monitoring. Prior to processing, ensured pre-process environmental monitoring had been performed.
8.11.4 Prepared 10 L Labtainer Bag In BSC, attach a 4" plasma transfer set to a 10 L Labtainer Bag via luer connection.
8.11.5 Prepared 10 L Labtainer Bag Label as "Supernatant", lot number, and initial/date.
8.11.6 Prepared 10 L Labtainer Bag. Closed all clamps before transferring out of the BSC. NOTE: Prepared one 10 L Labtainer Bag for every two G-Rex500MCS flasks to be harvested. NOTE: Supernatant bag(s) were used in Section 8.12, which could be run concurrently with Section 8.11.
8.11.7 Welded fluid transfer set. Outside the BSC, closed all clamps on 4S-4M60. Welded (per Process Note 5.11) repeater fluid transfer set to one of the male luer ends of 4S-4M60.
8.11.8 Passed materials into the BSC. Passed Plasmalyte-A and Human Albumin 25% into the BSC. Pass the 4S-4M60 and repeater fluid transfer set assembly into the BSC.

| Component Description | Amount Needed |
| --- | --- |
| Plasmalyte-A | 3000.0 mL |
| Human Albumin 25% | 120.0 mL |
| 4S-4M60 with Repeater Fluid Transfer Set | 1 Apparatus Step 8.11.7 |

8.11.9 Pumped Plasmalyte into 3000 mL bag. Spiked three bags of Plasmalyte-A to the 4S-4M60 Connector set. NOTE: Wipe the port cover with an alcohol swab (W3009488) prior to removing. NOTE: Maintain constant pressure while turning the spike in one direction. Ensure to not puncture the side of the port.
8.11.10 Pumped Plasmalyte into 3000 mL bag. Connected an Origen 3000 mL collection bag via luer connection to the larger diameter end of the repeater pump transfer set.
8.11.11 Pumped Plasmalyte into 3000 mL bag. Closed clamps on the unused lines of the 3000 mL Origen Bag.
8.11.12 Pumped Plasmalyte into 3000 mL bag. Staged the Baxa pump next to the BSC. Fed the transfer set tubing through the Baxa pump situated outside of the BSC. Set pump to "High" and "9".
8.11.13 Pumped Plasmalyte into 3000 mL bag. Opened all clamps from the Plasmalyte-A to the 3000 mL Origen Bag.
8.11.14 Pump Plasmalyte into 3000 mL bag. Pumped all of the Plasmalyte-A into the 3000 mL Origen bag. Once all the Plasmalyte-A had been transferred, stopped the pump.
8.11.15 Pumped Plasmalyte into 3000 mL bag. If necessary, removed air from 3000 mL Origen bag by reversing the pump and manipulating the position of the bag.
8.11.16 Pumped Plasmalyte into 3000 mL bag. Closed all clamps. Remove the 3000 mL bag from the repeater pump fluid transfer set via luer connection and placed a red cap (W3012845) on the line to the bag.
8.11.17 Added Human Albumin 25% to 3000 mL Bag. Opened vented mini spike. Without compromising sterility of spike, ensured blue cap is securely fastened.
8.11.18 Added Human Albumin 25% to 3000 mL Bag. Spiked the septum of a Human Albumin 25% bottle with the vented mini spike. NOTE: Ensured to not compromise the sterility of the spike.
8.11.19 Added Human Albumin 25% to 3000 mL Bag. Repeated Step 8.11.17-Step 8.11.18 two times for a total of three (3) spiked Human Albumin 25% bottles.
8.11.20 Added Human Albumin 25% to 3000 mL Bag. Removed the blue cap from one vented mini spike and attach a 60 mL syringe to the Human Serum Albumin 25% bottle.
8.11.21 Added Human Albumin 25% to 3000 mL Bag. Draw up 60 mL of Human Serum Albumin 25%. NOTE: It may be necessary to use more than one bottle of Human Serum Albumin 25%. If necessary, disconnect the syringe from the vented mini spike and connect it to the next vented mini spike in a Human Serum Albumin 25% bottle. Do not remove vented mini spike from the Human Serum Albumin 25% bottle.
8.11.22 Added Human Albumin 25% to 3000 mL Bag. Once 60 mL has been obtained, remove the syringe from the vented mini spike.
8.11.23 Added Human Albumin 25% to 3000 mL Bag. Attach syringe to needleless injection port on 3000 mL Origen bag filled with Plasmalyte-A in Step 8.11.16. Dispensed all of the Human Albumin 25%. NOTE: Wiped needless injection port with an alcohol pad before each use.
8.11.24 Added Human Albumin 25% to 3000 mL Bag. Repeated Step 8.11.20-Step 8.11.23 to obtain a final volume of 120.0 mL of Human Albumin 25%.
8.11.25 Mixed Bag. Gently mixed the bag after all of the Human Albumin 25% had been added.
8.11.26 Labeled Bag. Labeled as "LOVOWash Buffer" and lot number, and assign a 24 hour expiry.
8.11.27 Prepared IL-2 Diluent. Using a 10 mL syringe, removed 5.0 mL of LOVO Wash Buffer using the needleless injection port on the LOVO Wash Buffer bag. Dispensed LOVO wash buffer into a 50 mL conical tube and label as "IL-2 Diluent" and the lot number. NOTE: Wiped the needless injection port with an alcohol pad before each use.
8.11.28 CRF Blank Bag LOVO Wash Buffer Aliquotted. Using a 100 mL syringe, drew up 70.0 mL of LOVO Wash Buffer from the needleless injection port. NOTE: Wiped the needleless injection port with an alcohol pad before each use.
8.11.29 CRF Blank Bag LOVO Wash Buffer Aliquotted. Placed a red cap on the syringe and label as "blank cryo bag" and lot number. NOTE: Held the syringe at room temp until needed in Step 8.14.3
8.11.30 Completed Wash Buffer Prep. Closed all clamps on the LOVO Wash Buffer bag.

8.11.31 Thawed IL-2. Thawed one 1.1 mL of IL-2 ($6\times10^6$ IU/mL)), until all ice has melted. Record IL-2 Lot number and Expiry. NOTE: Ensured IL-2 label is attached.

8.11.32 IL-2 Preparation. Added 504 IL-2 stock ($6\times10^6$ IU/mL) to the 50 mL conical tube labeled "IL-2 Diluent."

8.11.33 IL-2 Preparation. Relabeled conical as "IL-2 $6\times10^4$", the date, lot number, and 24 hour expiry. Cap and store at 2-8'C.

8.11.34 Cryopreservation Prep. Placed 5 cryo-cassettes at 2-8° C. to precondition them for final product cryopreservation.

8.11.35 Prepared Cell Count Dilutions. In the BSC, added 4.5 mL of AIM-V Media that has been labelled with lot number and "For Cell Count Dilutions" to 4 separate 15 mL conical tubes. Labeled the tubes with the batch record lot number and tube number (1-4). Set aside for use in Step 8.12.34

8.11.36 Prepared Cell Counts. Labeled 4 cryovials with vial number (1-4). Kept vials under BSC to be used in Step 8.12.33.

8.11.37 Reviewed Section 8.11

8.12 Day 22 TIL Harvest 8.12.1 Monitor Incubator. Monitored the incubator. Incubator Parameters Temperature LED display: 37±2.0° C., CO2 Percentage: 5%±1.5%. NOTE: Section 8.12 could be run concurrently with Section 8.11.

8.12.2 Removed G-Rex500MCS Flasks from Incubator. Performed check below to ensure incubation parameters were met before removing G-Rex500MCS from incubator.

the GatheRex. Installed the clear harvest line from the G-Rex500MCS to the bottom clamp (marked with a blue line) and tubing guides on the GatheRex.

8.12.9 GatheRex Setup. Attached the gas line from the GatheRex to the sterile filter of the G-Rex500MCS. NOTE: Before removing the supernatant from the G-Rex500MCS, ensured all clamps on the cell removal lines were closed.

8.12.10 Volume Reduction. Transferred ~4.5 L of supernatant from the G-Rex500MCS to the Supernatant bag. Visually inspected G-Rex500MCS to ensure flask is level and media had been reduced to the end of the aspirating dip tube. Repeat step if needed. NOTE: If the GatheRex stopped prematurely, it may be restarted by pressing the button with the arrow pointing to the right again.

8.12.11 Prepared flask for TIL Harvest. After removal of the supernatant, closed all clamps to the red line.

8.12.12 Initiated collection of TIL. Recorded the start time of the TIL harvest.

8.12.13 Initiated collection of TIL. Vigorously tap flask and swirl media to release cells. Performed an inspection of the flask to ensure all cells have detached. Placed "TIL Suspension" 3000 mL collection bag on dry wipes on a flat surface. NOTE: Contacted area management if cells did not detach.

8.12.14 Initiated collection of TIL. Tilted the flask to ensure hose is at the edge of the flask. NOTE: If the cell collection hose was not at the junction of the wall and bottom membrane, rapping the flask while tilted at a 45° angle is usually sufficient to properly position the hose.

| Flask | Shelf | Lower limit from Step 8.10.83 B (DDMMMYY HHMM) | Upper limit from Step 8.10.83 C (DDMMMYY HHMM) | Time of Removal from Incubator (DDMMMYY HHMM) | Is 8.10.83 B < Time of Removal from Incubator < Step 8.10.83 C Yes/No* |
|---|---|---|---|---|---|

NOTE:
This step must was performed as each flask is removed from the incubator.

8.12.3 Prepared TIL collection bag Labeled a 3000 mL collection bag as "TIL Suspension", lot number, and initial/date.

8.12.4 Sealed off extra connections. Heat sealed off two leur connections on the collection bag near the end of each connection per Process Note 5.12.

8.12.5 GatheRex Setup. Sterile welded (per Process Note 5.11) the red media removal line from the G-Rex500MCS to the 10 L labtainer bag prepared in Step 8.11.5. NOTE: Referenced Process Note 5.16 for use of multiple GatheRex devices.

8.12.6 GatheRex Setup. Sterile welded (per Process Note 5.11) the clear cell removal line from the G-Rex500MCS to the TIL Suspension collection bag prepared in Step 8.12.3. NOTE: Reference Process Note 5.16 for use of multiple GatheRex devices.

8.12.7 GatheRex Setup. Placed the G-Rex500MCS flask on the left side of the GatheRex. Placed the supernatant Labtainer bag and pooled TIL suspension collection bag to the right side.

8.12.8 GatheRex Setup. Installed the red media removal line from the G-Rex500MCS to the top clamp (marked with a red line) and tubing guides on 8.12.15 TIL Harvest. Released all clamps leading to the TIL suspension collection bag.

8.12.16 TIL Harvest. Using the GatheRex, transferred the TIL suspension into the 3000 mL collection bag. NOTE: Maintained the tilted edge until all cells and media were collected.

8.12.17 TIL Harvest. Inspect membrane for adherent cells.

8.12.18 Rinsed flask membrane. Rinsed the bottom of the G-Rex500MCS. Covered ~¼ of gas exchange membrane with rinse media.

8.12.19 Close clamps on G-Rex500MCS. Ensure all clamps are closed.

8.12.20 Heat sealed. Heat seal (per Process Note 5.12) the collection bag containing the TIL as close to the weld as possible so that the overall tubing length remained approximately the same.

8.12.21 Heat Sealed. Heat sealed (per Process Note 5.12) the Supernatant bag.

8.12.22 Completed harvest of remaining G-Rex 500 MCS flasks. Repeat Steps 8.12.2 and 8.12.5-8.12.21, pooling all TIL into the same collection bag.

NOTE: IT WAS NECESSARY TO REPLACE THE 10 L SUPERNATANT BAG AFTER EVERY 2ND

FLASK. NOTE: Reference Process Note 5.16 for use of multiple GatheRex devices.

8.12.23 Prepared LOVO source bag. Obtained a new 3000 mL collection bag. Labeled as "LOVO Source Bag", lot number, and Initial/Date.

8.12.24 Prepared LOVO source bag. Heat sealed (per Process Note 5.12) the tubing on the "LOVO Source bag", removing the female luers, leaving enough line to weld.

8.12.25 Weighed LOVO Source Bag. Placed an appropriately sized plastic bin on the scale and tare. Place the LOVO Source Bag, including ports and lines, in the bin and record the dry weight 8.12.26 Transferred cell suspension into LOVO source bag. Closed all clamps of a 170 μm gravity blood filter.

8.12.27 Transferred cell suspension into LOVO source bag. Sterile welded (per Process Note 5.11) the long terminal end of the gravity blood filter to the LOVO source bag.

8.12.28 Transferred cell suspension into LOVO source bag. Sterile welded (per Process Note 5.11) one of the two source lines of the filter to "pooled TIL suspension" collection bag.

8.12.29 Transferred cell suspension into LOVO source bag. Once weld was complete, heat sealed (per Process Note 5.12) the unused line on the filter to remove it.

8.12.30 Transferred cell suspension into LOVO source bag. Opened all necessary clamps and elevate the TIL suspension by hanging the collection bag on an IV pole to initiate gravity-flow transfer of TIL through the blood filter and into the LOVO source bag. Gently rotated or knead the TIL Suspension bag while draining in order to keep the TIL in even suspension. Note: Did not allow the LOVO source bag to hang from the filtration apparatus. Laid LOVO source bag on dry wipes on a flat surface.

8.12.31 Closed all clamps. Once all TIL were transferred to the LOVO source bag, closed all clamps.

8.12.32 Heat Sealed. Heat sealed (per Process Note 5.12) as close to weld as possible to remove gravity blood filter.

8.12.33 Removed Cell Counts Samples. In the BSC, using separate 3 mL syringes for each sample, removed 4×1.0 mL cell count samples from the LOVO source bag using the needless injection port. Placed samples in the cryovials prepared in Step 8.11.36. NOTE: Wiped needless injection port with an alcohol pad and mix LOVO source bag between each sample.

8.12.34 Performed Cell Counts. Performed cell counts and calculations utilizing NC-200 and Process Note 5.14. Diluted cell count samples initially by adding 0.5 mL of cell suspension into 4.5 mL of AIM-V media prepared in Step 8.11.35. This gave a 1:10 dilution.

8.12.35 Recorded Cell Count sample volumes.
8.12.36 Determined Multiplication Factor

| Parameter | Formula | Result |
|---|---|---|
| Total cell count sample Volume | 8.12.35A + 8.12.35B | C. μL |
| Multiplication Factor | C ÷ 8.12.35A | D. |

8.12.37 Selected protocols and enter multiplication factors. Ensured the "Viable Cell Count Assay" protocol had been selected, all multiplication factors, and sample and diluent volumes had been entered. NOTE: If no dilution needed, enter "Sample [μL]"=200, "Dilution [μL]"=0

8.12.38 Record Cell Counts from Nucleoview 8.12.39 Determined the Average Viability, Viable Cell Concentration, and Total Nucleated Cell concentration of the cell counts performed.

| Parameter | Formula | Result |
|---|---|---|
| Viability | (8.12.38A + 8.12.38B) ÷ 2 | G. |
| Viable Cell Concentration | (8.12.38C + 8.12.38D) ÷ 2 | H. cells/mL |
| Total Nucleated Cell Concentration | (8.12.38E + 8.12.38F) ÷ 2 | I. cells/mL |

8.12.40 Determined Upper and Lower Limit for counts

| Parameter | Formula | Result |
|---|---|---|
| Lower Limit | 8.12.39H × 0.9 | J. cells/mL |
| Upper Limit | 8.12.39I × 1.1 | K. cells/mL |

8.12.41 Were both counts within acceptable limits?

| Parameter | Formula | Result (Yes/No) |
|---|---|---|
| Lower Limit | 8.12.38 C and D ≥ 8.12.40J | |
| Upper Limit | 8.12.38 C and D ≤ 8.12.40K | |

NOTE:
If either result was "No" performed second set of counts in steps 8.12.42-8.12.49.

NOTE: If either result was "No" performed second set of counts in steps 8.12.42-8.12.49.

8.12.42 If Applicable: Performed cell counts. Performed cell counts and calculations in utilizing NC-200 and Process Note 5.14. NOTE: Dilution may be adjusted according based off the expected concentration of cells.

8.12.43 If Applicable: Recorded Cell Count sample volumes 8.12.44 If Applicable: Determined Multiplication Factor

| Parameter | Formula | Result |
|---|---|---|
| Total cell count sample Volume | 8.12.43A + 8.12.43B | C. μL |
| Multiplication Factor | C ÷ 8.12.43A | D. |

8.12.45 If Applicable: Selected protocols and enter multiplication factors. Ensure the "Viable Cell Count Assay" protocol had been selected, all multiplication factors, and sample and diluent volumes had been entered. NOTE: If no dilution needed, enter "Sample [μL]"=200, "Dilution [μL]"=0

8.12.46 If Applicable: Record Cell Counts from Nucleoview 8.12.47 If Applicable: Determine the Average Viability, Viable Cell Concentration, and Total Nucleated Cell concentration of the cell counts performed.

| Parameter | Formula | Result |
|---|---|---|
| Viability | (8.12.46A + 8.12.46B) ÷ 2 | G. |
| Viable Cell Concentration | (8.12.46C + 8.12.46D) ÷ 2 | H. cells/mL |
| Total Nucleated Cell Concentration | (8.12.46E + 8.12.46F) ÷ 2 | I. cells/mL |

8.12.48 If Applicable: Determined Upper and Lower Limit for counts

| Parameter | Formula | Result |
|---|---|---|
| Lower Limit | 8.12.47 H × 0.9 | J. cells/mL |
| Upper Limit | 8.12.47 H × 1.1 | K. cells/mL |

8.12.49 If Applicable: Were counts within acceptable limits?

| Parameter | Formula | Result (Yes/No) |
|---|---|---|
| Lower Limit | 8.12.46 C and D ≥ 8.12.48J | |
| Upper Limit | 8.12.46 C and D ≤ 8.12.48K | |

NOTE:
If either result was "No" continue to Step 8.12.50 to determine an average 8.12.50 If Applicable: Determined an average Viable Cell Concentration and average Total Nucleated Cell Concentration from all four counts performed.

8.12.51 QA Review of Cell Counts. QA personnel review calculations performed in steps 8.12.38-8.12.50.

8.12.52 Weighed LOVO Source Bag. Placed an appropriately sized plastic bin on the scale and tare. Placed the full LOVO source bag in the bin and record the weight. Calculated the volume of cell suspension.

8.12.53 Calculate Total Viable TIL Cells.

| Parameter | Formula | Result |
|---|---|---|
| Average Viable Cell Concentraion* | 8.12.39 H* -or- 8.12.47 H* -or- | A. cells/mL |
| Total Volume | 8.12.52 C | B. mL |
| Total Viable Cells | A × B | C. cells |
| Is C ≥ 1.5 × $10^9$? | | Yes/No** |

*Circled step reference used to determine Viable Cell Concentration.
**If "Yes," proceeded. If "No," contacted Area Management.

8.12.54 Calculate Total Nucleated Cells.

| Parameter | Formula | Result |
|---|---|---|
| Average Total Nucleated Cell Concentraion* | 8.12.39 I* -or- 8.12.47 I* -or- | A. cells/mL |
| Total Volume | 8.5.52 C | B. mL |
| Total Nucleated Cells | A × B | C. cells |

*Circled step reference used to determine Total Nucleated Cell Concentration.

8.12.55 Prepared *Mycoplasma* Diluent. In the BSC, removed 10.0 mL from one supernatant bag via Luer sample port and placed in a 15 mL conical. Label 15 mL conical "*Mycoplasma* Diluent" and keep in the BSC for use in Step 8.14.69.

8.12.56 Review Section 8.12

8.13 LOVO 8.13.1 Turned on the LOVO using the switch on the back left of the instrument. NOTE: Steps 8.13.1-8.13.13 may be performed concurrently with Sections 8.11-8.12.

8.13.2 Checked weigh scales and pressure sensor.

8.13.3 Made sure there was nothing hanging on any of the weigh scales and reviewed the reading for each scale. Recorded values in Step 8.13.5. Note: If any of the scales read outside of a range of 0+/−2 g, performed weigh scale calibration 8.13.4 If all scales were in tolerance with no weight hanging, proceeded to hang a 1-kg weight on each scale (#1-4) and reviewed the reading. Recorded Values in Step 8.13.5.

8.13.5 Scale Checked. Recorded the displayed values for each scale. If values were in range, continue processing. If values were not in range, perform Calibration.

8.13.6 Reviewed the pressure sensor reading on the Instrument Operation Profile Screen and recorded. The acceptable range for the pressure reading was 0+/−10 mmHg. If displayed value was out of this range, stored a new atmospheric pressure setting, per the machine instructions.

8.13.7 Repeated steps. If a new weigh scale calibration had been performed or a new atmospheric pressure setting had been stored, repeated Steps 8.13.3-8.13.6.

8.13.8 Started the "TIL G-Rex Harvest" protocol from the drop-down menu.

8.13.9 The Solution 1 Screen displayed: Buffer type read PlasmaLyte 8.13.10-8.13.16 Followed the LOVO touch screen prompts.

8.13.17 Determined the final product target volume. NOTE: Using the total nucleated cells (TNC) value from Step 8.12.54 C and the chart below, determined the final product target volume. Recorded the Final Product Volume (mL)

| Cell Range | Final Product (Retentate) Volume to Target (mL) |
|---|---|
| 0 < Total (Viable + Dead) Cells ≤ 7.1 × $10^{10}$ | 165 |
| 7.1 × $10^{10}$ < Total (Viable + Dead) Cells ≤ 1.1 × $10^{11}$ | 215 |
| 1.1 × $10^{11}$ < Total (Viable + Dead) Cells ≤ 1.5 × $10^{11}$ | 265 |

Note:
If TVC from Step 8.12.53 C was >1.5 × $10^{11}$ contacted Area Management.

8.13.18-8.13.22 Followed the LOVO touch screen prompts.

8.13.23 Loaded disposable kit. Prior to loading the disposable kit, wipe pressure sensor port with an alcohol wipe followed by a lint-free wipe. Load the disposable kit. Follow screen directions on loading the disposable kit.

8.13.24 Removed filtrate bag. When the standard LOVO disposable kit had been loaded, touched the Next button. The Container Information and Location Screen displayed. Removed filtrate bag from scale 8.13.25 Ensured Filtrate container was New and Off-Scale 8.13.26 Entered Filtrate capacity. Sterile welded a LOVO Ancillary Bag onto the male luer line of the existing Filtrate Bag. Ensured all clamps are open and fluid path is clear. Touch the Filtrate Container Capacity entry field. A numeric keypad displays. Enter the total new Filtrate capacity (5,000 mL). Touch the button to accept the entry. NOTE: Estimated Filtrate Volume should not exceed 5000 mL.

8.13.27 Placed Filtrate container on benchtop. NOTE: If tubing was removed from the F clamp during welding, placed the tubing back into the clamp. Placed the new Filtrate container on the benchtop. DID NOT hang the Filtrate bag on weigh scale #3. Weigh scale #3 will be empty during the procedure.

8.13.28 Followed the LOVO touch screen prompts after changes to the filtrate container.

8.13.29 Ensured kit was loaded properly. The Disposable Kit Dry Checks overlay displays. Checked that the kit was loaded properly and all clamps were open. Checked all tubing for kinks or other obstructions and correct if possible. Ensured kit was properly installed and check all Robert's clamps. Pressed the Yes button. All LOVO mechanical clamps closed automatically and the Checking Disposable Kit Installation screen displays. The LOVO went through a series of pressurizing steps to check the kit.

8.13.30 Kit Check Results. If the Kit check passed, proceeded to the next step. *If No, a second Kit Check could be performed after checks have been complete. *If No, Checked all tubing for kinks or other obstructions and correct *If No, Ensured kit was properly installed and check all Robert's clamps. If the 2nd kit check failed: Contact area management and prepare to installation of new kit in Section 10.0. Repeat Step 8.13.23-Step 8.13.30 needed.

8.13.31 Attached PlasmaLyte. The Connect Solutions screen displayed. The wash value would always be 3000 mL. Entered this value on screen. Sterile welded the 3000 mL bag of PlasmaLyte to the tubing passing through Clamp 1 per Process Note 5.11. Hung the PlasmaLyte bag on an IV pole placing both corner bag loops on the hook.

8.13.32 Verified that the PlasmaLyte was attached. Opened any plastic clamps. Verified that the Solution Volume entry was 3000 mL. Touched the "Next" button. The Disposable Kit Prime overlay displayed. Verified that the PlasmaLyte was attached and any welds and plastic clamps on the tubing leading to the PlasmaLyte bag were open, then touched the Yes button 8.13.33 Observed that the PlasmaLyte is moving. Disposable kit prime starts and the Priming Disposable Kit Screen displays. Visually observed that Plasma-Lyte moving through the tubing connected to the bag of PlasmaLyte. If no fluid was moving, pressed the Pause Button on the screen and determined if a clamp or weld was still closed. Once the problem had been solved, pressed the Resume button on the screen to resume the Disposable Kit Prime. When disposable kit prime finished successfully, the Connect Source Screen displayed.

8.13.34-8.13.35 Followed the LOVO touch screen prompts.

8.13.36 Attached Source container to tubing. Sterile weld the LOVO Source Bag prepared in Step 8.12.31 to the tubing passing through Clamp S per Process Note 5.11. It could be necessary to remove the tubing from the clamp. Note: Made sure to replace source tubing into the S clamp if removed.

8.13.37 Hung Source container. Hung the Source container on the IV pole placing both corner bag loops on the hook. DID NOT hang the Source on weigh scale #1. Opened all clamps to the source bag.

8.13.38 Verified Source container was attached. Touched the Next button. The Source Prime overlay displayed. Verified that the Source was attached to the disposable kit, and that any welds and plastic clamps on the tubing leading to the Source were open. Touched the Yes button.

8.13.39 Confirm PlasmaLyte was moving. Source prime started and the Priming Source Screen displayed. Visually observed that PlasmaLyte is moving through the tubing attached to the Source bag. If no fluid is moving, press the Pause Button on the screen and determine if a clamp or weld is still closed. Once the problem was solved, pressed the Resume button on the screen to resume the Source Prime.

8.13.40 Started Procedure Screen. When the Source prime finishes successfully, the Start Procedure Screen displays. Pressed Start, the "Pre-Wash Cycle 1" pause screen appears immediately after pressing start.

8.13.41 Inverted In Process Bag. Removed the In Process Bag from weigh scale #2 (can also remove tubing from the In Process top port tubing guide) and manually invert it to allow the wash buffer added during the disposable kit prime step to coat all interior surfaces of the bag. Re-hang the In Process Bag on weigh scale #2 (label on the bag was facing to the left). Replace the top port tubing in the tubing guide, if it was removed.

8.13.42 Inverted Source bag. Before pressing the Start button, mixed the Source bag without removing it from the IV pole by massaging the bag corners and gently agitating the cells to create a homogeneous cell suspension. Pressed the Resume button. The LOVO started processing fluid from the Source bag and the Wash Cycle 1 Screen displays.

8.13.43 Source Rinse Pause. The Rinse Source Pause screen displayed once the source container is drained and the LOVO had added wash buffer to the Source bag. Without removing the Source bag from IV pole, massaged the corners and mixed well. Pressed Resume.

8.13.44 Mix In Process Bag Pause. To prepare cells for another pass through the spinner, the In Process Bag was diluted with wash buffer. After adding the wash buffer to the In Process Bag, the LOVO pauses automatically and displays the "Mix In Process Bag"

Pause Screen. Without removing the bag from the weigh scale, mixed the product well by gently squeezing the bag. Press Resume.

8.13.45 Massage In Process Corners Pause. When the In Process Bag was empty, wash buffer was added to the bottom port of the In Process Bag to rinse the bag. After adding the rinse fluid, the LOVO paused automatically and displayed the "Massage IP corners" Pause Screen. When the "Massage IP corners" Pause Screen displayed, DO NOT remove the bag from weigh scale #2. With the In Process Bag still hanging on weigh scale #2, massage the corners of the bag to bring any residual cells into suspension. Ensured the bag was not swinging on the weigh scale and pressed the Resume button.

8.13.46 Wait for Remove Products Screen. At the end of the LOVO procedure, the Remove Products Screen displayed. When this Screen displays, all bags on the LOVO kit could be manipulated. Note: Did not touch any bags until the Remove Products displayed.

8.13.47 Removed retentate bag. Placed a hemostat on the tubing very close to the port on the Retentate bag to keep the cell suspension from settling into the tubing. Heat sealed (per Process Note 5.12) below the hemostat, making sure to maintain enough line to weld in Step 8.13.48. Removed the retentate bag.

8.13.48 Prepared retentate bag for formulation. Welded (per Process Note 5.11) the female luer lock end of a 4" Plasma Transfer Set to the retentate bag. Transferred the retentate bag to the BSC for use in Step 8.14.11.

8.13.49 Removed Products. Followed the instructions on the Remove Products Screen. Closed all clamps on the LOVO kit to prevent fluid movement.

8.13.50 Removed Products. Touched the Next button. All LOVO mechanical clamps opened and the Remove Kit Screen displayed.

8.13.51 Recorded Data. Followed the instructions on the Remove Kit screen. Touched the "Next" button. All LOVO mechanical clamps close and the Results Summary Screen displays. Recorded the data from the results summary screen in table exactly as they are displayed. Closed all pumps and filter support. Removed the kit when prompted to do so by the LOVO. *NOTE: All Times recorded were recorded directly from the LOVO Results Summary Screen in HH:MM:SS format and (HH:MM:SS) format when applicable 8.13.52-8.13.54 Protocol Selection through LOVO shutdown. Follow the LOVO screen prompts.

8.13.55 Review Section 8.13

8.14 Final Formulation and Fill 8.14.1 Target volume/bag calculation. From the table below, selected the number of CS750 bags to be filled, target fill volume per bag, volume removed for retain per bag, and final target volume per bag that corresponded to the Volume of LOVO Retentate from Step 8.13.22.

| Volume of LOVO product | Volume of CS10 to add to product | Final Predicted Volume of formulated product | Number of bags to be filled | Target Fill Volume per bag | Volume removed for retain per bag | Final Target Volume per bag |
|---|---|---|---|---|---|---|
| 165 mL | 165 mL | 330 mL | 3 | 107 mL | 7 mL | 100 mL |
| 215 mL | 215 mL | 430 mL | 4 | 105 mL | 5 mL | 100 mL |
| 265 mL | 265 mL | 530 mL | 4 | 130 mL | 5 mL | 125 mL |

8.14.2 Prepared CRF Blank. Calculated volume of CS-10 and LOVO wash buffer to formulate blank bag.

| Final Target Volume per Bag 8.14.1E | Blank LOVO Wash Buffer Volume | Blank CS-10 Volume (mL) |
|---|---|---|
| A | B = A/2 | C = B |
| mL | mL | mL |

8.14.3 Prepared CRF Blank. Outside of the BSC, using the syringe of LOVO Wash Buffer prepared in Step 8.11.29, added volume calculated in Step 8.14.2 B to an empty CS750 bag via luer connection. Note: Blank CS750 bag formulation does not need to be done aseptically.

8.14.4 Prepared CRF Blank Using an appropriately sized syringe, added the volume of CS-10 calculated in Step 8.14.2 to the same CS750 bag prepared in Step 8.14.3. Placed a red cap on the CS750 bag.

8.14.5 Prepared CRF Blank. Removed as much air as possible from the CS-750 bag as possible. Heat sealed (per Process Note 5.12) the CS750 bag as close to the bag as possible, removing the tubing.

8.14.6 Prepared CRF Blank.Label CS750 bag with "CRF Blank", lot number, and initial/date. Placed the CRF Blank on cold packs until it was placed in the CRF.

8.14.7 Calculated required volume of IL-2. Calculated the volume of IL-2 to add to the Final Product

| Parameter | Formula | Result |
|---|---|---|
| Final Retentate Volume | Step 8.13.51 | A. mL |
| Final Formulated Volume | B = A × 2 | B. mL |
| Final IL-2 Concentration desired (IU/mL) | 300 IU/mL | C. 300 IU/mL |
| IU of IL-2 Required | D = B × C | D. IU |
| IL-2 Working Stock from Step 8.11.33 | $6 \times 10^4$ IU/mL | E. $6 \times 10^4$ IU/mL |
| Volume of IL-2 to Add to Final Product | F = D ÷ E | F. mL |

8.14.8 Assembled Connect apparatus. Sterile welded (per Process Note 5.11) a 4S-4M60 to a CC2 Cell Connect replacing a single spike of the Cell Connect apparatus (B) with the 4-spike end of the 4S-4M60 manifold at (G).

8.14.9 Assembled Connected apparatus. Sterile welded (per Process Note 5.11) the CS750 Cryobags to the harness prepared in Step 8.14.8, connecting one of the four male luer ends (E) with each bag. Reference Step 8.14.1 to determine the number of bags needed.

8.14.10 Assembled Connected apparatus. Welded (per Process Note 5.11) CS-10 bags to spikes of the 4S-4M60. Kept CS-10 cold by placing the bags between two cold packs conditioned at 2-8° C.

8.14.11 Passed materials into the BSC.

| Item | Item # or Step | Quantity |
|---|---|---|
| 4" plasma transfer set | | 1 |
| IL-2 ($6.0 \times 10^4$) aliquot | 8.11.33 | 1 |
| Appropriate size syringe to add IL2 | 8.14.7F | 1 |
| LOVO retentate bag | 8.13.48 | 1 |
| Red Caps | | 5 |

8.14.12 Prepared TIL with IL-2. Using an appropriately sized syringe, removed amount of IL-2 determined in Step 8.14.7 from the "IL-2 $6\times10^4$" aliquot.

8.14.13 Prepared TIL with IL-2. Connect the syringe to the retentate bag prepared in Step 8.13.48 via the Luer connection and inject IL-2.

8.14.14 Prepare TIL with IL-2 Clear the line by pushing air from the syringe through the line.

8.14.15 Labeled Formulated TIL Bag. Closed the clamp on the transfer set and label bag as "Formulated TIL" and passed the bag out of the BSC.

8.14.16 If applicable: Sample per sample plan. If there was remaining "IL-2 $6\times10^4$" aliquot prepared in step 8.11.33, remove a ~5 mL sample retain according to the sample plan using an appropriately sized syringe and dispense into a 50 mL conical tube.

8.14.17 If applicable: Sampled per sample plan. Labeled with sample plan inventory label and stored at 2-8° C. until submitted to Login for testing per Sample Plan.

8.14.18 If applicable: Sampled per sample plan. Ensured that LIMS sample plan sheet was filled out for removal of the sample.

8.14.19 Added the Formulated TIL bag to the apparatus. Once IL-2 had been added, welded (per Process Note 5.11) the "Formulated TIL" bag to the remaining spike (A) on the apparatus prepared in Step 8.14.10.

8.14.20 Added CS10. Passed the assembled apparatus with attached Formulated TIL, CS-750 bags, and CS-10 into the BSC. NOTE: The CS-10 bag and all CS-750 bags were placed between two cold packs preconditioned at 2-8° C. Did not place Formulated TIL bag on cold packs.

8.14.21 Added CS 10. Ensured all clamps were closed on the apparatus. Turn the stopcock so the syringe was closed.

8.14.22 Switched Syringes. Drew ~10 mL of air into a 100 mL syringe and replaced the 60 mL syringe on the apparatus.

8.14.23 Added CS10. Turned stopcock so that the line to the CS750 bags is closed. Open clamps to the CS-10 bags and pull volume calculated in Step 8.14.1B into syringe. NOTE: Multiple syringes will be used to add appropriate volume of CS-10. NOTE: Record volume from each syringe in Step 8.14.26

8.14.24 Added CS10. Closed clamps to CS-10 and open clamps to the Formulated TIL bag and add the CS-10. Note: Add first 10.0 mL of CS10 at approximately 10.0 mL/minute. Add remaining CS-10 at approximate rate of 1.0 mL/sec. Note: Multiple syringes were used to add appropriate volume of CS-10. Did not reuse a syringe once it had been dispensed.

8.14.25 Added CS10. Recorded time. NOTE: The target time from first addition of CS-10 to beginning of freeze is 30

8.14.26 Added CS10. Recorded the volume of each CS10 addition and the total volume added. Total volume match calculated volume from Step 8.14.1B 8.14.27 Added CS 10. Closed all clamps to the CS 10 bags.

8.14.28 Prepared CS-750 bags. Turned the stopcock so that the syringe was open. Opened clamps to the Formulated TIL bag and drew up suspension stopping just before the suspension reaches the stopcock.

8.14.29 Prepared CS-750 bags. Closed clamps to the formulated TIL bag. Turned stopcock so that it was open to the empty CS750 final product bags.

8.14.30 Prepared CS-750 bags. Using a new syringe, removed as much air as possible from the CS750 final product bags by drawing the air out. While maintaining pressure on the syringe plunger, clamped the bags shut.

8.14.31 Prepared CS-750 bags. Draw ~20 mL air into a new 100 mL syringe and connect to the apparatus.

NOTE: Each CS-750 final product bag should be between two cold packs to keep formulated TIL suspension cold.

8.14.32 Dispensed cells. Turned the stopcock so the line to the final product bags was closed. Pulled the volume calculated in Step 8.14.1 from the Formulated TIL bag into the syringe. NOTE: Multiple syringes could be used to obtain correct volume.

8.14.33 Dispensed cells. Turned the stopcock so the line to the formulated TIL bag is closed. Working with one final product bag at a time, dispense cells into a final product bag. Recorded volume of cells added to each CS750 bag in Step 8.14.35

8.14.34 Dispensed cells. Cleared the line with air from the syringe so that the cells are even with the top of the spike port. Closed the clamp on the filled bag. Repeated Step 8.14.29-Step 8.14.34 for each final product bag, gently mixing formulated TIL bag between each.

8.14.35 Dispensed cells. Record volume of TIL placed in each final product bag below.

8.14.36 Removed air from final product bags and take retain. Once the last final product bag was filled, closed all clamps.

8.14.37 Removed air from final product bags and take retain. Drew 10 mL of air into a new 100 mL syringe and replace the syringe on the apparatus.

8.14.38 Removed air from final product bags and take retain. Manipulating a single bag at a time, drew all of the air from each product bag plus the volume of product for retain determined in Step 8.14.1 D. NOTE: Upon removal of sample volume, inverted the syringe and used air to clear the line to the top port of the product bag. Clamped the line to the bag once the retain volume and air was removed.

8.14.39 Recorded Volume Removed. Recorded volume of retain removed from each bag.

8.14.40 Dispensed Retain. Dispensed retain into a 50 mL conical tube and label tube as "Retain" and lot number. Repeat Step 8.14.37-Step 8.14.39 for each bag.

8.14.41 Prepared final product for cryopreservation. With a hemostat, clamped the lines close to the bags. Removed syringe and red cap luer connection on the apparatus that the syringe was on. Passed apparatus out of the BSC.

8.14.42 Prepared final product for cryopreservation. Heat sealed (per Process Note 5.12) at F, removing the empty retentate bag and the CS-10 bags. NOTE: Retained luer connection for syringe on the apparatus. Disposed of empty retentate and CS-10 Bags.

8.14.43 Performed visual inspection. NOTE: Step 8.14.43-Step 8.14.46 may be performed concurrently with Step 8.14.47-Step 8.14.68.

8.14.44 Final Product Label Sample. Labeled final product bags. Attached sample final product label below.

8.14.45 Prepared final product for cryopreservation. Held the cryobags on cold pack or at 2-8° C. until cryopreservation.

8.14.46 Prepared external labels. Ensured the QA issued external labels that will be attached to the cassettes labels match corresponding final product label. Attached QA issued external labels to cassettes. Attached a sample external label below:

8.14.47 Removed Cell Count Sample. Using an appropriately sized pipette, remove 2.0 mL of retain removed in Step 8.14.38 and place in a 15 mL conical tube to be used for cell counts.

8.14.48 Performed Cell Counts. Performed cell counts and calculations utilizing the NC-200 per SOP-00314 and Process Note 5.14. NOTE: Diluted only one sample to appropriate dilution to verify dilution is sufficient. Diluted additional samples to appropriate dilution factor and proceed with counts.

8.14.49 Recorded Cell Count sample volumes. NOTE: If no dilution needed, "Sample [μL]"=200, "Dilution [μL]"

8.14.50 Determined Multiplication Factor

| Parameter | Formula | Result |
|---|---|---|
| Total cell count sample Volume | 8.14.49A + 8.14.49B | C. μL |
| Multiplication Factor | C ÷ 8.14.49A | D. |

8.14.51 Select protocols and enter multiplication factors. Ensure the "Viable Cell Count Assay" protocol has been selected, all multiplication factors, and sample and diluent volumes have been entered per SOP-00314 NOTE: If no dilution needed, enter "Sample [μL]"=200, "Dilution [μL]"=0

8.14.52 Recorded File Name, Viability and Cell Counts from Nucleoview.

8.14.53 Determined the Average of Viable Cell Concentration and Viability of the cell counts performed.

| Parameter | Formula | Result |
|---|---|---|
| Viability | (8.14.52A + 8.14.52B) ÷ 2 | E. % |
| Viable Cell Concentration | (8.14.52C + 8.14.52D) ÷ 2 | F. cells/mL |

8.14.54 Determined Upper and Lower Limit for counts.

| Parameter | Formula | Result |
|---|---|---|
| Lower Limit | 8.14.53F × 0.9 | G. cells/mL |
| Upper Limit | 8.14.53F × 1.1 | H. cells/mL |

8.14.55 Were both counts within acceptable limits?

| Parameter | Formula | Result (Yes/No) |
|---|---|---|
| Lower Limit | 8.14.52 C and D ≥ 8.14.54G | |
| Upper Limit | 8.14.52 C and D ≤ 8.14.54H | |

NOTE:
If either result is "No" perform second set of counts in steps 8.14.56-8.14.63

8.14.56 If Applicable: Performed cell counts. Performed cell counts and calculations in utilizing NC-200 per SOP-00314 and Process Note 5.14. NOTE: Dilution may be adjusted according based off the expected concentration of cells.

8.14.57 If Applicable: Recorded Cell Count sample volumes.

8.14.58 If Applicable: Determined Multiplication Factor

| Parameter | Formula | Result |
|---|---|---|
| Total cell count sample Volume | 8.14.57A + 8.14.57B | C. mL |
| Multiplication Factor | C ÷ 8.14.57A | D. |

8.14.59 If Applicable: Selected protocols and entered multiplication factors. Ensured the "Viable Cell Count Assay" protocol had been selected, all multiplication factors, and sample and diluent volumes had been entered. NOTE: If no dilution needed, enter "Sample [μL]"=200, "Dilution [μL]"=0

8.14.60 If Applicable: Recorded Cell Counts from Nucleoview 8.14.61 If Applicable: Determined the Average of Viable Cell Concentration and Viability of the cell counts performed.

| Parameter | Formula | Result |
|---|---|---|
| Viability | (8.14.60A + 8.14.60B) ÷ 2 | E. % |
| Viable Cell Concentration | (8.14.60C + 8.14.60D) ÷ 2 | F. cells/mL |

8.14.62 If Applicable: Determined Upper and Lower Limit for counts.

| Parameter | Formula | Result |
|---|---|---|
| Lower Limit | 8.14.61F × 0.9 | G. cells/mL |
| Upper Limit | 8.14.61F × 1.1 | H. cells/mL |

8.14.63 If Applicable: Were counts within acceptable limits?

| Parameter | Formula | Result (Yes/No) |
|---|---|---|
| Lower Limit | 8.14.60 C and D ≥ 8.14.62G | |
| Upper Limit | 8.14.60 C and D ≤ 8.14.62H | |

NOTE:

If either result is "No" continue to Step 8.14.64 to determine an average.

8.14.64 If Applicable: Determined an average Viable Cell Concentration from all four counts performed.

8.14.65 Calculated Flow. Cytometry Sample. Performed calculation to ensure sufficient cell concentration for flow cytometry sampling.

| Viable Cell Concentration From Step 8.14.53 F* Or Step 8.14.61 F* Or Step 8.14.64 E* A | Target Volume Required for $6 \times 10^7$ TVC B = $6 \times 10^7$ cells/A | Is B ≤ 1.0 mL? (Yes/No**) |
|---|---|---|
| cells/mL | mL | |

*Circle step reference used to determine Viable Cell Concentration
**NOTE:
If "No", contact area management.

8.14.66 Calculated IFN-γ. Sample Performed calculation to ensure sufficient cell concentration for IFN-γ sampling

| Viable Cell Concentration From Step 8.14.53 F* Or Step 8.14.61 F* Or Step 8.14.64 E* A | Volume Required for Minimum $1.5 \times 10^7$ TVC B = $1.5 \times 10^7$ cells/A | Is B ≤ 1.0 mL? (Yes/No**) |
|---|---|---|
| cells/mL | mL | |

*Circle step reference used to determine Viable Cell Concentration
**NOTE:
If "No", contact area management.

8.14.67 Reported Results. Completed forms for submission with samples.

8.14.68 Heat Sealed. Once sample volumes had been determined, heat sealed (per Process Note 5.12) Final Product Bags as close to the bags as possible to remove from the apparatus.

8.14.69 Labeled and Collected Samples per Sample Plan.

| Sample | Number of Containers | Sample Volume to Add to | Container Type | Destination |
|---|---|---|---|---|
| *Mycoplasma | 1 | 1.0 mL | 15 mL Conical | Login |
| Endotoxin | 2 | 1.0 mL | 2 mL Cryovial | Login |
| Gram Stain | 1 | 1.0 mL | 2 mL Cryovial | Login |
| IFN-g | 1 | 1.0 mL | 2 mL Cryovial | Login |
| Flow Cytometry | 1 | 1.0 mL | 2 mL Cryovial | Login |
| **Bac-T Sterility | 2 | 1.0 mL | Bac-T Bottle | Login |
| QC Retain | 4 | 1.0 mL | 2 mL Cryovial | CRF |
| Satellite Vials | 10 | 0.5 mL | 2 mL Cryovial | CRF |

*NOTE:
For the Mycoplasma sample, add formulated cell suspension volume to the 15 mL conical labelled "Mycoplasma Diluent" from Step 8.12.55.

**NOTE:
Proceed to Step 8.14.70 for Bac-T inoculation.

8.14.70 Sterility & BacT. Testing Sampling. In the BSC, remove a 1.0 mL sample from the retained cell suspension collected in Step 8.14.38 using an appropriately sized syringe and inoculate the anaerobic bottle. Repeat the above for the aerobic bottle. NOTE: Store Bac-T bottles are room temperature and protect from light.

8.14.71 Labeled and stored samples. Labeled all samples with sample plan inventory labels and store appropriately until transfer to Login. NOTE: Proceeded to Section 8.15 for cryopreservation of final product and samples.

8.14.72 Signed for sampling. Ensured that LIMS sample plan sheet is completed for removal of the samples.

8.14.73 Sample Submission. Submitted all Day 22 testing samples to Login.

8.14.74 Environmental Monitoring. After processing, verified BSC and personnel monitoring had been performed.

8.14.75 Review Section 8.14

8.15 Final Product Cryopreservation 8.15.1 Prepared Controlled Rate Freezer. Verified the CRF had been set up prior to freeze. Record CRF Equipment. Cryopreservation is performed.

8.15.2 Set up CRF probes. Punctured the septum on the CRF blank bag. Inserted the 6 mL vial temperature probe.

8.15.3 Placed final product and samples in CRF. Placed blank bag into preconditioned cassette and transferred into the approximate middle of the CRF rack. Transferred final product cassettes into CRF rack and vials into CRF vial rack.

8.15.4 Placed final product and samples in CRF. Transferred product racks and vial racks into the CRF. Recorded the time that the product is transferred into the CRF and the chamber temperature in Step 8.15.5. NOTE: Evenly distributed the cassettes and vial rack in the CRF, allowed as much space as possible between each shelf.

8.15.5 Determined the time needed to reach 4° C.±1.5° C. and proceed with the CRF run. Once the chamber temperature reached 4° C.±1.5° C., started the run. Recorded time.

| Parameter | Formula | Value |
|---|---|---|
| Time Final Product is transferred to CRF | (HHMM) | |
| Temperature Final Product is transferred into CRF | From monitor | °C. |
| B. CRF Start Time | (HHMM) | |
| Elapsed Time from Formulation to CRF Start | C = B − Step 8.14.25A | min |

8.15.6 CRF Completed and Stored. Stopped the CRF after the completion of the run. Remove cassettes and vials from CRF. Transferred cassettes and vials to vapor phase LN2 for storage. Recorded storage location Post Processing Summary
  Post-Processing: Final Drug Product
    (Day 22) Determination of CD3+ Cells on Day 22 REP by Flow Cytometry
    (Day 22) Gram Staining Method (GMP)
    (Day 22) Bacterial Endotoxin Test by Gel Clot LAL Assay (GMP)
    (Day 16) BacT Sterility Assay (GMP)
    (Day 16) *Mycoplasma* DNA Detection by TD-PCR (GMP)
    Acceptable Appearance Attributes (Step 8.14.43)
    (Day 22) BacT Sterility Assay (GMP)
    (Day 22) IFN-gamma Assay Example 2. Genetic Editing of a Cryopreserved TIL Therapy Using TALE Nucleases This example describes the use of a genetic editing step in conjunction with a TIL manufacturing process, such as the process shown in FIG. 20.

Optimization of human TIL electroporation is performed as follows. Four-6 pre-REP TIL lines derived from melanoma will be identified that express >25% PD1. Selected TIL lines will be thawed, rested, and activated, working 1 line at a time. Five-million activated TILs will be electroporated with each of the following control or test RNA: no Electroporation control (NE); no RNA control; green fluorescent protein (GFP) mRNA transfection control, CD52 TALEN KO control, PD1 TALEN, LAG-3 TALEN, and TIM-3 TALEN. Viable cells will be counted and an aliquot set aside for transfection efficiency measurements (GFP expression). Electroporated cells will be expanded by REP. Post-REP TILs will be assessed for cell viability and fold expansion (cell counter) and target gene knockdown (flow and qPCR). The target results are >80% viability or within 10% of NE; >70% transfection; fold expansion of TILs to within 30% of NE; and >50% knockout.

Implementation of TALEN-mediated PD-1 knockout to the TIL manufacturing process is performed as follows. Up to 6 fresh tumors from several histologies that may include melanoma, sarcoma, and breast and lung cancer will be used. Research-scale preps will be performed according to the processes shown in FIGS. 20 and 21. Electroporation conditions from prior experiments will be applied at predetermined time points of each of the processes. Post-REP TILs will be assessed for: Cell viability and fold expansion (cell counter); Cell phenotypes (flow cytometry); TCR Vβ repertoire (flow); T cell effector functions (IFN-γ production upon re-stimulation); and target gene knockdown (flow and qPCR). The target results are: >80% viability or within 10% of NE; >70% transfection; fold expansion within 30% of NE; T cell lineages/subsets maintained compared to TILs produced by process 2A; adequate TIL potency; and >50% knockout of PD-1. Following this work, one full-scale preparation of PD-1 knockdown TILs will be carried out and fully characterized.

Validation of the silencing of two additional target genes in addition to PD-1 will also be tested.

Example 3. TALEN-Mediated Inactivation of PD-1 in TILs

This example describes TALEN-mediated inactivation of PD-1 in conjunction with a TIL manufacturing process described herein, such as a process shown in FIG. 20 or FIG. 21. The TIL manufacturing process may include early addition of OKT-3 and/or a 4-1BB agonist to the cell culture medium e.g., as illustrated in Embodiment 2 of FIG. 21. The OKT-3 and/or 4-1BB agonist may optionally be added beginning on Day 0 or Day 1 of the first expansion or the second expansion.

TALEN construction and electroporation may be carried out according to methods described by Menger, et al., *Cancer Res.*, 2016 Apr. 15; 76(8):2087-93, Gautron, et al., et al., *Molecular Therapy: Nucleic Acids* 2017, 9:312-321, or U.S. Pat. No. 9,458,439, the disclosures of each of which are incorporated by reference herein. TALEN targeting the PD-1 gene will be produced, e.g., using a solid phase assembly method described by Daboussi et al., *Nat Commun* 2014; 5:3831, which is incorporated by reference herein, or may be obtained commercially from Trilink Biotechnologies or other providers as described in Gautron, et al., et al., *Molecular Therapy: Nucleic Acids* 2017, 9:312-321. The procedure described in Gautron, et al., et al., *Molecular Therapy: Nucleic Acids* 2017, 9:312-321, and described elsewhere herein, for activation of TILs, may be employed, wherein TILs are activated using Dynabeads human T-cell activator CD3/CD28 beads (available commercially from Invitrogen) at ratio of 1:1 CD3$^+$ bead:cell or human T-cell activator CD3/CD28 antibody complexes such as Immunocult CD3/CD28 activator (available commercially from StemCell Technologies). A total of 5×10$^6$ TILs/180 μL of BTX cytoporation medium T may be mixed with about 10 to 20 μg of the in vitro transcribed TALEN mRNA (mMESSAGE mMACHINE T7 kit; Ambion), before electroporation using an Agile Pulse BTX system (Harvard Apparatus). Electroporated cells may be expanded by pre-REP and REP methods described elsewhere herein. Post-REP TILs will be assessed for cell viability and fold expansion (cell counter) and PD-1 knockdown (flow and qPCR). The target results are >80% viability or within 10% of a "no electroporation" (NE) control; >70% transfection; fold expansion of TILs to within 30% of NE; and >50% PD-1 knockout. Electroporation methods known in the art, such as those described in U.S. Pat. Nos. 6,010,613 and 6,078,490, the disclosures of which are incorporated by reference herein, may be used.

Pulsed electroporation optimization may be performed using methods described herein or as follows. A first set of experiments were performed on TILs in order to determine a voltage range in which cells could be transfected. Five different Programs were tested

| | Group 1 | | | | Group 2 | | | | Group 3 | | | |
|---|---|---|---|---|---|---|---|---|---|---|---|---|
| Program | Pulses | V | Duration (ms) | Interval (ms) | Pulses | V | Duration (ms) | Interval (ms) | Pulses | V | Duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 |

TILs may be electroporated in 0.4 cm gap cuvette (on the order of about $10^6$ cells/mL) with about 20 μg of plasmids encoding GFP and control plasmids pUC using the different electroporation programs. About 24 hours post electroporation, GFP expression was analyzed in electroporated cells by flow cytometry to determine the efficiency of transfection. The minimal voltage required for plasmid electroporation in TILs has been previously reported in International Patent Application Publication No. WO 2014/184744 and U.S Patent Application Publication No. US 2013/0315884 A1, the disclosures of which are incorporated by reference herein, and program 3 and 4 each allow for an efficient TALEN incorporation process for TILs.

Figure 23:
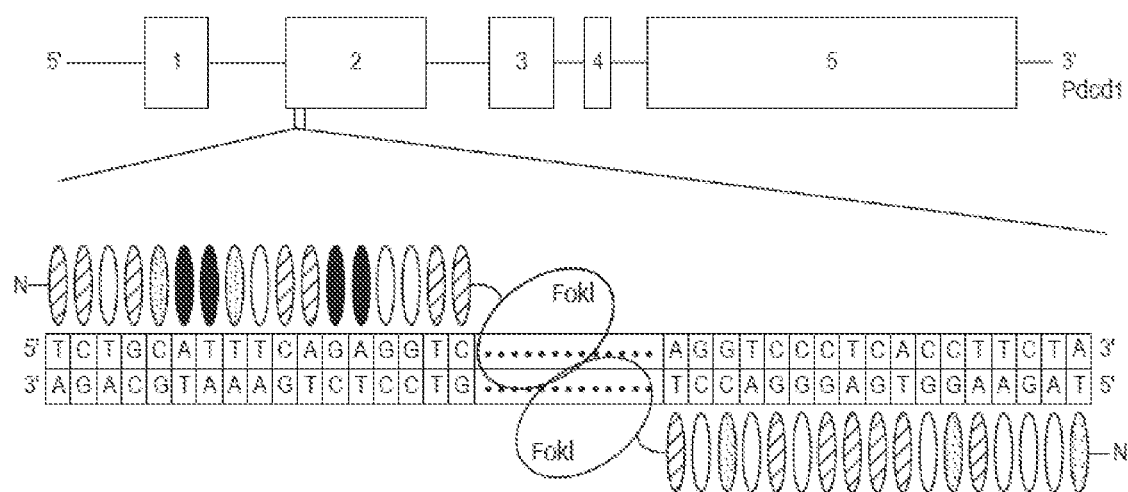
FIG. 23: Depiction of a TALEN construct that targets exon 2 of the Pdcd1 gene.

The TALEN construct shown in FIG. 23 targets exon 2 of the Pdcd1 gene, as shown, and may be used for the inactivation of PD1.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

Listing of Selected Sequences

```
<210> 127
<211> 49
<212> DNA
<213> Artificial Sequence
<223> PD-1 target sequence 1
<400> SEQ ID NO: 127
ttctccccag ccctgctcgt ggtgaccgaa ggggacaacg ccaccttca          49

<210> 128
<211> 49
<212> DNA
<213> Artificial Sequence
<223> PD-1 target sequence 2
<400> SEQ ID NO: 128
tacctctgtg gggccatctc cctggccccc aaggcgcaga tcaaagaga          49

<210> 129
<211> 530
<212> PRT
<213> Artificial Sequence
<223> Repeat PD-1-left
<400> SEQ ID NO: 129
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
```

-continued

```
            65                  70                  75                  80
Gly Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
            100                 105                 110
Ser His Asp Gly Gly Lys Gln Ala Leu Glu Thr Val Gln Arg Leu Leu
            115                 120                 125
Pro Val Leu Cys Gln Ala His Gly Leu Thr Pro Glu Gln Val Val Ala
            130                 135                 140
Ile Ala Ser His Asp Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Glu
            195                 200                 205
Gln Val Val Ala Ile Ala Ser His Asp Gly Gly Lys Gln Ala Leu Glu
            210                 215                 220
Thr Val Gln Arg Leu Leu Pro Val Leu Cys Gln Ala His Gly Leu Thr
225                 230                 235                 240
Pro Glu Gln Val Val Ala Ile Ala Ser Asn Ile Gly Gly Lys Gln Ala
                245                 250                 255
Leu Glu Thr Val Gln Ala Leu Leu Pro Val Leu Cys Gln Ala His Gly
            260                 265                 270
Leu Thr Pro Gln Gln Val Val Ala Ile Ala Ser Asn Asn Gly Gly Lys
            275                 280                 285
Gln Ala Leu Glu Thr Val Gln Arg Leu Leu Pro Val Leu Cys Gln Ala
            290                 295                 300
His Gly Leu Thr Pro Glu Gln Val Val Ala Ile Ala Ser His Asp Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser His
            340                 345                 350
Asp Gly Gly Lys Gln Ala Leu Glu Thr Val Gln Arg Leu Leu Pro Val
            355                 360                 365
Leu Cys Gln Ala His Gly Leu Thr Pro Glu Gln Val Val Ala Ile Ala
            370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Gln Gln Val Val Ala
                405                 410                 415
Ile Ala Ser Asn Gly Gly Gly Lys Gln Ala Leu Glu Thr Val Gln Arg
            420                 425                 430
Leu Leu Pro Val Leu Cys Gln Ala His Gly Leu Thr Pro Gln Gln Val
            435                 440                 445
Val Ala Ile Ala Ser Asn Asn Gly Gly Lys Gln Ala Leu Glu Thr Val
            450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
```

```
                      500                 505                 510
Pro Gln Gln Val Val Ala Ile Ala Ser Asn Gly Gly Arg Pro Ala
            515                 520                 525
Leu Glu
    530

<210> 130
<211> 529
<212> PRT
<213> Artificial Sequence
<223> Repeat PD-1-right
<400> SEQ ID NO: 130
Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
            35                  40                  45

Gly Lys Gln Ala Leu Glu Thr Val Gln Ala Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
            130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
            195                 200                 205

Gln Val Val Ala Ile Ala Ser Asn Asn Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Gly Gly Lys Gln
            275                 280                 285

Ala Leu Glu Thr Val Gln Arg Leu Leu Pro Val Leu Cys Gln Ala His
            290                 295                 300

Gly Leu Thr Pro Gln Gln Val Val Ala Ile Ala Ser Asn Asn Gly Gly
305                 310                 315                 320

Lys Gln Ala Leu Glu Thr Val Gln Arg Leu Leu Pro Val Leu Cys Gln
                325                 330                 335

Ala His Gly Leu Thr Pro Gln Gln Val Val Ala Ile Ala Ser Asn Gly
            340                 345                 350

Gly Gly Lys Gln Ala Leu Glu Thr Val Gln Arg Leu Leu Pro Val Leu
```

```
                              -continued
         355                   360                   365
     Cys Gln Ala His Gly Leu Thr Pro Gln Gln Val Val Ala Ile Ala Ser
         370                   375                   380

Asn Gly Gly Gly Lys Gln Ala Leu Glu Thr Val Gln Arg Leu Leu Pro
     385                 390                   395                 400

Val Leu Cys Gln Ala His Gly Leu Thr Pro Gln Gln Val Val Ala Ile
                     405                   410                   415

Ala Ser Asn Asn Gly Gly Lys Gln Ala Leu Glu Thr Val Gln Arg Leu
                     420                   425                   430

Leu Pro Val Leu Cys Gln Ala His Gly Leu Thr Pro Gln Gln Val Val
                     435                   440                   445

Ala Ile Ala Ser Asn Gly Gly Gly Lys Gln Ala Leu Glu Thr Val Gln
                     450                   455                   460

Arg Leu Leu Pro Val Leu Cys Gln Ala His Gly Leu Thr Pro Glu Gln
     465                 470                   475                 480

Val Val Ala Ile Ala Ser His Asp Gly Gly Lys Gln Ala Leu Glu Thr
                     485                   490                   495

Val Gln Arg Leu Leu Pro Val Leu Cys Gln Ala His Gly Leu Thr Pro
                     500                   505                   510

Gln Gln Val Val Ala Ile Ala Ser Asn Gly Gly Gly Arg Pro Ala Leu
                     515                   520                   525

Glu

<210> 131
     <211> 530
     <212> PRT
     <213> Artificial Sequence
     <223> Repeat PD-1-left
     <400> SEQ ID NO: 131
     Leu Thr Pro Glu Gln Val Val Ala Ile Ala Ser Asn Ile Gly Gly Lys
     1               5                   10                  15

Gln Ala Leu Glu Thr Val Gln Ala Leu Leu Pro Val Leu Cys Gln Ala
                     20                  25                  30

His Gly Leu Thr Pro Glu Gln Val Val Ala Ile Ala Ser His Asp Gly
                     35                  40                  45

Gly Lys Gln Ala Leu Glu Thr Val Gln Arg Leu Leu Pro Val Leu Cys
             50                  55                  60

Gln Ala His Gly Leu Thr Pro Glu Gln Val Val Ala Ile Ala Ser His
     65                  70                  75                  80

Asp Gly Gly Lys Gln Ala Leu Glu Thr Val Gln Arg Leu Leu Pro Val
                     85                  90                  95

Leu Cys Gln Ala His Gly Leu Thr Pro Gln Gln Val Val Ala Ile Ala
                     100                 105                 110

Ser Asn Gly Gly Gly Lys Gln Ala Leu Glu Thr Val Gln Arg Leu Leu
                     115                 120                 125

Pro Val Leu Cys Gln Ala His Gly Leu Thr Pro Glu Gln Val Val Ala
                     130                 135                 140

Ile Ala Ser His Asp Gly Gly Lys Gln Ala Leu Glu Thr Val Gln Arg
     145                 150                 155                 160

Leu Leu Pro Val Leu Cys Gln Ala His Gly Leu Thr Pro Gln Gln Val
                     165                 170                 175

Val Ala Ile Ala Ser Asn Gly Gly Lys Gln Ala Leu Glu Thr Val
                     180                 185                 190

Gln Arg Leu Leu Pro Val Leu Cys Gln Ala His Gly Leu Thr Pro Gln
                     195                 200                 205

Gln Val Val Ala Ile Ala Ser Asn Asn Gly Gly Lys Gln Ala Leu Glu
                     210                 215                 220
```

-continued

```
Thr Val Gln Arg Leu Leu Pro Val Leu Cys Gln Ala His Gly Leu Thr
225                 230                 235                 240

Pro Gln Gln Val Val Ala Ile Ala Ser Asn Gly Gly Lys Gln Ala
            245                 250                 255

Leu Glu Thr Val Gln Arg Leu Leu Pro Val Leu Cys Gln Ala His Gly
        260                 265                 270

Leu Thr Pro Gln Gln Val Val Ala Ile Ala Ser Asn Gly Gly Lys
    275                 280                 285

Gln Ala Leu Glu Thr Val Gln Arg Leu Leu Pro Val Leu Cys Gln Ala
290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
        340                 345                 350

Asn Gly Gly Lys Gln Ala Leu Glu Thr Val Gln Arg Leu Leu Pro Val
    355                 360                 365

Leu Cys Gln Ala His Gly Leu Thr Pro Gln Gln Val Val Ala Ile Ala
370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser His Asp Gly Gly Lys Gln Ala Leu Glu Thr Val Gln Arg
        420                 425                 430

Leu Leu Pro Val Leu Cys Gln Ala His Gly Leu Thr Pro Glu Gln Val
    435                 440                 445

Val Ala Ile Ala Ser His Asp Gly Gly Lys Gln Ala Leu Glu Thr Val
450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
            485                 490                 495

Thr Val Gln Ala Leu Leu Pro Val Leu Cys Gln Ala His Gly Leu Thr
        500                 505                 510

Pro Gln Gln Val Val Ala Ile Ala Ser Asn Gly Gly Arg Pro Ala
    515                 520                 525

Leu Glu
530

<210> 132
<211> 529
<212> PRT
<213> Artificial Sequence
<223> Repeat PD-1-right
<400> SEQ ID NO: 132
Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Lys
    50                  55                  60

Gln Ala His Gly Leu Thr Pro Glu Gln Val Val Ala Ile Ala Ser His
65                  70                  75                  80
```

-continued

```
Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Gly Gly Lys Gln Ala Leu Glu Thr Val Gln Arg Leu
            420                 425                 430

Leu Pro Val Leu Cys Gln Ala His Gly Leu Thr Pro Gln Gln Val Val
        435                 440                 445

Ala Ile Ala Ser Asn Asn Gly Gly Lys Gln Ala Leu Glu Thr Val Gln
    450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
            500                 505                 510
```

```
Gln Gln Val Val Ala Ile Ala Ser Asn Gly Gly Gly Arg Pro Ala Leu
        515                 520                 525

Glu

<210> 133
<211> 2814
<212> DNA
<213> Artificial Sequence
<223> PD-1-left TALEN
<400> SEQ ID NO: 133
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa caccggcag cgttagggac cgtcgctgtc    240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca gattgcaaa acgtggcgcg   420 gtgaccgcag tggaggcagt gcatgcatgg cgcaatgcac tgacgggtgc cccgctcaac   480
ttgacccccc agcaggtggt ggccatcgcc agcaatggcg gtggcaagca ggcgctggag   540
acggtccagc ggctgttgcc ggtgctgtgc caggcccacg gcttgacccc ggagcaggtg   600
gtggccatcg ccagccacga tgcggcaag caggcgctgg agacggtcca gcggctgttg    660
ccggtgctgt gccaggccca cggcttgacc cccagcagg tggtggccat cgccagcaat   720
ggcggtggca gcaggcgct ggagacggtc agcggctgt tgccggtgct gtgccaggcc    780
cacggcttga ccccggagca ggtggtggcc atcgccagcc acgatggcgg caagcaggcg   840
ctggagacgg tccagcggct gttgccggtg ctgtgccagg cccacggctt gaccccggag   900
caggtggtgg ccatcgccag ccacgatggc ggcaagcagg cgctggagac ggtccagcgg   960
ctgttgccgg tgctgtgcca ggcccacggc ttgaccccgg agcaggtggt ggccatcgcc  1020
agccacgatg cggcaagca ggcgctggag acggtccagc ggctgttgcc ggtgctgtgc   1080
caggcccacg gcttgacccc ggagcaggtg gtggccatcg ccagccacga tgcggcaag  1140 caggcgctgg agacggtcca gcggctgttg ccggtgctgt gccaggccca cggcttgacc  1200
ccggagcagg tggtggccat cgccagcaat attggtggca agcaggcgct ggagacggtg  1260
caggcgctgt gccggtgct gtgccaggcc cacggcttga ccccccagca ggtggtggcc    1320
atcgccagca ataatggtgg caagcaggcg ctggagacgg tccagcggct gttgccggtg  1380
ctgtgccagg cccacggctt gaccccggag caggtggtgg ccatcgccag ccacgatggc  1440
ggcaagcagg cgctggagac ggtccagcgg ctgttgccgg tgctgtgcca ggcccacggc  1500
ttgaccccgg agcaggtggt ggccatcgcc agccacgatg cggcaagca ggcgctggag   1560 acggtccagc ggctgttgcc ggtgctgtgc caggcccacg gcttgacccc ggagcaggtg  1620
gtggccatcg ccagccacga tgcggcaag caggcgctgg agacggtcca gcggctgttg   1680
ccggtgctgt gccaggccca cggcttgacc cccagcagg tggtggccat cgccagcaat  1740
ggcggtggca gcaggcgct ggagacggtc agcggctgt tgccggtgct gtgccaggcc   1800
cacggcttga ccccccagca ggtggtggcc atcgccagca ataatggtgg caagcaggcg  1860
ctggagacgg tccagcggct gttgccggtg ctgtgccagg cccacggctt gaccccggag  1920
caggtggtgg ccatcgccag ccacgatggc ggcaagcagg cgctggagac ggtccagcgg  1980
ctgttgccgg tgctgtgcca ggcccacggc ttgaccccct cagcaggtgg tggccatcgcc  2040 agcaatggcg gcggcaggcc ggcgctggag agcattgttg cccagttatc tcgccctgat  2100
```

-continued

```
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acgcgccat ctacaccgtg gctcccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca cccccaacga gtggtggaag    2580
gtgtaccccc tccagcgtga ccgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> 134
<211> 2829
<212> DNA
<213> Artificial Sequence
<223> PD-1-right TALEN
<400> SEQ ID NO: 134

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccccag caagtcgtcg caatcgccag caataacgga    540
gggaagcaag ccctcgaaac cgtgcagcgg ttgcttcctg tgctctgcca ggcccacggc    600
cttacccctg agcaggtggt ggccatcgca agtaacattg gaggaaagca agccttggag    660
acagtgcagg ccctgttgcc cgtgctgtgc aggcacacg gcctcacacc agagcaggtc    720
gtggccattg cctccaacat cgggggaaaa caggctctgg agaccgtcca ggccctgctg    780
cccgtcctct gtcaagctca cggcctgact ccccaacaag tggtcgccat cgcctctaat    840
aacggcggga agcaggcact ggaaacagtg cagagactgc tccctgtgct ttgccaagct    900
catgggttga cccccaaca ggtcgtcgct attgcctcaa caacgggggg caagcaggcc    960
cttgagactg tgcagaggct gttgccagtg ctgtgtcagg ctcacggcct cactccacaa    1020
caggtggtcg caattgccag caacggcggc ggaaagcaag ctcttgaaac cgtgcaacgc    1080
ctcctgcccg tgctctgtca ggctcatggc ctgacaccac aacaagtcgt ggccatcgcc    1140
agtaataatg gcgggaaaca ggctcttgag accgtccaga ggctgctccc agtgctctgc    1200
caggcacacg gctgaccccc ccagcaggtg gtggctatcg ccagcaataa tggggggcaag    1260 caggccctgg aaacagtcca gcgcctgctg ccagtgcttt gccaggctca cgggctcact    1320
cccgaacagg tcgtggcaat cgcctccaac ggagggaagc aggctctgga gaccgtgcag    1380
agactgctgc ccgtcttgtg ccaggcccac ggactcacac ctcagcaggt cgtcgccatt    1440
gcctctaaca cgggggcaa acaagccctg gagacagtgc agcggctgtt gcctgtgttg    1500
```

```
tgccaagccc acggcttgac tcctcaacaa gtggtcgcca tcgcctcaaa tggcggcgga  1560
aaacaagctc tggagacagt gcagaggttg ctgcccgtcc tctgccaagc ccacggcctg  1620
actccccaac aggtcgtcgc cattgccagc aacggcggag gaaagcaggc tctcgaaact  1680
gtgcagcggc tgcttcctgt gctgtgtcag gctcatgggc tgaccccca gcaagtggtg  1740 gctattgcct ctaacaatgg aggcaagcaa gcccttgaga cagtccagag gctgttgcca  1800
gtgctgtgcc aggcccacgg gctcacaccc cagcaggtgg tcgccatcgc cagtaacggc  1860
gggggcaaac aggcattgga aaccgtccag cgcctgcttc cagtgctctg ccaggcacac  1920
ggactgacac ccgaacaggt ggtggccatt gcatcccatg atggggggcaa gcaggccctg  1980 gagaccgtgc agagactcct gccagtgttg tgccaagctc acggcctcac ccctcagcaa  2040
gtcgtggcca tcgcctcaaa cggggggggc cggcctgcac tggagagcat tgttgcccag  2100
ttatctcgcc ctgatccggc gttggccgcg ttgaccaacg accacctcgt cgccttggcc  2160
tgcctcggcg gcgtcctgc gctggatgca gtgaaaaagg gattggggga tcctatcagc  2220
cgttcccagc tggtgaagtc cgagctggag gagaagaaat ccgagttgag gcacaagctg  2280
aagtacgtgc cccacgagta catcgagctg atcgagatcg cccggaacag cacccaggac  2340
cgtatcctgg agatgaaggt gatggagttc ttcatgaagg tgtacggcta caggggcaag  2400
cacctgggcg gctccaggaa gcccgacggc gccatctaca ccgtgggctc ccccatcgac  2460
tacggcgtga tcgtggacac caaggcctac tccggcggct acaacctgcc catcggccag  2520
gccgacgaaa tgcagaggta cgtggaggag aaccagacca ggaacaagca catcaacccc  2580
aacgagtggt ggaaggtgta ccctccagc gtgaccgagt tcaagttcct gttcgtgtcc  2640
ggccacttca agggcaacta caaggcccag ctgaccaggc tgaaccacat caccaactgc  2700
aacggcgccg tgctgtccgt ggaggagctc ctgatcggcg gcgagatgat caaggccggc  2760
accctgaccc tggaggaggt gaggaggaag ttcaacaacg gcgagatcaa cttcgcggcc  2820
gactgataa                                                         2829

<210> 135
<211> 2814
<212> DNA
<213> Artificial Sequence
<223> PD-1-left TALEN
<400> SEQ ID NO: 135
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca gattgcaaa acgtggcggc   420 gtgaccgcag tggaggcagt gcatgcatgg cgcaatgcac tgacgggtgc cccgctcaac   480
ttgaccccgg agcaggtggt ggccatcgcc agcaatattg gtggcaagca ggcgctggag   540
acggtgcagg cgctgttgcc ggtgctgtgc caggcccacg gcttgacccc ggagcaggtg   600
gtggccatcg ccagccacga tggcggcaag caggcgctgg agacggtcca gcggctgttg   660
ccggtgctgt gccaggccca cggcttgacc ccggagcagg tggtggccat cgccagccac   720
gatggcggca gcaggcgct ggagacggtc agcggctgt tgccggtgct gtgccaggcc   780
cacggcttga ccccccagca ggtggtgcc atcgccagca atggcggtgg caagcaggcg   840
ctggagacgg tccagcggct gttgccggtg ctgtgccagg cccacggctt gaccccggag   900
```

-continued

```
caggtggtgg ccatcgccag ccacgatggc ggcaagcagg cgctggagac ggtccagcgg    960
ctgttgccgg tgctgtgcca ggcccacggc ttgaccccc agcaggtggt ggccatcgcc   1020
agcaatggcg gtggcaagca ggcgctggag acggtccagc ggctgttgcc ggtgctgtgc   1080
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccccagcagg tggtggccat cgccagcaat ggcggtggca agcaggcgct ggagacggtc   1260
cagcggctgt tgccggtgct gtgccaggcc cacggcttga ccccccagca ggtggtggcc   1320
atcgccagca ataatggtgg caagcaggcg ctggagacgg tccagcggct gttgccggtg   1380
ctgtgccagg cccacggctt gacccccag caggtggtgg ccatcgccag caataatggt   1440
ggcaagcagg cgctggagac ggtccagcgg ctgttgccgg tgctgtgcca ggcccacggc   1500
ttgacccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc cagcggctgt tgccggtgct gtgccaggcc   1800
cacggcttga ccccggagca ggtggtggcc atcgccagcc acgatggcgg caagcaggcg   1860
ctggagacgg tccagcggct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agtgaagta cgtgcccac   2280 gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctcccca tcgactacgg cgtgatcgtg   2460
gacaccaagg cctactccgg cggctacaac ctgcccatcg ccaggccga cgaaatgcag   2520 aggtacgtgg aggagaacca gaccaggaac aagcacatca ccccaacga gtggtggaag   2580 gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
tccgtggagg agctcctgat cggcggcgag atgatcaagg ccggcaccct gacccctgag   2760
gaggtgagga ggaagttcaa caacggcgag atcaacttcg cggccgactg ataa        2814
```

```
<210> 136
<211> 2829
<212> DNA
<213> Artificial Sequence
<223> PD-1-right TALEN
<400> SEQ ID NO: 136
```

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
```

-continued

| | | | | | |
|---|---|---|---|---|---|
|gaagcgatcg|ttggcgtcgg|caaacagtgg|tccggcgcac|gcgctctgga|ggccttgctc|360|
|acggtggcgg|gagagttgag|aggtccaccg|ttacagttgg|acacaggcca|acttctcaag|420|
|attgcaaaac|gtggcggcgt|gaccgcagtg|gaggcagtgc|atgcatggcg|caatgcactg|480|
|acgggtgccc|cgctcaactt|gaccccgag|caagtcgtcg|caatcgccag|ccatgatgga|540|
|gggaagcaag|ccctcgaaac|cgtgcagcgg|ttgcttcctg|tgctctgcca|ggcccacggc|600|
|cttacccctc|agcaggtggt|ggccatcgca|agtaacggag|gaggaaagca|agccttggag|660|
|acagtgcagc|gcctgttgcc|cgtgctgtgc|caggcacacg|gcctcacacc|agagcaggtc|720|
|gtggccattg|cctcccatga|cgggggaaa|caggctctgg|agaccgtcca|gaggctgctg|780|
|cccgtcctct|gtcaagctca|cggcctgact|ccccaacaag|tggtcgccat|cgcctctaat|840|
|ggcggcggga|agcaggcact|ggaaacagtg|cagagactgc|tccctgtgct|ttgccaagct|900|
|catgggttga|ccccccaaca|ggtcgtcgct|attgcctcaa|acggggggg|caagcaggcc|960|
|cttgagactg|tgcagaggct|gttgccagtg|ctgtgtcagg|ctcacgggct|cactccacaa|1020|
|caggtggtcg|caattgccag|caacggcggc|ggaaagcaag|ctcttgaaac|cgtgcaacgc|1080|
|ctcctgcccg|tgctctgtca|ggctcatggc|ctgacaccac|aacaagtcgt|ggccatcgcc|1140|
|agtaataatg|gcgggaaaca|ggctcttgag|accgtccaga|ggctgctccc|agtgctctgc|1200|
|caggcacacg|ggctgacccc|cgagcaggtg|gtggctatcg|ccagcaatat|tggggcaag|1260|
|caggccctgg|aaacagtcca|ggccctgctg|ccagtgcttt|gccaggctca|cgggctcact|1320|
|ccccagcagg|tcgtggcaat|cgcctccaac|ggcggaggga|agcaggctct|ggagaccgtg|1380|
|cagagactgc|tgcccgtctt|gtgccaggcc|acggactca|cacctgaaca|ggtcgtcgcc|1440|
|attgcctctc|acgatggggg|caaacaagcc|ctggagacag|tgcagcggct|gttgcctgtg|1500|
|ttgtgccaag|cccacggctt|gactcctcaa|caagtggtcg|ccatcgcctc|aaatggcggc|1560|
|ggaaaacaag|ctctggagac|agtgcagagg|ttgctgcccg|tcctctgcca|agcccacggc|1620|
|ctgactcccc|aacaggtcgt|cgccattgcc|agcaacaacg|gaggaaagca|ggctctcgaa|1680|
|actgtgcagc|ggctgcttcc|tgtgctgtgt|caggctcatg|ggctgacccc|cgagcaagtg|1740|
|gtggctattg|cctctaatgg|aggcaagcaa|gcccttgaga|cagtccagag|gctgttgcca|1800|
|gtgctgtgcc|aggcccacgg|gctcacaccc|cagcaggtgg|tcgccatcgc|cagtaacaac|1860|
|ggggcaaac|aggcattgga|aaccgtccag|cgcctgcttc|cagtgctctg|ccaggcacac|1920|
|ggactgacac|ccgaacaggt|ggtggccatt|gcatcccatg|atgggggcaa|gcaggccctg|1980|
|gagaccgtgc|agagactcct|gccagtgttg|tgccaagctc|acggcctcac|ccctcagcaa|2040|
|gtcgtggcca|tcgcctcaaa|cggggggc|cggcctgcac|tggagagcat|tgttgcccag|2100|
|ttatctcgcc|ctgatccggc|gttggccgcg|ttgaccaacg|accacctcgt|cgccttggcc|2160|
|tgcctcggcg|ggcgtcctgc|gctggatgca|gtgaaaaagg|gattggggga|tcctatcagc|2220|
|cgttcccagc|tggtgaagtc|cgagctggag|gagaagaaat|ccgagttgag|gcacaagctg|2280|
|aagtacgtgc|cccacgagta|catcgagctg|atcgagatcg|cccggaacag|cacccaggac|2340|
|cgtatcctgg|agatgaaggt|gatggagttc|ttcatgaagg|tgtacggcta|caggggcaag|2400|
|cacctgggcg|gctccaggaa|gcccgacggc|gccatctaca|ccgtgggctc|ccccatcgac|2460|
|tacggcgtga|tcgtggacac|caaggcctac|tccggcggct|acaacctgcc|catcggccag|2520|
|gccgacgaaa|tgcagaggta|cgtggaggag|aaccagacca|ggaacaagca|catcaacccc|2580|
|aacgagtggt|ggaaggtgta|cccctccagc|gtgaccgagt|tcaagttcct|gttcgtgtcc|2640|
|ggccacttca|agggcaacta|caaggcccag|ctgaccaggc|tgaaccacat|caccaactgc|2700|
|aacggcgccg|tgctgtccgt|ggaggagctc|ctgatcggcg|gcgagatgat|caaggccggc|2760|

```
accctgaccc tggaggaggt gaggaggaag ttcaacaacg gcgagatcaa cttcgcggcc    2820
gactgataa                                                            2829
```

---

SEQUENCE LISTING

```
Sequence total quantity: 136
SEQ ID NO: 1            moltype = AA   length = 450
FEATURE                 Location/Qualifiers
REGION                  1..450
                        note = Muromonab heavy chain
source                  1..450
                        mol_type = protein
                        organism = synthetic construct
SEQUENCE: 1
QVQLQQSGAE LARPGASVKM SCKASGYTFT RYTMHWVKQR PGQGLEWIGY INPSRGYTNY    60
NQKFKDKATL TTDKSSSTAY MQLSSLTSED SAVYYCARYY DDHYCLDYWG QGTTLTVSSA    120
KTTAPSVYPL APVCGGTTGS SVTLGCLVKG YFPEPVTLTW NSGSLSSGVH TFPAVLQSDL    180
YTLSSSVTVT SSTWPSQSIT CNVAHPASST KVDKKIEPRP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 2            moltype = AA   length = 213
FEATURE                 Location/Qualifiers
REGION                  1..213
                        note = Muromonab light chain
source                  1..213
                        mol_type = protein
                        organism = synthetic construct
SEQUENCE: 2
QIVLTQSPAI MSASPGEKVT MTCSASSSVS YMNWYQQKSG TSPKRWIYDT SKLASGVPAH    60
FRGSGSGTSY SLTISGMEAE DAATYYCQQW SSNPFTFGSG TKLEINRADT APTVSIFPPS    120
SEQLTSGGAS VVCFLNNFYP KDINVKWKID GSERQNGVLN SWTDQDSKDS TYSMSSTLTL    180
TKDEYERHNS YTCEATHKTS TSPIVKSFNR NEC                                  213

SEQ ID NO: 3            moltype = AA   length = 134
FEATURE                 Location/Qualifiers
REGION                  1..134
                        note = recombinant human IL-2 (rhIL-2)
source                  1..134
                        mol_type = protein
                        organism = synthetic construct
SEQUENCE: 3
MAPTSSSTKK TQLQLEHLLL DLQMILNGIN NYKNPKLTRM LTFKFYMPKK ATELKHLQCL    60
EEELKPLEEV LNLAQSKNFH LRPRDLISNI NVIVLELKGS ETTFMCEYAD ETATIVEFLN    120
RWITFCQSII STLT                                                      134

SEQ ID NO: 4            moltype = AA   length = 132
FEATURE                 Location/Qualifiers
REGION                  1..132
                        note = Aldesleukin
source                  1..132
                        mol_type = protein
                        organism = synthetic construct
SEQUENCE: 4
PTSSSTKKTQ LQLEHLLLDL QMILNGINNY KNPKLTRMLT FKFYMPKKAT ELKHLQCLEE    60
ELKPLEEVLN LAQSKNFHLR PRDLISNINV IVLELKGSET TFMCEYADET ATIVEFLNRW    120
ITFSQSIIST LT                                                        132

SEQ ID NO: 5            moltype = AA   length = 130
FEATURE                 Location/Qualifiers
REGION                  1..130
                        note = recombinant human IL-4 (rhIL-4)
source                  1..130
                        mol_type = protein
                        organism = synthetic construct
SEQUENCE: 5
MHKCDITLQE IIKTLNSLTE QKTLCTELTV TDIFAASKNT TEKETFCRAA TVLRQFYSHH    60
EKDTRCLGAT AQQFHRHKQL IRFLKRLDRN LWGLAGLNSC PVKEANQSTL ENFLERLKTI    120
MREKYSKCSS                                                           130

SEQ ID NO: 6            moltype = AA   length = 153
FEATURE                 Location/Qualifiers
REGION                  1..153
```

```
                        note = recombinant human IL-7 (rhIL-7)
source                  1..153
                        mol_type = protein
                        organism = synthetic construct
SEQUENCE: 6
MDCDIEGKDG KQYESVLMVS IDQLLDSMKE IGSNCLNNEF NFFKRHICDA NKEGMFLFRA    60
ARKLRQFLKM NSTGDFDLHL LKVSEGTTIL LNCTGQVKGR KPAALGEAQP TKSLEENKSL   120
KEQKKLNDLC FLKRLLQEIK TCWNKILMGT KEH                                153

SEQ ID NO: 7            moltype = AA   length = 115
FEATURE                 Location/Qualifiers
REGION                  1..115
                        note = recombinant human IL-15 (rhIL-15)
source                  1..115
                        mol_type = protein
                        organism = synthetic construct
SEQUENCE: 7
MNWVNVISDL KKIEDLIQSM HIDATLYTES DVHPSCKVTA MKCFLLELQV ISLESGDASI    60
HDTVENLIIL ANNSLSSNGN VTESGCKECE ELEEKNIKEF LQSFVHIVQM FINTS        115

SEQ ID NO: 8            moltype = AA   length = 132
FEATURE                 Location/Qualifiers
REGION                  1..132
                        note = recombinant human IL-21 (rhIL-21)
source                  1..132
                        mol_type = protein
                        organism = synthetic construct
SEQUENCE: 8
MQDRHMIRMR QLIDIVDQLK NYVNDLVPEF LPAPEDVETN CEWSAFSCFQ KAQLKSANTG    60
NNERIINVSI KKLKRKPPST NAGRRQKHRL TCPSCDSYEK KPPKEFLERF KSLLQKMIHQ   120
HLSSRTHGSE DS                                                       132

SEQ ID NO: 9            moltype = AA   length = 255
FEATURE                 Location/Qualifiers
REGION                  1..255
                        note = human 4-1BB, Tumor necrosis factor receptor
                           superfamily, member 9(Homo sapiens)
source                  1..255
                        mol_type = protein
                        organism = synthetic construct
SEQUENCE: 9
MGNSCYNIVA TLLLVLNFER TRSLQDPCSN CPAGTFCDNN RNQICSPCPP NSFSSAGGQR    60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                    255

SEQ ID NO: 10           moltype = AA   length = 256
FEATURE                 Location/Qualifiers
REGION                  1..256
                        note = murine 4-1BB, Tumor necrosis factor receptor
                           superfamily, member9 (Mus musculus)
source                  1..256
                        mol_type = protein
                        organism = synthetic construct
SEQUENCE: 10
MGNNCYNVVV IVLLLVGCEK VGAVQNSCDN CQPGTFCRKY NPVCKSCPPS TFSSIGGQPN    60
CNICRVCAGY FRFKKFCSST HNAECECIEG FHCLGPQCTR CEKDCRPGQE LTKQGCKTCS   120
LGTFNDQNGT GVCRPWTNCS LDGRSVLKTG TTEKDVVCGP PVVSFSPSTT ISVTPEGGPG   180
GHSLQVLTLF LALTSALLLA LIFITLLFSV LKWIRKKFPH IFKQPFKKTT GAAQEEDACS   240
CRCPQEEEGG GGGYEL                                                   256

SEQ ID NO: 11           moltype = AA   length = 441
FEATURE                 Location/Qualifiers
REGION                  1..441
                        note = heavy chain for utomilumab
source                  1..441
                        mol_type = protein
                        organism = synthetic construct
SEQUENCE: 11
EVQLVQSGAE VKKPGESLRI SCKGSGYSFS TYWISWVRQM PGKGLEWMGK IYPGDSYTNY    60
SPSFQGQVTI SADKSISTAY LQWSSLKASD TAMYYCARGY GIFDYWGQGT LVTVSSASTK   120
GPSVFPLAPC SRSTSESTAA LGCLVKDYFP EPVTVSWNSG ALTSGVHTFP AVLQSSGLYS   180
LSSVVTVPSS NFGTQTYTCN VDHKPSNTKV DKTVERKCCV ECPPCPAPPV AGPSVFLFPP   240
KPKDTLMISR TPEVTCVVVD VSHEDPEVQF NWYVDGVEVH NAKTKPREEQ FNSTFRVVSV   300
LTVVHQDWLN GKEYKCKVSN KGLPAPIEKT ISKTKGQPRE PQVYTLPPSR EEMTKNQVSL   360
TCLVKGFYPS DIAVEWESNG QPENNYKTTP PMLDSDGSFF LYSKLTVDKS RWQQGNVFSC   420
SVMHEALHNH YTQKSLSLSP G                                             441
```

```
SEQ ID NO: 12            moltype = AA  length = 214
FEATURE                  Location/Qualifiers
REGION                   1..214
                         note = light chain for utomilumab
source                   1..214
                         mol_type = protein
                         organism = synthetic construct
SEQUENCE: 12
SYELTQPPSV SVSPGQTASI TCSGDNIGDQ YAHWYQQKPG QSPVLVIYQD KNRPSGIPER    60
FSGSNSGNTA TLTISGTQAM DEADYYCATY TGFGSLAVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 13            moltype = AA  length = 116
FEATURE                  Location/Qualifiers
REGION                   1..116
                         note = heavy chain variable region for utomilumab
source                   1..116
                         mol_type = protein
                         organism = synthetic construct
SEQUENCE: 13
EVQLVQSGAE VKKPGESLRI SCKGSGYSFS TYWISWVRQM PGKGLEWMGK IYPGDSYTNY    60
SPSFQGQVTI SADKSISTAY LQWSSLKASD TAMYYCARGY GIFDYWGQGT LVTVSS       116

SEQ ID NO: 14            moltype = AA  length = 108
FEATURE                  Location/Qualifiers
REGION                   1..108
                         note = light chain variable region for utomilumab
source                   1..108
                         mol_type = protein
                         organism = synthetic construct
SEQUENCE: 14
SYELTQPPSV SVSPGQTASI TCSGDNIGDQ YAHWYQQKPG QSPVLVIYQD KNRPSGIPER    60
FSGSNSGNTA TLTISGTQAM DEADYYCATY TGFGSLAVFG GGTKLTVL                108

SEQ ID NO: 15            moltype = AA  length = 6
FEATURE                  Location/Qualifiers
REGION                   1..6
                         note = heavy chain CDR1 for utomilumab
source                   1..6
                         mol_type = protein
                         organism = synthetic construct
SEQUENCE: 15
STYWIS                                                                6

SEQ ID NO: 16            moltype = AA  length = 17
FEATURE                  Location/Qualifiers
REGION                   1..17
                         note = heavy chain CDR2 for utomilumab
source                   1..17
                         mol_type = protein
                         organism = synthetic construct
SEQUENCE: 16
KIYPGDSYTN YSPSFQG                                                   17

SEQ ID NO: 17            moltype = AA  length = 8
FEATURE                  Location/Qualifiers
REGION                   1..8
                         note = heavy chain CDR3 for utomilumab
source                   1..8
                         mol_type = protein
                         organism = synthetic construct
SEQUENCE: 17
RGYGIFDY                                                              8

SEQ ID NO: 18            moltype = AA  length = 11
FEATURE                  Location/Qualifiers
REGION                   1..11
                         note = light chain CDR1 for utomilumab
source                   1..11
                         mol_type = protein
                         organism = synthetic construct
SEQUENCE: 18
SGDNIGDQYA H                                                         11

SEQ ID NO: 19            moltype = AA  length = 7
FEATURE                  Location/Qualifiers
REGION                   1..7
                         note = light chain CDR2 for utomilumab
```

```
source                    1..7
                          mol_type = protein
                          organism = synthetic construct
SEQUENCE: 19
QDKNRPS                                                                 7

SEQ ID NO: 20             moltype = AA  length = 11
FEATURE                   Location/Qualifiers
REGION                    1..11
                          note = light chain CDR3 for utomilumab
source                    1..11
                          mol_type = protein
                          organism = synthetic construct
SEQUENCE: 20
ATYTGFGSLA V                                                           11

SEQ ID NO: 21             moltype = AA  length = 448
FEATURE                   Location/Qualifiers
REGION                    1..448
                          note = heavy chain for urelumab
source                    1..448
                          mol_type = protein
                          organism = synthetic construct
SEQUENCE: 21
QVQLQQWGAG LLKPSETLSL TCAVYGGSFS GYYWSWIRQS PEKGLEWIGE INHGGYVTYN       60
PSLESRVTIS VDTSKNQFSL KLSSVTAADT AVYYCARDYG PGNYDWYFDL WGRGTLVTVS      120
SASTKGPSVF PLAPCSRSTS ESTAALGCLV KDYFPEPVTV SWNSGALTSG VHTFPAVLQS      180
SGLYSLSSVV TVPSSSLGTK TYTCNVDHKP SNTKVDKRVE SKYGPPCPPC PAPEFLGGPS      240
VFLFPPKPKD TLMISRTPEV TCVVVDVSQE DPEVQFNWYV DGVEVHNAKT KPREEQFNST      300
YRVVSVLTVL HQDWLNGKEY KCKVSNKGLP SSIEKTISKA KGQPREPQVY TLPPSQEEMT      360
KNQVSLTCLV KGFYPSDIAV EWESNGQPEN NYKTTPPVLD SDGSFFLYSR LTVDKSRWQE      420
GNVFSCSVMH EALHNHYTQK SLSLSLGK                                         448

SEQ ID NO: 22             moltype = AA  length = 216
FEATURE                   Location/Qualifiers
REGION                    1..216
                          note = light chain for urelumab
source                    1..216
                          mol_type = protein
                          organism = synthetic construct
SEQUENCE: 22
EIVLTQSPAT LSLSPGERAT LSCRASQSVS SYLAWYQQKP GQAPRLLIYD ASNRATGIPA       60
RFSGSGSGTD FTLTISSLEP EDFAVYYCQQ RSNWPPALTF GGGTKVEIKR TVAAPSVFIF      120
PPSDEQLKSG TASVVCLLNN FYPREAKVQW KVDNALQSGN SQESVTEQDS KDSTYSLSST      180
LTLSKADYEK HKVYACEVTH QGLSSPVTKS FNRGEC                                216

SEQ ID NO: 23             moltype = AA  length = 120
FEATURE                   Location/Qualifiers
REGION                    1..120
                          note = variable heavy chain for urelumab
source                    1..120
                          mol_type = protein
                          organism = synthetic construct
SEQUENCE: 23
MKHLWFFLLL VAAPRWVLSQ VQLQQWGAGL LKPSETLSLT CAVYGGSFSG YYWSWIRQSP       60
EKGLEWIGEI NHGGYVTYNP SLESRVTISV DTSKNQFSLK LSSVTAADTA VYYCARDYGP      120

SEQ ID NO: 24             moltype = AA  length = 110
FEATURE                   Location/Qualifiers
REGION                    1..110
                          note = variable light chain for urelumab
source                    1..110
                          mol_type = protein
                          organism = synthetic construct
SEQUENCE: 24
MEAPAQLLFL LLLWLPDTTG EIVLTQSPAT LSLSPGERAT LSCRASQSVS SYLAWYQQKP       60
GQAPRLLIYD ASNRATGIPA RFSGSGSGTD FTLTISSLEP EDFAVYYCQQ                 110

SEQ ID NO: 25             moltype = AA  length = 5
FEATURE                   Location/Qualifiers
REGION                    1..5
                          note = heavy chain CDR1 for urelumab
source                    1..5
                          mol_type = protein
                          organism = synthetic construct
SEQUENCE: 25
GYYWS                                                                   5

SEQ ID NO: 26             moltype = AA  length = 16
```

```
FEATURE                 Location/Qualifiers
REGION                  1..16
                        note = heavy chain CDR2 for urelumab
source                  1..16
                        mol_type = protein
                        organism = synthetic construct
SEQUENCE: 26
EINHGGYVTY NPSLES                                                      16

SEQ ID NO: 27           moltype = AA  length = 13
FEATURE                 Location/Qualifiers
REGION                  1..13
                        note = heavy chain CDR3 for urelumab
source                  1..13
                        mol_type = protein
                        organism = synthetic construct
SEQUENCE: 27
DYGPGNYDWY FDL                                                         13

SEQ ID NO: 28           moltype = AA  length = 11
FEATURE                 Location/Qualifiers
REGION                  1..11
                        note = light chain CDR1 for urelumab
source                  1..11
                        mol_type = protein
                        organism = synthetic construct
SEQUENCE: 28
RASQSVSSYL A                                                           11

SEQ ID NO: 29           moltype = AA  length = 7
FEATURE                 Location/Qualifiers
REGION                  1..7
                        note = light chain CDR2 for urelumab
source                  1..7
                        mol_type = protein
                        organism = synthetic construct
SEQUENCE: 29
DASNRAT                                                                 7

SEQ ID NO: 30           moltype = AA  length = 11
FEATURE                 Location/Qualifiers
REGION                  1..11
                        note = light chain CDR3 for urelumab
source                  1..11
                        mol_type = protein
                        organism = synthetic construct
SEQUENCE: 30
QQRSDWPPAL T                                                           11

SEQ ID NO: 31           moltype = AA  length = 230
FEATURE                 Location/Qualifiers
REGION                  1..230
                        note = Fc domain
source                  1..230
                        mol_type = protein
                        organism = synthetic construct
SEQUENCE: 31
KSCDKTHTCP PCPAPELLGG PSVFLFPPKP KDTLMISRTP EVTCVVVDVS HEDPEVKFNW       60
YVDGVEVHNA KTKPREEQYN STYRVVSVLT VLHQDWLNGK EYKCKVSNKA LPAPIEKTIS      120
KAKGQPREPQ VYTLPPSREE MTKNQVSLTC LVKGFYPSDI AVEWESNGQP ENNYKTTPPV      180
LDSDGSFFLY SKLTVDKSRW QQGNVFSCSV MHEALHNHYT QKSLSLSPGK                 230

SEQ ID NO: 32           moltype = AA  length = 22
FEATURE                 Location/Qualifiers
REGION                  1..22
                        note = linker
source                  1..22
                        mol_type = protein
                        organism = synthetic construct
SEQUENCE: 32
GGPGSSKSCD KTHTCPPCPA PE                                               22

SEQ ID NO: 33           moltype = AA  length = 22
FEATURE                 Location/Qualifiers
REGION                  1..22
                        note = linker
source                  1..22
                        mol_type = protein
                        organism = synthetic construct
```

```
SEQUENCE: 33
GGSGSSKSCD KTHTCPPCPA PE                                                  22

SEQ ID NO: 34          moltype = AA  length = 27
FEATURE                Location/Qualifiers
REGION                 1..27
                       note = linker
source                 1..27
                       mol_type = protein
                       organism = synthetic construct
SEQUENCE: 34
GGPGSSSSSS SKSCDKTHTC PPCPAPE                                             27

SEQ ID NO: 35          moltype = AA  length = 27
FEATURE                Location/Qualifiers
REGION                 1..27
                       note = linker
source                 1..27
                       mol_type = protein
                       organism = synthetic construct
SEQUENCE: 35
GGSGSSSSSS SKSCDKTHTC PPCPAPE                                             27

SEQ ID NO: 36          moltype = AA  length = 29
FEATURE                Location/Qualifiers
REGION                 1..29
                       note = linker
source                 1..29
                       mol_type = protein
                       organism = synthetic construct
SEQUENCE: 36
GGPGSSSSSS SSSKSCDKTH TCPPCPAPE                                           29

SEQ ID NO: 37          moltype = AA  length = 29
FEATURE                Location/Qualifiers
REGION                 1..29
                       note = linker
source                 1..29
                       mol_type = protein
                       organism = synthetic construct
SEQUENCE: 37
GGSGSSSSSS SSSKSCDKTH TCPPCPAPE                                           29

SEQ ID NO: 38          moltype = AA  length = 24
FEATURE                Location/Qualifiers
REGION                 1..24
                       note = linker
source                 1..24
                       mol_type = protein
                       organism = synthetic construct
SEQUENCE: 38
GGPGSSGSGS SDKTHTCPPC PAPE                                                24

SEQ ID NO: 39          moltype = AA  length = 23
FEATURE                Location/Qualifiers
REGION                 1..23
                       note = linker
source                 1..23
                       mol_type = protein
                       organism = synthetic construct
SEQUENCE: 39
GGPGSSGSGS DKTHTCPPCP APE                                                 23

SEQ ID NO: 40          moltype = AA  length = 21
FEATURE                Location/Qualifiers
REGION                 1..21
                       note = linker
source                 1..21
                       mol_type = protein
                       organism = synthetic construct
SEQUENCE: 40
GGPSSSGSDK THTCPPCPAP E                                                   21

SEQ ID NO: 41          moltype = AA  length = 25
FEATURE                Location/Qualifiers
REGION                 1..25
                       note = linker
source                 1..25
                       mol_type = protein
```

```
                        organism = synthetic construct
SEQUENCE: 41
GGSSSSSSSS GSDKTHTCPP CPAPE                                           25

SEQ ID NO: 42           moltype = AA  length = 246
FEATURE                 Location/Qualifiers
REGION                  1..246
                        note = Fc domain
source                  1..246
                        mol_type = protein
                        organism = synthetic construct
SEQUENCE: 42
METDTLLLWV LLLWVPAGNG DKTHTCPPCP APELLGGPSV FLFPPKPKDT LMISRTPEVT      60
CVVVDVSHED PEVKFNWYVD GVEVHNAKTK PREEQYNSTY RVVSVLTVLH QDWLNGKEYK     120
CKVSNKALPA PIEKTISKAK GQPREPQVYT LPPSREEMTK NQVSLTCLVK GFYPSDIAVE     180
WESNGQPENN YKTTPPVLDS DGSFFLYSKL TVDKSRWQQG NVFSCSVMHE ALHNHYTQKS     240
LSLSPG                                                                246

SEQ ID NO: 43           moltype = AA  length = 11
FEATURE                 Location/Qualifiers
REGION                  1..11
                        note = linker
source                  1..11
                        mol_type = protein
                        organism = synthetic construct
SEQUENCE: 43
SGSGSGSGSG S                                                           11

SEQ ID NO: 44           moltype = AA  length = 12
FEATURE                 Location/Qualifiers
REGION                  1..12
                        note = linker
source                  1..12
                        mol_type = protein
                        organism = synthetic construct
SEQUENCE: 44
SSSSSSGSGS GS                                                          12

SEQ ID NO: 45           moltype = AA  length = 16
FEATURE                 Location/Qualifiers
REGION                  1..16
                        note = linker
source                  1..16
                        mol_type = protein
                        organism = synthetic construct
SEQUENCE: 45
SSSSSSGSGS GSGSGS                                                      16

SEQ ID NO: 46           moltype = AA  length = 254
FEATURE                 Location/Qualifiers
REGION                  1..254
                        note = 4-1BBL
source                  1..254
                        mol_type = protein
                        organism = synthetic construct
SEQUENCE: 46
MEYASDASLD PEAPWPPAPR ARACRVLPWA LVAGLLLLLL LAAACAVFLA CPWAVSGARA      60
SPGSAASPRL REGPELSPDD PAGLLDLRQG MFAQLVAQNV LLIDGPLSWY SDPGLAGVSL     120
TGGLSYKEDT KELVVAKAGV YYVFFQLELR RVVAGEGSGS VSLALHLQPL RSAAGAAALA     180
LTVDLPPASS EARNSAFGFQ GRLLHLSAGQ RLGVHLHTEA RARHAWQLTQ GATVLGLFRV     240
TPEIPAGLPS PRSE                                                       254

SEQ ID NO: 47           moltype = AA  length = 168
FEATURE                 Location/Qualifiers
REGION                  1..168
                        note = 4-1BBL soluble domain
source                  1..168
                        mol_type = protein
                        organism = synthetic construct
SEQUENCE: 47
LRQGMFAQLV AQNVLLIDGP LSWYSDPGLA GVSLTGGLSY KEDTKELVVA KAGVYYVFFQ      60
LELRRVVAGE GSGSVSLALH LQPLRSAAGA AALTVDLP PASSEARNSA FGFQGRLLHL      120
SAGQRLGVHL HTEARARHAW QLTQGATVLG LFRVTPEIPA GLPSPRSE                  168

SEQ ID NO: 48           moltype = AA  length = 118
FEATURE                 Location/Qualifiers
REGION                  1..118
                        note = variable heavy chain for 4B4-1-1 version 1
source                  1..118
```

```
                        mol_type = protein
                        organism = synthetic construct
SEQUENCE: 48
QVQLQQPGAE LVKPGASVKL SCKASGYTFS SYWMHWVKQR PGQVLEWIGE INPGNGHTNY    60
NEKFKSKATL TVDKSSSTAY MQLSSLTSED SAVYYCARSF TTARGFAYWG QGTLVTVS    118

SEQ ID NO: 49           moltype = AA  length = 107
FEATURE                 Location/Qualifiers
REGION                  1..107
                        note = variable light chain for 4B4-1-1 version 1
source                  1..107
                        mol_type = protein
                        organism = synthetic construct
SEQUENCE: 49
DIVMTQSPAT QSVTPGDRVS LSCRASQTIS DYLHWYQQKS HESPRLLIKY ASQSISGIPS    60
RFSGSGSGSD FTLSINSVEP EDVGVYYCQD GHSFPPTFGG GTKLEIK               107

SEQ ID NO: 50           moltype = AA  length = 119
FEATURE                 Location/Qualifiers
REGION                  1..119
                        note = variable heavy chain for 4B4-1-1 version 2
source                  1..119
                        mol_type = protein
                        organism = synthetic construct
SEQUENCE: 50
QVQLQQPGAE LVKPGASVKL SCKASGYTFS SYWMHWVKQR PGQVLEWIGE INPGNGHTNY    60
NEKFKSKATL TVDKSSSTAY MQLSSLTSED SAVYYCARSF TTARGFAYWG QGTLVTVSA   119

SEQ ID NO: 51           moltype = AA  length = 108
FEATURE                 Location/Qualifiers
REGION                  1..108
                        note = variable light chain for 4B4-1-1 version 2
source                  1..108
                        mol_type = protein
                        organism = synthetic construct
SEQUENCE: 51
DIVMTQSPAT QSVTPGDRVS LSCRASQTIS DYLHWYQQKS HESPRLLIKY ASQSISGIPS    60
RFSGSGSGSD FTLSINSVEP EDVGVYYCQD GHSFPPTFGG GTKLEIKR              108

SEQ ID NO: 52           moltype = AA  length = 120
FEATURE                 Location/Qualifiers
REGION                  1..120
                        note = variable heavy chain for H39E3-2
source                  1..120
                        mol_type = protein
                        organism = synthetic construct
SEQUENCE: 52
MDWTWRILFL VAAATGAHSE VQLVESGGGL VQPGGSLRLS CAASGFTFSD YWMSWVRQAP    60
GKGLEWVADI KNDGSYTNYA PSLTNRFTIS RDNAKNSLYL QMNSLRAEDT AVYYCARELT   120

SEQ ID NO: 53           moltype = AA  length = 109
FEATURE                 Location/Qualifiers
REGION                  1..109
                        note = variable light chain for H39E3-2
source                  1..109
                        mol_type = protein
                        organism = synthetic construct
SEQUENCE: 53
MEAPAQLLFL LLLWLPDTTG DIVMTQSPDS LAVSLGERAT INCKSSQSLL SSGNQKNYLW    60
YQQKPGQPPK LLIYYASTRQ SGVPDRFSGS GSGTDFTLTI SSLQAEDVA             109

SEQ ID NO: 54           moltype = AA  length = 277
FEATURE                 Location/Qualifiers
REGION                  1..277
                        note = human OX40 (Homo sapiens)
source                  1..277
                        mol_type = protein
                        organism = synthetic construct
SEQUENCE: 54
MCVGARRLGR GPCAALLLLG LGLSTVTGLH CVGDTYPSND RCCHECRPGN GMVSRCSRSQ    60
NTVCRPCGPG FYNDVVSSKP CKPCTWCNLR SGSERKQLCT ATQDTVCRCR AGTQPLDSYK   120
PGVDCAPCPP GHFSPGDNQA CKPWTNCTLA GKHTLQPASN SSDAICEDRD PPATQPQETQ   180
GPPARPITVQ PTEAWPRTSQ GPSTRPVEVP GGRAVAAILG LGLVLGLLGP LAILLALYLL   240
RRDQRLPPDA HKPPGGGSFR TPIQEEQADA HSTLAKI                          277

SEQ ID NO: 55           moltype = AA  length = 272
FEATURE                 Location/Qualifiers
REGION                  1..272
                        note = murine OX40 (Mus musculus)
```

```
                        source          1..272
                                        mol_type = protein
                                        organism = synthetic construct
SEQUENCE: 55
MYVWVQQPTA LLLLGLTLGV TARRLNCVKH TYPSGHKCCR ECQPGHGMVS RCDHTRDTLC   60
HPCETGFYNE AVNYDTCKQC TQCNHRSGSE LKQNCTPTQD TVCRCRPGTQ PRQDSGYKLG  120
VDCVPCPPGH FSPGNNQACK PWTNCTLSGK QTRHPASDSL DAVCEDRSLL ATLLWETQRP  180
TFRPTTVQST TVWPRTSELP SPPTLVTPEG PAFAVLLGLG LGLLAPLTVL LALYLLRKAW  240
RLPNTPKPCW GNSFRTPIQE EHTDAHFTLA KI                                272

SEQ ID NO: 56           moltype = AA  length = 451
FEATURE                 Location/Qualifiers
REGION                  1..451
                        note = heavy chain for tavolixizumab
source                  1..451
                        mol_type = protein
                        organism = synthetic construct
SEQUENCE: 56
QVQLQESGPG LVKPSQTLSL TCAVYGGSFS SGYWNWIRKH PGKGLEYIGY ISYNGITYHN   60
PSLKSRITIN RDTSKNQYSL QLNSVTPEDT AVYYCARYKY DYDGGHAMDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 57           moltype = AA  length = 214
FEATURE                 Location/Qualifiers
REGION                  1..214
                        note = light chain for tavolixizumab
source                  1..214
                        mol_type = protein
                        organism = synthetic construct
SEQUENCE: 57
DIQMTQSPSS LSASVGDRVT ITCRASQDIS NYLNWYQQKP GKAPKLLIYY TSKLHSGVPS   60
RFSGSGSGTD YTLTISSLQP EDFATYYCQQ GSALPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 58           moltype = AA  length = 118
FEATURE                 Location/Qualifiers
REGION                  1..118
                        note = heavy chain variable region for tavolixizumab
source                  1..118
                        mol_type = protein
                        organism = synthetic construct
SEQUENCE: 58
QVQLQESGPG LVKPSQTLSL TCAVYGGSFS SGYWNWIRKH PGKGLEYIGY ISYNGITYHN   60
PSLKSRITIN RDTSKNQYSL QLNSVTPEDT AVYYCARYKY DYDGGHAMDY WGQGTLVT   118

SEQ ID NO: 59           moltype = AA  length = 108
FEATURE                 Location/Qualifiers
REGION                  1..108
                        note = light chain variable region for tavolixizumab
source                  1..108
                        mol_type = protein
                        organism = synthetic construct
SEQUENCE: 59
DIQMTQSPSS LSASVGDRVT ITCRASQDIS NYLNWYQQKP GKAPKLLIYY TSKLHSGVPS   60
RFSGSGSGTD YTLTISSLQP EDFATYYCQQ GSALPWTFGQ GTKVEIKR              108

SEQ ID NO: 60           moltype = AA  length = 9
FEATURE                 Location/Qualifiers
REGION                  1..9
                        note = heavy chain CDR1 for tavolixizumab
source                  1..9
                        mol_type = protein
                        organism = synthetic construct
SEQUENCE: 60
GSFSSGYWN                                                            9

SEQ ID NO: 61           moltype = AA  length = 13
FEATURE                 Location/Qualifiers
REGION                  1..13
                        note = heavy chain CDR2 for tavolixizumab
source                  1..13
                        mol_type = protein
                        organism = synthetic construct
```

```
SEQUENCE: 61
YIGYISYNGI TYH                                                           13

SEQ ID NO: 62          moltype = AA  length = 14
FEATURE                Location/Qualifiers
REGION                 1..14
                       note = heavy chain CDR3 for tavolixizumab
source                 1..14
                       mol_type = protein
                       organism = synthetic construct
SEQUENCE: 62
RYKYDYDGGH AMDY                                                          14

SEQ ID NO: 63          moltype = AA  length = 8
FEATURE                Location/Qualifiers
REGION                 1..8
                       note = light chain CDR1 for tavolixizumab
source                 1..8
                       mol_type = protein
                       organism = synthetic construct
SEQUENCE: 63
QDISNYLN                                                                 8

SEQ ID NO: 64          moltype = AA  length = 11
FEATURE                Location/Qualifiers
REGION                 1..11
                       note = light chain CDR2 for tavolixizumab
source                 1..11
                       mol_type = protein
                       organism = synthetic construct
SEQUENCE: 64
LLIYYTSKLH S                                                             11

SEQ ID NO: 65          moltype = AA  length = 8
FEATURE                Location/Qualifiers
REGION                 1..8
                       note = light chain CDR3 for tavolixizumab
source                 1..8
                       mol_type = protein
                       organism = synthetic construct
SEQUENCE: 65
QQGSALPW                                                                 8

SEQ ID NO: 66          moltype = AA  length = 444
FEATURE                Location/Qualifiers
REGION                 1..444
                       note = heavy chain for 11D4
source                 1..444
                       mol_type = protein
                       organism = synthetic construct
SEQUENCE: 66
EVQLVESGGG LVQPGGSLRL SCAASGFTFS SYSMNWVRQA PGKGLEWVSY ISSSSSTIDY         60
ADSVKGRFTI SRDNAKNSLY LQMNSLRDED TAVYYCARES GWYLFDYWGQ GTLVTVSSAS        120
TKGPSVFPLA PCSRSTSEST AALGCLVKDY FPEPVTVSWN SGALTSGVHT FPAVLQSSGL        180
YSLSSVVTVP SSNFGTQTYT CNVDHKPSNT KVDKTVERKC CVECPPCPAP PVAGPSVFLF        240
PPKPKDTLMI SRTPEVTCVV VDVSHEDPEV QFNWYVDGVE VHNAKTKPRE EQFNSTFRVV        300
SVLTVVHQDW LNGKEYKCKV SNKGLPAPIE KTISKTKGQP REPQVYTLPP SREEMTKNQV        360
SLTCLVKGFY PSDIAVEWES NGQPENNYKT TPPMLDSDGS FFLYSKLTVD KSRWQQGNVF        420
SCSVMHEALH NHYTQKSLSL SPGK                                               444

SEQ ID NO: 67          moltype = AA  length = 214
FEATURE                Location/Qualifiers
REGION                 1..214
                       note = light chain for 11D4
source                 1..214
                       mol_type = protein
                       organism = synthetic construct
SEQUENCE: 67
DIQMTQSPSS LSASVGDRVT ITCRASQGIS SWLAWYQQKP EKAPKSLIYA ASSLQSGVPS         60
RFSGSGSGTD FTLTISSLQP EDFATYYCQQ YNSYPPTFGG GTKVEIKRTV AAPSVFIFPP        120
SDEQLKSGTA SVVCLLNNFY PREAKVQWKV DNALQSGNSQ ESVTEQDSKD STYSLSSTLT        180
LSKADYEKHK VYACEVTHQG LSSPVTKSFN RGEC                                    214

SEQ ID NO: 68          moltype = AA  length = 118
FEATURE                Location/Qualifiers
REGION                 1..118
                       note = heavy chain variable region for 11D4
source                 1..118
                       mol_type = protein
```

```
                          organism = synthetic construct
SEQUENCE: 68
EVQLVESGGG LVQPGGSLRL SCAASGFTFS SYSMNWVRQA PGKGLEWVSY ISSSSSTIDY     60
ADSVKGRFTI SRDNAKNSLY LQMNSLRDED TAVYYCARES GWYLFDYWGQ GTLVTVSS     118

SEQ ID NO: 69           moltype = AA   length = 107
FEATURE                 Location/Qualifiers
REGION                  1..107
                        note = light chain variable region for 11D4
source                  1..107
                        mol_type = protein
                        organism = synthetic construct
SEQUENCE: 69
DIQMTQSPSS LSASVGDRVT ITCRASQGIS SWLAWYQQKP EKAPKSLIYA ASSLQSGVPS     60
RFSGSGSGTD FTLTISSLQP EDFATYYCQQ YNSYPPTFGG GTKVEIK                 107

SEQ ID NO: 70           moltype = AA   length = 5
FEATURE                 Location/Qualifiers
REGION                  1..5
                        note = heavy chain CDR1 for 11D4
source                  1..5
                        mol_type = protein
                        organism = synthetic construct
SEQUENCE: 70
SYSMN                                                                  5

SEQ ID NO: 71           moltype = AA   length = 17
FEATURE                 Location/Qualifiers
REGION                  1..17
                        note = heavy chain CDR2 for 11D4
source                  1..17
                        mol_type = protein
                        organism = synthetic construct
SEQUENCE: 71
YISSSSSTID YADSVKG                                                    17

SEQ ID NO: 72           moltype = AA   length = 9
FEATURE                 Location/Qualifiers
REGION                  1..9
                        note = heavy chain CDR3 for 11D4
source                  1..9
                        mol_type = protein
                        organism = synthetic construct
SEQUENCE: 72
ESGWYLFDY                                                              9

SEQ ID NO: 73           moltype = AA   length = 11
FEATURE                 Location/Qualifiers
REGION                  1..11
                        note = light chain CDR1 for 11D4
source                  1..11
                        mol_type = protein
                        organism = synthetic construct
SEQUENCE: 73
RASQGISSWL A                                                          11

SEQ ID NO: 74           moltype = AA   length = 7
FEATURE                 Location/Qualifiers
REGION                  1..7
                        note = light chain CDR2 for 11D4
source                  1..7
                        mol_type = protein
                        organism = synthetic construct
SEQUENCE: 74
AASSLQS                                                                7

SEQ ID NO: 75           moltype = AA   length = 9
FEATURE                 Location/Qualifiers
REGION                  1..9
                        note = light chain CDR3 for 11D4
source                  1..9
                        mol_type = protein
                        organism = synthetic construct
SEQUENCE: 75
QQYNSYPPT                                                              9

SEQ ID NO: 76           moltype = AA   length = 450
FEATURE                 Location/Qualifiers
REGION                  1..450
```

```
                        note = heavy chain for 18D8
source                  1..450
                        mol_type = protein
                        organism = synthetic construct
SEQUENCE: 76
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAKDQ STADYYFYYG MDVWGQGTTV   120
TVSSASTKGP SVFPLAPCSR STSESTAALG CLVKDYFPEP VTVSWNSGAL TSGVHTFPAV   180
LQSSGLYSLS SVVTVPSSNF GTQTYTCNVD HKPSNTKVDK TVERKCCVEC PPCPAPPVAG   240
PSVFLFPPKP KDTLMISRTP EVTCVVVDVS HEDPEVQFNW YVDGVEVHNA KTKPREEQFN   300
STFRVVSVLT VVHQDWLNGK EYKCKVSNKG LPAPIEKTIS KTKGQPREPQ VYTLPPSREE   360
MTKNQVSLTC LVKGFYPSDI AVEWESNGQP ENNYKTTPPM LDSDGSFFLY SKLTVDKSRW   420
QQGNVFSCSV MHEALHNHYT QKSLSLSPGK                                   450

SEQ ID NO: 77           moltype = AA   length = 213
FEATURE                 Location/Qualifiers
REGION                  1..213
                        note = light chain for 18D8
source                  1..213
                        mol_type = protein
                        organism = synthetic construct
SEQUENCE: 77
EIVVTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TKVEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 78           moltype = AA   length = 124
FEATURE                 Location/Qualifiers
REGION                  1..124
                        note = heavy chain variable region for 18D8
source                  1..124
                        mol_type = protein
                        organism = synthetic construct
SEQUENCE: 78
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAKDQ STADYYFYYG MDVWGQGTTV   120
TVSS                                                               124

SEQ ID NO: 79           moltype = AA   length = 106
FEATURE                 Location/Qualifiers
REGION                  1..106
                        note = light chain variable region for 18D8
source                  1..106
                        mol_type = protein
                        organism = synthetic construct
SEQUENCE: 79
EIVVTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TKVEIK                 106

SEQ ID NO: 80           moltype = AA   length = 5
FEATURE                 Location/Qualifiers
REGION                  1..5
                        note = heavy chain CDR1 for 18D8
source                  1..5
                        mol_type = protein
                        organism = synthetic construct
SEQUENCE: 80
DYAMH                                                                5

SEQ ID NO: 81           moltype = AA   length = 17
FEATURE                 Location/Qualifiers
REGION                  1..17
                        note = heavy chain CDR2 for 18D8
source                  1..17
                        mol_type = protein
                        organism = synthetic construct
SEQUENCE: 81
GISWNSGSIG YADSVKG                                                  17

SEQ ID NO: 82           moltype = AA   length = 15
FEATURE                 Location/Qualifiers
REGION                  1..15
                        note = heavy chain CDR3 for 18D8
source                  1..15
                        mol_type = protein
                        organism = synthetic construct
SEQUENCE: 82
DQSTADYYFY YGMDV                                                    15
```

```
SEQ ID NO: 83            moltype = AA   length = 11
FEATURE                  Location/Qualifiers
REGION                   1..11
                         note = light chain CDR1 for 18D8
source                   1..11
                         mol_type = protein
                         organism = synthetic construct
SEQUENCE: 83
RASQSVSSYL A                                                              11

SEQ ID NO: 84            moltype = AA   length = 7
FEATURE                  Location/Qualifiers
REGION                   1..7
                         note = light chain CDR2 for 18D8
source                   1..7
                         mol_type = protein
                         organism = synthetic construct
SEQUENCE: 84
DASNRAT                                                                   7

SEQ ID NO: 85            moltype = AA   length = 8
FEATURE                  Location/Qualifiers
REGION                   1..8
                         note = light chain CDR3 for 18D8
source                   1..8
                         mol_type = protein
                         organism = synthetic construct
SEQUENCE: 85
QQRSNWPT                                                                  8

SEQ ID NO: 86            moltype = AA   length = 120
FEATURE                  Location/Qualifiers
REGION                   1..120
                         note = heavy chain variable region for Hu119-122
source                   1..120
                         mol_type = protein
                         organism = synthetic construct
SEQUENCE: 86
EVQLVESGGG LVQPGGSLRL SCAASEYEFP SHDMSWVRQA PGKGLELVAA INSDGGSTYY          60
PDTMERRFTI SRDNAKNSLY LQMNSLRAED TAVYYCARHY DDYYAWFAYW GQGTMVTVSS         120

SEQ ID NO: 87            moltype = AA   length = 111
FEATURE                  Location/Qualifiers
REGION                   1..111
                         note = light chain variable region for Hu119-122
source                   1..111
                         mol_type = protein
                         organism = synthetic construct
SEQUENCE: 87
EIVLTQSPAT LSLSPGERAT LSCRASKSVS TSGYSYMHWY QQKPGQAPRL LIYLASNLES          60
GVPARFSGSG SGTDFTLTIS SLEPEDFAVY YCQHSRELPL TFGGGTKVEI K                  111

SEQ ID NO: 88            moltype = AA   length = 5
FEATURE                  Location/Qualifiers
REGION                   1..5
                         note = heavy chain CDR1 for Hu119-122
source                   1..5
                         mol_type = protein
                         organism = synthetic construct
SEQUENCE: 88
SHDMS                                                                     5

SEQ ID NO: 89            moltype = AA   length = 17
FEATURE                  Location/Qualifiers
REGION                   1..17
                         note = heavy chain CDR2 for Hu119-122
source                   1..17
                         mol_type = protein
                         organism = synthetic construct
SEQUENCE: 89
AINSDGGSTY YPDTMER                                                        17

SEQ ID NO: 90            moltype = AA   length = 11
FEATURE                  Location/Qualifiers
REGION                   1..11
                         note = heavy chain CDR3 for Hu119-122
source                   1..11
                         mol_type = protein
```

```
                        organism = synthetic construct
SEQUENCE: 90
HYDDYYAWFA Y                                                                 11

SEQ ID NO: 91           moltype = AA   length = 15
FEATURE                 Location/Qualifiers
REGION                  1..15
                        note = light chain CDR1 for Hu119-122
source                  1..15
                        mol_type = protein
                        organism = synthetic construct
SEQUENCE: 91
RASKSVSTSG YSYMH                                                             15

SEQ ID NO: 92           moltype = AA   length = 7
FEATURE                 Location/Qualifiers
REGION                  1..7
                        note = light chain CDR2 for Hu119-122
source                  1..7
                        mol_type = protein
                        organism = synthetic construct
SEQUENCE: 92
LASNLES                                                                       7

SEQ ID NO: 93           moltype = AA   length = 9
FEATURE                 Location/Qualifiers
REGION                  1..9
                        note = light chain CDR3 for Hu119-122
source                  1..9
                        mol_type = protein
                        organism = synthetic construct
SEQUENCE: 93
QHSRELPLT                                                                     9

SEQ ID NO: 94           moltype = AA   length = 122
FEATURE                 Location/Qualifiers
REGION                  1..122
                        note = heavy chain variable region for Hu106-222
source                  1..122
                        mol_type = protein
                        organism = synthetic construct
SEQUENCE: 94
QVQLVQSGSE LKKPGASVKV SCKASGYTFT DYSMHWVRQA PGQGLKWMGW INTETGEPTY  60
ADDFKGRFVF SLDTSVSTAY LQISSLKAED TAVYYCANPY YDYVSYYAMD YWGQGTTVTV 120
SS                                                                          122

SEQ ID NO: 95           moltype = AA   length = 107
FEATURE                 Location/Qualifiers
REGION                  1..107
                        note = light chain variable region for Hu106-222
source                  1..107
                        mol_type = protein
                        organism = synthetic construct
SEQUENCE: 95
DIQMTQSPSS LSASVGDRVT ITCKASQDVS TAVAWYQQKP GKAPKLLIYS ASYLYTGVPS  60
RFSGSGSGTD FTFTISSLQP EDIATYYCQQ HYSTPRTFGQ GTKLEIK                 107

SEQ ID NO: 96           moltype = AA   length = 5
FEATURE                 Location/Qualifiers
REGION                  1..5
                        note = heavy chain CDR1 for Hu106-222
source                  1..5
                        mol_type = protein
                        organism = synthetic construct
SEQUENCE: 96
DYSMH                                                                         5

SEQ ID NO: 97           moltype = AA   length = 17
FEATURE                 Location/Qualifiers
REGION                  1..17
                        note = heavy chain CDR2 for Hu106-222
source                  1..17
                        mol_type = protein
                        organism = synthetic construct
SEQUENCE: 97
WINTETGEPT YADDFKG                                                           17

SEQ ID NO: 98           moltype = AA   length = 13
FEATURE                 Location/Qualifiers
```

```
REGION                         1..13
                               note = heavy chain CDR3 for Hu106-222
source                         1..13
                               mol_type = protein
                               organism = synthetic construct
SEQUENCE: 98
PYYDYVSYYA MDY                                                          13

SEQ ID NO: 99                  moltype = AA  length = 11
FEATURE                        Location/Qualifiers
REGION                         1..11
                               note = light chain CDR1 for Hu106-222
source                         1..11
                               mol_type = protein
                               organism = synthetic construct
SEQUENCE: 99
KASQDVSTAV A                                                            11

SEQ ID NO: 100                 moltype = AA  length = 7
FEATURE                        Location/Qualifiers
REGION                         1..7
                               note = light chain CDR2 for Hu106-222
source                         1..7
                               mol_type = protein
                               organism = synthetic construct
SEQUENCE: 100
SASYLYT                                                                  7

SEQ ID NO: 101                 moltype = AA  length = 9
FEATURE                        Location/Qualifiers
REGION                         1..9
                               note = light chain CDR3 for Hu106-222
source                         1..9
                               mol_type = protein
                               organism = synthetic construct
SEQUENCE: 101
QQHYSTPRT                                                                9

SEQ ID NO: 102                 moltype = AA  length = 183
FEATURE                        Location/Qualifiers
REGION                         1..183
                               note = OX40L
source                         1..183
                               mol_type = protein
                               organism = synthetic construct
SEQUENCE: 102
MERVQPLEEN VGNAARPRFE RNKLLLVASV IQGLGLLLCF TYICLHFSAL QVSHRYPRIQ        60
SIKVQFTEYK KEKGFILTSQ KEDEIMKVQN NSVIINCDGF YLISLKGYFS QEVNISLHYQ       120
KDEEPLFQLK KVRSVNSLMV ASLTYKDKVY LNVTTDNTSL DDFHVNGGEL ILIHQNPGEF       180
CVL                                                                    183

SEQ ID NO: 103                 moltype = AA  length = 131
FEATURE                        Location/Qualifiers
REGION                         1..131
                               note = OX40L soluble domain
source                         1..131
                               mol_type = protein
                               organism = synthetic construct
SEQUENCE: 103
SHRYPRIQSI KVQFTEYKKE KGFILTSQKE DEIMKVQNNS VIINCDGFYL ISLKGYFSQE        60
VNISLHYQKD EEPLFQLKKV RSVNSLMVAS LTYKDKVYLN VTTDNTSLDD FHVNGGELIL       120
IHQNPGEFCV L                                                           131

SEQ ID NO: 104                 moltype = AA  length = 128
FEATURE                        Location/Qualifiers
REGION                         1..128
                               note = OX40L soluble domain (alternative)
source                         1..128
                               mol_type = protein
                               organism = synthetic construct
SEQUENCE: 104
YPRIQSIKVQ FTEYKKEKGF ILTSQKEDEI MKVQNNSVII NCDGFYLISL KGYFSQEVNI        60
SLHYQKDEEP LFQLKKVRSV NSLMVASLTY KDKVYLNVTT DNTSLDDFHV NGGELILIHQ       120
NPGEFCVL                                                               128

SEQ ID NO: 105                 moltype = AA  length = 120
FEATURE                        Location/Qualifiers
REGION                         1..120
                               note = variable heavy chain for 008
```

```
source                    1..120
                          mol_type = protein
                          organism = synthetic construct
SEQUENCE: 105
EVQLVESGGG LVQPGGSLRL SCAASGFTFS NYTMNWVRQA PGKGLEWVSA ISGSGGSTYY    60
ADSVKGRFTI SRDNSKNTLY LQMNSLRAED TAVYYCAKDR YSQVHYALDY WGQGTLVTVS   120

SEQ ID NO: 106            moltype = AA  length = 108
FEATURE                   Location/Qualifiers
REGION                    1..108
                          note = variable light chain for 008
source                    1..108
                          mol_type = protein
                          organism = synthetic construct
SEQUENCE: 106
DIVMTQSPDS LPVTPGEPAS ISCRSSQSLL HSNGYNYLDW YLQKAGQSPQ LLIYLGSNRA    60
SGVPDRFSGS GSGTDFTLKI SRVEAEDVGV YYCQQYYNHP TTFGQGTK                108

SEQ ID NO: 107            moltype = AA  length = 120
FEATURE                   Location/Qualifiers
REGION                    1..120
                          note = variable heavy chain for 011
source                    1..120
                          mol_type = protein
                          organism = synthetic construct
SEQUENCE: 107
EVQLVESGGG VVQPGRSLRL SCAASGFTFS DYTMNWVRQA PGKGLEWVSS ISGGSTYYAD    60
SRKGRFTISR DNSKNTLYLQ MNNLRAEDTA VYYCARDRYF RQQNAFDYWG QGTLVTVSSA   120

SEQ ID NO: 108            moltype = AA  length = 108
FEATURE                   Location/Qualifiers
REGION                    1..108
                          note = variable light chain for 011
source                    1..108
                          mol_type = protein
                          organism = synthetic construct
SEQUENCE: 108
DIVMTQSPDS LPVTPGEPAS ISCRSSQSLL HSNGYNYLDW YLQKAGQSPQ LLIYLGSNRA    60
SGVPDRFSGS GSGTDFTLKI SRVEAEDVGV YYCQQYYNHP TTFGQGTK                108

SEQ ID NO: 109            moltype = AA  length = 120
FEATURE                   Location/Qualifiers
REGION                    1..120
                          note = variable heavy chain for 021
source                    1..120
                          mol_type = protein
                          organism = synthetic construct
SEQUENCE: 109
EVQLVESGGG LVQPRGSLRL SCAASGFTFS SYAMNWVRQA PGKGLEWVAV ISYDGSNKYY    60
ADSVKGRFTI SRDNSKNTLY LQMNSLRAED TAVYYCAKDR YITLPNALDY WGQGTLVTVS   120

SEQ ID NO: 110            moltype = AA  length = 108
FEATURE                   Location/Qualifiers
REGION                    1..108
                          note = variable light chain for 021
source                    1..108
                          mol_type = protein
                          organism = synthetic construct
SEQUENCE: 110
DIQMTQSPVS LPVTPGEPAS ISCRSSQSLL HSNGYNYLDW YLQKPGQSPQ LLIYLGSNRA    60
SGVPDRFSGS GSGTDFTLKI SRVEAEDVGV YYCQQYKSNP PTFGQGTK                108

SEQ ID NO: 111            moltype = AA  length = 120
FEATURE                   Location/Qualifiers
REGION                    1..120
                          note = variable heavy chain for 023
source                    1..120
                          mol_type = protein
                          organism = synthetic construct
SEQUENCE: 111
EVQLVESGGG LVHPGGSLRL SCAGSGFTFS SYAMHWVRQA PGKGLEWVSA IGTGGGTYYA    60
DSVMGRFTIS RDNSKNTLYL QMNSLRAEDT AVYYCARYDN VMGLYWFDYW GQGTLVTVSS   120

SEQ ID NO: 112            moltype = AA  length = 108
FEATURE                   Location/Qualifiers
REGION                    1..108
                          note = variable light chain for 023
source                    1..108
                          mol_type = protein
```

```
                        organism = synthetic construct
SEQUENCE: 112
EIVLTQSPAT LSLSPGERAT LSCRASQSVS SYLAWYQQKP GQAPRLLIYD ASNRATGIPA      60
RFSGSGSGTD FTLTISSLEP EDFAVYYCQQ RSNWPPAFGG GTKVEIKR                  108

SEQ ID NO: 113          moltype = AA  length = 119
FEATURE                 Location/Qualifiers
REGION                  1..119
                        note = heavy chain variable region
source                  1..119
                        mol_type = protein
                        organism = synthetic construct
SEQUENCE: 113
EVQLQQSGPE LVKPGASVKM SCKASGYTFT SYVMHWVKQK PGQGLEWIGY INPYNDGTKY      60
NEKFKGKATL TSDKSSSTAY MELSSLTSED SAVYYCANYY GSSLSMDYWG QGTSVTVSS      119

SEQ ID NO: 114          moltype = AA  length = 108
FEATURE                 Location/Qualifiers
REGION                  1..108
                        note = light chain variable region
source                  1..108
                        mol_type = protein
                        organism = synthetic construct
SEQUENCE: 114
DIQMTQTTSS LSASLGDRVT ISCRASQDIS NYLNWYQQKP DGTVKLLIYY TSRLHSGVPS      60
RFSGSGSGTD YSLTISNLEQ EDIATYFCQQ GNTLPWTFGG GTKLEIKR                  108

SEQ ID NO: 115          moltype = AA  length = 121
FEATURE                 Location/Qualifiers
REGION                  1..121
                        note = heavy chain variable region
source                  1..121
                        mol_type = protein
                        organism = synthetic construct
SEQUENCE: 115
EVQLQQSGPE LVKPGASVKI SCKTSGYTFK DYTMHWVKQS HGKSLEWIGG IYPNNGGSTY      60
NQNFKDKATL TVDKSSSTAY MEFRSLTSED SAVYYCARMG YHGPHLDFDV WGAGTTVTVS     120
P                                                                    121

SEQ ID NO: 116          moltype = AA  length = 108
FEATURE                 Location/Qualifiers
REGION                  1..108
                        note = light chain variable region
source                  1..108
                        mol_type = protein
                        organism = synthetic construct
SEQUENCE: 116
DIVMTQSHKF MSTSLGDRVS ITCKASQDVG AAVAWYQQKP GQSPKLLIYW ASTRHTGVPD      60
RFTGGGSGTD FTLTISNVQS EDLTDYFCQQ YINYPLTFGG GTKLEIKR                  108

SEQ ID NO: 117          moltype = AA  length = 122
FEATURE                 Location/Qualifiers
REGION                  1..122
                        note = heavy chain variable region of humanized antibody
source                  1..122
                        mol_type = protein
                        organism = synthetic construct
SEQUENCE: 117
QIQLVQSGPE LKKPGETVKI SCKASGYTFT DYSMHWVKQA PGKGLKWMGW INTETGEPTY      60
ADDFKGRFAF SLETSASTAY LQINNLKNED TATYFCANPY YDYVSYYAMD YWGHGTSVTV     120
SS                                                                   122

SEQ ID NO: 118          moltype = AA  length = 122
FEATURE                 Location/Qualifiers
REGION                  1..122
                        note = heavy chain variable region of humanized antibody
source                  1..122
                        mol_type = protein
                        organism = synthetic construct
SEQUENCE: 118
QVQLVQSGSE LKKPGASVKV SCKASGYTFT DYSMHWVRQA PGQGLKWMGW INTETGEPTY      60
ADDFKGRFVF SLDTSVSTAY LQISSLKAED TAVYYCANPY YDYVSYYAMD YWGQGTTVTV     120
SS                                                                   122

SEQ ID NO: 119          moltype = AA  length = 107
FEATURE                 Location/Qualifiers
REGION                  1..107
                        note = light chain variable region of humanized antibody
source                  1..107
```

```
                        mol_type = protein
                        organism = synthetic construct
SEQUENCE: 119
DIVMTQSHKF MSTSVRDRVS ITCKASQDVS TAVAWYQQKP GQSPKLLIYS ASYLYTGVPD    60
RFTGSGSGTD FTFTISSVQA EDLAVYYCQQ HYSTPRTFGG GTKLEIK                 107

SEQ ID NO: 120          moltype = AA  length = 107
FEATURE                 Location/Qualifiers
REGION                  1..107
                        note = light chain variable region of humanized antibody
source                  1..107
                        mol_type = protein
                        organism = synthetic construct
SEQUENCE: 120
DIVMTQSHKF MSTSVRDRVS ITCKASQDVS TAVAWYQQKP GQSPKLLIYS ASYLYTGVPD    60
RFTGSGSGTD FTFTISSVQA EDLAVYYCQQ HYSTPRTFGG GTKLEIK                 107

SEQ ID NO: 121          moltype = AA  length = 120
FEATURE                 Location/Qualifiers
REGION                  1..120
                        note = heavy chain variable region of humanized antibody
source                  1..120
                        mol_type = protein
                        organism = synthetic construct
SEQUENCE: 121
EVQLVESGGG LVQPGESLKL SCESNEYEFP SHDMSWVRKT PEKRLELVAA INSDGGSTYY    60
PDTMERRFII SRDNTKKTLY LQMSSLRSED TALYYCARHY DDYYAWFAYW GQGTLVTVSA   120

SEQ ID NO: 122          moltype = AA  length = 120
FEATURE                 Location/Qualifiers
REGION                  1..120
                        note = heavy chain variable region of humanized antibody
source                  1..120
                        mol_type = protein
                        organism = synthetic construct
SEQUENCE: 122
EVQLVESGGG LVQPGGSLRL SCAASEYEFP SHDMSWVRQA PGKGLELVAA INSDGGSTYY    60
PDTMERRFTI SRDNAKNSLY LQMNSLRAED TAVYYCARHY DDYYAWFAYW GQGTMVTVSS   120

SEQ ID NO: 123          moltype = AA  length = 111
FEATURE                 Location/Qualifiers
REGION                  1..111
                        note = light chain variable region of humanized antibody
source                  1..111
                        mol_type = protein
                        organism = synthetic construct
SEQUENCE: 123
DIVLTQSPAS LAVSLGQRAT ISCRASKSVS TSGYSYMHWY QQKPGQPPKL LIYLASNLES    60
GVPARFSGSG SGTDFTLNIH PVEEEDAATY YCQHSRELPL TFGAGTKLEL K            111

SEQ ID NO: 124          moltype = AA  length = 111
FEATURE                 Location/Qualifiers
REGION                  1..111
                        note = light chain variable region of humanized antibody
source                  1..111
                        mol_type = protein
                        organism = synthetic construct
SEQUENCE: 124
EIVLTQSPAT LSLSPGERAT LSCRASKSVS TSGYSYMHWY QQKPGQAPRL LIYLASNLES    60
GVPARFSGSG SGTDFTLTIS SLEPEDFAVY YCQHSRELPL TFGGGTKVEI K            111

SEQ ID NO: 125          moltype = AA  length = 138
FEATURE                 Location/Qualifiers
REGION                  1..138
                        note = heavy chain variable region
source                  1..138
                        mol_type = protein
                        organism = synthetic construct
SEQUENCE: 125
MYLGLNYVFI VFLLNGVQSE VKLEESGGGL VQPGGSMKLS CAASGFTFSD AWMDWVRQSP    60
EKGLEWVAEI RSKANNHATY YAESVNGRFT ISRDDSKSSV YLQMNSLRAE DTGIYYCTWG   120
EVFYFDYWGQ GTTLTVSS                                                 138

SEQ ID NO: 126          moltype = AA  length = 126
FEATURE                 Location/Qualifiers
REGION                  1..126
                        note = light chain variable region
source                  1..126
                        mol_type = protein
```

```
                        organism = synthetic construct
SEQUENCE: 126
MRPSIQFLGL LLFWLHGAQC DIQMTQSPSS LSASLGGKVT ITCKSSQDIN KYIAWYQHKP    60
GKGPRLLIHY TSTLQPGIPS RFSGSGSGRD YSFSISNLEP EDIATYYCLQ YDNLLTFGAG   120
TKLELK                                                              126

SEQ ID NO: 127          moltype = DNA   length = 49
FEATURE                 Location/Qualifiers
misc_feature            1..49
                        note = synthetic construct PD-1 target sequence 1
source                  1..49
                        mol_type = other DNA
                        organism = synthetic construct
SEQUENCE: 127
ttctccccag ccctgctcgt ggtgaccgaa ggggacaacg ccaccttca                49

SEQ ID NO: 128          moltype = DNA   length = 49
FEATURE                 Location/Qualifiers
misc_feature            1..49
                        note = synthetic construct PD-1 target sequence 1
source                  1..49
                        mol_type = other DNA
                        organism = synthetic construct
SEQUENCE: 128
tacctctgtg gggccatctc cctggccccc aaggcgcaga tcaaagaga                49

SEQ ID NO: 129          moltype = AA   length = 530
FEATURE                 Location/Qualifiers
REGION                  1..530
                        note = synthetic construct Repeat PD-1-left
source                  1..530
                        mol_type = protein
                        organism = synthetic construct
SEQUENCE: 129
LTPQQVVAIA SNGGGKQALE TVQRLLPVLC QAHGLTPEQV VAIASHDGGK QALETVQRLL    60
PVLCQAHGLT PQQVVAIASN GGGKQALETV QRLLPVLCQA HGLTPEQVVA IASHDGGKQA   120
LETVQRLLPV LCQAHGLTPE QVVAIASHDG GKQALETVQR LLPVLCQAHG LTPEQVVAIA   180
SHDGGKQALE TVQRLLPVLC QAHGLTPEQV VAIASHDGGK QALETVQRLL PVLCQAHGLT   240
PEQVVAIASN IGGKQALETV QALLPVLCQA HGLTPQQVVA IASNNGGKQA LETVQRLLPV   300
LCQAHGLTPE QVVAIASHDG GKQALETVQR LLPVLCQAHG LTPEQVVAIA SHDGGKQALE   360
TVQRLLPVLC QAHGLTPEQV VAIASHDGGK QALETVQRLL PVLCQAHGLT PQQVVAIASN   420
GGGKQALETV QRLLPVLCQA HGLTPQQVVA IASNNGGKQA LETVQRLLPV LCQAHGLTPE   480
QVVAIASHDG GKQALETVQR LLPVLCQAHG LTPQQVVAIA SNGGGRPALE              530

SEQ ID NO: 130          moltype = AA   length = 529
FEATURE                 Location/Qualifiers
REGION                  1..529
                        note = synthetic construct Repeat PD-1-right
source                  1..529
                        mol_type = protein
                        organism = synthetic construct
SEQUENCE: 130
LTPQQVVAIA SNNGGKQALE TVQRLLPVLC QAHGLTPEQV VAIASNIGGK QALETVQALL    60
PVLCQAHGLT PEQVVAIASN IGGKQALETV QALLPVLCQA HGLTPQQVVA IASNNGGKQA   120
LETVQRLLPV LCQAHGLTPQ QVVAIASNNG GKQALETVQR LLPVLCQAHG LTPQQVVAIA   180
SNGGGKQALE TVQRLLPVLC QAHGLTPQQV VAIASNNGGK QALETVQRLL PVLCQAHGLT   240
PQQVVAIASN NGGKQALETV QRLLPVLCQA HGLTPQQVVA IASNGGGKQAL ETVQRLLPVL   300
CQAHGLTPQQ VVAIASNNGG KQALETVQRL LPVLCQAHGL TPQQVVAIAS NGGGKQALET   360
VQRLLPVLCQ AHGLTPQQVV AIASNGGGKQ ALETVQRLLP VLCQAHGLTP QQVVAIASNN   420
GGKQALETVQ RLLPVLCQAH GLTPQQVVAI ASNGGGKQAL ETVQRLLPVL CQAHGLTPEQ   480
VVAIASHDGG KQALETVQRL LPVLCQAHGL TPQQVVAIAS NGGGRPALE               529

SEQ ID NO: 131          moltype = AA   length = 530
FEATURE                 Location/Qualifiers
REGION                  1..530
                        note = synthetic construct Repeat PD-1-left
source                  1..530
                        mol_type = protein
                        organism = synthetic construct
SEQUENCE: 131
LTPEQVVAIA SNIGGKQALE TVQALLPVLC QAHGLTPEQV VAIASHDGGK QALETVQRLL    60
PVLCQAHGLT PEQVVAIASH DGGKQALETV QRLLPVLCQA HGLTPQQVVA IASNGGGKQA   120
LETVQRLLPV LCQAHGLTPE QVVAIASHDG GKQALETVQR LLPVLCQAHG LTPQQVVAIA   180
SNGGGKQALE TVQRLLPVLC QAHGLTPQQV VAIASNNGGK QALETVQRLL PVLCQAHGLT   240
PQQVVAIASN GGGKQALETV QRLLPVLCQA HGLTPQQVVA IASNNGGKQA LETVQRLLPV   300
LCQAHGLTPQ QVVAIASNNG GKQALETVQR LLPVLCQAHG LTPQQVVAIA SNGGKQALE    360
TVQRLLPVLC QAHGLTPQQV VAIASNNGGK QALETVQRLL PVLCQAHGLT PEQVVAIASH   420
DGGKQALETV QRLLPVLCQA HGLTPEQVVA IASHDGGKQA LETVQRLLPV LCQAHGLTPE   480
QVVAIASNIG GKQALETVQA LLPVLCQAHG LTPQQVVAIA SNGGGRPALE              530
```

```
SEQ ID NO: 132            moltype = AA  length = 529
FEATURE                   Location/Qualifiers
REGION                    1..529
                          note = synthetic construct Repeat PD-1-right
source                    1..529
                          mol_type = protein
                          organism = synthetic construct
SEQUENCE: 132
LTPEQVVAIA SHDGGKQALE TVQRLLPVLC QAHGLTPQQV VAIASNGGGK QALETVQRLL    60
PVLCQAHGLT PEQVVAIASH DGGKQALETV QRLLPVLCQA HGLTPQQVVA IASNGGGKQA   120
LETVQRLLPV LCQAHGLTPQ QVVAIASNGG GKQALETVQR LLPVLCQAHG LTPQQVVAIA   180
SNGGGKQALE TVQRLLPVLC QAHGLTPQQV VAIASNNGGK QALETVQRLL PVLCQAHGLT   240
PEQVVAIASN IGGKQALETV QALLPVLCQA HGLTPQQVVA IASNGGGKQA LETVQRLLPV   300
LCQAHGLTPE QVVAIASHDG GKQALETVQR LLPVLCQAHG LTPQQVVAIA SNGGGKQALE   360
TVQRLLPVLC QAHGLTPQQV VAIASNNGGK QALETVQRLL PVLCQAHGLT PEQVVAIASN   420
GGKQALETVQ RLLPVLCQAH GLTPQQVVAI ASNNGGKQAL ETVQRLLPVL CQAHGLTPEQ   480
VVAIASHDGG KQALETVQRL LPVLCQAHGL TPQQVVAIAS NGGGRPALE              529

SEQ ID NO: 133            moltype = DNA  length = 2814
FEATURE                   Location/Qualifiers
misc_feature              1..2814
                          note = synthetic construct PD-1-left TALEN
source                    1..2814
                          mol_type = other DNA
                          organism = synthetic construct
SEQUENCE: 133
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa caccccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacggtgc cccgctcaac   480
ttgacccccc agcaggtggt ggccatcgcc agcaatggcg gtggcaagca ggcgctggag   540
acggtccagc ggctgttgcc ggtgctgtgc caggcccacg gcttgacccc ggagcaggtg   600
gtggccatcg ccagccacga tggcggcaag caggcgctgg agacggtcca gcggctgttg   660
ccggtgctgt gccaggccca cggcttgacc cccagcaggt ggtggccat cgccagcaat   720
ggcggtggca agcaggcgct ggagacggtc agcggctgt gccggtgct gtgccaggcc   780
cacggcttga cccccggagca ggtggtggcc atcgccagcc acgatggcgg caagcaggcg   840
ctggagacgt ccagcggct gttgccggtg ctgtgccagg cccacggctt gaccccggag   900
caggtggtgg ccatcgccag ccacgatggc ggcaagcagg cgctggagac ggtccagcgg   960
ctgttgccgg tgctgtgcca ggcccacggc ttgaccccgg agcaggtggt ggccatcgcc  1020
agccacgatg cggcaagca ggcgctggag acggtccagc ggctgttgcc ggtgctgtgc  1080
caggcccacg gcttgacccc ggagcaggtg gtggccatcg ccagccacga tggcggcaag  1140
caggcgctgg agacggtcca gcggctgttg ccggtgctgt gccaggccca cggcttgacc  1200
ccggagcagg tggtggccat cgccagcaat attggtggca agcaggcgct ggagacggtc  1260
cagggcgtgt gccggtgct gtgccaggcc acggcttga cccccagca ggtggtggcc  1320
atcgccagca taatggtgg caagcaggcg ctggagacgg tccagcggct gttgccggtc  1380
ctgtgccagg cccacggctt gaccccggag caggtggtgg ccatcgccag ccacgatggc  1440
ggcaagcagg cgctgagac ggtccagcgg ctgttgccgg tgctgtgcca ggcccacggc  1500
ttgaccccgg agcaggtggt ggccatcgcc agccacgatg cggcaagca ggcgctggag  1560
acggtccagc ggctgttgcc ggtgctgtgc caggcccacg gcttgacccc ggagcaggtg  1620
gtggccatcg ccagccacga tggcggcaag caggcgctgg agacggtcca gcggctgttg  1680
ccggtgctgt gccaggccca cggcttgacc cccagcagg tggtggccat cgccagcaat  1740
ggcggtggca agcaggcgct ggagacggtc cagcggctgt tgccggtgct gtgccaggcc  1800
cacggcttga cccccagca ggtggtggcc atcgccagca taatggtgg caagcaggcg  1860
ctggagacgg tccagcggct gttgccggtg ctgtgccagg cccacggctt gaccccggag  1920
caggtggtgg ccatcgccag ccacgatggc ggcaagcagg cgctggagac ggtccagcgg  1980
ctgttgccgg tgctgtgcca ggcccacggc ttgaccccctc agcaggtggt ggccatcgcc  2040
agcaatggcg gcggcaggcc ggcgctggag agcattgttg cccagttatc tgccctgat  2100
ccggcgttgg ccgcgttgac caacgaccac ctcgtcgcct tggcctgcct cggcgggcgt  2160
cctgcgctgg atgcagtgaa aaagggattg ggggatccta tcagccgttc ccagctgtg  2220
aagtccgagc tggaggagaa gaaatccgag ttgaggcaca agctgaagta cgtgccccac  2280
gagtacatcg agctgatcga gatcgcccgg aacagcaccc aggaccgtat cctggagatg  2340
aaggtgatgg agttcttcat gaaggtgtac ggctacaggg gcaagcacct gggcggctcc  2400
aggaagcccg acggcgccat ctacaccgtg gctcccca tcgactacgg cgtgatcgtg  2460
gacaccaagg cctactccgg cggctacaac ctgcccatcg gccaggcga cgaaatgcag  2520
aggtacgtgg aggagaacca gaccaggaac aagcacatcg accccaacga gtggtggaag  2580
gtgtaccccct ccagcgtgac cgagttcaag ttcctgttcg tgtccggcca cttcaagggc  2640
aactacaagg cccagctgac caggctgaac cacatcacca ctgcaacgg cgccgtgctg  2700
tccgtggagg agctcctgat cggcggcgag atgatcaagg ccggcaccct gacccctgag  2760
gaggtgagga ggaagttcaa caacggcgag atcaacttcg cggccgactg ataa         2814

SEQ ID NO: 134            moltype = DNA  length = 2829
FEATURE                   Location/Qualifiers
misc_feature              1..2829
                          note = synthetic construct PD-1-right TALEN
```

```
source                  1..2829
                        mol_type = other DNA
                        organism = synthetic construct
SEQUENCE: 134
atgggcgatc ctaaaaagaa acgtaaggtc atcgataagg agaccgccgc tgccaagttc    60
gagagacagc acatggacag catcgatatc gccgatctac gcacgctcgg ctacagccag   120
cagcaacagg agaagatcaa accgaaggtt cgttcgacag tggcgcagca ccacgaggca   180
ctggtcggcc acgggtttac acacgcgcac atcgttgcgt taagccaaca cccggcagcg   240
ttagggaccg tcgctgtcaa gtatcaggac atgatcgcac cgttgccaga ggcgacacac   300
gaagcgatcg ttggcgtcgg caaacagtgg tccggcgcac gcgctctgga ggccttgctc   360
acggtggcgg gagagttgag aggtccaccg ttacagttgg acacaggcca acttctcaag   420
attgcaaaac gtggcggcgt gaccgcagtg gaggcagtgc atgcatggcg caatgcactg   480
acgggtgccc cgctcaactt gaccccccag caagtcgtcg caatcgccag caataacgga   540
gggaagcaag ccctcgaaac cgtgcagcgg ttgcttcctg tgctctgcca ggcccacggc   600
cttacccctg agcaggtggt ggccatcgca agtaacattg gaggaaagca agcccttgga   660
acagtgcagg ccctgttgcc cgtgctgtgc caggcacacg gcctcacacc agagcaggtc   720
gtggccattg cctccaacat cggggggaaa caggctctga gaccgtcca ggccctgctg   780
cccgtcctct gtcaagctca cggcctgact ccccaacaag tggtcgccat gcctctaat   840
aacggcggga gcaggcact ggaaacagtg cagagactgc tccctgtgct ttgccaagct   900
catgggttga ccccccaaca ggtcgtcgct attgcctcaa caacgggggg caagcaggcc   960
cttgagactg tgcagaggct gttgccagtg ctgtgtcagg ctcacgggct cactccacaa  1020
caggtggtcg caattgccag caacggcggc ggaaagcaag ctcttgaaac cgtgcaacgt  1080
ctcctgcccg tgctctgtca ggctcatggc ctgacaccac aacaagtcgt ggccatcgcc  1140
agtaataatg gcgggaaaca ggctcttgag accgtccaga ggctgctccc agtgctctgc  1200
caggcacacg ggctgacccc ccagcaggtg gtggctatcg ccagcaataa tgggggcaag  1260
caggccctgg aaacagtcca gcgcctgctg ccagtgcttt gccaggctca cgggctcact  1320
cccgaacagg tcgtggcaat cgcctccaac ggagggaagc aggctctgga gaccgtgcag  1380
agactgctgc ccgtcttgtg ccaggcccac ggactcacac ctcagcaggt cgtcgccatt  1440
gcctctaaca acgggggcaa acaagccctg agacagtgc agcggctgtt gcctgtgttg  1500
tgccaagccc acggcttgac tcctcaacaa gtggtcgcca tcgcctcaaa tggcggcgga  1560
aaacaagctc tggagacagt gcagaggttg ctgcccgtcc tctgccaagc ccacggcctg  1620
actccccaac aggtcgtcgc cattgccagc aacggcggag aaagcaggc tctgaaact  1680
gtgcagcggc tgcttcctgt gctgtgtcag gctcatgggc tgacccccca gcaagtggtg  1740
gctattgcct ctaacaatgg aaggcaagcaa gcccttgaga cagtccagag gctgttgcca  1800
gtgctgtgcc aggcccacgg gctcacaccc cagcaggtgg tcgccatcgc cagtaacgcc  1860
gggggcaaac aggcattgga aaccgtccag cgcctgcttc cagtgctctg ccaggcacac  1920
ggactgacac ccgaacaggt ggtggccatt gcatcccatg atgggggcaa gcaggccctg  1980
gagaccgtgc agagactcct gccagtgttg tgccaagctc acggcctcac ccctcagcaa  2040
gtcgtggcca tcgcctcaaa cggggggggc cggctgccac tggagagcat tgttgcccag  2100
ttatctcgcc ctgatccggc gttggccgcg ttgaccaacg accaccgtcg cgccttggcc  2160
tgcctcggcg gcgtcctgc gctggatgca gtgaaaaagg gattggggga tcctatcagc  2220
cgttcccagc tggtgaagtc cgagctggag gagaagaat ccgagttgag gcacaagctg  2280
aagtacgtgc cccacgagta catcgacgtg atcgagatcg ccggaaacag cacccaggac  2340
cgtatcctgg agatgaaggt gatggagttc ttcatgaagg tgtacggcta caggggcaag  2400
cacctggggcg gctccaggaa gcccgacggc gccatctaca ccgtgggctc ccccatcgac  2460
tacggcgtga tcgtggacac caaggcctac tccggcggct acaacctgcc catcggccag  2520
gccgacgaaa tgcagaggta cgtggaggag aaccagacca tcaaccccg  2580
aacgagtggt ggaaggtgta cccctccagc gtgaccgagt tcaagttcct gttcgtgtcc  2640
ggccacttca agggcaacta caaggcccag ctgaccaggc tgaaccacat caccaactgc  2700
aacggcgccg tgctgtccgt ggaggagctc ctgatcggcg gcgagatgat caaggccggc  2760
accctgaccc tggaggaggt gaggaggaag ttcaacaacg gcgagatcaa cttcgcggcc  2820
gactgataa                                                         2829
SEQ ID NO: 135         moltype = DNA  length = 2814
FEATURE                Location/Qualifiers
misc_feature           1..2814
                        note = synthetic construct PD-1-left TALEN
source                  1..2814
                        mol_type = other DNA
                        organism = synthetic construct
SEQUENCE: 135
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtgcgcag caccacgagg ccacgggttt   180
acacacgcgc acatcgttgc gttaagccaa cacccggcag cgttagggac cgtcgctgtc   240
aagtatcagg acatgatcgc accgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgacccccg agcaggtggt ggccatcgcc agcaatattg tggcaagca ggcgctggag   540
acggtgcagg cgctgttgcc ggtgctgtgc caggcccacg gcttgacccc ggagcaggtg   600
gtggccatcg ccagccacga tggcggcaag caggcgctgg agacggtcca gcggctgttg   660
ccggtgctgt gccaggccca cggcttgacc cggagcaggt ggtggccat cgccagccac   720
gatggcggca agcaggcgtg gagacggtcca gcggctgttg ccggtgctgt gccaggccca   780
cggcttgacc ccccagcagg tggtggccat cgccagcaca tggcggtgg caagcaggcg   840
ctggagacgg tccagcggct gttgccgtg ctgtgccagg cccacggctt gaccccggag   900
caggtggtgg ccatcgccag ccacgatggc ggcaagcagg cgctggagac ggtccagcgg   960
ctgttgccgg tgctgtgcca ggcccacggc ttgaccccc agcaggtggt ggccatcgcc  1020
agcaatggcg gtggcaagca ggcgctggag acggtccagc ggctgttgcc ggtgctgtgc  1080
```

```
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccccagcagg tggtggccat cgccagcaat ggcggtggca agcaggcgct ggagacggtc   1260
cagcggctgt gccggtgct gtgccaggcc cacggcttga ccccccagca ggtggtggcc   1320
atcgccagca ataatggtgg caagcggcg ctggagacg tccagcggct gttgccggtg   1380
ctgtgccagg cccacggctt gacccccag caggtggtgg ccatcgccag caataatggt   1440
ggcaagcagg cgctggagac ggtccagcgg ctgttgccgg tgctgtgcca ggcccacggc   1500
ttgaccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc cagcggctgt gccggtgct gtgccaggcc   1800
cacggcttga ccccggagca ggtggtggcc atcgccagcc acgatggcgg caagcaggcg   1860
ctggagacgg tccagcggct gttgccggtg ctgtgcccac ggcttga ccccggagcag   1920
caggtggtgg ccatcgccag caatattggt ggcaagcagg cgctggagac ggtgcaggcg   1980
ctgttgccgg tgctgtgcca ggcccacggc ttgaccccctc agcaggtggt ggccatcgcc   2040
agcaatggcg cggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg gggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg ccaggccga cgaaatgcag   2520
aggtacgtgg aggagaacca gaccaggaac aagcacatca accccaacga gtggtggaag   2580
gtgtaccccct ccagcgtgac cgagttcaag ttcctgttcg tgtccggcca cttcaaggc   2640
aactacaagg cccagctgac caggctgaac cacatcacca actgcaacgg cgccgtgctg   2700
tccgtggagg agctcctgat cggcggcgag atgatcaagg ccggcaccct gaccctggag   2760
gaggtgagga ggaagttcaa caacggcgag atcaacttcg cggccgactg ataa         2814
```

SEQ ID NO: 136      moltype = DNA length = 2829
FEATURE             Location/Qualifiers
misc_feature        1..2829
                       note = synthetic construct PD-1-right TALEN
source               1..2829
                       mol_type = other DNA
                       organism = synthetic construct
SEQUENCE: 136

```
atgggcgatc ctaaaaagaa acgtaaggtc atcgataagg agaccgccgc tgccaagttc   60
gagagacagc acatggacag catcgatatc gccgatctac gcacgctcgg ctacagccag   120
cagcaacagg agaagatcaa accgaaggtt cgttcgacag tggcgcagca ccacgagca   180
ctggtcggca acgggtttac acacgcgcac atcgttgcgt taagccaaca cccggcagcg   240
ttagggaccg tcgctgtcaa gtatcaggac atgatcgcag cgttgccaga ggcgacacac   300
gaagcgatcg ttggcgtcgg caaacagtgg tccggcgcac gcgctctgga ggccttgctc   360
acggtggcgg gagagttgag aggtccaccg ttacagttgg acacaggcca acttctcaag   420
attgcaaaac gtgggcggcgt gaccgcagtg gaggcagtgc atgcatggcg caatgcactg   480
acgggtgccc cgctcaactt gaccccgag caagtcgtcg caatcgccag ccatgatgga   540
gggaagcaag ccctcgaaac cgtgcagcgg ttgcttcctg tgctctgcca ggcccacggc   600
cttacccctc agcaggtggt ggccatcgca gtaacggag gagaaagca agccttggag   660
acagtgcagc gcctgttgcc cgtgctgtgc aggcacacg gcctcacacc agagcaggtc   720
gtggccattg cctcccatga cgggggaaa caggctctgg agaccgtcca ggcgctgtg   780
cccgtcctct gtcaagctca cggcctgact cccaacaag tggtcgccat cgcctctaat   840
ggcggcggga agcaggcact ggaaacagtg cagagactgc tccctgtgct ttgccaagct   900
catgggttga ccccccaaca ggtcgtcgct attgcctcaa cgggggggg caagcaggcc   960
cttgagactg tgcagaggct gttgccagtg ctgtgtcagg ctcacgggct cactccacaa   1020
caggtggtcg caattgccag caacggcggc ggaaagcaag ctcttgaaac cgtgcaacgc   1080
ctcctgcccg tgctctgtca ggctcatggc ctgacaccac aacagtcgt ggccatcgcc   1140
agtaataatg gcgggaaaca ggctcttgag accgtccaga ggctgctccc agtgctctgc   1200
caggcacacg gcctgaccc ccagcaggtg gtggctatcg ccagcaatat tggggcaag   1260
caggccctgg aaacagtcca ggccctgctg ccagtgcttt gccaggctca cgggctcact   1320
ccccagcagg tcgtggcaat cgcctccaac ggcggaggga agcaggctct ggagaccgtg   1380
cagagactgc tgcccgtctt gtgccaggcc acggactca cacctgaaca ggtcgtcgcc   1440
attgcctctc acgatgggggg caaacaagcc ctggagacag tgcagcggct gttgcctgtg   1500
ttgtgccaag cccacggctt gactcctcaa caagtgctcg ccatcgcctc aaatggcggc   1560
ggaaaacaag ctctggagac agtgcagagg ttgctgcccg tcctctgcca gcccacggc   1620
ctgactcccc aacaggtcgt cgccattgcc agcaacaacg gagaaagca ggctctcgaa   1680
actgtgcagc ggctgcttcc tgtgctgtgt caggctcatg gctgacccc cgagcaagtg   1740
gtggctattg cctctaatgg aggcaagcaa gcccttgaga cagtccagag gctgttgcca   1800
gtgctgtgcc aggcccacgg gctcacacc cagcaggtgg tcgccatcgc cagtaacaac   1860
gggggcaaac aggcattgga aaccgtccag cgctgcttc cagtgctctg ccaggcacac   1920
ggactgacac ccgaacaggt ggtggccatt gcatcccatg atggggggcaa gcaggccctg   1980
gagaccgtgc agagactcct gccagtgttg tgccaagctc acggcctcac cctcagcaa   2040
gtcgtggcca tcgcctcaaa cggggggggc cggcctgcac tggagagcat tgttgcccag   2100
ttatctgatc cggttggccg tgaccaacg ccacctcgt cgccttggcc   2160
tgcctcggcg gcgtcctgc gctggatgca gtgaaaaagg gattggggga tcctatcagc   2220
cgttccagc tggtgaagtc cgagctggag gagaagaaat ccgagttgag gcacaagctg   2280
aagtacgtgc ccacgagta catcgagctg atcgagatcg cccggaacag cacccaggac   2340
cgtatcctgg agatgaaggt gatggagttc ttcatgaagg tgtacggcta caggggcaag   2400
cacctgggcg gctccaggaa gcccgacggc gccatctaca ccgtgggctc ccccatcgac   2460
```

-continued

```
tacggcgtga tcgtggacac caaggcctac tccggcggct acaacctgcc catcggccag  2520
gccgacgaaa tgcagaggta cgtggaggag aaccagacca ggaacaagca catcaacccc  2580
aacgagtggt ggaaggtgta ccctccagc gtgaccgagt tcaagttcct gttcgtgtcc   2640
ggccacttca agggcaacta caaggcccag ctgaccaggc tgaaccacat caccaactgc  2700
aacggcgccg tgctgtccgt ggaggagctc ctgatcggcg gcgagatgat caaggccggc  2760
accctgaccc tggaggaggt gaggaggaag ttcaacaacg gcgagatcaa cttcgcggcc  2820
gactgataa                                                          2829
```

What is claimed is:

1. A method for expanding tumor infiltrating lymphocytes (TILs) into a therapeutic population of TILs comprising:
   (a) obtaining a first population of TILs from a tumor resected from a patient by processing a tumor sample obtained from the patient into multiple tumor fragments;
   (b) performing a first expansion by culturing the first population of TILs in a cell culture medium comprising IL-2, and optionally OKT-3, to produce a second population of TILs, wherein the first expansion is performed for about 3-12 days;
   (c) activating the second population of TILs using CD3 and CD28 activating beads or antibodies for 1 to 5 days;
   (d) gene-editing at least a portion of the second population of TILs to obtain a third population of TILs; and
   (e) performing a second expansion of the third population of TILs in a cell culture medium comprising IL-2, optionally OKT-3, and antigen presenting cells (APCs), to produce a fourth population of TILs, wherein the second expansion is performed for about 7-12 days to obtain the fourth population of TILs, wherein the fourth population of TILs comprises a therapeutic population of TILs.

2. The method of claim 1, wherein the gene-editing causes expression of one or more immune checkpoint genes to be silenced or reduced in at least a portion of the therapeutic population of TILs.

3. The method of claim 2, wherein said one or more immune checkpoint genes is/are selected from the group comprising PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

4. The method of claim 2, wherein said one or more immune checkpoint genes is/are selected from the group comprising PD-1, CTLA-4, LAG-3, HAVCR2 (TIM-3), Cish, TGFβ, TIGIT, and PKA.

5. The method of claim 2, wherein said one or more immune checkpoint genes comprise PD-1.

6. The method of claim 2, wherein said one or more immune checkpoint genes comprise LAG-3, TIGIT, or CTLA-4.

7. The method of claim 2, wherein said one or more immune checkpoint genes comprise PD-1 and LAG-3.

8. The method of claim 2, wherein said one or more immune checkpoint genes comprise PD-1 and TIGIT.

9. The method of claim 2, wherein said one or more immune checkpoint genes comprise PD-1 and CTLA-4.

10. The method of claim 2, wherein the gene-editing comprises the use of a programmable nuclease that mediates the generation of a double-strand or single-strand break at said one or more immune checkpoint genes.

11. The method of claim 10, wherein the gene-editing comprises the delivery of a Clustered Regularly Interspersed Short Palindromic Repeat (CRISPR) system, a Transcription Activator-Like Effector (TALE) system, or a zinc finger system.

12. The method of claim 10, wherein the gene-editing comprises the delivery of a TALE system.

13. The method of claim 12, wherein the gene-editing comprises introducing an mRNA molecule encoding a TALE nuclease into the second population of TILs by electroporation.

14. The method of claim 13, wherein the one or more immune checkpoint genes is/are selected from the group comprising PD-1, CTLA-4, LAG-3, HAVCR2 (TIM-3), Cish, TGFβ, TIGIT, and PKA.

15. The method of claim 13, wherein the one or more immune checkpoint genes are PD-1 and CTLA-4.

16. The method of claim 13, wherein the one or more immune checkpoint genes are PD-1 and TIGIT.

17. The method of claim 13, wherein the one or more immune checkpoint genes are PD-1 and LAG-3.

18. The method of claim 1, wherein the number of TILs sufficient for a therapeutically effective dosage is from about $2.3 \times 10^{10}$ to about $13.7 \times 10^{10}$.

19. The method of claim 1, wherein the first expansion is performed for about 3-11 days.

20. The method of claim 1, wherein the second expansion is performed within a period of about 11 days.

21. The method of claim 1, wherein the first expansion and the second expansion are each individually performed within a period of 10 days or 11 days.

22. The method of claim 1, wherein the first expansion and the second expansion are each individually performed within a period of about 11 days.

23. The method of claim 1, further comprising the step of:
   (f) harvesting the therapeutic population of TILs.

24. The method of claim 23, further comprising the step of:
   (g) transferring the harvested TIL population from step (f) to an infusion bag.

25. The method of claim 24, further comprising the step of:
   (h) cryopreserving the infusion bag from step (g).

26. The method of claim 1, wherein steps (b), (c) and (e) are performed in a closed system.

27. The method of claim 25, wherein the gene-editing causes expression of one or more immune checkpoint genes to be silenced or reduced in at least a portion of the therapeutic population of TILs, wherein the one or more immune checkpoint genes is/are selected from the group comprising PD-1, CTLA-4, LAG-3, HAVCR2 (TIM-3), Cish, TGFβ, TIGIT, and PKA.

28. The method of claim 27, wherein the one or more immune checkpoint genes are PD-1 and CTLA-4.

29. The method of claim 27, wherein the one or more immune checkpoint genes are PD-1 and TIGIT.

30. The method of claim 27, wherein the one or more immune checkpoint genes are PD-1 and LAG-3.

* * * * *